(12) United States Patent
Liang et al.

(10) Patent No.: US 9,708,325 B2
(45) Date of Patent: Jul. 18, 2017

(54) SULFONIMIDOYLPURINONE COMPOUNDS AND DERIVATIVES FOR THE TREATMENT AND PROPHYLAXIS OF VIRUS INFECTION

(71) Applicant: Hoffmann-La Roche Inc., Little Falls, NJ (US)

(72) Inventors: Chungen Liang, Shanghai (CN); Jianping Wang, Shanghai (CN); Kun Miao, Shanghai (CN); Hongying Yun, Shanghai (CN); Xiufang Zheng, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/148,309

(22) Filed: May 6, 2016

(65) Prior Publication Data

US 2016/0326177 A1   Nov. 10, 2016

(30) Foreign Application Priority Data

May 8, 2015   (WO) ................ PCT/CN2015/078507
Apr. 8, 2016   (WO) ................ PCT/CN2016/078785

(51) Int. Cl.
*A61K 31/522*   (2006.01)
*C07D 473/24*   (2006.01)

(52) U.S. Cl.
CPC ................. *C07D 473/24* (2013.01)

(58) Field of Classification Search
USPC ........................... 514/253.13, 263.1, 263.21
See application file for complete search history.

(56) References Cited

U.S. PATENT DOCUMENTS

| | | | |
|---|---|---|---|
| 7,642,350 B2 | 1/2010 | Pryde | |
| 2010/0143301 A1 | 6/2010 | Desai et al. | |
| 2011/0150836 A1 | 6/2011 | Halcomb | |

FOREIGN PATENT DOCUMENTS

| | | |
|---|---|---|
| CN | 101239980 | 8/2008 |
| CN | 101239980 A | 8/2008 |
| JP | 11-193282 A | 7/1999 |
| JP | 11193282 | 7/1999 |
| WO | 2006/117670 A1 | 11/2006 |
| WO | WO 2006/117670 A1 * | 11/2006 ........... A61K 31/522 |
| WO | 2016/023511 A1 | 2/2016 |
| WO | 2016023511 | 2/2016 |

OTHER PUBLICATIONS

Asselah et al., "Interferon therapy for chronic hepatitis B" Clin Liver Dis 11:839-849 (2007).
Connolly et al., "New developments in Tool-like receptor targeted therapeutics" Current Opinion in Pharmacology 12:510-518 (2012).
Gane et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 (Nov. 2013).
Hemmi et al., "Small anti-viral compounds activate immune cells via the TLR7 MyD88-dependent signaling pathway" Nature Immunology 3(2):196 ( 2002).
Kaisho et al., "Turning NF-kB and IRFs on and off in DC" Trends in Immunology 29(7):329-336 ( 2008).
Roethle et al., "Identification and Optimization of Pteridinone Toll-like Receptor 7 (TLR7) Agonists for the Oral Treatment of Viral Hepatitis" Journal of Medicinal Chemistry 56(18):7324-7333 (Sep. 26, 2013).

* cited by examiner

*Primary Examiner* — Pancham Bakshi
(74) *Attorney, Agent, or Firm* — Jonathan Duffield

(57) ABSTRACT

The present invention relates to compounds of formula (I),

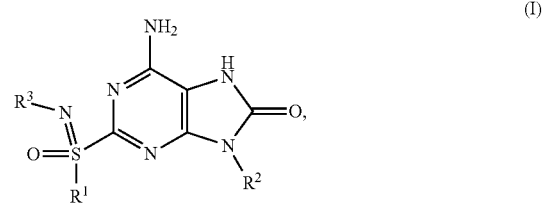

wherein $R^1$, $R^2$ and $R^3$ are as described herein, and their prodrugs or pharmaceutically acceptable salt, enantiomer or diastereomer thereof, and compositions including the compounds and methods of using the compounds.

21 Claims, No Drawings

SULFONIMIDOYLPURINONE COMPOUNDS AND DERIVATIVES FOR THE TREATMENT AND PROPHYLAXIS OF VIRUS INFECTION

The present invention relates to novel sulfonimidoylpurinones and their derivatives that have Toll-like receptor agonism activity and their prodrugs thereof, as well as their manufacture, pharmaceutical compositions containing them and their potential use as medicaments.

FIELD OF THE INVENTION

The present invention relates to compounds of formula (I),

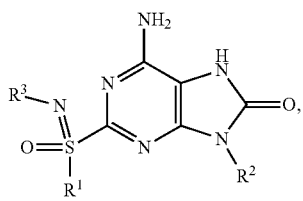

and their prodrugs, formula (Ia),

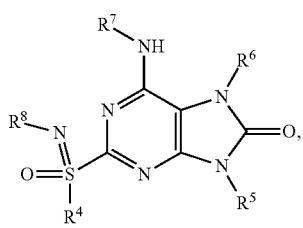

wherein $R^1$ to $R^8$ are described below, or pharmaceutically acceptable salt, enantiomer or diastereomer thereof.

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7 TLR8, and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. A J O'Neill, Current Opinion in Pharmacology 2012, 12:510-518, P. A. Roethle et al, J. Med. Chem. 2013, 56, 7324-7333).

The current therapy of chronic HBV infection is based on two different types of drugs: the traditional antiviral nucleos(t)ide analogues and the more recent Pegylated IFN-α (PEG-IFN-α). The oral nucleos(t)ide analogues act by suppressing the HBV replication. This is a life-long course of treatment during which drug resistance often occurs. As an alternative option, Pegylated IFN-α (PEG-IFN-α) has been used to treat some chronic infected HBV patients within finite therapy duration. Although it has achieved seroconversion in HBeAg at least in a small percentage of HBV patients, the adverse effect makes it poorly tolerable. Notably, functional cure defined as HBsAg seroconversion is very rare with both current therapies. A new generation therapeutic option to treat HBV patients for a functional cure is therefore of urgent need. Treatment with an oral TLR7 agonist represents a promising solution to provide greater efficacy with better tolerability. Pegylated IFN-α (PEG-IFN-α) is currently used to treat chronic HBV and is an alternative to potentially life-long treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleos(t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

In fact, several identified TLR7 agonists have been considered for therapeutic purposes. So far Imiquimod (AL-DARA™) is a U.S. FDA approved TLR7 agonist drug for topical use to treat skin lesions by human papillomavirus. The TLR7/8 dual agonist resiquimod (R-848) and the TLR7 agonist 852A have been evaluated for treating human genital herpes and chemotherapy-refractory metastatic melanoma, respectively. ANA773 is an oral pro-drug TLR7 agonist, developed for the treatment of patients with chronic hepatitis C virus (HCV) infection and chronic hepatitis B infection. GS-9620 is an orally available TLR7 agonist. A phase Ib study demonstrated that treatment with GS-9620 was safe, well tolerated and resulted in dose-dependent ISG15 mRNA induction in patients with chronic hepatitis B (E. J. Gane et al, Annu Meet Am Assoc Study Liver Dis (November 1-5, Washington, D.C.) 2013, Abst 946). Therefore there is high unmet clinical need for developing potent and safe TLR7 agonists as new HBV treatment to offer more therapeutic solutions or replace existing partly effective treatment.

SUMMARY OF THE INVENTION

The present invention provides a series of novel 6-amino-2-sulfonimidoyl-9-substituted-7H-purin-8-one compounds that have Toll-like receptor agonism activity and their pro-drugs. The invention also provides the bio-activity of such compounds to induce SEAP level increase by activating Toll-like receptors, such as TLR7 receptor, the metabolic conversion of prodrugs to parent compounds in the presence of human hepatocytes, and the therapeutic or prophylactic use of such compounds and their pharmaceutical compositions comprising these compounds and their prodrugs to treat or prevent infectious disease like HBV or HCV. The present invention also provides compounds with superior activity. In addition, the compounds of formula (I) and/or (Ia) also show good solubility, selectivity over TLR8, in vitro and in vivo clearance, Ames, hERG, GSH, PK and safety profiles.

The present invention relates to novel compounds of formula (I),

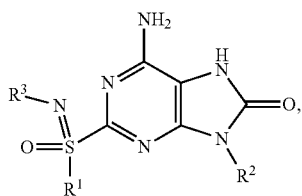

(I)

wherein
$R^1$ is $C_{1-6}$alkyl, halo$C_{1-6}$alkyl, $C_{3-7}$cylcoalkyl$C_{1-6}$alkyl, $C_{1-6}$alkoxy$C_{1-6}$alkyl or pyrrolidinyl$C_{1-6}$alkyl;
$R^2$ is $C_{1-6}$alkyl, phenyl$C_{1-6}$alkyl, pyridinyl$C_{1-6}$alkyl or pyrimidinyl$C_{1-6}$alkyl, said phenyl$C_{1-6}$alkyl, pyridinyl$C_{1-6}$alkyl and pyrimidinyl$C_{1-6}$alkyl are unsubstituted or substituted by one, two or three substituents independently selected from halogen, $C_{1-6}$alkyl, $C_{1-6}$alkoxy, cyano, carboxy, carbamoyl, halo$C_{1-6}$alkyl, $C_{1-6}$alkylsulfonyl, $C_{1-6}$alkoxycarbonyl, $C_{1-6}$alkoxy$C_{1-6}$alkylaminocarbonyl, pyrrolidinylcarbonyl and piperidinylcarbonyl;
$R^3$ is H;
or pharmaceutically acceptable salt, enantiomer or diastereomer thereof.

The present invention also relates to the prodrugs of formula (Ia),

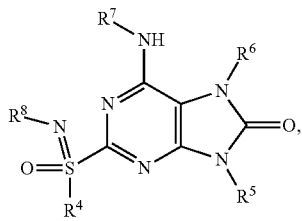

(Ia)

wherein
$R^4$ is $C_{1-6}$alkyl, halo$C_{1-6}$alkyl, $C_{3-7}$cylcoalkyl$C_{1-6}$alkyl, $C_{1-6}$alkoxy$C_{1-6}$alkyl or pyrrolidinyl$C_{1-6}$alkyl;
$R^5$ is $C_{1-6}$alkyl, phenyl$C_{1-6}$alkyl, pyridinyl$C_{1-6}$alkyl or pyrimidinyl$C_{1-6}$alkyl, said phenyl$C_{1-6}$alkyl, pyridinyl$C_{1-6}$alkyl and pyrimidinyl$C_{1-6}$alkyl are unsubstituted or substituted by one, two or three substituents independently selected from halogen, $C_{1-6}$alkyl, $C_{1-6}$alkoxy, cyano, carboxy, carbamoyl, halo$C_{1-6}$alkyl, $C_{1-6}$alkylsulfonyl, $C_{1-6}$alkoxycarbonyl, $C_{1-6}$alkoxy$C_{1-6}$alkylaminocarbonyl, pyrrolidinylcarbonyl and piperidinylcarbonyl;
$R^6$ is H or $C_{1-6}$alkyl-C(O)O—$C_{1-6}$alkyl-;
$R^7$ is H, $C_{1-6}$alkyl, $C_{3-7}$cycloalkyl or $C_{1-10}$alkylcarbonyl;
$R^8$ is H, $C_{1-6}$alkylcarbonyl, carboxy$C_{1-6}$alkylcarbonyl, $C_{1-6}$alkyoxycarbonyl$C_{1-6}$alkylcarbonyl or benzoyl;
or pharmaceutically acceptable salt, enantiomer or diastereomer thereof.

The invention also relates to their manufacture, medicaments based on a compound in accordance with the invention and their production as well as the use of compounds of formula (I) or their prodrugs, formula (Ia), thereof as TLR7 agonist. Accordingly, the compounds of formula (I) or their prodrugs, formula (Ia), are useful for the treatment or prophylaxis of HBV and/or HCV infection with Toll-like receptors agonism.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

DEFINITIONS

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "$C_{1-10}$alkyl" denotes a saturated, linear or branched chain alkyl group containing 1 to 10, particularly 1 to 7 carbon atoms, Particular "$C_{1-10}$alkyl" group is propylbutyl.

The term "$C_{3-7}$cycloalkyl" denotes to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" group is cyclopropyl.

The term "$C_{1-6}$alkoxy" denotes a group of the formula $C_{1-6}$alkyl-O—. Examples of $C_{1-6}$alkoxy group include, but not limited to, methoxy, ethoxy, n-propoxy, isopropoxy, n-butoxy, isobutoxy and tert-butoxy. Particular "$C_{1-6}$alkoxy" groups are methoxy, ethoxy and isopropoxy. A more particular $C_{1-6}$alkoxy group is ethoxy.

The term "halogen" and "halo" are used interchangeably herein and denote fluoro, chloro, bromo, or iodo.

The term "halo$C_{1-6}$alkyl" denotes an alkyl group wherein at least one of the hydrogen atoms of the alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl, trifluoromethyl and trifluoroethyl.

The term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero$C_{3-7}$cycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amino are methylamino, ethylamino, propylamino, isopropylamino, phenyl amino, benzylamino dimethylamino, diethylamino, dipropylamino, diisopropylamino, methoxyethylamino, methylethylamino, chlorobutylmethylamino, dibutylamino and methylbutylamino.

The term "carbonyl" alone or in combination refers to the group —C(O)—.

The term "$C_{1-6}$alkylcarbonyl" refers to a group $C_{1-6}$alkyl-C(O)—, wherein the "$C_{1-6}$alkyl" is as defined above. Particular "$C_{1-6}$alkylcarbonyl" group is acetyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 Agonist and Prodrug

The present invention relates to a compound of formula (I),

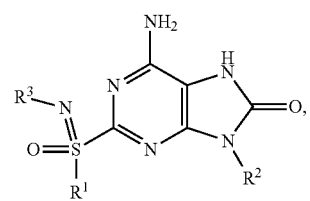

wherein $R^1$ is $C_{1-6}$alkyl, halo$C_{1-6}$alkyl, $C_{3-7}$cylcoalkyl$C_{1-6}$alkyl, $C_{1-6}$alkoxy$C_{1-6}$alkyl or pyrrolidinyl$C_{1-6}$alkyl;

$R^2$ is $C_{1-6}$alkyl, phenyl$C_{1-6}$alkyl, pyridinyl$C_{1-6}$alkyl or pyrimidinyl$C_{1-6}$alkyl, said phenyl$C_{1-6}$alkyl, pyridinyl$C_{1-6}$alkyl and pyrimidinyl$C_{1-6}$alkyl are unsubstituted or substituted by one, two or three substituents independently selected from halogen, $C_{1-6}$alkyl, $C_{1-6}$alkoxy, cyano, carboxy, carbamoyl, halo$C_{1-6}$alkyl, $C_{1-6}$alkylsulfonyl, $C_{1-6}$alkoxycarbonyl, $C_{1-6}$alkoxy$C_{1-6}$alkylaminocarbonyl, pyrrolidinyl carbonyl and piperidinylcarbonyl;

$R^3$ is H;

or pharmaceutically acceptable salt, enantiomer or diastereomer thereof.

A further embodiment of present invention is (ii) a compound of formula (I), wherein $R^1$ is methyl, ethyl, propyl, butyl, chloropropyl, cyclohexylmethyl, methoxyethyl, methoxypropyl, pyrrolidinylpropyl or trifluoroethyl;

$R^2$ is isobutyl, benzyl, chlorobenzyl, fluorobenzyl, bromobenzyl, chlorofluorobenzyl, chloromethylbenzyl, dichlorobenzyl, difluorobenzyl, methylbenzyl, methoxybenzyl, cyanobenzyl, carbamoylbenzyl, trifluoromethylbenzyl, methylsulfonylbenzyl, methoxycarbonylbenzyl, carboxybenzyl, methoxyethylaminocarbonylbenzyl, piperidinylcarbonylbenzyl, pyrrolidinylcarbonylbenzyl, pyridinylmethyl, chloropyridinylmethyl, methylpyridinylmethyl, pyrimidinylmethyl or methylpyrimidinylmethyl;
$R^3$ is H;
or pharmaceutically acceptable salt, enantiomer or diastereomer thereof.

A further embodiment of present invention is (iii) a compound of formula (I), wherein $R^1$ is $C_{1-6}$alkyl, halo$C_{1-6}$alkyl or $C_{1-6}$alkoxy$C_{1-6}$alkyl; or pharmaceutically acceptable salt, enantiomer or diastereomer thereof.

A further embodiment of present invention is a compound of formula (I), wherein $R^1$ is methyl, propyl, chloropropyl, methoxyethyl or trifluoroethyl; or pharmaceutically acceptable salt, enantiomer or diastereomer thereof.

A further embodiment of present invention is (iv) a compound of formula (I), wherein $R^1$ is methyl, ethyl, propyl, butyl, chloropropyl, trifluoroethyl, methoxyethyl or methoxypropyl; or pharmaceutically acceptable salt, enantiomer or diastereomer thereof.

A further embodiment of present invention is (v) a compound of formula (I), wherein $R^1$ is $C_{1-6}$alkyl; or pharmaceutically acceptable salt, enantiomer or diastereomer thereof.

A further embodiment of present invention is (vi) a compound of formula (I), wherein $R^1$ is methyl, ethyl or propyl; or pharmaceutically acceptable salt, enantiomer or diastereomer thereof.

A further embodiment of present invention is (vii) a compound of formula (I), wherein $R^1$ is ethyl; or pharmaceutically acceptable salt, enantiomer or diastereomer thereof.

A further embodiment of present invention is a compound of formula (I), wherein $R^2$ is phenyl$C_{1-6}$alkyl, said phenyl$C_{1-6}$alkyl is unsubstituted or substituted by one to three substituents independently selected from halogen, $C_{1-6}$alkyl, carboxy and $C_{1-6}$alkoxycarbonyl; or pharmaceutically acceptable salt, enantiomer or diastereomer thereof.

A further embodiment of present invention is (viii) a compound of formula (I), wherein $R^2$ is phenyl$C_{1-6}$alkyl, said phenyl$C_{1-6}$alkyl is unsubstituted or substituted by halogen, carbamoyl, $C_{1-6}$alkyl, carboxy, cyano, $C_{1-6}$alkoxy, $C_{1-6}$alkylsulfonyl and $C_{1-6}$alkoxy$C_{1-6}$alkylaminocarbonyl; pyridinyl$C_{1-6}$alkyl, said pyridinyl$C_{1-6}$alkyl is unsubstituted or substituted by $C_{1-6}$alkyl; or pyrimidinyl$C_{1-6}$alkyl, said pyrimidinyl$C_{1-6}$alkyl is unsubstituted or substituted by $C_{1-6}$alkyl; or pharmaceutically acceptable salt, enantiomer or diastereomer thereof.

A further embodiment of present invention is (ix) a compound of formula (I), wherein $R^2$ is benzyl, methylbenzyl, chlorobenzyl, fluorobenzyl, difluorobenzyl, cyanobenzyl, carboxybenzyl, methoxybenzyl, methylsulfonylbenzyl, methoxyethylaminocarbonylbenzyl, pyridinylmethyl, methylpyridinylmethyl, pyrimidinylmethyl or methylpyrimidinylmethyl; or pharmaceutically acceptable salt, enantiomer or diastereomer thereof.

A further embodiment of present invention is a compound of formula (I), wherein $R^2$ is benzyl, methylbenzyl, chlorobenzyl, fluorobenzyl, bromobenzyl, chlorofluorobenzyl, chloromethylbenzyl, dichlorobenzyl, difluorobenzyl, carboxybenzyl or methoxycarbonylbenzyl; or pharmaceutically acceptable salt, enantiomer or diastereomer thereof.

A further embodiment of present invention is (x) a compound of formula (I), wherein $R^2$ is benzyl, methylbenzyl, chlorobenzyl, fluorobenzyl, difluorobenzyl, carboxybenzyl or methylpyridinylmethyl; or pharmaceutically acceptable salt, enantiomer or diastereomer thereof.

A further embodiment of present invention is (xi) a compound of formula (I), wherein $R^2$ is methylbenzyl or chlorobenzyl; or pharmaceutically acceptable salt, enantiomer or diastereomer thereof.

Another embodiment of present invention is (xii) a compound of formula (I), wherein
$R^1$ is $C_{1-6}$alkyl or $C_{1-6}$alkoxy$C_{1-6}$alkyl;
$R^2$ is phenyl$C_{1-6}$alkyl, said phenyl$C_{1-6}$alkyl is unsubstituted or substituted by halogen, carbamoyl, $C_{1-6}$alkyl, carboxy, cyano and $C_{1-6}$alkoxy$C_{1-6}$alkylaminocarbonyl; or pyrimidinyl$C_{1-6}$alkyl, said pyrimidinyl$C_{1-6}$alkyl is unsubstituted or substituted by $C_{1-6}$alkyl;
$R^3$ is H;
or pharmaceutically acceptable salt, enantiomer or diastereomer thereof.

A further embodiment of present invention is (xiii) a compound of formula (I), wherein
$R^1$ is methyl, ethyl, propyl, butyl or methoxyethyl;
$R^2$ is benzyl, methylbenzyl, chlorobenzyl, fluorobenzyl, cyanobenzyl, carboxybenzyl, methoxyethylaminocarbonylbenzyl, pyrimidinylmethyl or methylpyrimidinylmethyl;
$R^3$ is H;
or pharmaceutically acceptable salt, enantiomer or diastereomer thereof.

Another embodiment of present invention is (xiv) a compound of formula (I), wherein
$R^1$ is $C_{1-6}$alkyl;
$R^2$ is phenyl$C_{1-6}$alkyl, said phenyl$C_{1-6}$alkyl is unsubstituted or substituted by halogen or $C_{1-6}$alkyl;
$R^3$ is H;
or pharmaceutically acceptable salt, enantiomer or diastereomer thereof.

A further embodiment of present invention is (xv) a compound of formula (I), wherein
$R^1$ is ethyl or propyl;
$R^2$ is benzyl, chlorobenzyl or methylbenzyl;
$R^3$ is H;
or pharmaceutically acceptable salt, enantiomer or diastereomer thereof.

Another embodiment of present invention is that (xvi) particular compounds of formula (I) are the following:
6-Amino-9-benzyl-2-(methylsulfonimidoyl)-7H-purin-8-one;
6-Amino-9-benzyl-2-(ethylsulfonimidoyl)-7H-purin-8-one;
6-Amino-9-benzyl-2-(2-methoxyethylsulfonimidoyl)-7H-purin-8-one;
6-Amino-9-benzyl-2-(propylsulfonimidoyl)-7H-purin-8-one;
6-Amino-9-benzyl-2-(butylsulfonimidoyl)-7H-purin-8-one;
6-Amino-9-benzyl-2-(3-methoxypropylsulfonimidoyl)-7H-purin-8-one;
6-Amino-9-benzyl-2-(2,2,2-trifluoroethylsulfonimidoyl)-7H-purin-8-one;
6-Amino-9-benzyl-2-(cyclohexylmethylsulfonimidoyl)-7H-purin-8-one;
6-Amino-9-[(4-chlorophenyl)methyl]-2-(propylsulfonimidoyl)-7H-purin-8-one;
6-Amino-9-[(4-methoxyphenyl)methyl]-2-(methylsulfonimidoyl)-7H-purin-8-one;
6-Amino-2-(3-chloropropylsulfonimidoyl)-9-[(4-methoxyphenyl)methyl]-7H-purin-8-one;

6-Amino-9-[(4-methoxyphenyl)methyl]-2-(3-pyrrolidin-1-ylpropylsulfonimidoyl)-7H-purin-8-one;
6-Amino-9-[(4-chlorophenyl)methyl]-2-(methylsulfonimidoyl)-7H-purin-8-one;
6-Amino-9-[(6-chloro-3-pyridyl)methyl]-2-(propylsulfonimidoyl)-7H-purin-8-one;
6-Amino-9-[(2-chlorophenyl)methyl]-2-(propylsulfonimidoyl)-7H-purin-8-one;
6-Amino-2-(methylsulfonimidoyl)-9-(3-pyridylmethyl)-7H-purin-8-one;
3-[[6-Amino-8-oxo-2-(propylsulfonimidoyl)-7H-purin-9-yl]methyl]benzonitrile;
3-[[6-amino-8-oxo-2-(propylsulfonimidoyl)-7H-purin-9-yl]methyl]benzamide;
6-Amino-2-(methylsulfonimidoyl)-9-(2-pyridylmethyl)-7H-purin-8-one;
6-Amino-2-(methylsulfonimidoyl)-9-(4-pyridylmethyl)-7H-purin-8-one;
6-Amino-9-isobutyl-2-(propylsulfonimidoyl)-7H-purin-8-one;
6-Amino-9-[(3-chlorophenyl)methyl]-2-(propylsulfonimidoyl)-7H-purin-8-one;
6-Amino-2-(propylsulfonimidoyl)-9-[[4-(trifluoromethyl)phenyl]methyl]-7H-purin-8-one;
6-Amino-9-[(4-fluorophenyl)methyl]-2-(propylsulfonimidoyl)-7H-purin-8-one;
6-Amino-9-[(4-bromophenyl)methyl]-2-(propylsulfonimidoyl)-7H-purin-8-one;
6-Amino-9-[(3,4-dichlorophenyl)methyl]-2-(propylsulfonimidoyl)-7H-purin-8-one;
6-Amino-9-(3,4-difluorophenylmethyl)-2-(propylsulfonimidoyl)-7H-purin-8-one;
6-Amino-9-[(4-chloro-3-methyl-phenyl)methyl]-2-(propylsulfonimidoyl)-7H-purin-8-one;
6-Amino-2-(propylsulfonimidoyl)-9-(p-tolylmethyl)-7H-purin-8-one;
6-Amino-9-[(4-chloro-3-fluorophenyl)methyl]-2-(propylsulfonimidoyl)-7H-purin-8-one;
6-Amino-9-[(2,4-difluorophenyl)methyl]-2-(propylsulfonimidoyl)-7H-purin-8-one;
4-[[6-Amino-8-oxo-2-(propylsulfonimidoyl)-7H-purin-9-yl]methyl]benzonitrile;
4-[[6-Amino-8-oxo-2-(propylsulfonimidoyl)-7H-purin-9-yl]methyl]benzamide;
6-Amino-9-[(6-methyl-3-pyridyl)methyl]-2-(propylsulfonimidoyl)-7H-purin-8-one;
6-Amino-9-[(2-methyl-4-pyridyl)methyl]-2-(propylsulfonimidoyl)-7H-purin-8-one;
6-Amino-9-[(3-chloro-4-methyl-phenyl)methyl]-2-(propylsulfonimidoyl)-7H-purin-8-one;
6-Amino-9-[(4-methylsulfonylphenyl)methyl]-2-(propylsulfonimidoyl)-7H-purin-8-one;
Methyl 4-[[6-amino-8-oxo-2-(propylsulfonimidoyl)-7H-purin-9-yl]methyl]benzoate;
4-[[6-Amino-8-oxo-2-(propylsulfonimidoyl)-7H-purin-9-yl]methyl]benzoic acid;
4-[[6-Amino-8-oxo-2-(propylsulfonimidoyl)-7H-purin-9-yl]methyl]-N-(2-methoxyethyl)benzamide;
6-Amino-9-[[4-(piperidine-1-carbonyl)phenyl]methyl]-2-(propylsulfonimidoyl)-7H-purin-8-one;
6-Amino-2-(S-propylsulfonimidoyl)-9-[[4-(pyrrolidine-1-carbonyl)phenyl]methyl]-7H-purin-8-one;
6-Methyl-2-(propylsulfonimidoyl)-9-(pyrimidin-5-ylmethyl)-7H-purin-8-one;
6-Methyl-9-[(2-methylpyrimidin-5-yl)methyl]-2-(propylsulfonimidoyl)-7H-purin-8-one;
6-Amino-9-[(4-chlorophenyl)methyl]-2-(ethylsulfonimidoyl)-7H-purin-8-one;
6-Amino-2-(ethylsulfonimidoyl)-9-(p-tolylmethyl)-7H-purin-8-one; and
6-Amino-2-(ethylsulfonimidoyl)-9-[(4-fluorophenyl)methyl]-7H-purin-8-one;

or pharmaceutically acceptable salt, enantiomer or diastereomer thereof.

Another embodiment of present invention is that (xvii) more particular compounds of formula (I) are the following:
6-Amino-9-benzyl-2-(propylsulfonimidoyl)-7H-purin-8-one;
6-Amino-9-[(4-chlorophenyl)methyl]-2-(propylsulfonimidoyl)-7H-purin-8-one;
6-Amino-9-[(6-chloro-3-pyridyl)methyl]-2-(propylsulfonimidoyl)-7H-purin-8-one;
6-Amino-9-[(4-fluorophenyl)methyl]-2-(propylsulfonimidoyl)-7H-purin-8-one;
6-Amino-9-[(4-bromophenyl)methyl]-2-(propylsulfonimidoyl)-7H-purin-8-one;
6-Amino-2-(propylsulfonimidoyl)-9-(p-tolylmethyl)-7H-purin-8-one;
6-Amino-9-[(6-methyl-3-pyridyl)methyl]-2-(propylsulfonimidoyl)-7H-purin-8-one;
Methyl 4-[[6-amino-8-oxo-2-(propylsulfonimidoyl)-7H-purin-9-yl]methyl]benzoate;
4-[[6-Amino-8-oxo-2-(propylsulfonimidoyl)-7H-purin-9-yl]methyl]benzoic acid;
6-Methyl-9-[(2-methylpyrimidin-5-yl)methyl]-2-(propylsulfonimidoyl)-7H-purin-8-one;
6-Amino-9-[(4-chlorophenyl)methyl]-2-(ethylsulfonimidoyl)-7H-purin-8-one; and
6-Amino-2-(ethylsulfonimidoyl)-9-(p-tolylmethyl)-7H-purin-8-one;

or pharmaceutically acceptable salt, enantiomer or diastereomer thereof.

Another embodiment of present invention is that (xviii) the most particular compounds of formula (I) are the following:
6-Amino-9-[(4-chlorophenyl)methyl]-2-(ethylsulfonimidoyl)-7H-purin-8-one; and
6-Amino-2-(ethylsulfonimidoyl)-9-(p-tolylmethyl)-7H-purin-8-one;

or pharmaceutically acceptable salt, enantiomer or diastereomer thereof.

Another embodiment of present invention is (xix) a compound of formula (Ia),

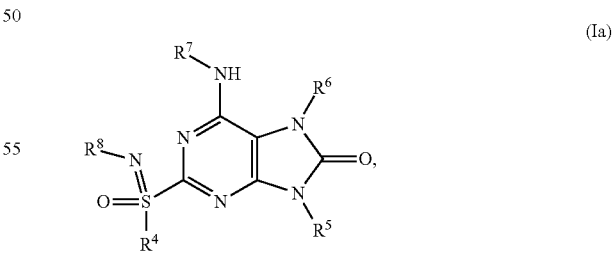

wherein
$R^4$ is $C_{1-6}$alkyl, halo$C_{1-6}$alkyl, $C_{3-7}$cylcoalkyl$C_{1-6}$alkyl, $C_{1-6}$alkoxy$C_{1-6}$alkyl or pyrrolidinyl$C_{1-6}$alkyl;
$R^5$ is $C_{1-6}$alkyl, phenyl$C_{1-6}$alkyl, pyridinyl$C_{1-6}$alkyl or pyrimidinyl$C_{1-6}$alkyl, said phenyl$C_{1-6}$alkyl, pyridinyl$C_{1-6}$alkyl and pyrimidinyl$C_{1-6}$alkyl are unsubstituted or substituted by one, two or three substituents independently selected from halogen, $C_{1-6}$alkyl, $C_{1-6}$alkoxy, cyano, carboxy, carbamoyl, halo$C_{1-6}$alkyl, $C_{1-6}$alkylsulfonyl, $C_{1-6}$alkoxycarbonyl, $C_{1-6}$alkoxy$C_{1-6}$alkylaminocarbonyl, pyrrolidinylcarbonyl and piperidinylcarbonyl;

$R^6$ is H or $C_{1-6}$alkyl-C(O)O—$C_{1-6}$alkyl-;

$R^7$ is H, $C_{1-6}$alkyl, $C_{3-7}$cycloalkyl or $C_{1-10}$alkylcarbonyl;

$R^8$ is H, $C_{1-6}$alkylcarbonyl, carboxy$C_{1-6}$alkylcarbonyl, $C_{1-6}$alkyoxycarbonyl$C_{1-6}$alkylcarbonyl or benzoyl;

provided that $R^6$, $R^7$ and $R^8$ are not H simultaneously;

or pharmaceutically acceptable salt, enantiomer or diastereomer thereof.

A further embodiment of present invention is (xx) a compound of formula (Ia), wherein $R^4$ is methyl, ethyl, propyl, butyl, chloropropyl, cyclohexylmethyl, methoxyethyl, methoxypropyl, pyrrolidinylpropyl or trifluoroethyl;

$R^5$ is isobutyl, benzyl, chlorobenzyl, fluorobenzyl, bromobenzyl, chlorofluorobenzyl, chloromethylbenzyl, dichlorobenzyl, difluorobenzyl, methylbenzyl, methoxybenzyl, cyanobenzyl, carbamoylbenzyl, trifluoromethylbenzyl, methylsulfonylbenzyl, methoxycarbonylbenzyl, carboxybenzyl, methoxyethylaminocarbonylbenzyl, piperidinylcarbonylbenzyl, pyrrolidinylcarbonylbenzyl, pyridinylmethyl, chloropyridinylmethyl, methylpyridinylmethyl, pyrimidinylmethyl or methylpyrimidinylmethyl;

$R^6$ is H, acetoxymethyl, acetoxyethyl or dimethylpropanoyloxymethyl;

$R^7$ is H, ethyl, propyl, isopropyl, cyclopropyl, acetyl, pentanoyl, methylpentanoyl, propylpentanoyl, ethylbutanoyl, methylbutanoyl or dimethylpropanoyl;

$R^8$ is H, acetyl, pentanoyl, carboxypropanoyl, ethoxycarbonylpropanoyl or benzoyl;

provided that $R^6$, $R^7$ and $R^8$ are not H simultaneously;

or pharmaceutically acceptable salt, enantiomer or diastereomer thereof.

A further embodiment of present invention is (xxi) a compound of formula (Ia), wherein $R^4$ is $C_{1-6}$alkyl; or pharmaceutically acceptable salt, enantiomer or diastereomer thereof.

A further embodiment of present invention is (xxii) a compound of formula (Ia), wherein $R^4$ is methyl or propyl; or pharmaceutically acceptable salt, enantiomer or diastereomer thereof.

A further embodiment of present invention is (xxiii) a compound of formula (Ia), wherein $R^5$ is phenyl$C_{1-6}$alkyl or pyridinyl$C_{1-6}$alkyl, said phenyl$C_{1-6}$alkyl and pyridinyl$C_{1-6}$alkyl are unsubstituted or substituted by one to three substituents independently selected from halogen or $C_{1-6}$alkyl; or pharmaceutically acceptable salt, enantiomer or diastereomer thereof.

A further embodiment of present invention is a compound of formula (Ia), wherein $R^5$ is benzyl, methylbenzyl, chlorobenzyl or methylpyridinylmethyl; or pharmaceutically acceptable salt, enantiomer or diastereomer thereof.

A further embodiment of present invention is (xxiv) a compound of formula (Ia), wherein $R^5$ is benzyl, chlorobenzyl or methylpyridinylmethyl; or pharmaceutically acceptable salt, enantiomer or diastereomer thereof.

A further embodiment of present invention is (xxv) a compound of formula (Ia), wherein $R^7$ is H, $C_{1-6}$alkyl or $C_{1-10}$alkylcarbonyl; or pharmaceutically acceptable salt, enantiomer or diastereomer thereof.

A further embodiment of present invention is (xxvi) a compound of formula (Ia), wherein $R^7$ is H, ethyl, propyl, methylpentanoyl or propylpentanoyl; or pharmaceutically acceptable salt, enantiomer or diastereomer thereof.

A further embodiment of present invention is (xxvii) a compound of formula (Ia), wherein $R^8$ is H, $C_{1-6}$alkylcarbonyl or carboxy$C_{1-6}$alkylcarbonyl; or pharmaceutically acceptable salt, enantiomer or diastereomer thereof.

A further embodiment of present invention is (xxviii) a compound of formula (Ia), wherein $R^8$ is H, pentanoyl or carboxypropanoyl; or pharmaceutically acceptable salt, enantiomer or diastereomer thereof.

Another embodiment of present invention is that (xix) particular compounds of formula (Ia) are the following:

N-[(6-Amino-9-benzyl-8-oxo-7H-purin-2-yl)-oxo-propyl-$\lambda^4$-sulfanylidene]pentanamide;

N-[[6-Amino-9-[(4-chlorophenyl)methyl]-8-oxo-7H-purin-2-yl]-oxo-propyl-$\lambda^4$-sulfanylidene]acetamide;

N-[(6-Amino-9-benzyl-8-oxo-7H-purin-2-yl)-methyl-oxo-$\lambda^4$-sulfanylidene]acetamide;

4-[[(6-Amino-9-benzyl-8-oxo-7H-purin-2-yl)-oxo-propyl-$\lambda^4$-sulfanylidene]amino]-4-oxo-butanoic acid;

4-[[(6-Amino-9-benzyl-8-oxo-7H-purin-2-yl)-oxo-propyl-$\lambda^4$-sulfanylidene]amino]-4-oxo-butanoic acid;

4-[[(6-Amino-9-benzyl-8-oxo-7H-purin-2-yl)-oxo-propyl-$\lambda^4$-sulfanylidene]amino]-4-oxo-butanoic acid;

Ethyl 4-[[(6-amino-9-benzyl-8-oxo-7H-purin-2-yl)-oxo-propyl-$\lambda^4$-sulfanylidene]amino]-3-oxo-butanoate;

Ethyl 4-[[(6-amino-9-benzyl-8-oxo-7H-purin-2-yl)-oxo-propyl-$\lambda^4$-sulfanylidene]amino]-4-oxo-butanoate;

Ethyl 4-[[(6-amino-9-benzyl-8-oxo-7H-purin-2-yl)-oxo-propyl-$\lambda^4$-sulfanylidene]amino]-4-oxo-butanoate;

N-[(6-amino-9-benzyl-8-oxo-7H-purin-2-yl)-oxo-propyl-$\lambda^4$-sulfanylidene]benzamide;

N-[(6-Amino-9-benzyl-8-oxo-7H-purin-2-yl)-oxo-propyl-$\lambda^4$-sulfanylidene]benzamide;

N-[(6-Amino-9-benzyl-8-oxo-7H-purin-2-yl)-oxo-propyl-$\lambda^4$-sulfanylidene]benzamide;

9-Benzyl-6-(ethylamino)-2-(propylsulfonimidoyl)-7H-purin-8-one;

6-(Ethylamino)-9-[(6-methyl-3-pyridyl)methyl]-2-(S-propylsulfonimidoyl)-7H-purin-8-one;

9-[(4-Chlorophenyl)methyl]-6-(ethylamino)-2-(propylsulfonimidoyl)-7H-purin-8-one;

9-Benzyl-6-(propylamino)-2-(propylsulfonimidoyl)-7H-purin-8-one;

9-Benzyl-6-(isopropylamino)-2-(propylsulfonimidoyl)-7H-purin-8-one;

9-Benzyl-6-(cyclopropylamino)-2-(propylsulfonimidoyl)-7H-purin-8-one;

N-[9-[(4-Chlorophenyl)methyl]-8-oxo-2-(propylsulfonimidoyl)-7H-purin-6-yl]-2-propyl-pentanamide;

N-[9-[(4-Chlorophenyl)methyl]-8-oxo-2-(propylsulfonimidoyl)-7H-purin-6-yl]acetamide;

N-[9-Benzyl-8-oxo-2-(propylsulfonimidoyl)-7H-purin-6-yl]pentanamide;

N-[9-[(4-Chlorophenyl)methyl]-8-oxo-2-(propylsulfonimidoyl)-7H-purin-6-yl]-2-ethyl-butanamide;

N-[9-[(4-Chlorophenyl)methyl]-8-oxo-2-(propylsulfonimidoyl)-7H-purin-6-yl]-3-methyl-butanamide;

N-[9-[(4-Chlorophenyl)methyl]-8-oxo-2-(propylsulfonimidoyl)-7H-purin-6-yl]-2-methyl-pentanamide;

N-[9-[(4-chlorophenyl)methyl]-8-oxo-2-(propylsulfonimidoyl)-7H-purin-6-yl]-2,2-dimethyl-propanamide;

N-[9-Benzyl-8-oxo-2-(propylsulfonimidoyl)-7H-purin-6-yl]-2-propyl-pentanamide;

[6-Amino-9-benzyl-2-(methylsulfonimidoyl)-8-oxo-purin-7-yl]methyl acetate;

[6-Amino-9-benzyl-8-oxo-2-(propylsulfonimidoyl)purin-7-yl]methyl acetate;

[6-Amino-9-benzyl-8-oxo-2-(propylsulfonimidoyl)purin-7-yl]methyl 2,2-dimethylpropanoate; and 1-[6-Amino-9-benzyl-8-oxo-2-(propylsulfonimidoyl)purin-7-yl]ethyl acetate;

or pharmaceutically acceptable salt, enantiomer or diastereomer thereof.

In some embodiments, compounds of present invention were tested and compared with the following reference compounds:

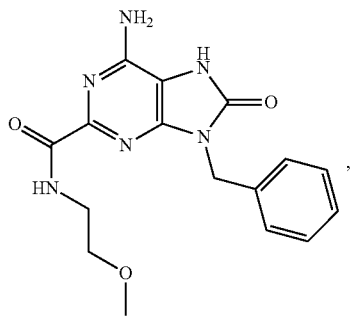
(P-2)

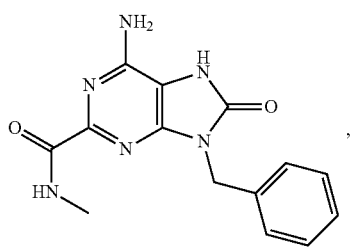
(P-5)

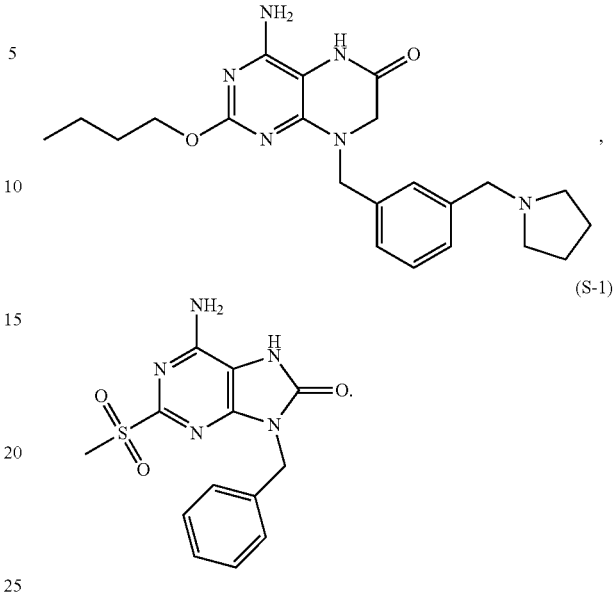

Compound P-2 and P-5 were disclosed in WO2006117670 as example 2 and 5 respectively, compound GS-9620 was disclosed in US20100143301 as example 49, compound S-1 was disclosed in JP1999193282.

Synthesis

The compounds of the present invention can be prepared by any conventional means. Suitable processes for synthesizing these compounds as well as their starting materials are provided in the schemes below and in the examples. All substituents, in particular, $R^1$ to $R^{11}$ are as defined above unless otherwise indicated. Furthermore, and unless explicitly otherwise stated, all reactions, reaction conditions, abbreviations and symbols have the meanings well known to a person of ordinary skill in organic chemistry.

Scheme 1

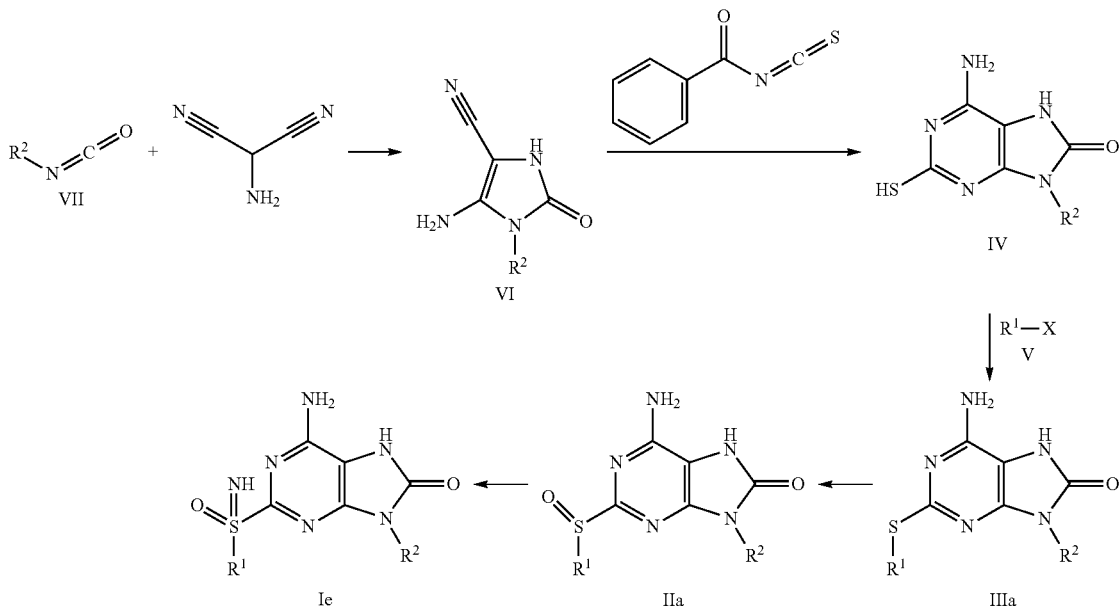

A compound of formula VI is prepared by cyclization of isocyanate VII with aminomalononitrile p-toluenesulfonate. Then bicycle IV is synthesized by reaction of compound of formula VI with benzoyl isothiocyanate with inorganic base, such as sodium hydroxide or potassium hydroxide. Alkylation of bicycle IV with alkylhalide V in the presence of base such as $K_2CO_3$, NaH or $Cs_2CO_3$, gives compound of formula IIIa. Then compound of formula IIa is prepared by oxidation of compound of formula IIIa with an oxidant, such as meta-chloroperoxybenzoic acid, urea-hydrogen peroxide adduct or $HIO_4$. Compound of formula Ie is obtained by imination of compound of formula IIa with imination reagent, such as sodium azide in acid, said acid is for example Eaton's reagent or PPA.

Scheme 2

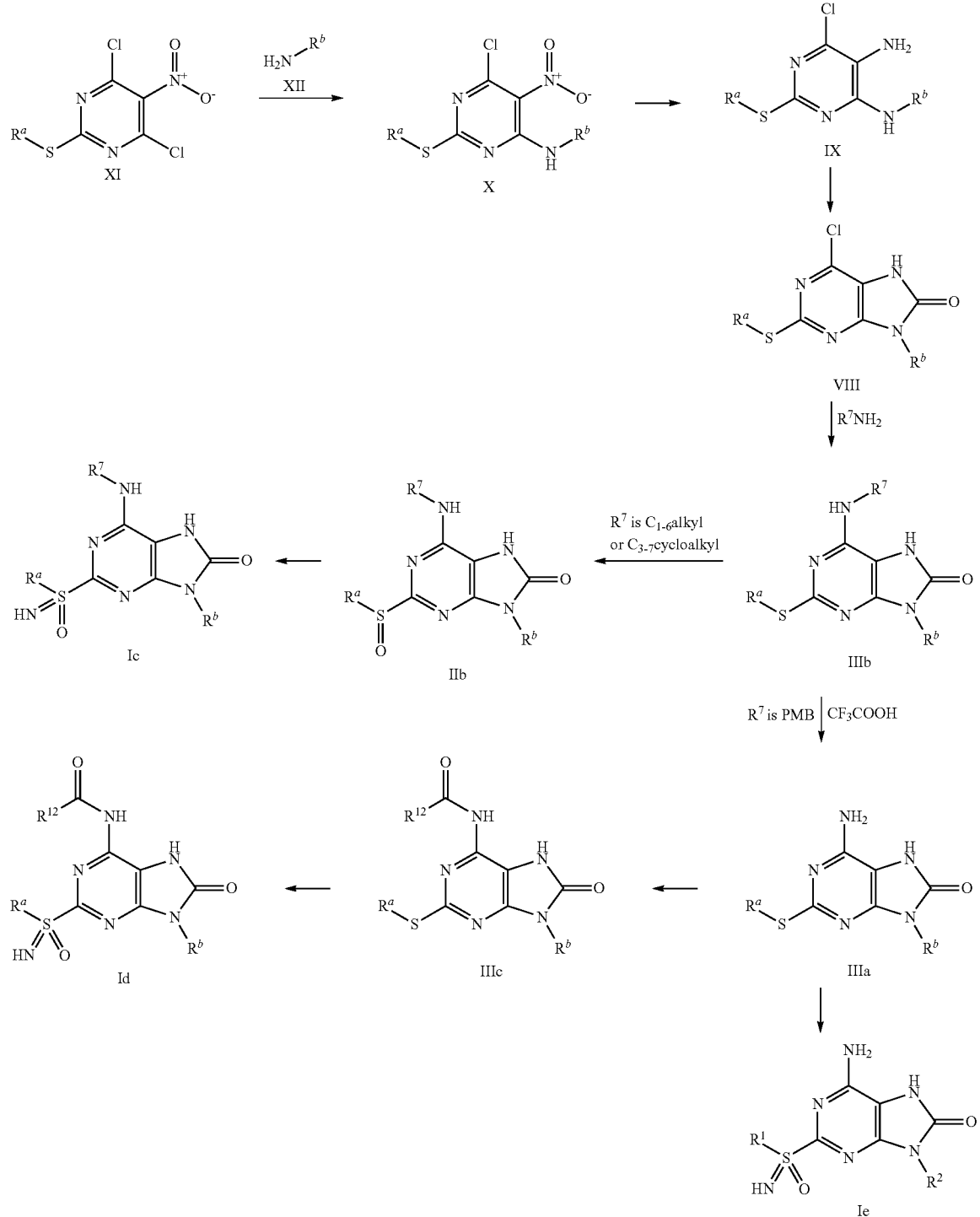

$R^a$ is $R^1$ or $R^4$, $R^b$ is $R^2$ or $R^5$, $R^7$ is $C_{1-6}$alkyl, $C_{3-7}$cycloalkyl or PMB, $R^{12}$ is $C_{1-10}$alkyl.

A compound of formula X is prepared by reaction of compound of formula XI with $R^bNH_2$. Reduction of compound X gives the compound of formula IX. Cyclization of compound of formula IX with cyclization reagents, such as phosgene, carbonyl diimidazole, diethyl carbonate or triphosgene affords compound of formula VIII. A compound of formula IIIb is prepared by treating the compound of formula VIII with $R^7NH_2$ upon heating. A compound of formula Ie is prepared by deprotection of compound of formula IIIb while $R^7$ is PMB with acid, such as $CF_3COOH$, followed by oxidation with an oxidant, such as meta-chloroperoxybenzoic acid, urea-hydrogen peroxide adduct or $HIO_4$, and imination with imination reagent, such as sodium azide in acid, said acid is for example Eaton's reagent or PPA. A compound of formula Ic is obtained by direct oxidation of compound of formula IIIb to give compound IIb while $R^7$ is alkyl or cycloalkyl, followed by imination with imination reagent, such as sodium azide in acid, said acid is for example Eaton's reagent or PPA. A compound of formula Id is obtained by acylation of compound of formula IIIa to give compound IIIc, followed by oxidation with an oxidant, such as meta-chloroperoxybenzoic acid, urea-hydrogen peroxide adduct or $HIO_4$, and imination with imination reagent, such as sodium azide in acid, said acid is for example Eaton's reagent or PPA.

Scheme 3

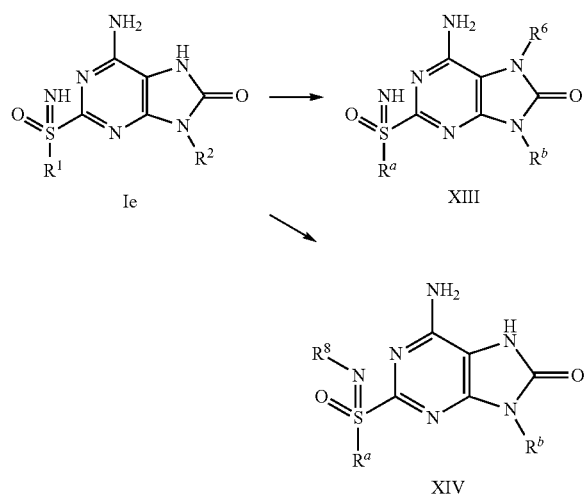

$R^a$ is $R^1$, $R^4$ or $R^9$; $R^b$ is $R^2$, $R^5$ or $R^{10}$.

Prodrugs of formula XIII or XIV can be prepared according Scheme 3.

Compound of formula XIII is synthesized by alkylation of active parent compounds of formula Ie with haloester, such as chloromethyl acetate. Compound of formula XIV is synthesized by reaction of active parent compound of formula Ie with carboxylic anhydride, such as acetic anhydride, or acylchloride, such as 4-chloro-4-oxo-butanoate.

This invention also relates to a process for the preparation of a compound of formula (I) or (Ia) comprising the reaction of:

(a) the reaction of a compound of formula (IIa),

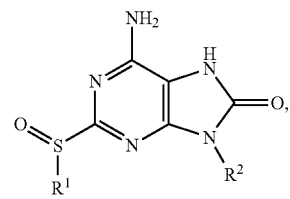

(IIa)

with an imination reagent;

(b) the reaction of a compound of formula (IIb),

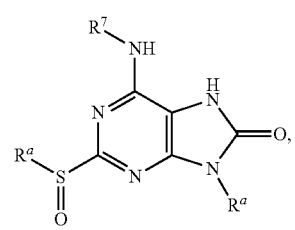

(IIb)

with an imination reagent; wherein $R^a$ is $R^1$ or $R^4$, $R^b$ is $R^2$ or $R^5$, $R^7$ is $C_{1-6}$alkyl or $C_{3-7}$cycloalkyl;

(c) the reaction of a compound of formula (IIIc),

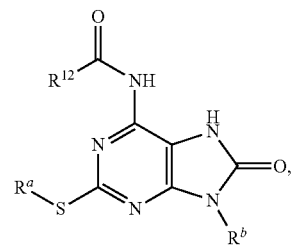

(IIIc)

with an oxidant followed by an imination reagent, wherein $R^a$ is $R^1$ or $R^4$, $R^b$ is $R^2$ or $R^5$, $R^{12}$ is $C_{1-10}$alkyl;

(d) the reaction of a compound of formula (IIIa),

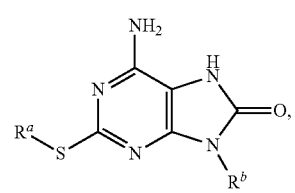

(IIIa)

with an oxidant followed by an imination reagent, wherein $R^a$ is $R^1$ or $R^4$, $R^b$ is $R^2$ or $R^5$;

(e) the reaction of a compound of formula (Ie),

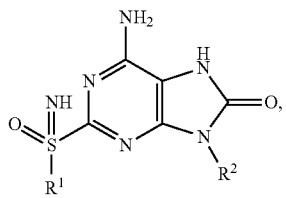

with haloester;

(f) the reaction of a compound of formula (Ie),

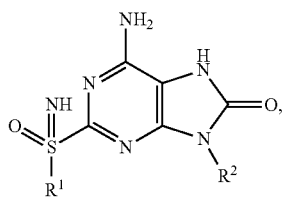

with carboxylic anhydride or acylchloride;
or wherein $R^a$, $R^b$, $R^1$, $R^2$, $R^4$, $R^5$, $R^7$ and $R^{12}$ are defined above.

In step (a), (b), (c) and (d), the imination reagent can be for example sodium azide in acid, said acid can be for example Eaton's reagent or PPA.

In step (c) and (d), the oxidant can be for example meta-chloroperoxybenzoic acid, urea-hydrogen peroxide adduct or $HIO_4$.

In step (e), the haloester can be for example chloromethyl acetate.

In step (f), the carboxylic anhydride can be for example acetic anhydride; the acylchloride can be 4-chloro-4-oxobutanoate.

A compound of formula (I) and (Ia) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) or their prodrugs may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or their prodrugs are formulated in an acetate buffer, at pH 5. In another embodiment, the compounds of formula (I) or their prodrugs are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 receptor and lead to produce INF-α and other cytokines, which can be used, but not limited, for the treatment or prevention of hepatitis B and/or C viral infected patients.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or its prodrugs, formula (Ia), or pharmaceutically acceptable salts or enantiomers or diastereomers thereof.

In a further embodiment includes a pharmaceutical composition comprising a compound of formula (I) or its prodrugs, formula (Ia), or pharmaceutically acceptable salts or enantiomers or diastereomers thereof, together with a pharmaceutically acceptable carrier or excipient.

Another embodiment includes a pharmaceutical composition comprising a compound of formula (I) or its prodrugs, formula (Ia), or pharmaceutically acceptable salts or enantiomers or diastereomers thereof for use in the treatment of hepatitis B virus infection.

Indications and Methods of Treatment

The present invention provides methods for treating or preventing a hepatitis B viral infection and/or hepatitis C viral infection in a patient in need thereof.

The present invention further provides methods for introducing a therapeutically effective amount of a compound of formula (I) or its prodrugs, or other compounds of the invention into the blood stream of a patient for the treatment and/or prevention of hepatitis B and/or C viral infection.

The methods of the present invention are particularly well suited for human patients. In particular, the methods and doses of the present invention can be useful for, but not limited to, HBV and/or HCV infected patients. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing hepatitis B viral infection and/or hepatitis C viral infection in a mammal in need of such treatment, wherein the method comprises administering to said mammal a therapeutically effective amount of a compound of formula (I), or enantiomers, diastereomers, prodrugs or pharmaceutically acceptable salts thereof.

EXAMPLES

The invention will be more fully understood by reference to the following examples. They should not, however, be construed as limiting the scope of the invention.

ABBREVIATIONS aq. aqueous
BSA: N,O-bis(trimethylsilyl)acetamide
CDCl$_3$: deuterated chloroform
CD$_3$OD: deuterated methanol
CDI: N,N'-carbonyldiimidazole
DIEPA: N, N-diethylpropylamine
DMF: dimethyl formamide
DMSO: dimethylsulfoxide
DBU: 1,8-Diazabicycloundec-7-ene
DPPA: diphenylphosphoryl azide
EC$_{50}$: the molar concentration of an agonist, which produces 50% of the maximum possible response for that agonist.
EDC: N1-((ethylimino)methylene)-N3,N3-dimethylpropane-1,3-diamine
EtOAc or EA: ethyl acetate
HATU: (1-[Bis(dimethylamino)methylene]-1H-1,2,3-triazolo[4,5-b]pyridinium 3-oxid hexafluorophosphate)
hr(s): hour(s)
HPLC: high performance liquid chromatography
HOBt: N-hydroxybenzotriazole
MS (ESI): mass spectroscopy (electron spray ionization)
m-CPBA: 3-chloroperbenzoic acid
min(s) minute(s)
MTEB: methyl tert-butyl ether
NMR: nuclear magnetic resonance
NMP: N-methylpyrrolidone
obsd. observed
PE: petroleum ether
PMB: p-methoxybenzyl
PPA: polyphosphoric acid
RT or rt: room temperature
sat. saturated
TFA: trifluoroacetic acid
THF: tetrahydrofuran
TEA: triethylamine
V/V volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in H$_2$O; B: 0.1% formic acid in acetonitrile;

Basic condition: A: 0.05% NH$_3$.H$_2$O in H$_2$O; B: acetonitrile.

Mass spectra (MS): generally only ions which indicate the parent mass are reported, and unless otherwise stated the mass ion quoted is the positive mass ion (M+H)$^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

Preparative Examples

Example 1

6-Amino-9-benzyl-2-(methylsulfonimidoyl)-7H-purin-8-one

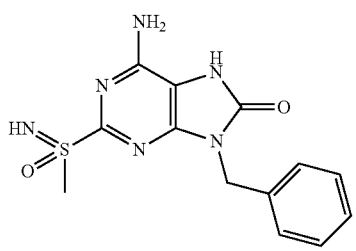

1

Step 1: Preparation of
4-amino-3-benzyl-2-oxo-1H-imidazole-5-carbonitrile

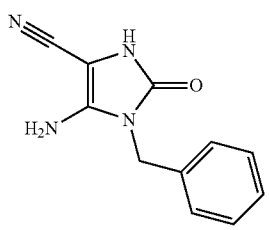

1a

To a solution of aminomalononitrile p-toluenesulfonate (25 g, 98.5 mmol, TCI, Catalog number: A1119-25G) in dry THF (100 mL) was added benzyl isocyanate (13.2 g, 98.5 mmol) and TEA (10.2 g, 79.0 mmol) at RT. After stirred at rt for 24 hrs, the reaction was concentrated in vacuo and the residue partitioned between EtOAc (500 mL) and water (250 mL). The separated organic layer was washed with brine (50 mL) two times, and extracted with sodium hydroxide solution (50 mL, 1N) two times. The combined sodium hydroxide solution layer was neutralized with 10 wt. % sodium hydrogen sulfate solution and extracted with EtOAc. The separated organic layer was washed with brine, dried over anhydrous $Na_2SO_4$, filtered and concentrated in vacuo. The residue was triturated in 2-isopropoxypropane and then the suspension was filtered to give 4-amino-3-benzyl-2-oxo-1H-imidazole-5-carbonitrile (compound 1a) as a yellow solid (15 g), the product was used in the next step without further purification. MS obsd. (ESI$^+$) [(M+H)$^+$]: 215.

Step 2: Preparation of
6-amino-9-benzyl-2-sulfanyl-7H-purin-8-one

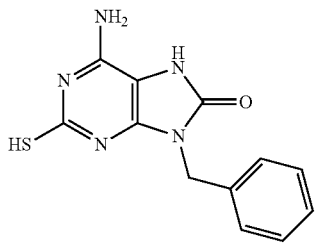

1b

To a solution of 4-amino-3-benzyl-2-oxo-1H-imidazole-5-carbonitrile (15.0 g, 70.0 mmol, compound 1a) in THF (700 mL) was added benzoylisothiocyanate (28.6 g, 175.1 mmol, TCI, Catalog number: A11596-100G) dropwise. After stirred at RT for 12 hrs, the reaction mixture was concentrated in vacuo. The residue was triturated in diethyl ether (100 mL) and the resulting precipitate was collected by filtration.

To a solution of the obtained precipitate in THF (700 mL) was added sodium hydroxide (70 mL, 2 N). The mixture was refluxed for 50 hrs, and then acidified to pH3 with 10% wt. aqueous sodium hydrogen sulfate solution. The resulting precipitate was collected by filtration to give a crude product 6-amino-9-benzyl-2-sulfanyl-7H-purin-8-one (8.1 g, compound 1b) as a yellow solid. The product was used in the next step without further purification. MS obsd. (ESI$^+$) [(M+H)$^+$]: 274.

Step 3: Preparation of
6-amino-9-benzyl-2-methylsulfanyl-7H-purin-8-one

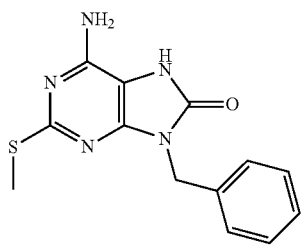

1c

To a solution of 6-amino-9-benzyl-2-sulfanyl-7H-purin-8-one (5.46 g, 20.0 mmol, compound 1b) in DMF was added potassium carbonate (2.76 g, 20.0 mmol). And then methyl iodide (2.84 g, 20.0 mmol) in DMF (5.0 mL) was slowly added to previous solution. After stirred at RT for 12 hrs, the reaction mixture was poured into water (200 mL), then acidified with 10 wt. % aqueous sodium hydrogen sulfate solution and extracted with EtOAc (100 mL) two times. The organic layer was washed with brine, dried and concentrated in vacuo to give the crude product, which was purified by flash chromatography on silica gel to give 6-amino-9-benzyl-2-methylsulfanyl-7H-purin-8-one (4.9 g, compound 1c) as a white solid. MS obsd. (ESI$^+$) [(M+H)$^+$]: 288.

Step 4: Preparation of
6-amino-9-benzyl-2-methylsulfinyl-7H-purin-8-one

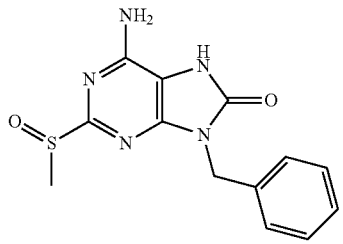

1d

To a suspension of compound 6-amino-9-benzyl-2-methylsulfanyl-7H-purin-8-one (2.5 g, 8.7 mmol, compound 1c) in DCM/MeOH (500 mL, V/V=1:1) was added 3-chloroperbenzoic acid (2.15 g, 8.7 mmol, 70% purity, Aldrich, Catalog number: 273031-100G). After reaction was stirred for 2 hrs, the volume of reaction mixture was reduced in vacuo to about 50 mL. The resulting precipitate was collected by filtration, washed with methanol and dried to give 6-amino-9-benzyl-2-methylsulfinyl-7H-purin-8-one (1.0 g, compound 1d) as a white solid. The product was used in the next step without further purification. MS obsd. (ESI$^+$) [(M+H)$^+$]: 304.

Step 5: Preparation of 6-amino-9-benzyl-2-(methylsulfonimidoyl)-7H-purin-8-one

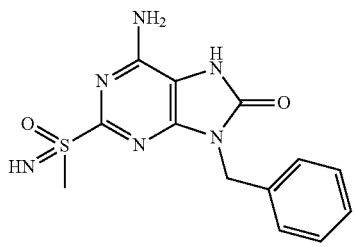

1

To a solution of 6-amino-9-benzyl-2-methylsulfinyl-7H-purin-8-one (1.4 g, 4.6 mmol, compound 1d) in Eaton's reagent (40 mL, phosphorus pentoxide, 7.5 wt. % in methanesulphonic acid, Aldrich, Catalog number: 380814-100ML) was added sodium azide (360 mg, 5.5 mmol) at 50° C. After being stirred at this temperature for 30 minutes, the reaction mixture was cooled to RT and poured into sat. aqueous sodium bicarbonate solution. The reaction mixture was extracted with n-BuOH (100 mL) two times, and the organic phase was concentrated in vacuo. The residue was submitted for purification by HPLC to give 6-amino-9-benzyl-2-(methylsulfonimidoyl)-7H-purin-8-one (900 mg, compound 1) as a white solid. $^1$H NMR (400 MHz, DMSO-d$_6$) δ ppm: 10.6 (br. s, 1H), 7.26-7.34 (m, 5H), 7.07 (br. s., 2H), 4.96 (s, 2H), 4.04 (s, 1H), 3.18 (s, 3H). MS obsd. (ESI$^+$) [(M$^+$H)$^+$]: 319.

Separation of compound of Example 1 by chiral HPLC afforded Example 1-A (faster eluting, 7.1 mg) and Example 1-B (slower eluting, 9.1 mg) as white solid. (Separation condition: methanol 5%-40% (0.05% DEA)/CO$_2$ on ChiralPak OJ-3 column.)

Example 1-A $^1$H NMR (400 MHz, DMSO-d$_6$) δ ppm: 10.06 (br. s., 1H), 7.27-7.36 (m, 5H), 6.98 (br. s., 2H), 4.97 (s, 2H), 4.06 (br. s., 1H), 3.18 (s, 3H). MS obsd. (ESI$^+$) [(M+H)$^+$]: 319.

Example 1-B $^1$H NMR (400 MHz, DMSO-d$_6$) δ ppm: 10.06 (br. s., 1H), 7.26-7.36 (m, 5H), 6.98 (br. s., 2H), 4.96 (s, 2H), 4.07 (br. s., 1H), 3.18 (s, 3H). MS obsd. (ESI$^+$) [(M+H)$^+$]: 319.

Example 2

6-Amino-9-benzyl-2-(ethylsulfonimidoyl)-7H-purin-8-one

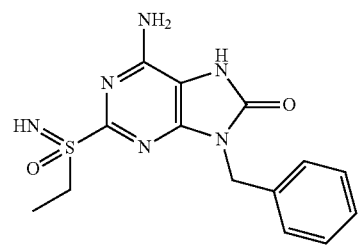

2

Step 1: Preparation of
6-amino-9-benzyl-2-ethylsulfanyl-7H-purin-8-one

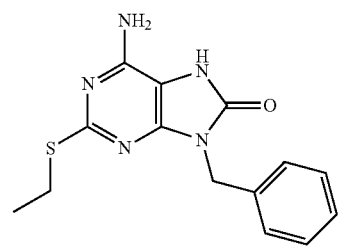

2a

Compound 2a was prepared in analogy to Example 1, Step 3 by using ethyl bromide instead of methyl iodide. 6-Amino-9-benzyl-2-ethylsulfanyl-7H-purin-8-one (500 mg, compound 2a) was obtained as a white solid. MS obsd. (ESI$^+$) [(M+H)$^+$]: 302.

Step 2: Preparation of
6-amino-9-benzyl-2-methylsulfinyl-7H-purin-8-one

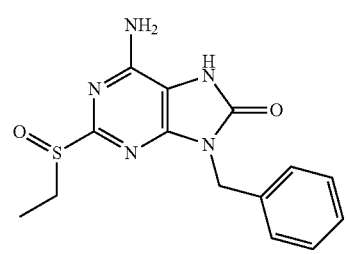

2b

Compound 2b was prepared in analogy to Example 1, Step 4 by using 6-amino-9-benzyl-2-ethylsulfanyl-7H-purin-8-one (compound 2a) instead of 6-amino-9-benzyl-2-methylsulfanyl-7H-purin-8-one (compound 1c). 6-Amino-9-benzyl-2-ethylsulfinyl-7H-purin-8-one (300 mg, compound 2b) was obtained as a white solid. MS obsd. (ESI⁺) [(M+H)⁺]: 318.

Step 3: Preparation of 6-amino-9-benzyl-2-(ethylsulfonimidoyl)-7H-purin-8-one

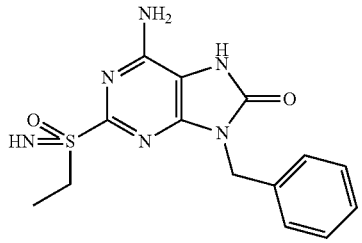

2

The title compound was prepared in analogy to Example 1, Step 5 by using 6-amino-9-benzyl-2-ethylsulfinyl-7H-purin-8-one (compound 2b) instead of 6-amino-9-benzyl-2-methylsulfinyl-7H-purin-8-one (compound 1d). 6-Amino-9-benzyl-2-(ethylsulfonimidoyl)-7H-purin-8-one (12 mg, compound 2) was obtained as a white solid. ¹H NMR (400 MHz, CD₃OD) δ ppm: 7.43 (d, J=7.03 Hz, 2H), 7.27-7.36 (m, 3H), 5.11 (s, 2H), 3.44-3.62 (m, 2H), 1.30 (t, J=7.40 Hz, 3H). MS obsd. (ESI⁺) [(M+H)⁺]: 333.

Example 3

6-Amino-9-benzyl-2-(2-methoxyethylsulfonimidoyl)-7H-purin-8-one

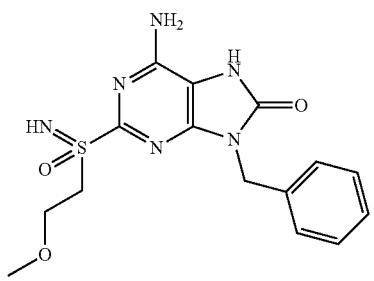

3

Step 1: Preparation of 6-amino-9-benzyl-2-(2-methoxyethylsulfanyl)-7H-purin-8-one

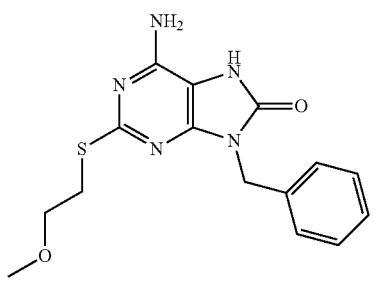

3a

Compound 3a was prepared in analogy to Example 1, Step 3 by using 2-bromoethyl methyl ether (TCI, Catalog number: B1242-250G) instead of methyl iodide. 6-Amino-9-benzyl-2-(2-methoxyethylsulfanyl)-7H-purin-8-one (600 mg, compound 3a) was obtained as a white solid. MS obsd. (ESI⁺) [(M+H)⁺]: 332.

Step 2: Preparation of 6-amino-9-benzyl-2-(2-methoxyethylsulfinyl)-7H-purin-8-one

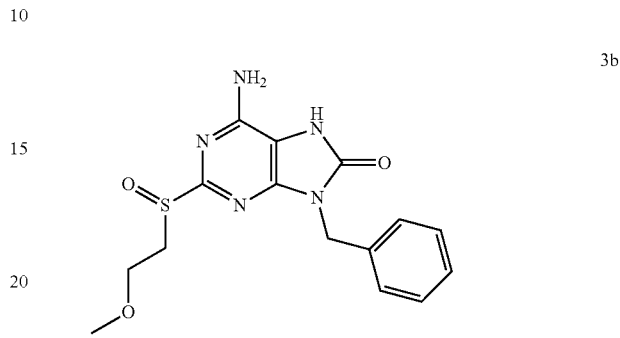

3b

Compound 3b was prepared in analogy to Example 1, Step 4 by using 6-amino-9-benzyl-2-(2-methoxyethylsulfanyl)-7H-purin-8-one (compound 3a) instead of 6-amino-9-benzyl-2-methylsulfanyl-7H-purin-8-one (compound 1c). 6-Amino-9-benzyl-2-(2-methoxyethylsulfinyl)-7H-purin-8-one (350 mg, compound 3b) was obtained as a white solid. MS obsd. (ESI⁺) [(M+H)⁺]: 348.

Step 3: Preparation of 6-amino-9-benzyl-2-(2-methoxyethylsulfonimidoyl)-7H-purin-8-one

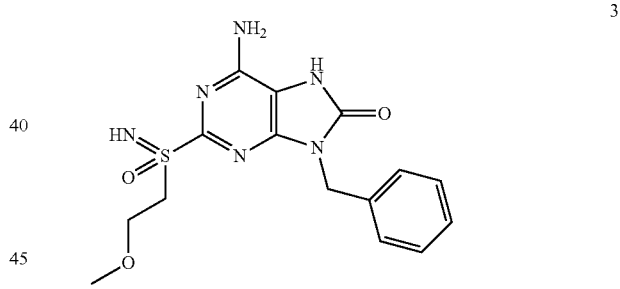

3

The title compound was prepared in analogy to Example 1, Step 5 by using 6-amino-9-benzyl-2-methoxyethylsulfinyl-7H-purin-8-one (compound 3b) instead of 6-amino-9-benzyl-2-methylsulfinyl-7H-purin-8-one (compound 1d). 6-amino-9-benzyl-2-(2-methoxyethylsulfonimidoyl)-7H-purin-8-one (21 mg, Example 3) was obtained as a white solid. ¹H NMR (400 MHz, CD₃OD) δ ppm: 7.44 (d, J=7.15 Hz, 2H), 7.25-7.36 (m, 3H), 5.12 (s, 2H), 3.75-3.82 (m, 4H), 3.17 (s, 3H). MS obsd. (ESI⁺) [(M+H)⁺]: 363.

Separation of compound of Example 3 by chiral HPLC afforded Example 3-A (faster eluting, 7.0 mg) and Example 3-B (slower eluting, 5.0 mg) as white solid. (Separation condition: methanol 5%-40% (0.05% DEA)/CO₂ on ChiralPak AS-3 column.)

Example 3-A

¹H NMR (400 MHz, CD₃OD) δ ppm: 7.43 (d, J=7.15 Hz, 2H), 7.25-7.36 (m, 3H), 5.12 (s, 2H), 3.75-3.82 (m, 4H), 3.17 (s, 3H). MS obsd. (ESI⁺) [(M+H)⁺]: 363.

Example 3-B $^1$H NMR (400 MHz, CD$_3$OD) δ ppm: 7.44 (d, J=7.15 Hz, 2H), 7.24-7.35 (m, 3H), 5.12 (s, 2H), 3.75-3.82 (m, 4H), 3.17 (s, 3H). MS obsd. (ESI$^+$) [(M+H)$^+$]: 363.

Example 4

6-Amino-9-benzyl-2-(propylsulfonimidoyl)-7H-purin-8-one

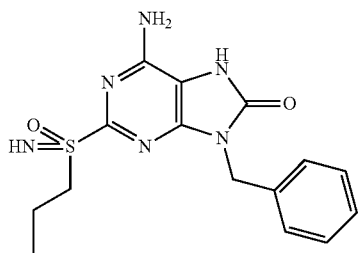

4

Step 1: Preparation of 6-amino-9-benzyl-2-(2-propylsulfanyl)-7H-purin-8-one

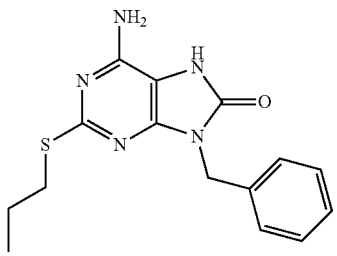

4a

Compound 4a was prepared in analogy to Example 1, Step 3 by using 1-bromopropane (TCI, Catalog number: B0638-500G) instead of methyl iodide. 6-Amino-9-benzyl-2-propylsulfanyl-7H-purin-8-one (240 mg, compound 4a) was obtained as a white solid. MS obsd. (ESI$^+$) [(M+H)$^+$]: 316.

Step 2: Preparation of 6-amino-9-benzyl-2-propylsulfinyl-7H-purin-8-one

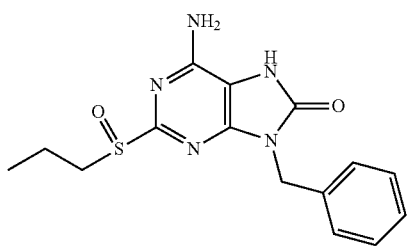

4b

Compound 4b was prepared in analogy to Example 1, Step 4 by using 6-amino-9-benzyl-2-propylsulfanyl-7H-purin-8-one (compound 4a) instead of 6-amino-9-benzyl-2-methylsulfanyl-7H-purin-8-one (compound 1c). 6-Amino-9-benzyl-2-(2-propylsulfinyl)-7H-purin-8-one (210 mg, compound 4b) was obtained as a white solid. MS obsd. (ESI$^+$) [(M+H)$^+$]: 332.

Step 3: Preparation of 6-amino-9-benzyl-2-(propylsulfonimidoyl)-7H-purin-8-one

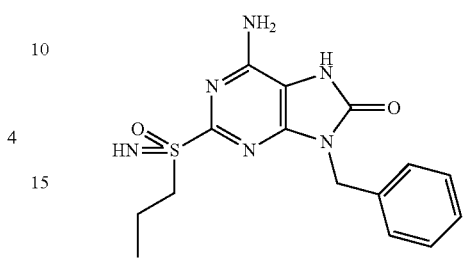

4

The title compound was prepared in analogy to Example 1, Step 5 by using 6-amino-9-benzyl-2-(2-propylsulfinyl)-7H-purin-8-one (compound 4b) instead of 6-amino-9-benzyl-2-(2-methylsulfinyl)-7H-purin-8-one (compound 1d). 6-Amino-9-benzyl-2-(propylsulfonimidoyl)-7H-purin-8-one (80 mg, Example 4) was obtained as a white solid. $^1$H NMR (400 MHz, DMSO-d$_6$) δ ppm: 10.65 (br. s., 1H), 7.26-7.37 (m, 5H), 6.98 (br. s., 2H), 4.97 (s, 2H), 4.02 (s, 1H), 3.33 (t, J=7.53 Hz, 2H), 1.55-1.74 (m, 2H), 0.92 (t, J=7.53 Hz, 3H) MS obsd. (ESI$^+$) [(M$^+$H)$^+$]: 347.

Separation of compound of Example 4 by chiral HPLC afforded Example 4-A (slower eluting, 500 mg) and Example 4-B (faster eluting, 490 mg) as white solid. (Separation condition: methanol 5%-40% (0.05% DEA)/CO$_2$ on ChiralPak AS-3 column.)

Example 4-A $^1$H NMR (400 MHz, DMSO-d$_6$) δ ppm: 10.52 (br. s., 1H), 7.25-7.41 (m, 5H), 6.96 (br. s., 2H), 4.96 (s, 2H), 4.03 (s, 1H), 3.24-3.42 (m, 2H), 1.52-1.75 (m, 2H), 0.92 (t, J=7.53 Hz, 3H).

Example 4-B $^1$H NMR (400 MHz, DMSO-d$_6$) δ ppm: 10.01 (br. s., 1H), 7.26-7.36 (m, 5H), 6.97 (br. s., 2H), 4.96 (s, 2H), 4.03 (s, 1H), 3.26-3.41 (m, 2H), 1.56-1.73 (m, 2H), 0.92 (t, J=7.53 Hz, 3H).

Example 5

6-Amino-9-benzyl-2-(butylsulfonimidoyl)-7H-purin-8-one

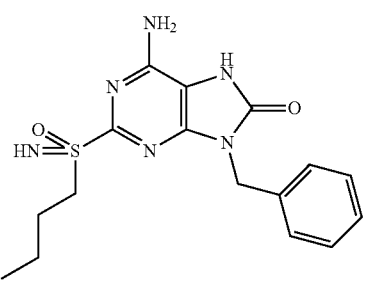

5

Step 1: Preparation of 6-amino-9-benzyl-2-butylsulfanyl-7H-purin-8-one

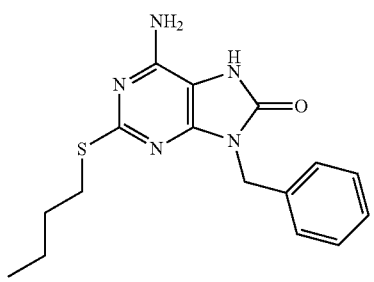

5a

Compound 5a was prepared in analogy to Example 1, Step 3 by using 1-bromobutane (TCI, Catalog number: B560-500G) instead of methyl iodide. 6-Amino-9-benzyl-2-butylsulfanyl-7H-purin-8-one (600 mg, compound 5a) was obtained as a white solid. MS obsd. (ESI$^+$) [(M+H)$^+$]: 330.

Step 2: Preparation of 6-amino-9-benzyl-2-butylsulfinyl-7H-purin-8-one

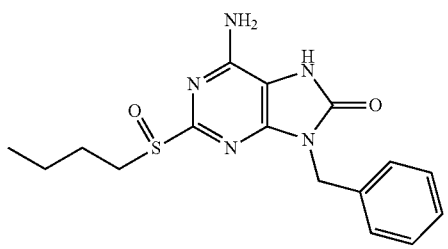

5b

Compound 5b was prepared in analogy to Example 1, Step 4 by using 6-amino-9-benzyl-2-butylsulfanyl-7H-purin-8-one (compound 5a) instead of 6-amino-9-benzyl-2-methylsulfanyl-7H-purin-8-one (compound 1c). 6-Amino-9-benzyl-2-(2-butylsulfinyl)-7H-purin-8-one (400 mg, compound 5b) was obtained as a white solid. MS obsd. (ESI$^+$) [(M+H)$^+$]: 346.

Step 3: Preparation of 6-amino-9-benzyl-2-(butylsulfonimidoyl)-7H-purin-8-one

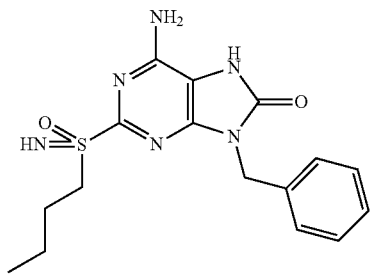

5

The title compound was prepared in analogy to Example 1, Step 5 by using 6-amino-9-benzyl-2-(2-butylsulfinyl)-7H-purin-8-one (compound 5b) instead of 6-amino-9-benzyl-2-(2-methylsulfinyl)-7H-purin-8-one (compound 1d). 6-Amino-9-benzyl-2-(butylsulfonimidoyl)-7H-purin-8-one (40 mg, Example 5) was obtained as a white solid. $^1$H NMR (400 MHz, DMSO-d$_6$) δ ppm: 10.59 (s, 1H), 7.24-7.39 (m, 5H), 6.97 (br. s., 2H), 4.96 (s, 2H), 4.03 (s, 1H), 3.35-3.46 (m, 2H), 1.51-1.61 (m, 2H), 1.27-1.39 (m, 2H), 0.84 (t, J=7.34 Hz, 3H). MS obsd. (ESI$^+$) [(M+H)$^+$]: 361.

Example 6

6-Amino-9-benzyl-2-(3-methoxypropylsulfonimidoyl)-7H-purin-8-one

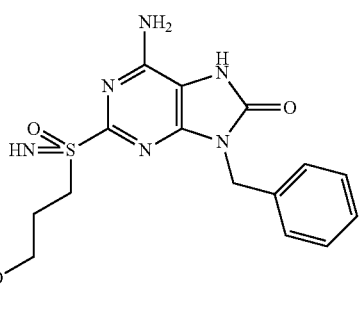

6

Step 1: Preparation of 6-amino-9-benzyl-2-(3-methoxypropylsulfanyl)-7H-purin-8-one

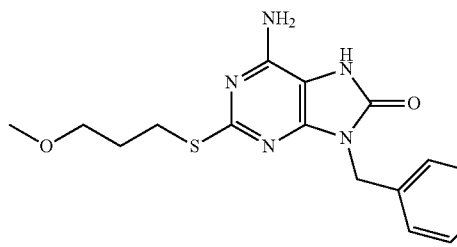

6a

Compound 6a was prepared in analogy to Example 1, Step 3 by using 1-bromo-3-methoxylpropane (TCI, Catalog number: B3499-25G) instead of methyl iodide. 6-Amino-9-benzyl-2-methoxypropylsulfanyl-7H-purin-8-one (220 mg, compound 6a) was obtained as a white solid. MS obsd. (ESI$^+$) [(M+H)$^+$]: 346.

Step 2: Preparation of 6-amino-9-benzyl-2-(3-methoxypropylsulfinyl)-7H-purin-8-one

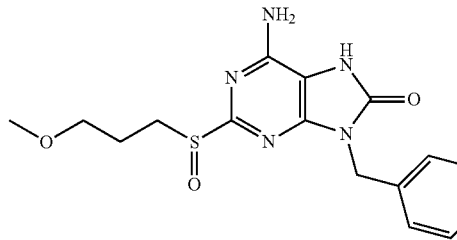

6b

Compound 6b was prepared in analogy to Example 1, Step 4 by using 6-amino-9-benzyl-2-propylsulfanyl-7H-purin-8-one (compound 6a) instead of 6-amino-9-benzyl-2- methylsulfanyl-7H-purin-8-one (compound 1c). 6-amino-9-benzyl-2-(2-methoxypropylsulfinyl)-7H-purin-8-one (110 mg, compound 6b) was obtained as a white solid. MS obsd. (ESI⁺) [(M+H)⁺]: 362.

Step 3: Preparation of 6-amino-9-benzyl-2-(butyl-sulfonimidoyl)-7H-purin-8-one

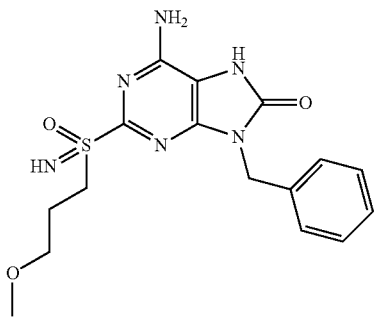

6

The title compound was prepared in analogy to Example 1, Step 5 by using 6-amino-9-benzyl-2-(2-methoxypropyl-sulfinyl)-7H-purin-8-one (compound 6b) instead of 6-amino-9-benzyl-2-(2-methylsulfinyl)-7H-purin-8-one (compound 1d). 6-Amino-9-benzyl-2-(methoxypropylsulfo-nimidoyl)-7H-purin-8-one (20 mg, Example 6) was obtained as a white solid. $^1$H NMR (400 MHz, DMSO-d$_6$) δ ppm: 10.59 (s, 1H), 7.29-7.34 (m, 5H), 7.00 (br. s., 2H), 4.96 (s, 2H), 4.13 (s, 1H), 4.10 (m, 4H), 3.20 (s, 3H), 1.86 (m, 2H). MS obsd. (ESI⁺) [(M+H)⁺]: 377.

Example 7

6-Amino-9-benzyl-2-(2,2,2-trifluoroethylsulfonimi-doyl)-7H-purin-8-one

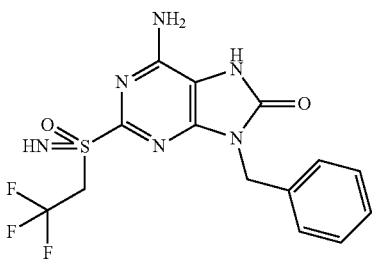

7

Step 1: Preparation of 6-amino-9-benzyl-2-(2,2,2-trifluoroethylsulfanyl)-7H-purin-8-one

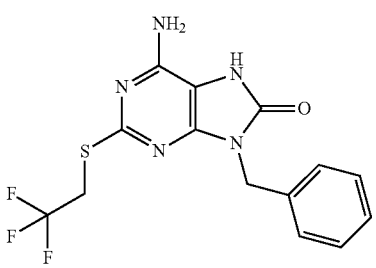

7a

Compound 7a was prepared in analogy to Example 1, Step 3 by using 2,2,2-trifluoroethyl iodide (TCI, Catalog number: T1148-25G) instead of methyl iodide. 6-Amino-9-benzyl-2-(2,2,2-trifluoroethyl)sulfanyl-7H-purin-8-one (compound 7a) was obtained as a white solid. MS obsd. (ESI⁺) [(M+H)⁺]: 356.

Step 2: Preparation of 6-amino-9-benzyl-2-(2,2,2-trifluoroethylsulfinyl)-7H-purin-8-one

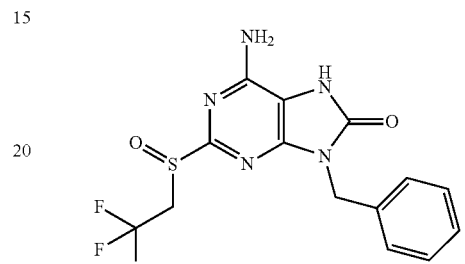

7b

Compound 7b was prepared in analogy to Example 1, Step 4 by using 6-amino-9-benzyl-2-2,2,2-trifluoroethylsul-fanyl sulfanyl-7H-purin-8-one (compound 7a) instead of 6-amino-9-benzyl-2-methylsulfanyl-7H-purin-8-one (compound 1c). 6-Amino-9-benzyl-2-(2-2,2,2-trifluoroethylsulfi-nyl)-7H-purin-8-one (compound 7b) was obtained as a white solid. MS obsd. (ESI⁺) [(M+H)⁺]: 372.

Step 3: Preparation of 6-amino-9-benzyl-2-(2,2,2-trifluoroethylsulfonimidoyl)-7H-purin-8-one

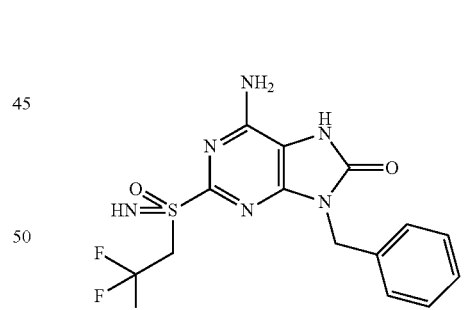

7

The title compound was prepared in analogy to Example 1, Step 5 by using 6-amino-9-benzyl-2-(2-2,2,2-trifluoroeth-ylsulfinyl)-7H-purin-8-one (compound 7b) instead of 6-amino-9-benzyl-2-(2-methylsulfinyl)-7H-purin-8-one (compound 1d). 6-Amino-9-benzyl-2-(2,2,2-trifluoroethyl-sulfonimidoyl)-7H-purin-8-one (20 mg, Example 7) was obtained as a white solid. $^1$H NMR (400 MHz, DMSO-d$_6$) δ ppm: 10.59 (br. s., 1H), 7.25-7.37 (m, 5H), 7.06 (br. s., 2H), 4.95-5.01 (m, 3H), 4.85 (qd, J=10.02, 15.37 Hz, 1H), 4.63 (qd, J=9.92, 15.40 Hz, 1H). MS obsd. (ESI⁺) [(M+H)⁺]: 387.

Example 8

6-Amino-9-benzyl-2-(cyclohexylmethylsulfonimidoyl)-7H-purin-8-one

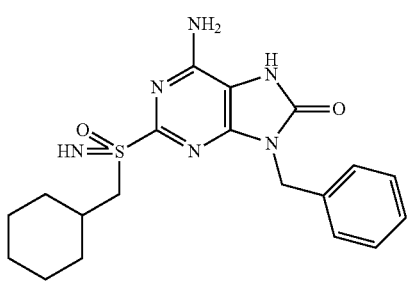

8

Step 1: Preparation of 6-amino-9-benzyl-2-(cyclohexylmethylsulfanyl)-7H-purin-8-one

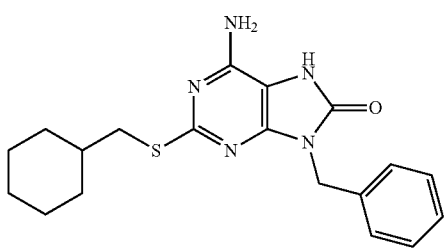

8a

Compound 8a was prepared in analogy to Example 1, Step 3 by using cyclohexylmethyl bromide (TCI, Catalog number: B1708-25G) instead of methyl iodide. 6-Amino-9-benzyl-2-cyclohexylmethylsulfanyl-7H-purin-8-one (260 mg, compound 8a) was obtained as a white solid. MS obsd. (ESI$^+$) [(M+H)$^+$]: 370.

Step 2: Preparation of 6-amino-9-benzyl-2-(cyclohexylmethylsulfinyl)-7H-purin-8-one

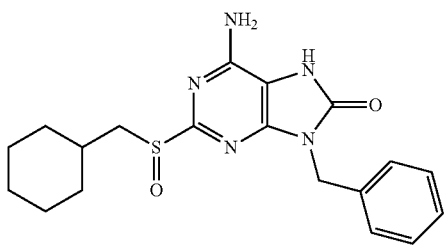

8b

Compound 8b was prepared in analogy to Example 1, Step 4 by using 6-amino-9-benzyl-2-cyclohexylmethylsulfanyl-7H-purin-8-one (compound 8a) instead of 6-amino-9-benzyl-2-methylsulfanyl-7H-purin-8-one (compound 1c). 6-Amino-9-benzyl-2-(2-cyclohexylmethylsulfinyl)-7H-purin-8-one (120 mg, compound 8b) was obtained as a white solid. MS obsd. (ESI$^+$) [(M+H)$^+$]: 386.

Step 3: Preparation of 6-amino-9-benzyl-2-(cyclohexylmethylsulfonimidoyl)-7H-purin-8-one

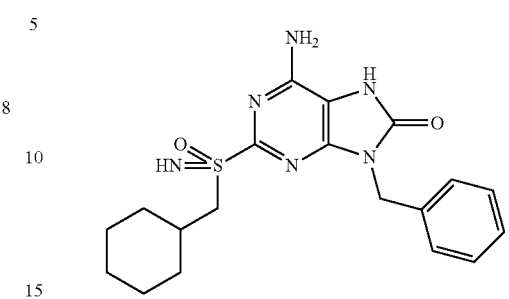

8

The title compound was prepared in analogy to Example 1, Step 5 by using 6-amino-9-benzyl-2-(2-cyclohexylmethylsulfinyl)-7H-purin-8-one (compound 8b) instead of 6-amino-9-benzyl-2-methylsulfinyl-7H-purin-8-one (compound 1d). 6-Amino-9-benzyl-2-(cyclohexylmethylsulfonimidoyl)-7H-purin-8-one (40 mg, Example 8) was obtained as a white solid. $^1$H NMR (400 MHz, DMSO-d$_6$) δ ppm: 10.59 (br. s., 1H), 7.27-7.33 (m, 5H), 6.97 (br. s., 2H), 4.97 (s, 2H), 4.03 (s, 1H), 3.26-3.29 (m, 2H), 1.54-1.86 (m, 5H), 0.89-1.12 (m, 6H). MS obsd. (ESI$^+$) [(M+H)$^+$]: 401.

Example 9

6-Amino-9-[(4-chlorophenyl)methyl]-2-(propylsulfonimidoyl)-7H-purin-8-one

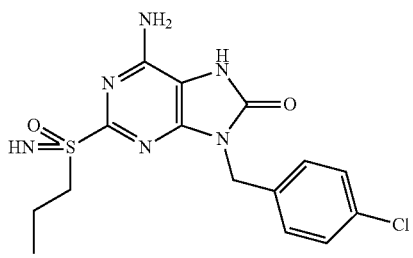

9

Step 1: Preparation of 4-amino-3-[(4-chlorophenyl)methyl]-2-oxo-1H-imidazole-5-carbonitrile

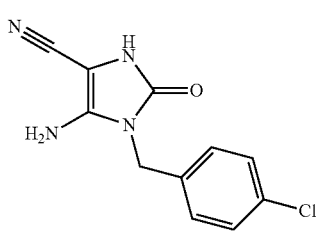

9a

To a solution of triphosgene (5.9 g, 20 mmol) in dry THF (40 mL) was added (4-chlorophenyl)methylamine (8.5 g, 60 mmol, Accela ChemBio Inc, Catalog number: SY004062-25 g) and DIPEA (12.4 g, 96 mmol) in dry THF (80 mL) at −80° C. The solution was stirred at −80° C. for 15 min. A solution of aminomalononitrile p-toluenesulfonate (15.2 g, 60 mmol, TCI, Catalog number: A1119-25G) and DIPEA (6.2 g, 48 mmol) in dry THF (40 mL) was added at −80° C. After stirred at RT for 24 hrs, the reaction was concentrated in vacuo and the residue was partitioned between EtOAc (300 mL) and water (150 mL). The separated organic layer was washed with brine (50 mL) two times, and extracted with sodium hydroxide solution (50 mL, 1 N) two times. The combined sodium hydroxide solution layer was neutralized with 10% wt. sodium hydrogen sulfate solution and extracted with EtOAc. Then the separated organic layer was washed with brine, dried over anhydrous sodium sulfate, filtered and concentrated in vacuo. The residue was triturated with diethyl ether and then the mixture was filtered to give 4-amino-3-[(4-chlorophenyl)methyl]-2-oxo-1H-imidazole-5-carbonitrile (8.0 g, compound 9a) as a yellow solid. MS obsd. (ESI$^+$) [(M+H)$^+$]: 249.

Step 2: Preparation of 6-amino-9-[(4-chlorophenyl)methyl]-2-sulfanyl-7H-purin-8-one

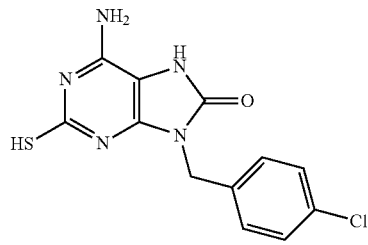

9b

To a solution of 4-amino-3-[(4-chlorophenyl)methyl]-2-oxo-1H-imidazole-5-carbonitrile (8.0 g, 32.0 mmol, compound 9a) in THF (100 mL) was added benzoylisothiocyanate (11.5 g, 70.4 mmol, TCI, Catalog number: A11596-100G) dropwise. After stirred at RT for 12 hrs, the reaction mixture was concentrated in vacuo. The residue was triturated in diethyl ether (100 mL) and the resulting precipitate was collected by filtration.

To a solution of the obtained precipitate in THF (300 mL) was added sodium hydroxide (30 mL, 2 N). The mixture was refluxed for 50 hrs, and then acidified to pH 3 with 10 wt. % aqueous sodium hydrogen sulfate solution. The resulting precipitate was collected by filtration to give a crude product 6-amino-9-[(4-chlorophenyl)methyl]-2-sulfanyl-7H-purin-8-one (compound 9b) as a yellow solid (6.4 g). The product was used in the next step without further purification. MS obsd. (ESI$^+$) [(M+H)$^+$]: 308.

Step 3: Preparation of 6-amino-9-[(4-chlorophenyl)methyl]-2-propylsulfanyl-7H-purin-8-one

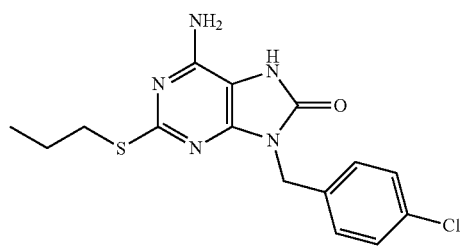

9c

Compound 9c was prepared in analogy to Example 1, Step 3 by using n-propyl bromide and 6-amino-9-[(4-chlorophenyl)methyl]-2-sulfanyl-7H-purin-8-one (compound 9b) instead of methyl iodide and 6-amino-9-phenylmethyl-2-sulfanyl-7H-purin-8-one (compound 1b). 6-Amino-9-[(4-chlorophenyl)methyl]-2-propylsulfanyl-7H-purin-8-one (800 mg, compound 9c) was obtained as a white solid. MS obsd. (ESI$^+$) [(M+H)$^+$]: 350.

Step 4: Preparation of 6-amino-9-[(4-chlorophenyl)methyl]-2-propylsulfinyl-7H-purin-8-one

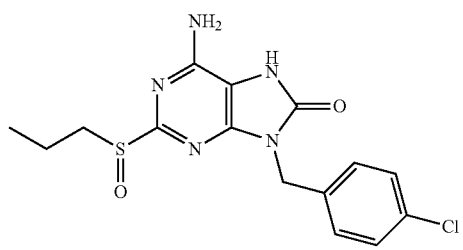

9d

Compound 9d was prepared in analogy to Example 1, Step 4 by using 6-amino-9-[(4-chlorophenyl)methyl]-2-propylsulfanyl-7H-purin-8-one (compound 9c) instead of 6-amino-9-benzyl-2-methylsulfanyl-7H-purin-8-one (compound 1c). 6-Amino-9-[(4-chlorophenyl)methyl]-2-propylsulfinyl-7H-purin-8-one (150 mg, compound 9d) was obtained as a white solid. MS obsd. (ESI$^+$) [(M+H)$^+$]: 366.

Step 5: Preparation of 6-amino-9-[(4-chlorophenyl)methyl]-2-(propylsulfonimidoyl)-7H-purin-8-one

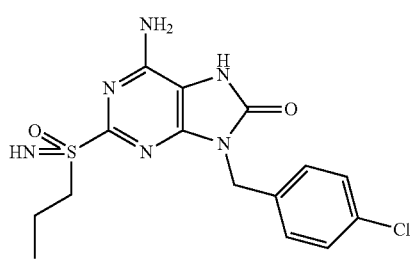

9

The title compound was prepared in analogy to Example 1, Step 5 by using 6-amino-9-[(4-chlorophenyl)methyl]-2-propylsulfinyl-7H-purin-8-one (compound 9d) instead of 6-amino-9-benzyl-2-(2-methylsulfinyl)-7H-purin-8-one (compound 1d). 6-Amino-9-[(4-chlorophenyl)methyl]-2-(propylsulfonimidoyl)-7H-purin-8-one (25 mg, Example 9) was obtained as a white solid.

$^1$H NMR (400 MHz, DMSO-d$_6$) δ ppm: 10.60 (br. s, 1H), 7.32-7.42 (m, 4H), 6.98 (br. s, 2H), 4.96 (s, 2H), 4.03 (s, 1H), 3.25-3.41 (m, 2H), 1.56-1.68 (m, 2H), 0.91 (t, J=8 Hz, 3H). MS obsd. (ESI$^+$) [(M$^+$H)$^+$]: 381.

Separation of compound of Example 9 by chiral HPLC afforded Example 9-A (faster eluting, 21 mg) and Example 9-B (slower eluting, 10 mg) as white solid. (Separation condition: methanol 5%-40% (0.05% DEA)/CO$_2$ on ChiralPak OJ-3 column.)

Example 9-A $^1$H NMR (400 MHz, DMSO-d$_6$) δ ppm: 10.63 (br. s, 1H), 7.34-7.41 (m, 4H), 6.99 (br. s, 2H), 4.96 (s, 2H), 4.05 (br. s, 1H), 3.29-3.38 (m, 2H), 1.58-1.66 (m, 2H), 0.91 (t, J=8 Hz, 3H). MS obsd. (ESI⁺) [(M+H)⁺]: 381.

Example 9-B

¹H NMR (400 MHz, DMSO-d₆) δ ppm: 10.63 (br. s, 1H), 7.34-7.41 (m, 4H), 6.99 (br. s, 2H), 4.96 (s, 2H), 4.05 (br. s, 1H), 3.29-3.38 (m, 2H), 1.58-1.66 (m, 2H), 0.91 (t, J=8 Hz, 3H). MS obsd. (ESI⁺) [(M+H)⁺]: 381.

Example 10

6-Amino-9-[(4-methoxyphenyl)methyl]-2-(methylsulfonimidoyl)-7H-purin-8-one

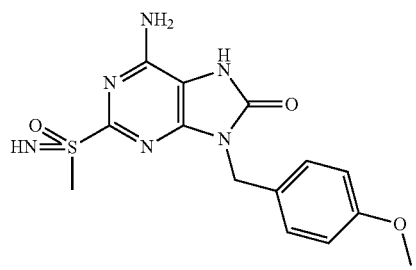

10

Step 1: Preparation of 4-amino-3-[(4-methoxyphenyl)methyl]-2-oxo-1H-imidazole-5-carbonitrile

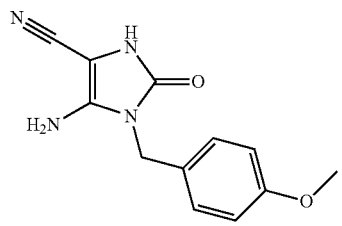

10a

Compound 10a was prepared in analogy to Example 9, Step 1 by using (4-methoxyphenyl)methylamine instead of 4-chloropenylmethylamine. 4-Amino-3-[(4-methoxyphenyl)methyl]-2-oxo-1H-imidazole-5-carbonitrile (7.5 g, compound 10a) was prepared as a yellow solid. MS obsd. (ESI⁺) [(M+H)⁺]: 245.

Step 2: Preparation of 6-amino-9-[(4-methoxyphenyl)methyl]-2-sulfanyl-7H-purin-8-one

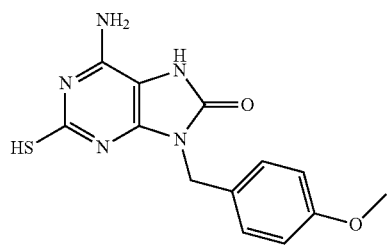

10b

Compound 10b was prepared in analogy to Example 9, Step 2 by using 4-amino-3-[(4-methoxyphenyl)methyl]-2-oxo-1H-imidazole-5-carbonitrile (compound 10a) instead of 4-amino-3-[(4-chlorophenyl)methyl]-2-oxo-1H-imidazole-5-carbonitrile (compound 9a). 6-Amino-9-[(4-methoxyphenyl)methyl]-2-sulfanyl-7H-purin-8-one (11.4 g, compound 10b) was prepared as a yellow solid. MS obsd. (ESI⁺) [(M+H)⁺]: 304.

Step 3: Preparation of 6-amino-9-[(4-methoxyphenyl)methyl]-2-methylsulfanyl-7H-purin-8-one

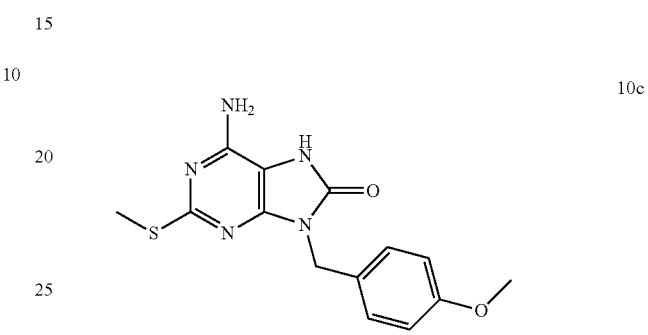

10c

Compound 10c was prepared in analogy to Example 1, Step 3 by using 6-amino-9-[(4-methoxyphenyl)methyl]-2-sulfanyl-7H-purin-8-one (compound 10b) instead of 6-amino-9-benzyl-2-sulfanyl-7H-purin-8-one (compound 1b). 6-Amino-9-[(4-methoxyphenyl)methyl]-2-methylsulfanyl-7H-purin-8-one (2.3 g, compound 10c) was prepared as a yellow solid. MS obsd. (ESI⁺) [(M+H)⁺]: 318.

Step 4: Preparation of 6-amino-9-[(4-methoxyphenyl)methyl]-2-methylsulfinyl-7H-purin-8-one

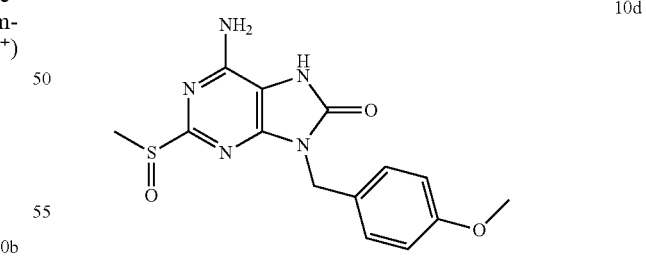

10d

Compound 10d was prepared in analogy to Example 1, Step 4 by using 6-amino-9-[(4-methoxyphenyl)methyl]-2-methylsulfanyl-7H-purin-8-one (compound 10c) instead of 6-amino-9-benzyl-2-methylsulfanyl-7H-purin-8-one (compound 1c). 6-Amino-9-[(4-methoxyphenyl)methyl]-2-methylsulfinyl-7H-purin-8-one (130 mg, compound 10d) was prepared as a yellow solid. MS obsd. (ESI⁺) [(M+H)⁺]: 334.

Step 5: Preparation of 6-amino-9-[(4-methoxyphenyl)methyl]-2-(methylsulfonimidoyl)-7H-purin-8-one

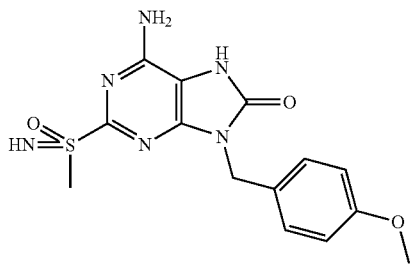

The title compound was prepared in analogy to Example 1, Step 5 by using 6-amino-9-[(4-methoxyphenyl)methyl]-2-methylsulfinyl-7H-purin-8-one (compound 10d) instead of 6-amino-9-benzyl-2-methylsulfinyl-7H-purin-8-one (compound 1d). 6-Amino-9-[(4-methoxyphenyl)methyl]-2-(methylsulfonimidoyl)-7H-purin-8-one (10 mg, Example 10) was prepared as a yellow solid. $^1$H NMR (400 MHz, DMSO-$d_6$) δ ppm: 10.53 (br. s, 1H), 7.32 (t, J=6.41 Hz, 2H), 6.95 (br. s, 2H), 6.89 (t, J=6.38 Hz, 2H), 4.89 (s, 2H), 4.07 (s, 1H), 3.72 (s, 3H), 3.21 (s, 3H). MS obsd. (ESI$^+$) [(M+H)$^+$]: 349.

Example 11

6-Amino-2-(3-chloropropylsulfonimidoyl)-9-[(4-methoxyphenyl)methyl]-7H-purin-8-one

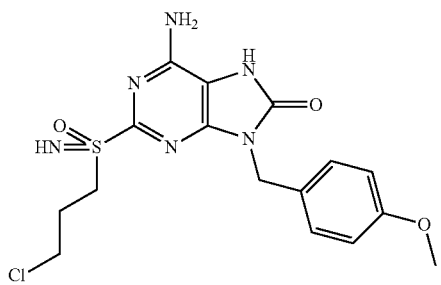

Step 1: Preparation of 6-amino-2-(3-chloropropylsulfanyl)-9-[(4-methoxyphenyl)methyl]-7H-purin-8-one

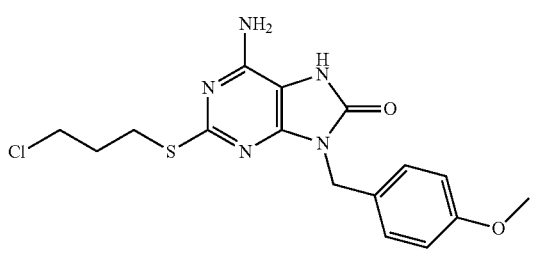

Compound 11a was prepared in analogy to Example 1, Step 3 by using 1-bromo-3-chloro-propane and 6-amino-9-[(4-methoxyphenyl)methyl]-2-sulfanyl-7H-purin-8-one (compound 10b) instead of methyl iodide and 6-amino-9-benzyl-2-sulfanyl-7H-purin-8-one (compound 1b). 6-Amino-2-(3-chloropropylsulfanyl)-9-[(4-methoxyphenyl)methyl]-7H-purin-8-one (3.2 g, compound 11a) was obtained as a white solid. MS obsd. (ESI$^+$) [(M+H)$^+$]: 380.

Step 2: Preparation of 6-amino-2-(3-chloropropylsulfinyl)-9-[(4-methoxyphenyl)methyl]-7H-purin-8-one

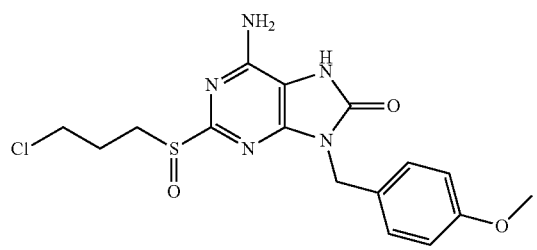

Compound 11b was prepared in analogy to Example 1, Step 4 by using 6-amino-2-(3-chloropropylsulfanyl)-9-[(4-methoxyphenyl)methyl]-7H-purin-8-one (compound 11a) instead of 6-amino-9-benzyl-2-methylsulfanyl-7H-purin-8-one (compound 1c). 6-Amino-2-(3-chloropropylsulfinyl)-9-[(4-methoxyphenyl)methyl]-7H-purin-8-one (1.3 g, compound 11b) was obtained as a white solid. MS obsd. (ESI$^+$) [(M+H)$^+$]: 396.

Step 3: Preparation of 6-amino-2-(3-chloropropylsulfonimidoyl)-9-[(4-methoxyphenyl)methyl]-7H-purin-8-one

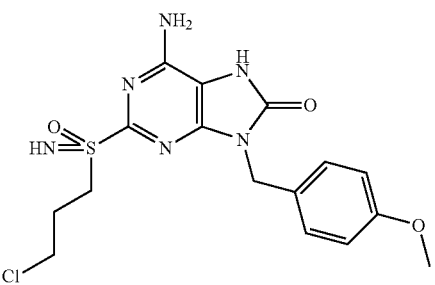

The title compound was prepared in analogy to Example 1, Step 5 by using 6-amino-2-(3-chloropropylsulfinyl)-9-[(4-methoxyphenyl)methyl]-7H-purin-8-one (compound 11b) instead of 6-amino-9-benzyl-2-(2-methylsulfanyl)-7H-purin-8-one (compound 1d). 6-Amino-2-(3-chloropropylsulfonimidoyl)-9-[(4-methoxyphenyl)methyl]-7H-purin-8-one (40 mg, Example 11) was obtained as a white solid. $^1$H NMR (400 MHz, DMSO-$d_6$) δ ppm: 10.53 (br. s, 1H), 7.32 (t, J=6.41 Hz, 2H), 6.95 (br. s, 2H), 6.89 (t, J=6.38 Hz, 2H), 4.89 (s, 2H), 4.07 (s, 1H), 3.89 (m, 2H), 3.72 (s, 3H), 3.52 (m, 2H), 2.13 (m, 2H). MS obsd. (ESI$^+$) [(M+H)$^+$]: 411.

Example 12

6-Amino-9-[(4-methoxyphenyl)methyl]-2-(3-pyrrolidin-1-ylpropylsulfonimidoyl)-7H-purin-8-one

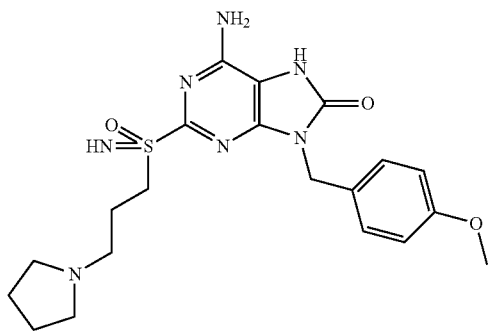

12

To a solution of 6-amino-2-(3-chloropropylsulfonimidoyl)-9-[(4-methoxyphenyl)methyl]-7H-purin-8-one (150 mg, compound 11) in DMSO (5 mL) was added pyrrolidine (0.9 mL, 11.0 mmol) drop wise. The mixture was stirred at 80° C. for 2 hrs. The resulting mixture was diluted with brine (60 mL), extracted with EtOAc (60 mL) three times. The organic layer was combined, washed with brine, dried over sodium sulfate and concentrated in vacuo. The residue was purified by prep-HPLC to give 6-amino-9-[(4-methoxyphenyl)methyl]-2-(3-pyrrolidin-1-ylpropylsulfonimidoyl)-7H-purin-8-one (26 mg, Example 12) as a light brown solid. $^1$H NMR (400 MHz, DMSO-d$_6$) δ ppm: 10.88 (br. s, 1H), 7.29 (t, J=6.41 Hz, 2H), 7.05 (br. s, 2H), 6.88 (t, J=6.38 Hz, 2H), 4.88 (s, 2H), 3.72 (m, 4H), 2.52 (m, 4H), 2.45 (m, 4H), 1.84 (m, 2H), 1.67 (m, 4H). MS obsd. (ESI$^+$) [(M$^+$H)$^+$]: 446.

Example 13

6-Amino-9-[(4-chlorophenyl)methyl]-2-(methylsulfonimidoyl)-7H-purin-8-one

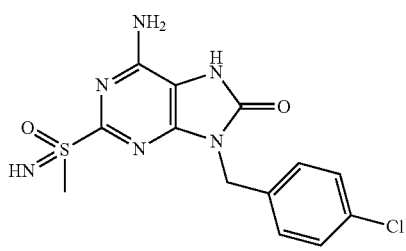

13

Step 1: Preparation of 6-amino-9-[(4-chlorophenyl)methyl]-2-methylsulfanyl-7H-purin-8-one

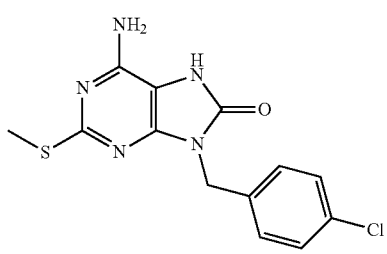

13a

Compound 13a was prepared in analogy to Example 1, Step 3 by using 6-amino-9-[(4-chlorophenyl)methyl]-2-sulfanyl-7H-purin-8-one (compound 9b) instead of 6-amino-9-benzyl-2-sulfanyl-7H-purin-8-one (compound 1b). 6-Amino-9-[(4-chlorophenyl)methyl]-2-methylsulfanyl-7H-purin-8-one (1.2 g, compound 13a) was obtained as a white solid. MS obsd. (ESI$^+$) [(M+H)$^+$]: 322.

Step 2: Preparation of 6-amino-9-[(4-chlorophenyl)methyl]-2-methylsulfinyl-7H-purin-8-one

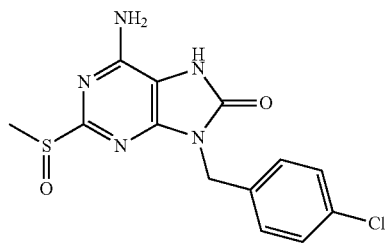

13b

Compound 13b was prepared in analogy to Example 1, Step 4 by using 6-amino-9-[(4-chlorophenyl)methyl]-2-methylsulfanyl-7H-purin-8-one (compound 13a) instead of 6-amino-9-benzyl-2-methylsulfanyl-7H-purin-8-one (compound 1c). 6-Amino-9-[(4-chlorophenyl)methyl]-2-methylsulfanyl-7H-purin-8-one (148 mg, compound 13b) was obtained as a white solid. MS obsd. (ESI$^+$) [(M+H)$^+$]: 338.

Step 3: Preparation of 6-amino-9-[(4-chlorophenyl)methyl]-2-(methylsulfonimidoyl)-7H-purin-8-one

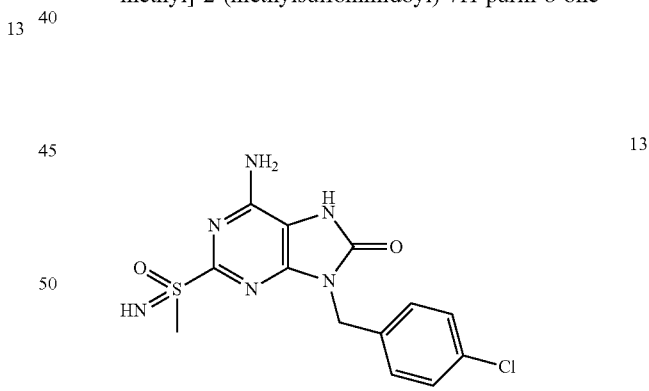

13

The title compound was prepared in analogy to Example 1, Step 5 by using 6-amino-9-[(4-chlorophenyl)methyl]-2-methylsulfanyl-7H-purin-8-one (compound 13b) instead of using 6-amino-9-benzyl-2-methylsulfanyl-7H-purin-8-one (compound 1d). 6-Amino-9-[(4-chlorophenyl)methyl]-2-methylsulfinyl-7H-purin-8-one (7 mg, Example 13) was obtained as a white solid. $^1$H NMR (400 MHz, DMSO-d$_6$) δ ppm: 10.53 (br. s, 1H), 7.36-7.51 (m, 4H), 6.98 (br. s, 2H), 4.96 (s, 2H), 4.07 (s, 1H), 3.18 (s, 3H). MS obsd. (ESI$^+$) [(M$^+$H)$^+$]: 353.

Example 14

6-Amino-9-[(6-chloro-3-pyridyl)methyl]-2-(propylsulfonimidoyl)-7H-purin-8-one

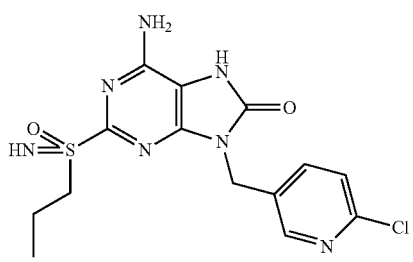

14

Step 1: Preparation of 4-amino-3-[(6-chloro-3-pyridyl)methyl]-2-oxo-1H-imidazole-5-carbonitrile

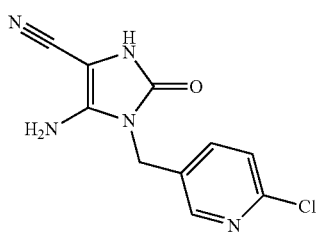

14a

Compound 14a was prepared in analogy to Example 9, Step 1 by using (6-chloro-3-pyridyl)methanamine (Alfa Aesar (China) Co., Ltd., Catalog number: L19283-25 g) instead of (4-chlorophenyl)methylamine. 4-Amino-3-[(6-chloro-3-pyridyl)methyl]-2-oxo-1H-imidazole-5-carbonitrile (7.8 g, compound 14a) was obtained as a white solid. MS obsd. (ESI$^+$) [(M+H)$^+$]: 250.

Step 2: Preparation of 6-amino-9-[(6-chloro-3-pyridyl)methyl]-2-sulfanyl-7H-purin-8-one

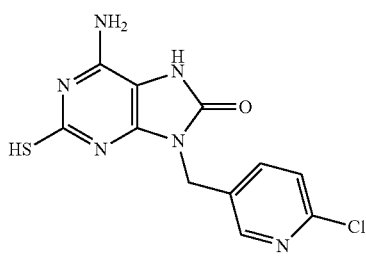

14b

Compound 14b was prepared in analogy to Example 9, Step 2 by using 4-amino-3-[(6-chloro-3-pyridyl)methyl]-2-oxo-1H-imidazole-5-carbonitrile (compound 14a) instead of 4-amino-3-[(4-chlorophenyl)methyl]-2-oxo-1H-imidazole-5-carbonitrile (compound 9a). 6-Amino-9-[(6-chloro-3-pyridyl)methyl]-2-sulfanyl-7H-purin-8-one (1.1 g, compound 14b) was obtained as a white solid. MS obsd. (ESI$^+$) [(M+H)$^+$]: 309.

Step 3: Preparation of 6-amino-9-[(6-chloro-3-pyridyl)methyl]-2-propylsulfanyl-7H-purin-8-one

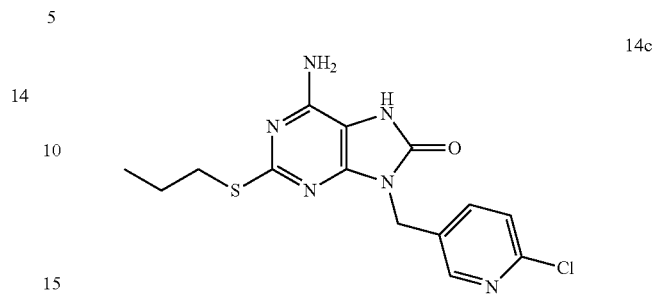

14c

Compound 14c was prepared in analogy to Example 1, Step 3 by using 6-amino-9-[(6-chloro-3-pyridyl)methyl]-2-sulfanyl-7H-purin-8-one (compound 14b) instead of 6-amino-9-benzyl-2-sulfanyl-7H-purin-8-one (compound 1b). 6-Amino-9-[(6-chloro-3-pyridyl)methyl]-2-propylsulfanyl-7H-purin-8-one (750 mg, compound 14c) was obtained as a white solid. MS obsd. (ESI$^+$) [(M+H)$^+$]: 351.

Step 4: Preparation of 6-amino-9-[(6-chloro-3-pyridyl)methyl]-2-propylsulfinyl-7H-purin-8-one

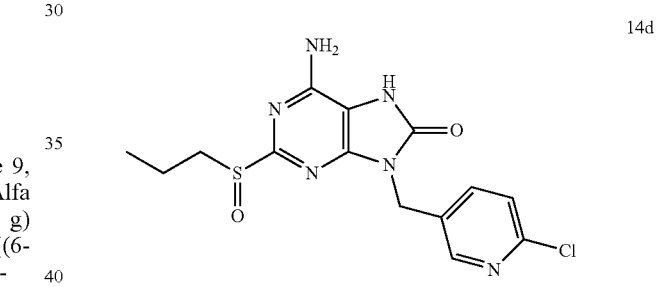

14d

Compound 14d was prepared in analogy to Example 1, Step 4 by using 6-amino-9-[(6-chloro-3-pyridyl)methyl]-2-propylsulfanyl-7H-purin-8-one (compound 14c) instead of 6-amino-9-benzyl-2-methylsulfanyl-7H-purin-8-one (compound 1c). 6-Amino-9-[(6-chloro-3-pyridyl)methyl]-2-propylsulfinyl-7H-purin-8-one (750 mg, compound 14d). MS obsd. (ESI$^+$) [(M+H)$^+$]: 367.

Step 5: Preparation of 6-amino-9-[(6-chloro-3-pyridyl)methyl]-2-(propylsulfonimidoyl)-7H-purin-8-one

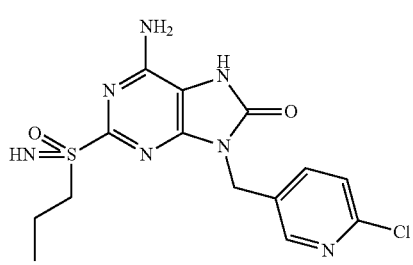

14

The title compound was prepared in analogy to Example 1, Step 5 by using 6-amino-9-[(6-chloro-3-pyridyl)methyl]-2-propylsulfanyl-7H-purin-8-one (compound 14d) instead of 6-amino-9-benzyl-2-methylsulfinyl-7H-purin-8-one (compound 1d). 6-Amino-9-[(6-chloro-3-pyridyl)methyl]-2-(propylsulfonimidoyl)-7H-purin-8-one (4 mg, Example 14) was obtained as a white solid. $^1$H NMR (400 MHz, DMSO-$d_6$) δ ppm: 10.80 (br. s, 1H), 8.45 (d, J=2.4 Hz, 1H), 7.81 (dd, J=2.4, 8.0 Hz, 1H), 7.49 (d, J=8.0 Hz, 1H), 7.04 (br. s, 2H), 5.01 (s, 2H), 4.06 (s, 1H), 3.24-3.43 (m, 2H), 1.53-1.73 (m, 2H), 0.92 (t, J=8.0 Hz, 3H). MS obsd. (ESI$^+$) [(M$^+$H)$^+$]: 382.

Example 15

6-Amino-9-[(2-chlorophenyl)methyl]-2-(propylsulfonimidoyl)-7H-purin-8-one

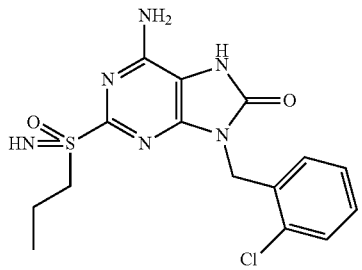

Step 1: Preparation of 6-chloro-N-[(2-chlorophenyl)methyl]-5-nitro-2-propylsulfanyl-pyrimidin-4-amine

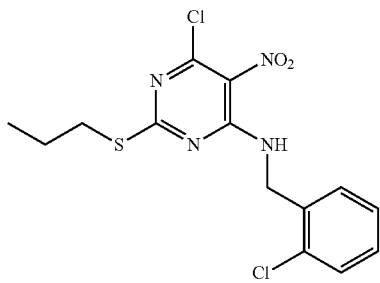

15a

To a solution of 4,6-dichloro-5-nitro-2-propylsulfanyl-pyrimidine (10 g, 37.0 mmol, J & K scientific, Catalog number: J92_090911_25G) and DIPEA (5.8 g, 45 mmol) in THF (200 mL) was added a solution of (2-chlorophenyl)methylamine (5.5 g, 39 mmol) in THF (50 mL) at −78° C. After the addition, the mixture was stirred at this temperature for 2 hrs. The resulting mixture was concentrated, extracted with EtOAc. The organic phase was washed with water, dried over anhydrous sodium sulfate, filtered and concentrated in vacuo. The residue was purified by column chromatography eluted with PE/EtOAc from 20/1 to 5/1 (V/V) to give 6-chloro-N-[(2-chlorophenyl)methyl]-5-nitro-2-propylsulfanyl-pyrimidin-4-amine (11 g, compound 15a) as a yellow solid. MS obsd. (ESI$^+$) [(M+H)$^+$]: 373.

Step 2: Preparation of 6-chloro-N4-[(2-chlorophenyl)methyl]-2-propylsulfanyl-pyrimidine-4,5-diamine

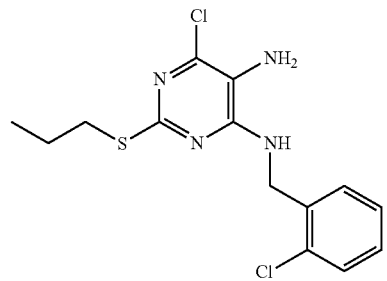

15b

To a solution of 6-chloro-N-[(2-chlorophenyl)methyl]-5-nitro-2-propylsulfanyl-pyrimidin-4-amine (11 g, 29.5 mmol, compound 15a) and HOAc (17.7 g, 295 mmol) in THF (400 mL) at 0° C. was added Zn dust (9.5 g, 147 mmol) in small portions. After the addition, the mixture was stirred at this temperature for 12 hrs and filtered. The filtrate was basified with NaHCO$_3$, extracted with DCM, dried over anhydrous sodium sulfate and concentrated in vacuo to give 6-chloro-N4-[(2-chlorophenyl)methyl]-2-propylsulfanyl-pyrimidine-4,5-diamine (9.0 g, compound 15b). MS obsd. (ESI$^+$) [(M+H)$^+$]: 343.

Step 3: Preparation of 6-chloro-9-[(2-chlorophenyl)methyl]-2-propylsulfanyl-7H-purin-8-one

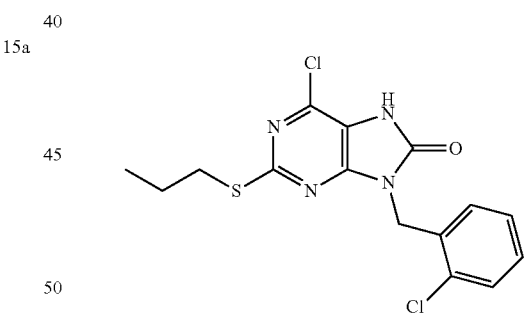

15c

To a solution of 6-chloro-N4-[(2-chlorophenyl)methyl]-2-propylsulfanyl-pyrimidine-4,5-diamine (9.0 g, 26.2 mmol, compound 15b) in THF (800 mg) was added CDI (21 g, 131 mmol). The reaction was kept at 80° C. for 12 hrs. The reaction mixture was cooled to RT, and then concentrated in vacuo. The residue was diluted with water (100 mL), extracted with EtOAc (125 mL) two times, dried over anhydrous sodium sulfate and concentrated in vacuo. The residue was purified by column eluted with PE/EtOAc from 10/1 to 1:1 (V/V) to give 6-chloro-9-[(2-chlorophenyl)methyl]-2-propylsulfanyl-7H-purin-8-one (9.5 g, compound 15c) as a gray solid. MS obsd. (ESI$^+$) [(M+H)$^+$]: 369.

Step 4: Preparation of 9-[(2-chlorophenyl)methyl]-6-[(4-methoxyphenyl)methylamino]-2-propylsulfanyl-7H-purin-8-one

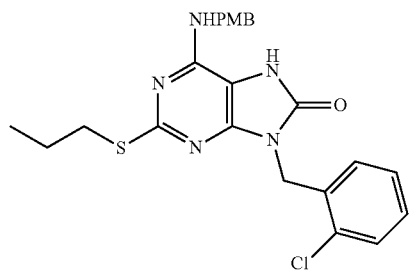

15d

To a solution of 6-chloro-9-[(2-chlorophenyl)methyl]-2-propylsulfanyl-7H-purin-8-one (9.0 g, 26.2 mmol, compound 15c) in n-BuOH (200 mL) was added PMBNH₂ (36 g, 262 mmol). The reaction was stirred at 130° C. for 12 hrs. The reaction mixture was cooled to 20° C., poured into PE. The formed precipitate was collected by filtration to give 9-[(2-chlorophenyl)methyl]-6-[(4-methoxyphenyl)methylamino]-2-propylsulfanyl-7H-purin-8-one as a white solid (10.2 g, compound 15d). MS obsd. (ESI⁺) [(M+H)⁺]: 470.

Step 5: Preparation of 6-amino-9-[(2-chlorophenyl)methyl]-2-propylsulfanyl-7H-purin-8-one

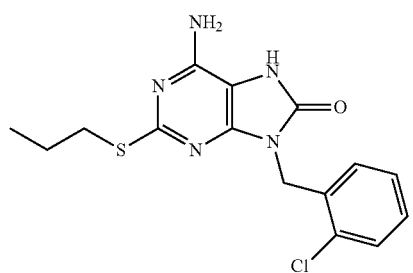

15e

9-[(2-Chlorophenyl)methyl]-6-[(4-methoxyphenyl)methylamino]-2-propylsulfanyl-7H-purin-8-one (2.0 g, 4.2 mmol, compound 15d) was dissolved in TFA (10 mL) and stirred at 60° C. for 12 hrs. The reaction mixture was concentrated in vacuo, and basified with NaHCO₃ solution. The resulting precipitate was collected by filtration and purified to give 6-amino-9-[(2-chlorophenyl)methyl]-2-propylsulfanyl-7H-purin-8-one (600 mg, compound 15e). MS obsd. (ESI⁺) [(M+H)⁺]: 350.

Step 6: Preparation of 6-amino-9-[(2-chlorophenyl)methyl]-2-propylsulfinyl-7H-purin-8-one

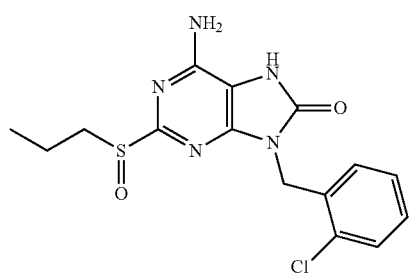

15f

To a solution of 6-amino-9-[(2-chlorophenyl)methyl]-2-propylsulfanyl-7H-purin-8-one (300 mg, 0.86 mmol, compound 15e) in THF (7 mL) was added m-CPBA (221 mg, 1.29 mmol) at 0° C. and the reaction mixture was stirred at 25° C. for 15 min. The mixture was filtered, and washed with THF (1 mL) three times. The obtained solid was co-evaporated with toluene two times to give 6-amino-9-[(2-chlorophenyl)methyl]-2-propylsulfinyl-7H-purin-8-one (150 mg, compound 15f) as a white solid. It was used in the next step without further purification. MS obsd. (ESI⁺) [(M+H)⁺]: 366.

Step 7: Preparation of 6-amino-9-[(2-chlorophenyl)methyl]-2-(propylsulfonimidoyl)-7H-purin-8-one

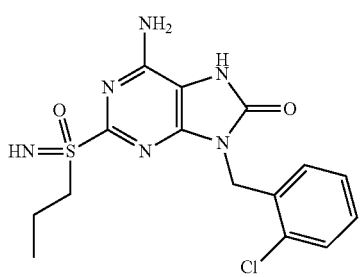

15

To a solution of 6-amino-9-[(2-chlorophenyl)methyl]-2-propylsulfinyl-7H-purin-8-one (100 mg, 0.27 mmol, compound 15f) in Eaton's reagent (1 mL) was added NaN₃ (53 mg, 0.81 mmol) and the mixture was stirred at 60° C. for 0.5 hr. The reaction mixture was added to ice water and basified with 0.88 N ammonium hydroxide solution, extracted with n-BuOH (10 mL) four times and concentrated in vacuo. The residue was purified by prep-HPLC to give 6-amino-9-[(2-chlorophenyl)methyl]-2-(propylsulfonimidoyl)-7H-purin-8-one (35 mg, Example 15) as a white solid. ¹H NMR (400 MHz DMSO-d₆) δ ppm: 10.78 (br. s., 1H), 7.51-7.49 (m, 1H), 7.33-7.28 (m, 2H), 7.14-7.12 (m, 1H), 7.04 (br. s., 2H), 5.05 (s, 2H), 3.98 (s, 1H), 3.35-3.24 (m, 2H), 1.62-1.55 (m, 2H), 0.86 (t, J=7.3 Hz, 3H). MS obsd. (ESI⁺) [(M+H)⁺]: 381.

Example 16

6-Amino-2-(methylsulfonimidoyl)-9-(3-pyridylmethyl)-7H-purin-8-one

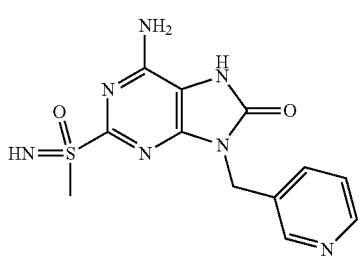

16

Step 1: Preparation of 6-chloro-2-methylsulfanyl-5-nitro-N-(3-pyridylmethyl)pyrimidin-4-amine

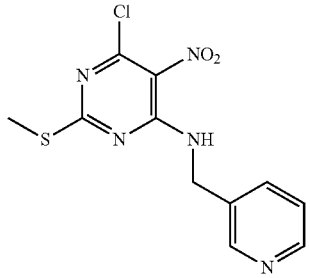

16a

Compound 16a was prepared in analogy to Example 15, Step 1 by using 4-pyridylmethylamine and 4,6-dichloro-2-methylsulfanyl-5-nitro-pyrimidine (J & K scientific, Catalog number: J92-058972-5G) instead of (2-chlorophenyl)methylamine and 4,6-dichloro-2-propylsulfanyl-5-nitro-pyrimidine. 6-Chloro-2-methylsulfanyl-5-nitro-N-(3-pyridylmethyl)pyrimidin-4-amine (compound 16a), which was used in the next step without further purification. MS obsd. (ESI$^+$) [(M+H)$^+$]: 312.

Step 2: Preparation of 6-chloro-2-methylsulfanyl-N4-(3-pyridylmethyl)pyrimidine-4,5-diamine

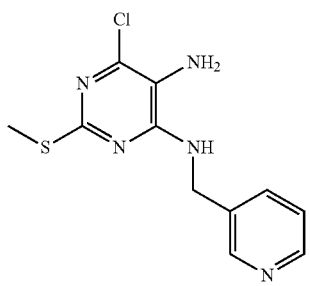

16b

Compound 16b was prepared in analogy to Example 15, Step 2 by using 6-chloro-2-methylsulfanyl-5-nitro-N-(3-pyridylmethyl)pyrimidin-4-amine (compound 16a) instead of 6-chloro-N-[(2-chlorophenyl)methyl]-5-nitro-2-propylsulfanyl-pyrimidin-4-amine (compound 15a). 6-Chloro-2-methylsulfanyl-N4-(3-pyridylmethyl)pyrimidine-4,5-diamine (700 mg, compound 16b) was obtained as a white solid. MS obsd. (ESI$^+$) [(M+H)$^+$]: 282.

Step 3: Preparation of 6-chloro-2-methylsulfanyl-9-(3-pyridylmethyl)-7H-purin-8-one

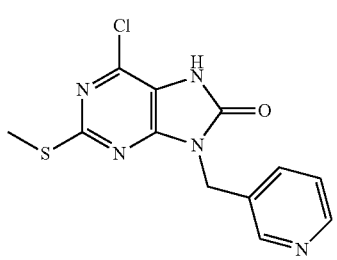

16c

Compound 16c was prepared in analogy to Example 15, Step 3 by using 6-chloro-2-methylsulfanyl-N4-(3-pyridylmethyl)pyrimidine-4,5-diamine (compound 16b) instead of 6-chloro-N-4-[(2-chlorophenyl)methyl]-2-propylsulfanyl-pyrimidine-4,5-diamine (compound 15b). 6-Chloro-2-methylsulfanyl-9-(3-pyridylmethyl)-7H-purin-8-one (600 mg, compound 16c) was obtained as a white solid. MS obsd. (ESI$^+$) [(M+H)$^+$]: 308.

Step 4: Preparation of 6-[(4-methoxyphenyl)methylamino]-2-methylsulfanyl-9-(3-pyridylmethyl)-7H-purin-8-one 16d Compound 16d was prepared in analogy to Example 15, Step 4 by using 6-chloro-2-methylsulfanyl-9-(3-pyridylmethyl)-7H-purin-8-one (compound 16c) instead of 6-chloro-9-[(2-chlorophenyl)methyl]-2-propylsulfanyl-7H-purin-8-one (compound 15c). 6-[(4-Methoxyphenyl)methylamino]-2-methylsulfanyl-9-(3-pyridylmethyl)-7H-purin-8-one (620 mg, compound 16d) was obtained as a white solid. MS obsd. (ESI$^+$) [(M+H)$^+$]: 409.

Step 5: Preparation of 6-amino-2-methylsulfanyl-9-(3-pyridylmethyl)-7H-purin-8-one 16e Compound 16e was prepared in analogy to Example 15, Step 5 by using 6-[(4-methoxyphenyl)methylamino]-2-methylsulfanyl-9-(3-pyridylmethyl)-7H-purin-8-one (compound 16d) instead of 9-[(2-chlorophenyl)methyl]-6-[(4-methoxyphenyl)methylamino]-2-propylsulfanyl-7H-purin-8-one (compound 15d). 6-Amino-2-methylsulfanyl-9-(3-pyridylmethyl)-7H-purin-8-one (380 mg, compound 16e) was obtained as a white solid. MS obsd. (ESI$^+$) [(M+H)$^+$]: 289.

Step 6: Preparation of 6-amino-2-methylsulfinyl-9-(3-pyridylmethyl)-7H-purin-8-one

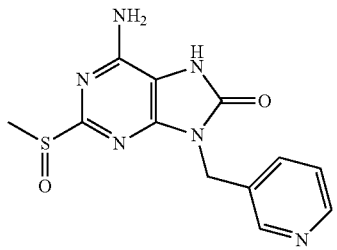

16f

Compound 16f was prepared in analogy to Example 15, Step 6 by 6-amino-2-methylsulfanyl-9-(3-pyridylmethyl)-7H-purin-8-one (compound 16e) instead of 6-amino-9-[(2-chlorophenyl)methyl]-2-propylsulfanyl-7H-purin-8-one (compound 15e). 6-Amino-2-methylsulfinyl-9-(3-pyridylmethyl)-7H-purin-8-one (105 mg, compound 16f) was obtained as a white solid. MS obsd. (ESI$^+$) [(M+H)$^+$]: 305.

Step 7: Preparation of 6-amino-2-(methylsulfonimidoyl)-9-(3-pyridylmethyl)-7H-purin-8-one

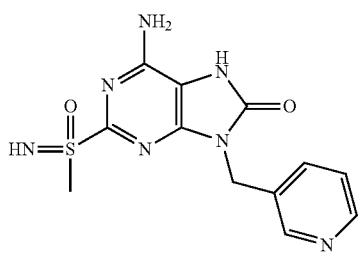

16

The title compound was prepared in analogy to Example 15, Step 7 by using 6-amino-2-methylsulfinyl-9-(3-pyridylmethyl)-7H-purin-8-one (200 mg, compound 16f) instead of 6-amino-9-[(2-chlorophenyl)methyl]-2-propylsulfinyl-7H-purin-8-one (compound 15f). 6-Amino-2-(methylsulfonimidoyl)-9-(3-pyridylmethyl)-7H-purin-8-one (38.2 mg, Example 16) was obtained as a white solid. $^1$H NMR (400 MHz, DMSO-d$_6$) δ ppm: 8.63 (s, 1H), 8.50 (d, J=4.52 Hz, 1H), 7.77 (d, J=8.03 Hz, 1H), 7.38 (dd, J=7.78, 5.02 Hz, 1H), 7.00 (br. s., 2H), 5.01 (s, 2H), 4.11 (br. s, 1H), 3.19 (s, 3H). MS obsd. (ESI$^+$) [(M+H)$^+$]: 320.

Separation of compound of Example 16 by chiral HPLC afforded Example 16-A (faster eluting, 5.0 mg) and Example 16-B (slower eluting, 7.1 mg) as white solid. (Separation condition: methanol 5%-40% (0.05% DEA)/CO$_2$ on ChiralPak OJ-3 column.)

Example 16-A $^1$H NMR (400 MHz, DMSO-d$_6$) δ ppm: 8.63 (s, 1H), 8.50 (d, J=4.52 Hz, 1H), 7.77 (d, J=8.03 Hz, 1H), 7.38 (dd, J=7.78, 5.02 Hz, 1H), 7.00 (br. s., 2H), 5.01 (s, 2H), 4.11 (br. s, 1H), 3.19 (s, 3H). MS obsd. (ESI$^+$) [(M+H)$^+$]: 320.

Example 16-B $^1$H NMR (400 MHz, DMSO-d$_6$) δ ppm: 8.63 (s, 1H), 8.50 (d, J=4.52 Hz, 1H), 7.77 (d, J=8.03 Hz, 1H), 7.38 (dd, J=7.78, 5.02 Hz, 1H), 7.00 (br. s., 2H), 5.01 (s, 2H), 4.11 (br. s, 1H), 3.19 (s, 3H). MS obsd. (ESI$^+$) [(M+H)$^+$]: 320.

Example 17 and Example 18

3-[[6-Amino-8-oxo-2-(propylsulfonimidoyl)-7H-purin-9-yl]methyl]benzonitrile (compound 17) and 3-[[6-amino-8-oxo-2-(propylsulfonimidoyl)-7H-purin-9-yl]methyl]benzamide (compound 18)

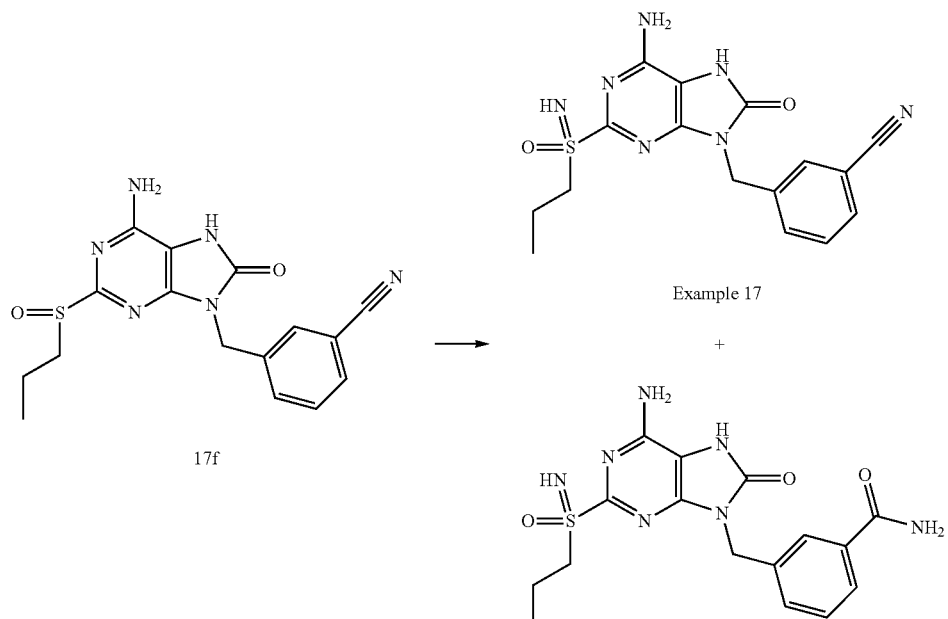

17f

Example 17

+

Example 18

Step 1: Preparation of 3-[[(6-chloro-5-nitro-2-propylsulfanyl-pyrimidin-4-yl)amino]methyl]benzonitrile

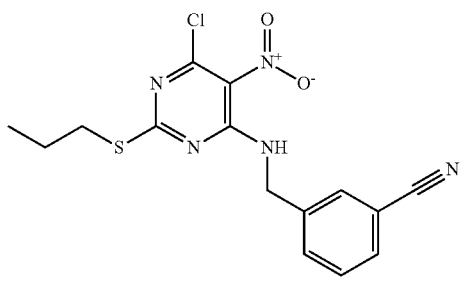

Compound 17a was prepared in analogy to Example 15, Step 1 by using 3-(aminomethyl)benzonitrile instead of (2-chlorophenyl)methylamine. 3-[[(6-Chloro-5-nitro-2-propylsulfanyl-pyrimidin-4-yl)amino]methyl]benzonitrile (2.75 g, compound 17a) was obtained as a yellow solid. MS obsd. (ESI$^+$) [(M+H)$^+$]: 364.

Step 2: Preparation of 3-[[(5-amino-6-chloro-2-propylsulfanyl-pyrimidin-4-yl)amino]methyl]benzonitrile

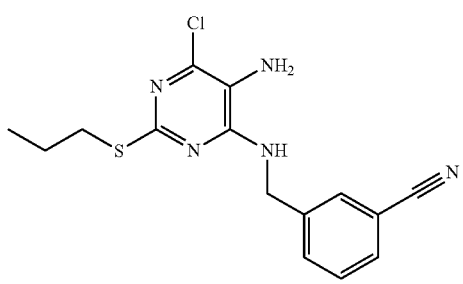

Compound 17b was prepared in analogy to Example 15, Step 2 by using 3-[[(6-chloro-5-nitro-2-propylsulfanyl-pyrimidin-4-yl)amino]methyl]benzonitrile (compound 17a) instead of 6-chloro-N-4-[(2-chlorophenyl)methyl]-5-nitro-2-propylsulfanyl-pyrimidin-4-amine (compound 15a). 3-[[(5-Amino-6-chloro-2-propylsulfanyl-pyrimidin-4-yl)amino]methyl]benzonitrile (1.1 g, compound 17b) was obtained as a white solid. MS obsd. (ESI$^+$) [(M+H)$^+$]: 334.

Step 3: Preparation of 3-[(6-chloro-2-propylsulfanyl-8-oxo-7H-purin-9-yl)methyl]benzonitrile

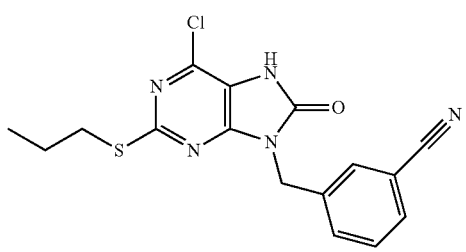

Compound 17c was prepared in analogy to Example 15, Step 3 by using 3-[[(5-amino-6-chloro-2-methylsulfanyl-pyrimidin-4-yl)amino]methyl]benzonitrile (compound 17b) instead of 6-chloro-N-4-[(2-chlorophenyl)methyl]-2-propyl-sulfanyl-pyrimidine-4,5-diamine (compound 15b). 3-[(6-Chloro-2-methylsulfanyl-8-oxo-7H-purin-9-yl)methyl]benzonitrile (700 mg, compound 17c) was obtained as a white solid. MS obsd. (ESI$^+$) [(M+H)$^+$]: 360.

Step 4: Preparation of 3-[[6-[(4-methoxyphenyl)methylamino]-2-propylsulfanyl-8-oxo-7H-purin-9-yl]methyl]benzonitrile

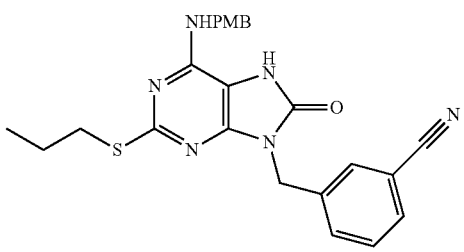

Compound 17d was prepared in analogy to Example 15, Step 4 by using 3-[(6-chloro-2-methylsulfanyl-8-oxo-7H-purin-9-yl)methyl]benzonitrile (compound 17c) instead of 6-chloro-9-[(2-chlorophenyl)methyl]-2-propylsulfanyl-7H-purin-8-one (compound 15c). 3-[[6-[(4-Methoxyphenyl)methylamino]-8-oxo-2-propylsulfanyl-7H-purin-9-yl]methyl]benzonitrile (900 mg, compound 17d) was obtained as a white solid. MS obsd. (ESI$^+$) [(M+H)$^+$]: 461.

Step 5: Preparation of 3-[(6-amino-8-oxo-2-propylsulfanyl-7H-purin-9-yl)methyl]benzonitrile

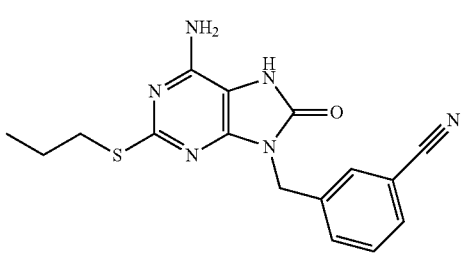

Compound 17e was prepared in analogy to Example 15, Step 5 by using 3-[[6-[(4-methoxyphenyl)methylamino]-2-propylsulfanyl-8-oxo-7H-purin-9-yl]methyl]benzonitrile (compound 17d) instead of 9-[(2-chlorophenyl)methyl]-6-[(4-methoxyphenyl)methylamino]-2-propylsulfanyl-7H-purin-8-one (compound 15d). 3-[(6-Amino-8-oxo-2-propylsulfanyl-7H-purin-9-yl)methyl]benzonitrile (600 mg, compound 17e) was obtained as a white solid. MS obsd. (ESI$^+$) [(M+H)$^+$]: 341.

Step 6: Preparation of 3-[(6-amino-8-oxo-2-propyl-sulfinyl-7H-purin-9-yl)methyl]benzonitrile

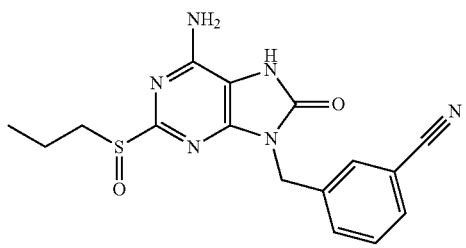

17f

Compound 17f was prepared in analogy to Example 15, Step 6 by using 6-amino-2-propylsulfanyl-9-(2-pyridylmethyl)-7H-purin-8-one (compound 17e) instead of 6-amino-9-[(2-chlorophenyl)methyl]-2-propylsulfanyl-7H-purin-8-one (compound 15e). 3-[(6-Amino-8-oxo-2-propylsulfinyl-7H-purin-9-yl)methyl]benzonitrile (610 mg, compound 17e) was obtained as a white solid. MS obsd. (ESI+) [(M+H)+]: 357.

Step 7: Preparation of 3-[[6-amino-8-oxo-2-(propyl-sulfonimidoyl)-7H-purin-9-yl]methyl]benzonitrile (compound 17) and 3-[[6-amino-8-oxo-2-(propyl-sulfonimidoyl)-7H-purin-9-yl]methyl]benzamide (compound 18)

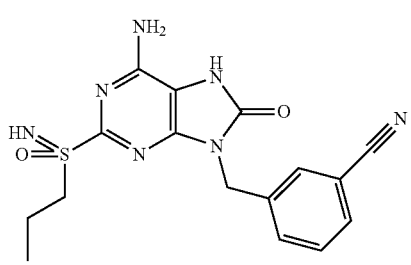

17

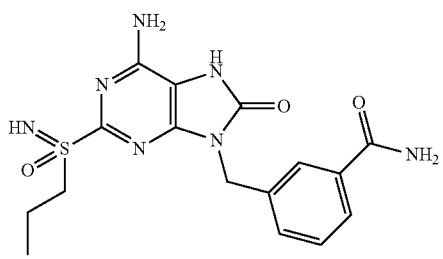

18

The title compound was prepared in analogy to Example 15, Step 7 by using 6-amino-2-methylsulfinyl-9-(2-pyridylmethyl)-7H-purin-8-one (270 mg, compound 17f) instead of 6-amino-9-[(2-chlorophenyl)methyl]-2-propylsulfinyl-7H-purin-8-one (compound 15f). 3-[[6-Amino-8-oxo-2-(propylsulfonimidoyl)-7H-purin-9-yl]methyl]benzonitrile (5 mg, Example 17) and 3-[[6-amino-8-oxo-2-(propylsulfonimidoyl)-7H-purin-9-yl]methyl]benzamide (41 mg, Example 18) was obtained as white solid.

Compound 17: $^1$H NMR (400 MHz, DMSO-d$_6$) δ ppm: 10.62 (br. s, 1H), 7.76-7.80 (m, 2H), 7.66 (d, J=8 Hz, 1H), 7.53-7.57 (m, 1H), 6.99 (br. s, 2H), 5.02 (s, 2H), 4.05 (s, 1H), 3.28-3.31 (m, 2H), 1.57-1.65 (m, 2H), 0.89 (t, J=8.0 Hz, 3H). MS obsd. (ESI+) [(M+H)+]: 372.

Compound 18: $^1$H NMR (400 MHz, DMSO-d$_6$) δ ppm: 10.85 (br. s, 1H), 7.97 (s, 1H), 7.84 (s, 1H), 7.77 (d, J=8 Hz, 1H), 7.47 (d, J=8 Hz, 1H), 7.37-7.42 (m, 2H), 7.06 (br. s, 2H), 5.00 (s, 2H), 4.01 (s, 1H), 3.28-3.30 (m, 2H), 1.55-1.67 (m, 2H), 0.88 (t, J=8.0 Hz, 3H). MS obsd. (ESI+) [(M+H)+]: 390.

Example 19

6-Amino-2-(methylsulfonimidoyl)-9-(2-pyridylmethyl)-7H-purin-8-one

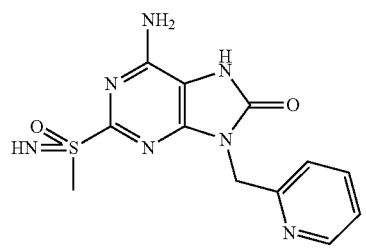

19

Step 1: Preparation of 6-chloro-2-methylsulfanyl-5-nitro-N-(2-pyridylmethyl)pyrimidin-4-amine

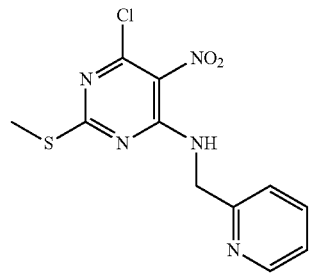

19a

Compound 19a was prepared in analogy to Example 15, Step 1 by using 2-pyridylmethylamine and 4,6-dichloro-2-methylsulfanyl-5-nitro-pyrimidine instead of (2-chlorophenyl)methylamine and 2-chlorophenylmethylamine and 4,6-dichloro-2-propylsulfanyl-5-nitro-pyrimidine. 6-Chloro-2-methylsulfanyl-5-nitro-N-(2-pyridylmethyl)pyrimidin-4-amine (4.64 g, compound 19a) was obtained as a white solid. MS obsd. (ESI+) [(M+H)+]: 312.

Step 2: Preparation of 6-chloro-2-methylsulfanyl-N4-(2-pyridylmethyl)pyrimidine-4,5-diamine

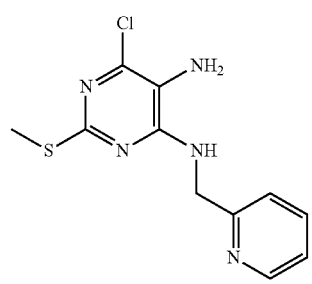

19b

Compound 19b was prepared in analogy to Example 15, Step 2 by using 6-chloro-2-methylsulfanyl-5-nitro-N-(2-pyridylmethyl)pyrimidin-4-amine (compound 19a) instead of 6-chloro-N-[(2-chlorophenyl)methyl]-5-nitro-2-propylsulfanyl-pyrimidin-4-amine (compound 15a). 6-Chloro-2-methylsulfanyl-N4-(2-pyridylmethyl)pyrimidine-4,5-diamine (2.3 g, compound 19b) was obtained as a white solid. MS obsd. (ESI⁺) [(M+H)⁺]: 282.

Step 3: Preparation of 6-chloro-2-methylsulfanyl-9-(2-pyridylmethyl)-7H-purin-8-one

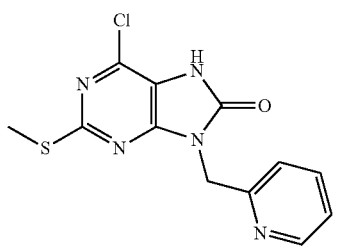

19c

Compound 19c was prepared in analogy to Example 15, Step 3 by using 6-chloro-2-methylsulfanyl-N4-(2-pyridylmethyl)pyrimidine-4,5-diamine (compound 19b) instead of 6-chloro-N-4-[(2-chlorophenyl)methyl]-2-propylsulfanyl-pyrimidine-4,5-diamine (compound 15b). 6-Chloro-2-methylsulfanyl-9-(2-pyridylmethyl)-7H-purin-8-one (2.0 g, compound 19c) was obtained as a white solid. MS obsd. (ESI⁺) [(M+H)⁺]: 308.

Step 4: Preparation of 6-[(4-methoxyphenyl)methylamino]-2-methylsulfanyl-9-(2-pyridylmethyl)-7H-purin-8-one

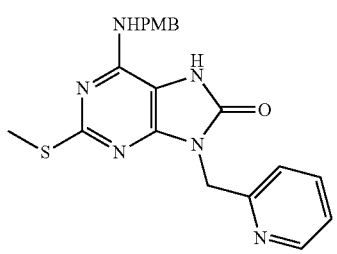

19d

Compound 19d was prepared in analogy to Example 15, Step 4 by using 6-chloro-2-methylsulfanyl-9-(2-pyridylmethyl)-7H-purin-8-one (compound 19c) instead of 6-chloro-9-[(2-chlorophenyl)methyl]-2-propylsulfanyl-7H-purin-8-one (compound 15c). 6-[(4-Methoxyphenyl)methylamino]-2-methylsulfanyl-9-(2-pyridylmethyl)-7H-purin-8-one (2.0 g, compound 19d) was obtained as a white solid. MS obsd. (ESI⁺) [(M+H)⁺]: 409.

Step 5: Preparation of 6-amino-2-methylsulfanyl-9-(2-pyridylmethyl)-7H-purin-8-one

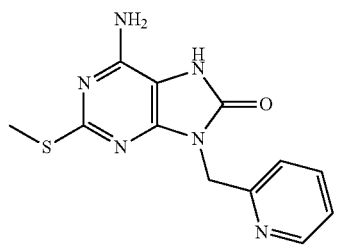

19e

Compound 19e was prepared in analogy to Example 15, Step 5 by using 6-[(4-methoxyphenyl)methylamino]-2-methylsulfanyl-9-(2-pyridylmethyl)-7H-purin-8-one (compound 19d) instead of 9-[(2-chlorophenyl)methyl]-6-[(4-methoxyphenyl)methylamino]-2-propylsulfanyl-7H-purin-8-one (compound 15d). 6-Amino-2-methylsulfanyl-9-(2-pyridylmethyl)-7H-purin-8-one (1.14 g, compound 19e) was obtained as a white solid. MS obsd. (ESI⁺) [(M+H)⁺]: 289.

Step 6: Preparation of 6-amino-2-methylsulfinyl-9-(2-pyridylmethyl)-7H-purin-8-one

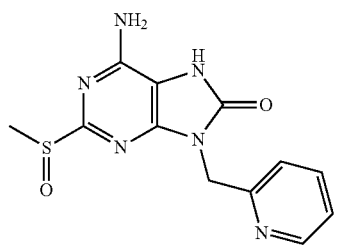

19f

Compound 19f was prepared in analogy to Example 15, Step 6 by using 6-amino-2-methylsulfanyl-9-(2-pyridylmethyl)-7H-purin-8-one (compound 19e) instead of 6-amino-9-[(2-chlorophenyl)methyl]-2-propylsulfanyl-7H-purin-8-one (compound 15e). 6-Amino-2-methylsulfinyl-9-(2-pyridylmethyl)-7H-purin-8-one (280 mg, compound 19f) was obtained as a white solid. MS obsd. (ESI⁺) [(M+H)⁺]: 305.

Step 7: Preparation of 6-amino-2-(methylsulfonimidoyl)-9-(2-pyridylmethyl)-7H-purin-8-one

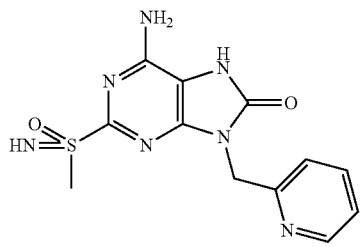

19

The title compound was prepared in analogy to Example 15, Step 7 by using 6-amino-2-methylsulfinyl-9-(2-pyridylmethyl)-7H-purin-8-one (compound 19f) instead 6-amino-9-[(2-chlorophenyl)methyl]-2-propylsulfinyl-7H-purin-8- one (compound 15f). 6-Amino-2-(methylsulfonimidoyl)-9-(2-pyridylmethyl)-7H-purin-8-one (50 mg, Example 19) was obtained as a white solid. ¹H NMR (400 MHz, DMSO-d₆) δ ppm: 8.47 (d, J=4.27 Hz, 1H), 7.77 (td, J=7.65, 1.51 Hz, 1H), 7.24-7.33 (m, 2H), 7.19 (br. s., 2H), 5.09 (s, 2H), 4.00 (br. s., 1H), 3.11 (s, 3H). MS obsd. (ESI⁺) [(M+H)⁺]: 320.

Example 20

6-Amino-2-(methylsulfonimidoyl)-9-(4-pyridylmethyl)-7H-purin-8-one

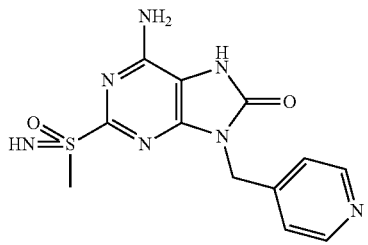

Step 1: Preparation of 6-chloro-2-methylsulfanyl-5-nitro-N-(4-pyridylmethyl)pyrimidin-4-amine

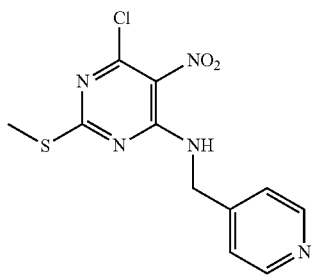

20a

Compound 20a was prepared in analogy to Example 15, Step 1 by using 4-pyridylmethylamine and 4,6-dichloro-2-methylsulfanyl-5-nitro-pyrimidine instead of (2-chlorophenyl)methylamine and 4,6-dichloro-2-propylsulfanyl-5-nitro-pyrimidine. 6-Chloro-2-methylsulfanyl-5-nitro-N-(4-pyridylmethyl)pyrimidin-4-amine (1.0 g, compound 20a) was obtained as a yellow solid. MS obsd. (ESI⁺) [(M+H)⁺]: 312.

Step 2: Preparation of 6-chloro-2-methylsulfanyl-N4-(4-pyridylmethyl)pyrimidine-4,5-diamine

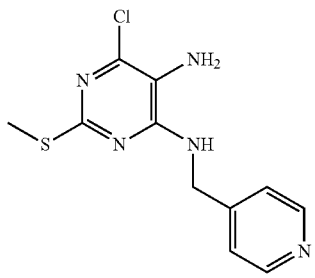

20b

Compound 20b was prepared in analogy to Example 15, Step 2 by using 6-chloro-2-methylsulfanyl-5-nitro-N-(4-pyridylmethyl)pyrimidin-4-amine (compound 20a) instead of 6-chloro-N-[(2-chlorophenyl)methyl]-5-nitro-2-propylsulfanyl-pyrimidin-4-amine (compound 15a). 6-Chloro-2-methylsulfanyl-N4-(4-pyridylmethyl)pyrimidine-4,5-diamine (900 mg, compound 20b) was obtained as a white solid. MS obsd. (ESI⁺) [(M+H)⁺]: 282.

Step 3: Preparation of 6-chloro-2-methylsulfanyl-9-(4-pyridylmethyl)-7H-purin-8-one

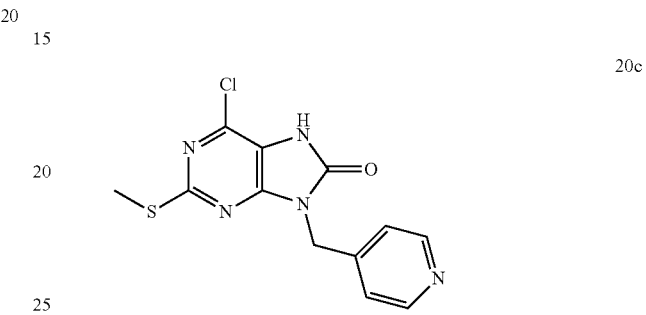

20c

Compound 20c was prepared in analogy to Example 15, Step 3 by using 6-chloro-2-methylsulfanyl-N4-(4-pyridylmethyl)pyrimidine-4,5-diamine (compound 20b) instead of 6-chloro-N-4-[(2-chlorophenyl)methyl]-2-propylsulfanyl-pyrimidine-4,5-diamine (compound 15b). 6-Chloro-2-methylsulfanyl-9-(4-pyridylmethyl)-7H-purin-8-one (620 mg, compound 20c) was obtained as a white solid. MS obsd. (ESI⁺) [(M+H)⁺]: 308.

Step 4: Preparation of 6-[(4-methoxyphenyl)methylamino]-2-methylsulfanyl-9-(4-pyridylmethyl)-7H-purin-8-one

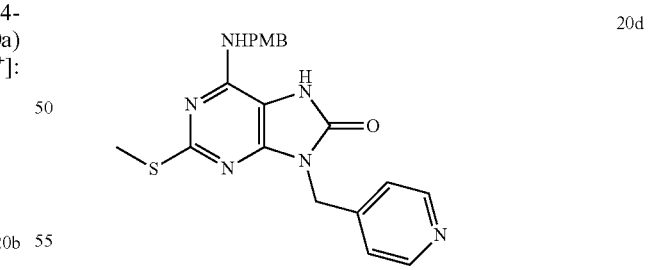

20d

Compound 20d was prepared in analogy to Example 15, Step 4 by using 6-Chloro-2-methylsulfanyl-9-(4-pyridylmethyl)-7H-purin-8-one (compound 20c) instead of 6-chloro-9-[(2-chlorophenyl)methyl]-2-propylsulfanyl-7H-purin-8-one (compound 15c). 6-[(4-Methoxyphenyl)methylamino]-2-methylsulfanyl-9-(4-pyridylmethyl)-7H-purin-8-one (700 mg, compound 20d) was obtained as a white solid. MS obsd. (ESI⁺) [(M+H)⁺]: 409.

Step 5: Preparation of 6-amino-2-methylsulfanyl-9-(4-pyridylmethyl)-7H-purin-8-one

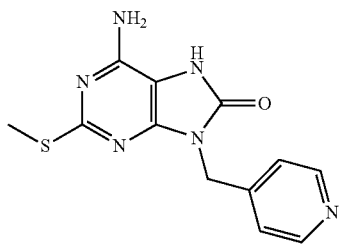

20e

Compound 20e was prepared in analogy to Example 15, Step 5 by using 6-[(4-methoxyphenyl)methylamino]-2-methylsulfanyl-9-(4-pyridylmethyl)-7H-purin-8-one (compound 20d) instead of 9-[(2-chlorophenyl)methyl]-6-[(4-methoxyphenyl)methylamino]-2-propylsulfanyl-7H-purin-8-one (compound 15d). 6-Amino-2-methylsulfanyl-9-(4-pyridylmethyl)-7H-purin-8-one (450 mg, compound 20e) was obtained as a white solid. MS obsd. (ESI$^+$) [(M+H)$^+$]: 289.

Step 6: Preparation of 6-amino-2-methylsulfinyl-9-(4-pyridylmethyl)-7H-purin-8-one

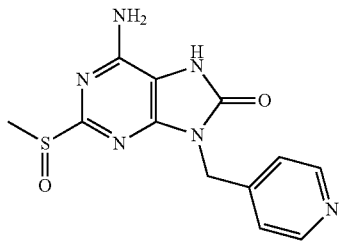

20f

Compound 20f was prepared in analogy to Example 15, Step 6 by using 6-amino-2-methylsulfanyl-9-(4-pyridylmethyl)-7H-purin-8-one (compound 20e) instead of 6-amino-9-[(2-chlorophenyl)methyl]-2-propylsulfanyl-7H-purin-8-one (compound 15e). 6-Amino-2-methylsulfinyl-9-(4-pyridylmethyl)-7H-purin-8-one (160 mg, compound 20f) was obtained as a white solid. MS obsd. (ESI$^+$) [(M+H)$^+$]: 305.

Step 7: Preparation of 6-amino-2-(methylsulfonimidoyl)-9-(4-pyridylmethyl)-7H-purin-8-one

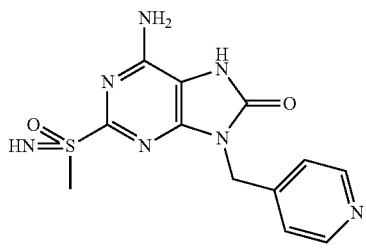

20

The title compound was prepared in analogy to Example 15, Step 7 by using 6-amino-2-methylsulfinyl-9-(4-pyridylmethyl)-7H-purin-8-one (200 mg, compound 20f) instead of 6-amino-9-[(2-chlorophenyl)methyl]-2-propylsulfinyl-7H-purin-8-one (compound 15f). 6-Amino-2-(methylsulfonimidoyl)-9-(4-pyridylmethyl)-7H-purin-8-one (27 mg, Example 20) was obtained as a white solid. $^1$H NMR (400 MHz, DMSO-d$_6$) δ ppm: 8.52 (d, J=5.77 Hz, 2H), 7.29 (d, J=5.52 Hz, 2H), 7.05 (br. s., 2H), 5.01 (s, 2H), 4.06 (s, 1H), 3.16 (s, 3H). MS obsd. (ESI$^+$) [(M+H)$^+$]: 320.

Example 21

6-Amino-9-isobutyl-2-(propylsulfonimidoyl)-7H-purin-8-one

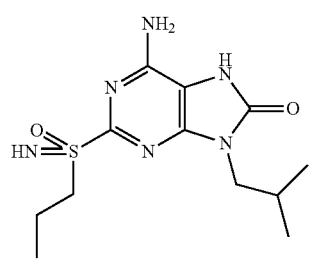

21

Step 1: Preparation of 6-chloro-N-isobutyl-5-nitro-2-propylsulfanyl-pyrimidin-4-amine

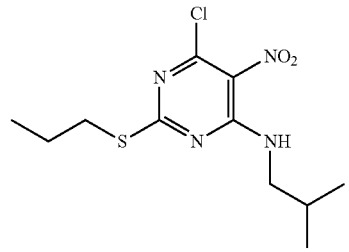

21a

Compound 21a was prepared in analogy to Example 15, Step 1 by using 2-methylpropan-1-amine instead of (2-chlorophenyl)methylamine. 6-Chloro-N-isobutyl-5-nitro-2-propylsulfanyl-pyrimidin-4-amine (compound 21a) was obtained as a light yellow solid. MS obsd. (ESI$^+$) [(M+H)$^+$]: 305.

Step 2: Preparation of 6-chloro-N4-isobutyl-2-propylsulfanyl-pyrimidine-4,5-diamine

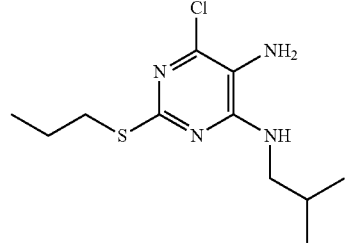

21b

Compound 21b was prepared in analogy to Example 15, Step 2 by using 6-chloro-N-isobutyl-5-nitro-2-propylsulfanyl-pyrimidin-4-amine (compound 21a) instead of 6-chloro- N-[(2-chlorophenyl)methyl]-5-nitro-2-propylsulfanyl-pyrimidin-4-amine (compound 15a). 6-Chloro-N4-isobutyl-2-propylsulfanyl-pyrimidine-4,5-diamine (4.5 g, compound 21b) was obtained as a white solid. MS obsd. (ESI⁺) [(M+H)⁺]: 275.

Step 3: Preparation of 6-chloro-9-isobutyl-2-propylsulfanyl-7H-purin-8-one

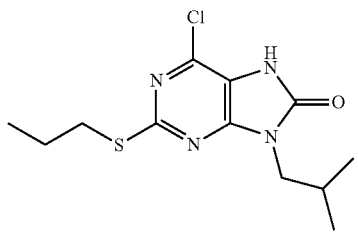

21c

Compound 21c was prepared in analogy to Example 15, Step 3 by using 6-chloro-N4-isobutyl-2-propylsulfanyl-pyrimidine-4,5-diamine (compound 21b) instead of 6-chloro-N-4-[(2-chlorophenyl)methyl]-2-propylsulfanyl-pyrimidine-4,5-diamine (compound 15b). 6-Chloro-9-isobutyl-2-propylsulfanyl-7H-purin-8-one (850 mg, compound 21c) was obtained as a white solid. MS obsd. (ESI⁺) [(M+H)⁺]: 301.

Step 4: Preparation of 9-isobutyl-6-[(4-methoxyphenyl)methylamino]-2-propylsulfanyl-7H-purin-8-one

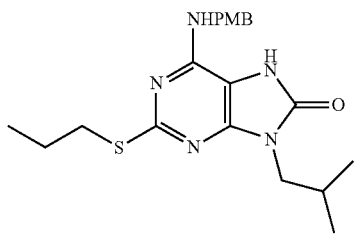

21d

Compound 21d was prepared in analogy to Example 15, Step 4 by using 6-chloro-9-isobutyl-2-propylsulfanyl-7H-purin-8-one (compound 21c) instead of 6-chloro-9-[(2-chlorophenyl)methyl]-2-propylsulfanyl-7H-purin-8-one (compound 15c). 9-Isobutyl-6-[(4-methoxyphenyl)methylamino]-2-propylsulfanyl-7H-purin-8-one (570 mg, compound 21d) was obtained as a white solid. MS obsd. (ESI⁺) [(M+H)⁺]: 402.

Step 5: Preparation of 6-amino-9-isobutyl-2-propylsulfanyl-7H-purin-8-one

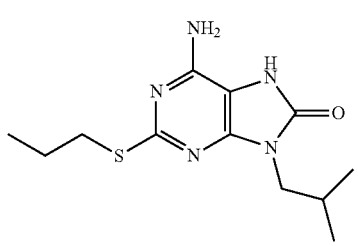

21e

Compound 21e was prepared in analogy to Example 15, Step 5 by using 9-isobutyl-6-[(4-methoxyphenyl)methylamino]-2-propylsulfanyl-7H-purin-8-one (compound 21d) instead of 9-[(2-chlorophenyl)methyl]-6-[(4-methoxyphenyl)methylamino]-2-propylsulfanyl-7H-purin-8-one (compound 15d). 6-Amino-9-isobutyl-2-propylsulfanyl-7H-purin-8-one (300 mg, compound 21e) was obtained as a white solid. MS obsd. (ESI⁺) [(M+H)⁺]: 282.

Step 6: Preparation of 6-amino-9-isobutyl-2-propylsulfinyl-7H-purin-8-one

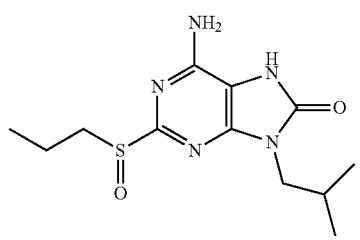

21f

Compound 21f was prepared in analogy to Example 15, Step 6 by using 6-amino-9-isobutyl-2-propylsulfanyl-7H-purin-8-one (compound 21e) instead of 6-amino-9-[(2-chlorophenyl)methyl]-2-propylsulfanyl-7H-purin-8-one (compound 15e). 6-Amino-9-isobutyl-2-propylsulfinyl-7H-purin-8-one (125 mg, compound 21f) was obtained as a white solid. MS obsd. (ESI⁺) [(M+H)⁺]: 298.

Step 7: Preparation of 6-amino-2-(methylsulfonimidoyl)-9-(4-pyridylmethyl)-7H-purin-8-one

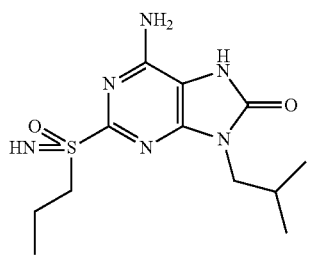

21

The title compound was prepared in analogy to Example 15, Step 7 by using 6-amino-9-isobutyl-2-propylsulfinyl-7H-purin-8-one (compound 21f) instead of 6-amino-9-[(2-chlorophenyl)methyl]-2-propylsulfinyl-7H-purin-8-one (compound 15f). 6-Amino-9-isobutyl-2-(propylsulfonimidoyl)-7H-purin-8-one (65.8 mg, Example 21) was obtained as a white solid. ¹H NMR (400 MHz, DMSO-d₆) δ ppm: 10.46 (s, 1H), 6.92 (br. s., 2H), 4.00 (s, 1H), 3.59 (d, J=1.6 Hz, 2H), 3.32-3.38 (m, 2H), 2.15 (m, 1H), 1.65-1.73 (m, 2H), 0.97 (t, J=73 Hz, 3H), 0.86 (m, 6H). MS obsd. (ESI⁺) [(M+H)⁺]: 313.

Example 22

6-Amino-9-[(3-chlorophenyl)methyl]-2-(propylsulfonimidoyl)-7H-purin-8-one

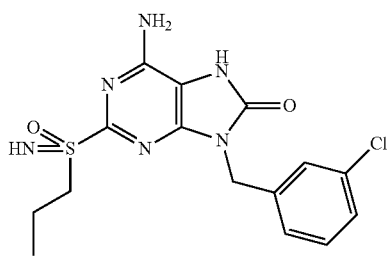

Step 1: Preparation of 6-chloro-N-[(3-chlorophenyl)methyl]-5-nitro-2-propylsulfanyl-pyrimidin-4-amine

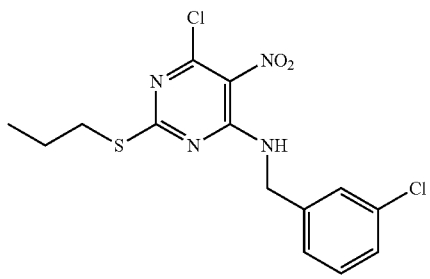

Compound 22a was prepared in analogy to Example 15, Step 1 by using (3-chlorophenyl)methylamine instead of (2-chlorophenyl)methylamine. 6-Chloro-N-[(3-chlorophenyl)methyl]-5-nitro-2-propylsulfanyl-pyrimidin-4-amine (13.9 g, compound 22a) was obtained as a yellow solid. MS obsd. (ESI+) [(M+H)+]: 373.

Step 2: Preparation of 6-chloro-N4-[(3-chlorophenyl)methyl]-2-propylsulfanyl-pyrimidine-4,5-diamine

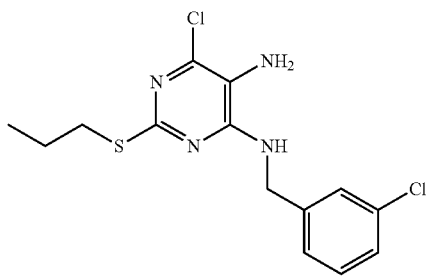

Compound 22b was prepared in analogy to Example 15, Step 2 by using 6-chloro-N-[(3-chlorophenyl)methyl]-5-nitro-2-propylsulfanyl-pyrimidin-4-amine (compound 22a) instead of 6-chloro-N-[(2-chlorophenyl)methyl]-5-nitro-2-propylsulfanyl-pyrimidin-4-amine (compound 15a). 6-Chloro-N4-[(3-chlorophenyl)methyl]-2-propylsulfanyl-pyrimidine-4,5-diamine (13.0 g, compound 22b) was obtained as a white solid. MS obsd. (ESI+) [(M+H)+]: 343.

Step 3: Preparation of 6-chloro-9-[(3-chlorophenyl)methyl]-2-propylsulfanyl-7H-purin-8-one

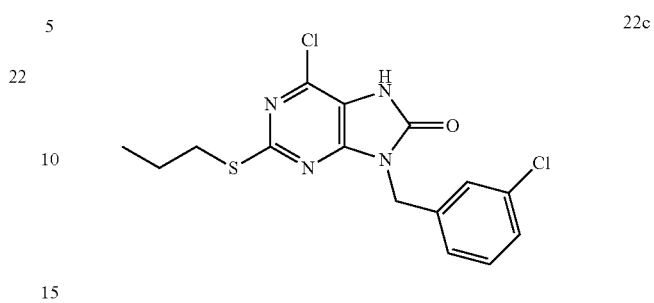

Compound 22c was prepared in analogy to Example 15, Step 3 by using 6-chloro-N-4-[(3-chlorophenyl)methyl]-2-propylsulfanyl-pyrimidine-4,5-diamine (compound 22b) instead of 6-chloro-N4-[(2-chlorophenyl)methyl]-2-propylsulfanyl-pyrimidine-4,5-diamine (compound 15b). 6-Chloro-9-[(3-chlorophenyl)methyl]-2-propylsulfanyl-7H-purin-8-one (13.0 g, compound 22c) was obtained as a white solid. MS obsd. (ESI+) [(M+H)+]: 369.

Step 4: Preparation of 9-[(3-chlorophenyl)methyl]-6-[(4-methoxyphenyl)methylamino]-2-propylsulfanyl-7H-purin-8-one

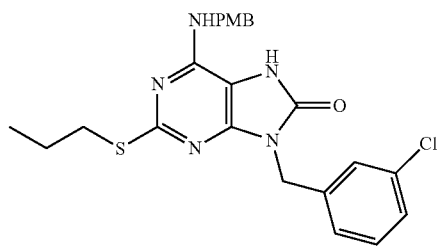

Compound 22d was prepared in analogy to Example 15, Step 4 by using 6-chloro-9-[(3-chlorophenyl)methyl]-2-propylsulfanyl-7H-purin-8-one (compound 22c) instead of 6-chloro-9-[(2-chlorophenyl)methyl]-2-propylsulfanyl-7H-purin-8-one (compound 15c). 9-[(3-Chlorophenyl)methyl]-6-[(4-methoxyphenyl)methylamino]-2-propylsulfanyl-7H-purin-8-one (6.0 g, compound 22d) was obtained as a white solid. MS obsd. (ESI+) [(M+H)+]: 470.

Step 5: Preparation of 6-amino-9-[(3-chlorophenyl)methyl]-2-propylsulfanyl-7H-purin-8-one

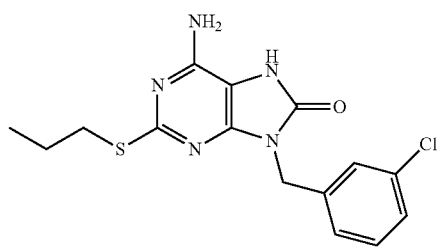

Compound 22e was prepared in analogy to Example 15, Step 5 by using 9-[(3-chlorophenyl)methyl]-6-[(4-methoxyphenyl)methylamino]-2-propylsulfanyl-7H-purin-8-one (compound 22d) instead of 9-[(2-chlorophenyl)methyl]-6-[(4-methoxyphenyl)methylamino]-2-propylsulfanyl-7H-purin-8-one (compound 15d). 6-Amino-9-[(3-chlorophenyl)methyl]-2-propylsulfanyl-7H-purin-8-one (300 mg, compound 22e) was obtained as a white solid. MS obsd. (ESI+) [(M+H)+]: 350.

Step 6: Preparation of 6-amino-9-[(3-chlorophenyl)methyl]-2-propylsulfinyl-7H-purin-8-one

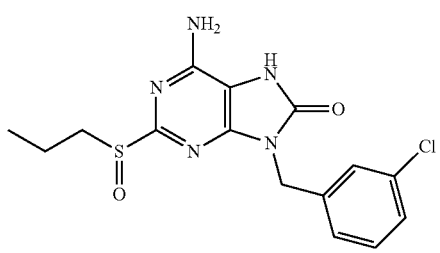

22f

Compound 22f was prepared in analogy to Example 15, Step 6 by using 6-amino-9-[(3-chlorophenyl)methyl]-2-propylsulfanyl-7H-purin-8-one (compound 22e) instead of 6-amino-9-[(2-chlorophenyl)methyl]-2-propylsulfanyl-7H-purin-8-one (compound 15e). 6-Amino-9-[(3-chlorophenyl)methyl]-2-propylsulfinyl-7H-purin-8-one (150 mg, compound 22f) was obtained as a yellow solid. MS obsd. (ESI+) [(M+H)+]: 366.

Step 7: Preparation of 6-amino-9-[(3-chlorophenyl)methyl]-2-(propylsulfonimidoyl)-7H-purin-8-one

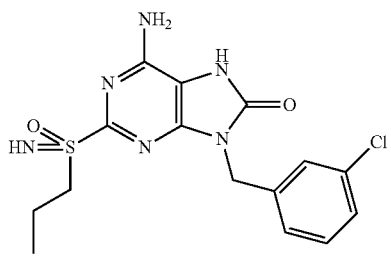

22

The title compound was prepared in analogy to Example 15, Step 7 by using 6-amino-9-[(3-chlorophenyl)methyl]-2-propylsulfinyl-7H-purin-8-one (100 mg, compound 22f) instead of 6-amino-9-[(2-chlorophenyl)methyl]-2-propylsulfinyl-7H-purin-8-one (compound 15f). 6-Amino-9-[(3-chlorophenyl)methyl]-2-(propylsulfonimidoyl)-7H-purin-8-one (43 mg, Example 22) was obtained as a white solid. $^1$H NMR (400 MHz DMSO-$d_6$) δ ppm: 7.41-7.36 (m, 3H), 7.030-7.28 (m, 1H), 7.01 (br. s., 2H), 4.96 (s, 2H), 4.03 (s, 1H), 3.34-3.27 (m, 2H), 1.67-1.59 (m, 2H), 0.91 (t, J=8.0 Hz, 3H). MS obsd. (ESI+) [(M+H)+]: 381.

Example 23

6-Amino-2-(propylsulfonimidoyl)-9-[[4-(trifluoromethyl)phenyl]methyl]-7H-purin-8-one

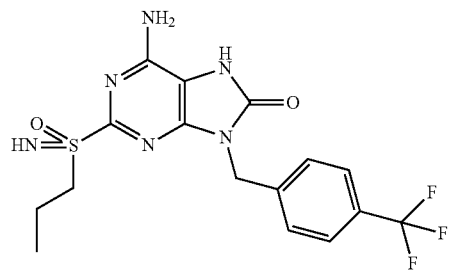

23

Step 1: Preparation of 6-chloro-N-[(4-trifluoromethylphenyl)methyl]-5-nitro-2-propylsulfanyl-pyrimidin-4-amine

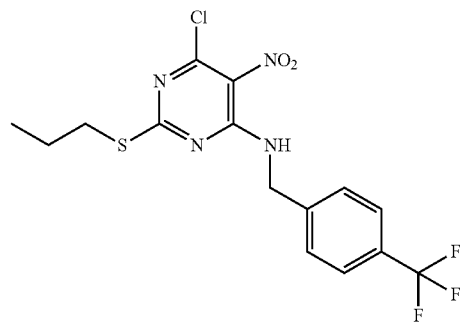

23a

Compound 23a was prepared in analogy to Example 15, Step 1 by using (4-trifluoromethylphenyl)methylamine instead of (2-chlorophenyl)methylamine. 6-Chloro-N-[(4-trifluoromethylphenylmethyl]-5-nitro-2-propylsulfanyl-pyrimidin-4-amine (7.0 g, compound 23a) was obtained as a white solid. MS obsd. (ESI+) [(M+H)+]: 407.

Step 2: Preparation of 6-chloro-2-propylsulfanyl-N4-[[4-(trifluoromethyl)phenyl]methyl]pyrimidine-4,5-diamine

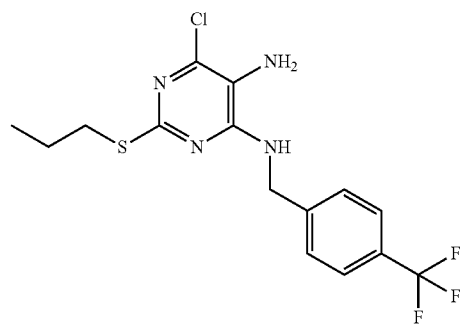

23b

Compound 23b was prepared in analogy to Example 15, Step 2 by using 6-chloro-N-[(4-trifluoromethylphenyl)methyl]-5-nitro-2-propylsulfanyl-pyrimidin-4-amine (compound 23a) instead of 6-chloro-N-[(2-chlorophenyl)methyl]-5-nitro-2-propylsulfanyl-pyrimidin-4-amine (compound 15a). 6-Chloro-N4-[(4-trifluoromethylphenyl)methyl]-2-propylsulfanyl-pyrimidine-4,5-diamine (3.1 g, compound 23b) was obtained as a white solid. MS obsd. (ESI+) [(M+H)+]: 377.

Step 3: Preparation of 6-chloro-9-[(4-trifluoromethylphenyl)methyl]-2-propylsulfanyl-7H-purin-8-one

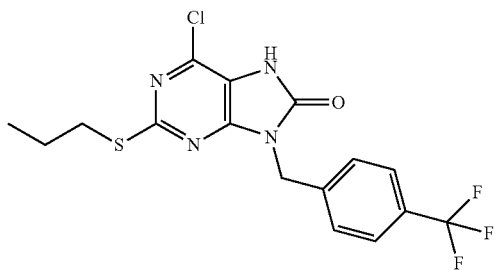

23c

Compound 23c was prepared in analogy to Example 15, Step 3 by using 6-chloro-N-4-[(4-trifluoromethylphenyl)methyl]-2-propylsulfanyl-pyrimidine-4,5-diamine (compound 23b) instead of 6-chloro-N4-[(2-chlorophenyl)methyl]-2-propylsulfanyl-pyrimidine-4,5-diamine (compound 15b). 6-Chloro-9-[(4-trifluoromethylphenyl)methyl]-2-propylsulfanyl-7H-purin-8-one (1.8 g, compound 23c) was obtained as a white solid. MS obsd. (ESI+) [(M+H)+]: 403.

Step 4: Preparation of 6-[(4-methoxyphenyl)methylamino]-2-propylsulfanyl-9-[[4-(trifluoromethyl)phenyl]methyl]-7H-purin-8-one

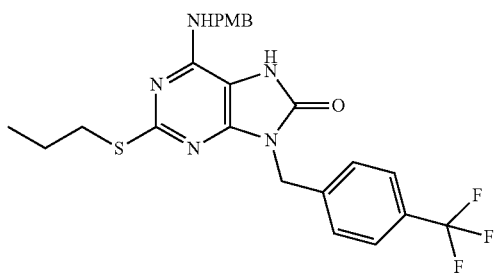

23d

Compound 23d was prepared in analogy to Example 15, Step 4 by using 6-chloro-9-[(4-trifluoromethylphenyl)methyl]-2-propylsulfanyl-7H-purin-8-one (compound 23c) instead of 6-chloro-9-[(2-chlorophenyl)methyl]-2-propylsulfanyl-7H-purin-8-one (compound 15c). 9-[(4-Trifluoromethylphenyl)methyl]-6-[(4-methoxyphenyl)methylamino]-2-propylsulfanyl-7H-purin-8-one (1.2 g, compound 23d) was obtained as a white solid. MS obsd. (ESI+) [(M+H)+]: 504.

Step 5: Preparation of 6-amino-9-[(4-trifluoromethylphenyl)methyl]-2-propylsulfanyl-7H-purin-8-one

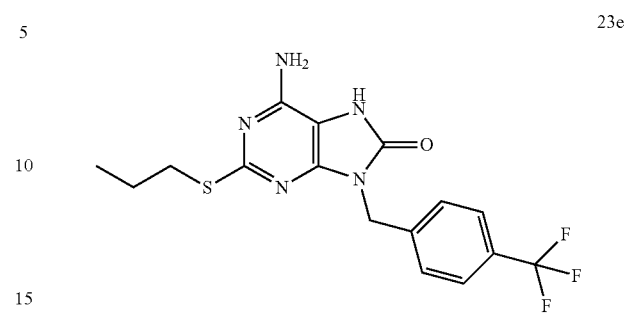

23e

Compound 23e was prepared in analogy to Example 15, Step 5 by using 9-[(4-trifluoromethylphenyl)methyl]-6-[(4-methoxyphenyl)methylamino]-2-propylsulfanyl-7H-purin-8-one (compound 23d) instead of 9-[(2-chlorophenyl)methyl]-6-[(4-methoxyphenyl)methylamino]-2-propylsulfanyl-7H-purin-8-one (compound 15d). 6-Amino-9-[(4-trifluoromethylphenyl)methyl]-2-propylsulfanyl-7H-purin-8-one (900 mg, compound 23e) was obtained as a white solid. MS obsd. (ESI+) [(M+H)+]: 384.

Step 6: Preparation of 6-amino-2-propylsulfinyl-9-[[4-(trifluoromethyl)phenyl]methyl]-7H-purin-8-one

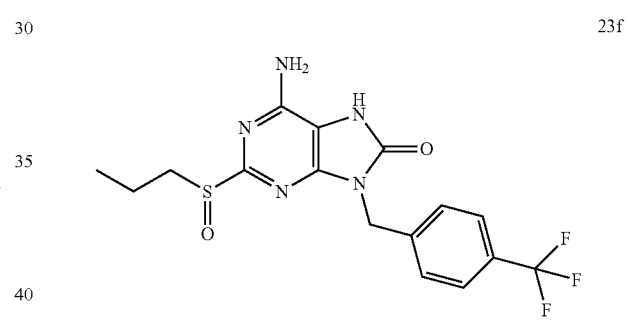

23f

Compound 23f was prepared in analogy to Example 15, Step 6 by using 6-amino-9-[(4-trifluoromethylphenyl)methyl]-2-propylsulfanyl-7H-purin-8-one (compound 23e) instead of 6-amino-9-[(2-chlorophenyl)methyl]-2-propylsulfanyl-7H-purin-8-one (compound 15e). 6-Amino-2-propylsulfinyl-9-[[4-(trifluoromethyl)phenyl]methyl]-7H-purin-8-one (200 mg, compound 23f) was obtained as a white solid. MS obsd. (ESI+) [(M+H)+]: 400.

Step 7: Preparation of 6-amino-2-(propylsulfonimidoyl)-9-[[4-(trifluoromethyl)phenyl]methyl]-7H-purin-8-one

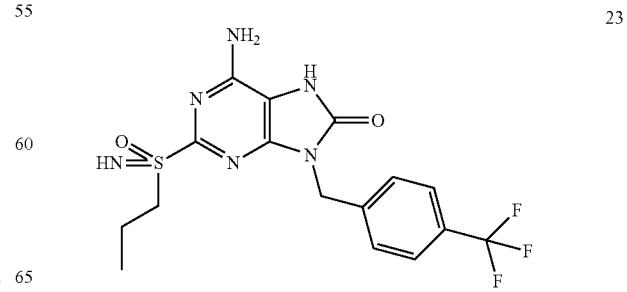

23

The title compound was prepared in analogy to Example 15, Step 7 by using 6-amino-9-[(4-trifluoromethylphenyl)methyl]-2-propylsulfinyl-7H-purin-8-one (200 mg, compound 23f) instead of 6-amino-9-[(2-chlorophenyl)methyl]-2-propylsulfinyl-7H-purin-8-one (compound 15f). 6-Amino-2-(propylsulfonimidoyl)-9-[[4-(trifluoromethyl)phenyl]methyl]-7H-purin-8-one (57 mg, Example 23) was obtained as a white solid. $^1$H NMR (400 MHz, DMSO-$d_6$) δ ppm: 7.70 (d, J=8.0 Hz, 2H), 7.53 (d, J=8.0 Hz, 2H), 7.01 (br. s., 2H), 5.07 (s, 2H), 4.06 (s, 1H), 3.41-3.27 (m, 2H), 1.6-1.57 (m, 2H), 0.86 (t, J=8.0 Hz, 3H). MS obsd. (ESI$^+$) [(M+H)$^+$]: 415.

Example 24

6-Amino-9-[(4-fluorophenyl)methyl]-2-(propylsulfonimidoyl)-7H-purin-8-one

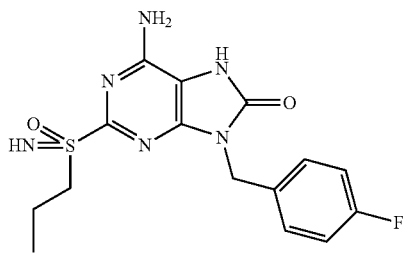

Step 1: Preparation of 6-chloro-N-[(4-fluorophenyl)methyl]-5-nitro-2-propylsulfanyl-pyrimidin-4-amine

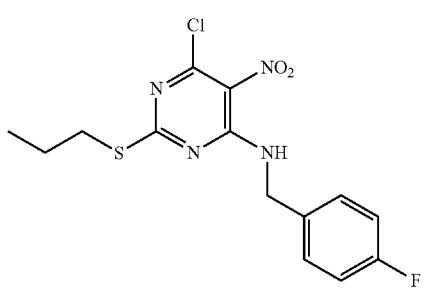

24a

Compound 24a was prepared in analogy to Example 15, Step 1 by using (4-fluorophenyl)methylamine instead of (2-chlorophenyl)methylamine. 6-Chloro-N-[(4-fluorophenylmethyl]-5-nitro-2-propylsulfanyl-pyrimidin-4-amine (6.4 g, compound 24a) was obtained as a white solid. MS obsd. (ESI$^+$) [(M+H)$^+$]: 357.

Step 2: Preparation of 6-chloro-N4-[(4-fluorophenyl)methyl]-2-propylsulfanyl-pyrimidine-4,5-diamine

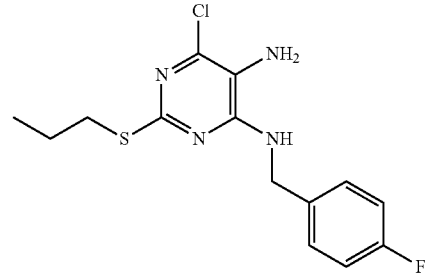

24b

Compound 24b was prepared in analogy to Example 15, Step 2 by using 6-chloro-N-[(4-fluorophenyl)methyl]-5-nitro-2-propylsulfanyl-pyrimidin-4-amine (compound 24a) instead of 6-chloro-N-[(2-chlorophenyl)methyl]-5-nitro-2-propylsulfanyl-pyrimidin-4-amine (compound 15a). 6-Chloro-N4-[(4-fluorophenyl)methyl]-2-propylsulfanyl-pyrimidine-4,5-diamine (6.0 g, compound 24b) was obtained as a white solid. MS obsd. (ESI$^+$) [(M+H)$^+$]: 327.

Step 3: Preparation of 6-chloro-9-[(4-fluorophenyl)methyl]-2-propylsulfanyl-7H-purin-8-one

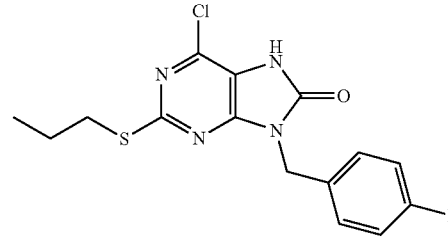

24c

Compound 24c was prepared in analogy to Example 15, Step 3 by using 6-chloro-N-4-[(4-fluorophenyl)methyl]-2-propylsulfanyl-pyrimidine-4,5-diamine (compound 24b) instead of 6-chloro-N4-[(2-chlorophenyl)methyl]-2-propylsulfanyl-pyrimidine-4,5-diamine (compound 15b). 6-Chloro-9-[(4-fluorophenyl)methyl]-2-propylsulfanyl-7H-purin-8-one (5.0 g, compound 24c) was obtained as a white solid. MS obsd. (ESI$^+$) [(M+H)$^+$]: 353.

Step 4: Preparation of 9-[(4-fluorophenyl)methyl]-6-[(4-methoxyphenyl)methylamino]-2-propylsulfanyl-7H-purin-8-one

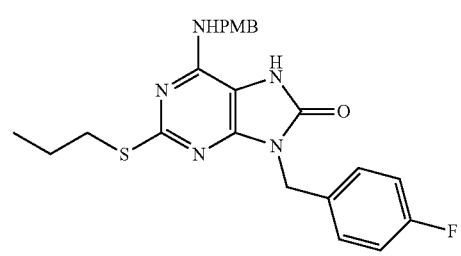

24d

Compound 24d was prepared in analogy to Example 15, Step 4 by using 6-chloro-9-[(4-fluorophenyl)methyl]-2-propylsulfanyl-7H-purin-8-one (compound 24c) instead of 6-chloro-9-[(2-chlorophenyl)methyl]-2-propylsulfanyl-7H-purin-8-one (compound 15c). 9-[(4-Fluorophenyl)methyl]-6-[(4-methoxyphenyl)methylamino]-2-propylsulfanyl-7H-purin-8-one (5.5 g, compound 24d) was obtained as a white solid. MS obsd. (ESI⁺) [(M+H)⁺]: 454.

Step 5: Preparation of 6-amino-9-[(4-fluorophenyl)methyl]-2-propylsulfanyl-7H-purin-8-one

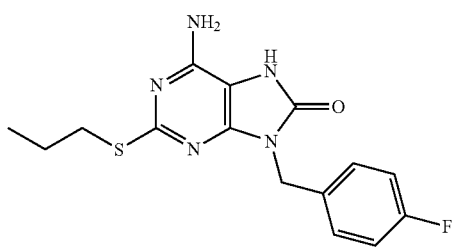

24e

Compound 24e was prepared in analogy to Example 15, Step 5 by using 9-[(4-fluorophenyl)methyl]-6-[(4-methoxyphenyl)methylamino]-2-propylsulfanyl-7H-purin-8-one (compound 24d) instead of 9-[(2-chlorophenyl)methyl]-6-[(4-methoxyphenyl)methylamino]-2-propylsulfanyl-7H-purin-8-one (compound 15d). 6-Amino-9-[(4-fluorophenyl)methyl]-2-propylsulfanyl-7H-purin-8-one (600 mg, compound 24e) was obtained as a white solid. MS obsd. (ESI⁺) [(M+H)⁺]: 334.

Step 6: Preparation of 6-amino-2-propylsulfinyl-9-[4-fluorophenylmethyl]-7H-purin-8-one

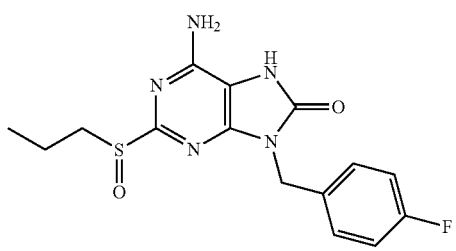

24f

Compound 24f was prepared in analogy to Example 15, Step 6 by using 6-amino-9-[(4-fluorophenyl)methyl]-2-propylsulfanyl-7H-purin-8-one (compound 24e) instead of 6-amino-9-[(2-chlorophenyl)methyl]-2-propylsulfanyl-7H-purin-8-one (compound 15e). 6-Amino-2-propylsulfinyl-9-[[4-fluorophenyl]methyl]-7H-purin-8-one (530 mg, compound 24f) was obtained as a white solid. MS obsd. (ESI⁺) [(M+H)⁺]: 350.

Step 7: Preparation of 6-amino-2-(propylsulfonimidoyl)-9-[[4-(trifluoromethyl)phenyl]methyl]-7H-purin-8-one

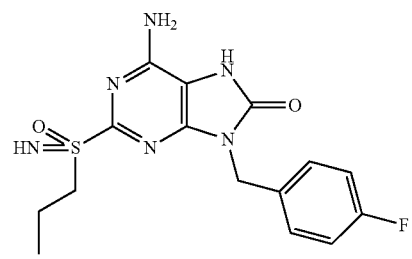

24

The title compound was prepared in analogy to Example 15, Step 5 by using 6-amino-9-[(4-fluorophenyl)methyl]-2-propylsulfinyl-7H-purin-8-one (250 mg, compound 24f) instead of 6-amino-9-[(2-chlorophenyl)methyl]-2-propylsulfinyl-7H-purin-8-one (compound 15f). 6-Amino-2-(propylsulfonimidoyl)-9-[[4-fluorophenyl]methyl]-7H-purin-8-one (41.6 mg, Example 24) was obtained as a gray solid. ¹H NMR (400 MHz, DMSO-d₆) δ ppm: 10.62 (br. s., 1H), 7.40-7.38 (m, 2H), 7.18-7.16 (m, 2H), 7.00 (br. s., 2H), 4.95 (s, 2H), 4.05 (s, 1H), 3.33-3.30 (m, 2H), 1.74-1.55 (m, 2H), 0.92 (t, J=8.0 Hz, 3H). MS obsd. (ESI⁺) [(M+H)⁺]: 365.

Example 25

6-Amino-9-[(4-bromophenyl)methyl]-2-(propylsulfonimidoyl)-7H-purin-8-one

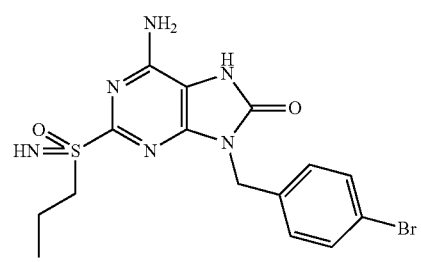

25

Step 1: Preparation of 6-chloro-N-[(4-bromophenyl)methyl]-5-nitro-2-propylsulfanyl-pyrimidin-4-amine

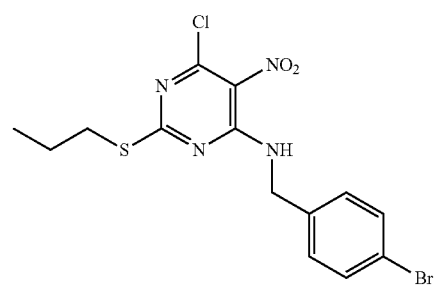

25a

Compound 25a was prepared in analogy to Example 15, Step 1 by using (4-bromophenyl)methylamine instead of (2-chlorophenyl)methylamine. 6-Chloro-N-[(4-bromophenylmethyl]-5-nitro-2-propylsulfanyl-pyrimidin-4-amine (7.0 g, compound 25a) was obtained as a white solid. MS obsd. (ESI$^+$) [(M+H)$^+$]: 417.

Step 2: Preparation of 6-chloro-N4-[(4-bromophenyl)methyl]-2-propylsulfanyl-pyrimidine-4,5-diamine

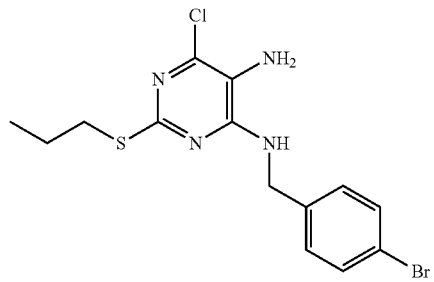

25b

Compound 25b was prepared in analogy to Example 15, Step 2 by using 6-chloro-N-[(4-bromophenyl)methyl]-5-nitro-2-propylsulfanyl-pyrimidin-4-amine (compound 25a) instead of 6-chloro-N-[(2-chlorophenyl)methyl]-5-nitro-2-propylsulfanyl-pyrimidin-4-amine (compound 15a). 6-Chloro-N4-[(4-bromophenyl)methyl]-2-propylsulfanyl-pyrimidine-4,5-diamine (3.2 g, compound 25b) was obtained as a white solid. MS obsd. (ESI$^+$) [(M+H)$^+$]: 387.

Step 3: Preparation of 6-chloro-9-[(4-bromophenyl)methyl]-2-propylsulfanyl-7H-purin-8-one

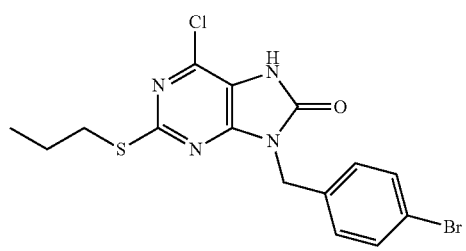

25c

Compound 25c was prepared in analogy to Example 15, Step 3 by using 6-chloro-N-4-[(4-bromophenyl)methyl]-2-propylsulfanyl-pyrimidine-4,5-diamine (compound 25b) instead of 6-chloro-N4-[(2-chlorophenyl)methyl]-2-propylsulfanyl-pyrimidine-4,5-diamine (compound 15b). 6-Chloro-9-[(4-bromophenyl)methyl]-2-propylsulfanyl-7H-purin-8-one (2.5 g, compound 25c) was obtained as a white solid. MS obsd. (ESI$^+$) [(M+H)$^+$]: 413.

Step 4: Preparation of 9-[(4-bromophenyl)methyl]-6-[(4-methoxyphenyl)methylamino]-2-propylsulfanyl-7H-purin-8-one

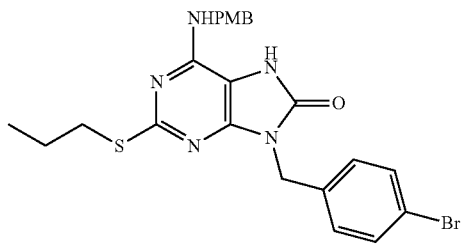

25d

Compound 25d was prepared in analogy to Example 15, Step 4 by using 6-chloro-9-[(4-bromophenyl)methyl]-2-propylsulfanyl-7H-purin-8-one (compound 25c) instead of 6-chloro-9-[(2-chlorophenyl)methyl]-2-propylsulfanyl-7H-purin-8-one (compound 15c). 9-[(4-Bromophenyl)methyl]-6-[(4-methoxyphenyl)methylamino]-2-propylsulfanyl-7H-purin-8-one (3.1 g, compound 25d) was obtained as a white solid. MS obsd. (ESI$^+$) [(M+H)$^+$]: 514.

Step 5: Preparation of 6-amino-9-[(4-bromophenyl)methyl]-2-propylsulfanyl-7H-purin-8-one

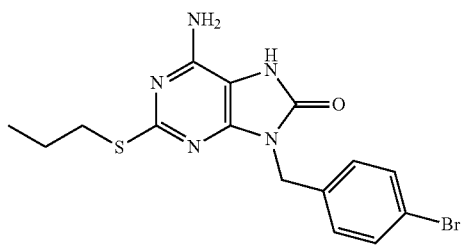

25e

Compound 25e was prepared in analogy to Example 15, Step 5 by using 9-[(4-bromophenyl)methyl]-6-[(4-methoxyphenyl)methylamino]-2-propylsulfanyl-7H-purin-8-one (compound 25d) instead of 9-[(2-chlorophenyl)methyl]-6-[(4-methoxyphenyl)methylamino]-2-propylsulfanyl-7H-purin-8-one (compound 15d). 6-Amino-9-[(4-bromophenyl)methyl]-2-propylsulfanyl-7H-purin-8-one (1.1 g, compound 25e) was obtained as a white solid. MS obsd. (ESI$^+$) [(M+H)$^+$]: 394.

Step 6: Preparation of 6-amino-2-propylsulfinyl-9-[4-bromophenylmethyl]-7H-purin-8-one

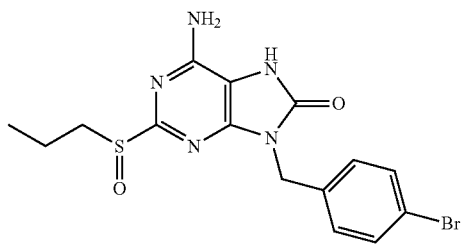

25f

Compound 25f was prepared in analogy to Example 15, Step 5 by using 6-amino-9-[(4-bromophenyl)methyl]-2-propylsulfanyl-7H-purin-8-one (compound 25e) instead of 6-amino-9-[(2-chlorophenyl)methyl]-2-propylsulfanyl-7H-purin-8-one (compound 15e). 6-Amino-2-propylsulfinyl-9-[[4-bromophenyl]methyl]-7H-purin-8-one (250 mg, compound 25f) was obtained as a white solid. MS obsd. (ESI$^+$) [(M+H)$^+$]: 410.

Step 7: Preparation of 6-amino-2-(propylsulfonimidoyl)-9-[[4-bromophenyl]methyl]-7H-purin-8-one

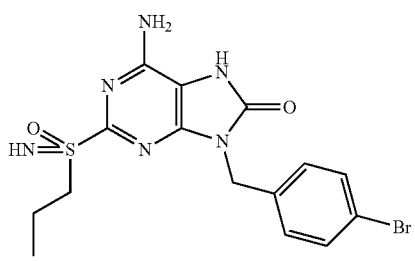

The title compound was prepared in analogy to Example 15, Step 5 by using 6-amino-9-[(4-bromophenyl)methyl]-2-propylsulfinyl-7H-purin-8-one (260 mg, compound 25f) instead of 6-amino-9-[(2-chlorophenyl)methyl]-2-propylsulfinyl-7H-purin-8-one (compound 15f). 6-Amino-2-(propylsulfonimidoyl)-9-[[4-bromophenyl]methyl]-7H-purin-8-one (70 mg, Example 25) was obtained as a white solid. $^1$H NMR (400 MHz, DMSO-d$_6$) δ ppm: 10.62 (br. s., 1H), 7.53 (d, J=8.0 Hz, 2H), 7.29 (d, J=8.0 Hz, 2H), 6.99 (br. s., 2H), 4.94 (s, 2H), 4.04 (s, 1H), 3.35-3.25 (m, 2H), 1.67-1.56 (m, 2H), 0.90 (t, J=8.0 Hz, 3H). MS obsd. (ESI$^+$) [(M+H)$^+$]: 425.

Example 26

6-Amino-9-[(3,4-dichlorophenyl)methyl]-2-(propylsulfonimidoyl)-7H-purin-8-one

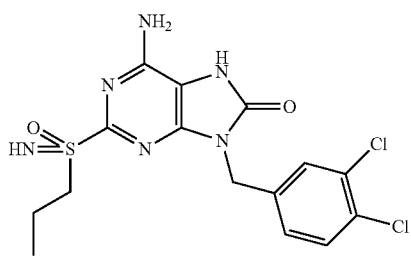

Step 1: Preparation of 6-chloro-N-[(3,4-dichlorophenyl)methyl]-5-nitro-2-propylsulfanyl-pyrimidin-4-amine

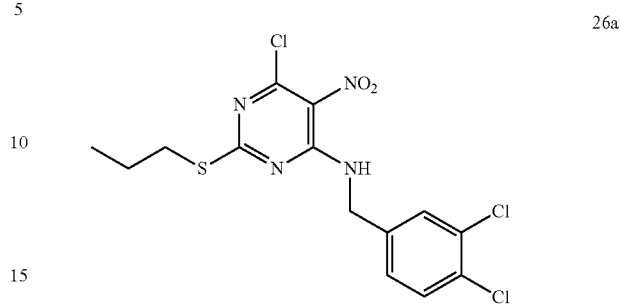

Compound 26a was prepared in analogy to Example 15, Step 1 by using (3,4-dichlorophenyl)methylamine instead of (2-chlorophenyl)methylamine. 6-Chloro-N-[(4-bromophenylmethyl]-5-nitro-2-propylsulfanyl-pyrimidin-4-amine (3.6 g, compound 26a) was obtained as a white solid. MS obsd. (ESI$^+$) [(M+H)$^+$]: 425.

Step 2: Preparation of 6-chloro-N4-[(3,4-dichlorophenyl)methyl]-2-propylsulfanyl-pyrimidine-4,5-diamine

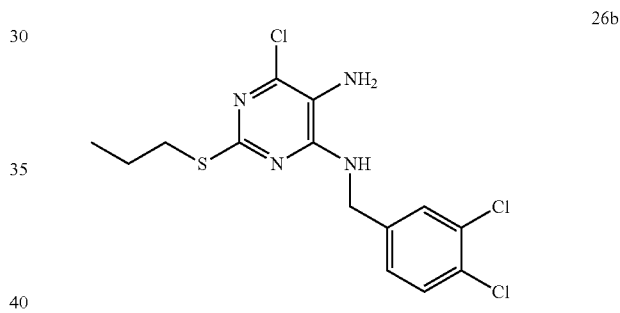

Compound 26b was prepared in analogy to Example 15, Step 2 by using 6-chloro-N-[(3,4-dichlorophenyl)methyl]-5-nitro-2-propylsulfanyl-pyrimidin-4-amine (compound 26a) instead of 6-chloro-N-[(2-chlorophenyl)methyl]-5-nitro-2-propylsulfanyl-pyrimidin-4-amine (compound 15a). 6-Chloro-N4-[(3,4-dichlorophenyl)methyl]-2-propylsulfanyl-pyrimidine-4,5-diamine (3.1 g, compound 26b) was obtained as a white solid. MS obsd. (ESI$^+$) [(M+H)$^+$]: 377.

Step 3: Preparation of 6-chloro-9-[(3,4-dichlorophenyl)methyl]-2-propylsulfanyl-7H-purin-8-one

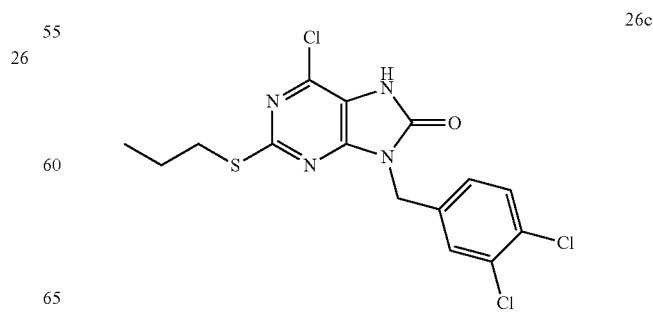

Compound 26c was prepared in analogy to Example 15, Step 3 by using 6-chloro-N-4-[(3,4-dichlorophenyl)methyl]-2-propylsulfanyl-pyrimidine-4,5-diamine (compound 26b) instead of 6-chloro-N4-[(2-chlorophenyl)methyl]-2-propylsulfanyl-pyrimidine-4,5-diamine (compound 15b). 6-Chloro-9-[(3,4-dichlorophenyl)methyl]-2-propylsulfanyl-7H-purin-8-one (1.8 g, compound 26c) was obtained as a white solid. MS obsd. (ESI+) [(M+H)+]: 403.

Step 4: Preparation of 9-[(3,4-dichlorophenyl)methyl]-6-[(4-methoxyphenyl)methylamino]-2-propylsulfanyl-7H-purin-8-one

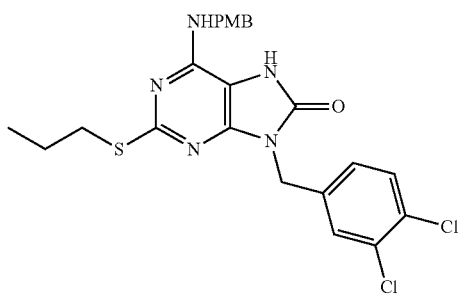

26d

Compound 26d was prepared in analogy to Example 15, Step 4 by using 6-chloro-9-[(3,4-dichlorophenyl)methyl]-2-propylsulfanyl-7H-purin-8-one (compound 26c) instead of 6-chloro-9-[(2-chlorophenyl)methyl]-2-propylsulfanyl-7H-purin-8-one (compound 15c). 9-[(3,4-Dichlorophenyl)methyl]-6-[(4-methoxyphenyl)methylamino]-2-propylsulfanyl-7H-purin-8-one (1.6 g, compound 26d) was obtained as a white solid. MS obsd. (ESI+) [(M+H)+]: 504.

Step 5: Preparation of 6-amino-9-[(3,4-dichlorophenyl)methyl]-2-propylsulfanyl-7H-purin-8-one

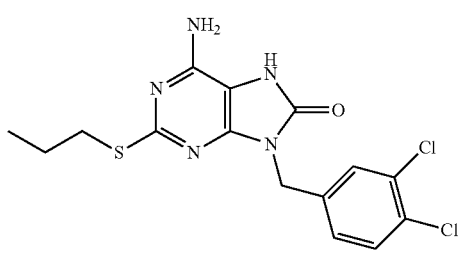

26e

Compound 26e was prepared in analogy to Example 15, Step 5 by using 9-[(3,4-dichlorophenyl)methyl]-6-[(4-methoxyphenyl)methylamino]-2-propylsulfanyl-7H-purin-8-one (compound 26d) instead of 9-[(2-chlorophenyl)methyl]-6-[(4-methoxyphenyl)methylamino]-2-propylsulfanyl-7H-purin-8-one (compound 15d). 6-Amino-9-[(3,4-dichlorophenyl)methyl]-2-propylsulfanyl-7H-purin-8-one (900 mg, compound 26e) was obtained as a white solid. MS obsd. (ESI+) [(M+H)+]: 384.

Step 6: Preparation of 6-amino-2-propylsulfinyl-9-[3,4-dichlorophenyl]-7H-purin-8-one

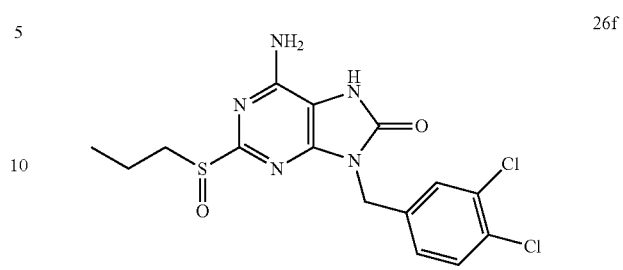

26f

Compound 26f was prepared in analogy to Example 15, Step 6 by using 6-amino-9-[(3,4-dichlorophenyl)methyl]-2-propylsulfanyl-7H-purin-8-one (compound 26e) instead of 6-amino-9-[(2-chlorophenyl)methyl]-2-propylsulfanyl-7H-purin-8-one (compound 15e). 6-Amino-2-propylsulfinyl-9-[[3,4-dichlorophenyl]methyl]-7H-purin-8-one (210 mg, compound 26f) was obtained as a white solid. MS obsd. (ESI+) [(M+H)+]: 401.

Step 7: Preparation of 6-amino-2-(propylsulfonimidoyl)-9-(3,4-dichlorophenylmethyl)-7H-purin-8-one

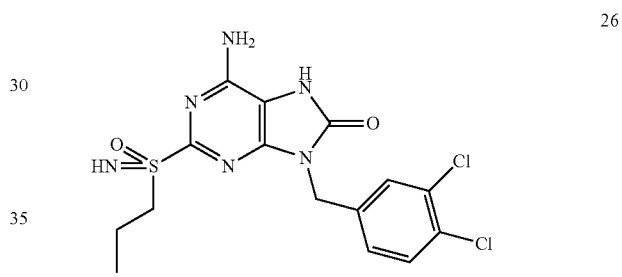

26

The title compound was prepared in analogy to Example 15, Step 7 by using 6-amino-9-[(3,4-dichlorophenylmethyl]-2-propylsulfinyl-7H-purin-8-one (compound 26f) instead of 6-amino-9-[(2-chlorophenyl)methyl]-2-propylsulfinyl-7H-purin-8-one (compound 15f). 6-Amino-2-(propylsulfonimidoyl)-9-(3,4-dichlorophenylmethyl)-7H-purin-8-one (47 mg, Example 26) was obtained as a white solid. $^1$H NMR (400 MHz, DMSO-$d_6$) δ ppm: 10.67 (br. s., 1H), 7.63-7.59 (m, 2H), 7.32-7.29 (m, 1H), 7.01 (br. s., 2H), 4.98 (s, 2H), 4.05 (s, 1H), 3.35-3.30 (m, 2H), 1.67-1.56 (m, 2H), 0.90 (t, J=8.0 Hz, 3H). MS obsd. (ESI+) [(M+H)+]: 415.

Example 27

6-Amino-9-(3,4-difluorophenylmethyl)-2-(propylsulfonimidoyl)-7H-purin-8-one

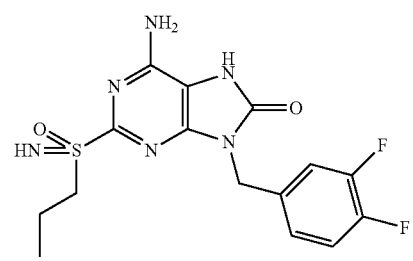

27

Step 1: Preparation of 6-chloro-N-[(3,4-difluorophenyl)methyl]-5-nitro-2-propylsulfanyl-pyrimidin-4-amine

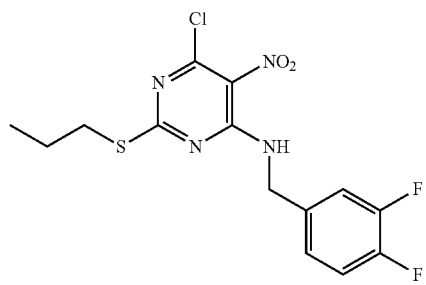

27a

Compound 27a was prepared in analogy to Example 15, Step 1 by using (3,4-difluorophenyl)methylamine instead of (2-chlorophenyl)methylamine. 6-Chloro-N-[(3,4-difluorophenyl)methyl]-5-nitro-2-propylsulfanyl-pyrimidin-4-amine (3.1 g, compound 27a) was obtained as a white solid. MS obsd. (ESI$^+$) [(M+H)$^+$]: 375.

Step 2: Preparation of 6-chloro-N4-[(3,4-difluorophenyl)methyl]-2-propylsulfanyl-pyrimidine-4,5-diamine

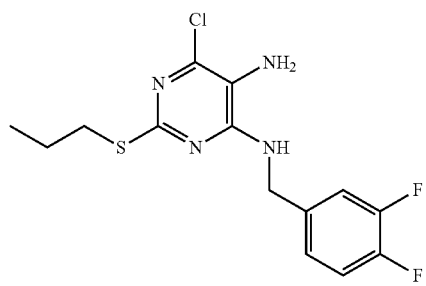

27b

Compound 27b was prepared in analogy to Example 15, Step 2 by using 6-chloro-N-[(3,4-difluorophenyl)methyl]-5-nitro-2-propylsulfanyl-pyrimidin-4-amine (compound 27a) instead of 6-chloro-N-[(2-chlorophenyl)methyl]-5-nitro-2-propylsulfanyl-pyrimidin-4-amine (compound 15a). 6-Chloro-N-4-[(3,4-difluorophenyl)methyl]-2-propylsulfanyl-pyrimidine-4,5-diamine (2.2 g, compound 27b) was obtained as a white solid. MS obsd. (ESI$^+$) [(M+H)$^+$]: 345.

Step 3: Preparation of 6-chloro-9-[(3,4-difluorophenyl)methyl]-2-propylsulfanyl-7H-purin-8-one

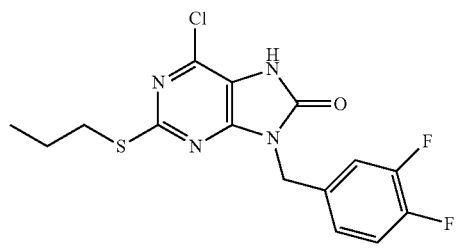

27c

Compound 27c was prepared in analogy to Example 15, Step 3 by using 6-chloro-N4-[(3,4-difluorophenyl)methyl]-2-propylsulfanyl-pyrimidine-4,5-diamine (compound 27b) instead of 6-chloro-N-4-[(2-chlorophenyl)methyl]-2-propylsulfanyl-pyrimidine-4,5-diamine (compound 15b). 6-Chloro-9-[(3,4-difluorophenyl)methyl]-2-propylsulfanyl-7H-purin-8-one (1.6 g, compound 27c) was obtained as a white solid. MS obsd. (ESI$^+$) [(M+H)$^+$]: 371.

Step 4: Preparation of 9-[(3,4-difluorophenyl)methyl]-6-[(4-methoxyphenyl)methylamino]-2-propylsulfanyl-7H-purin-8-one

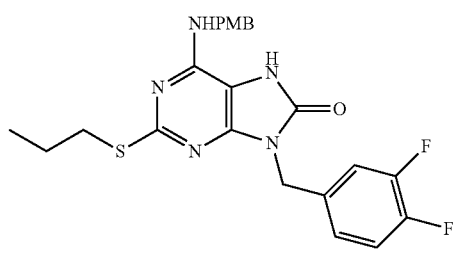

27d

Compound 27d was prepared in analogy to Example 15, Step 4 by using 6-chloro-9-[(3,4-difluorophenyl)methyl]-2-propylsulfanyl-7H-purin-8-one (compound 27c) instead of 6-chloro-9-[(2-chlorophenyl)methyl]-2-propylsulfanyl-7H-purin-8-one (compound 15c). 9-[(3,4-Difluorophenyl)methyl]-6-[(4-methoxyphenyl)methylamino]-2-propylsulfanyl-7H-purin-8-one (1.5 g, compound 27d) was obtained as a white solid. MS obsd. (ESI$^+$) [(M+H)$^+$]: 472.

Step 5: Preparation of 6-amino-9-[(3,4-difluorophenyl)methyl]-2-propylsulfanyl-7H-purin-8-one

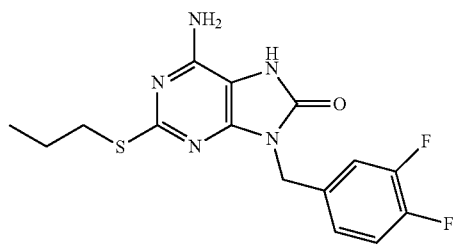

27e

Compound 27e was prepared in analogy to Example 15, Step 5 by using 9-[(3,4-difluorophenyl)methyl]-6-[(4-methoxyphenyl)methylamino]-2-propylsulfanyl-7H-purin-8-one (compound 27d) instead of 9-[(2-chlorophenyl)methyl]-6-[(4-methoxyphenyl)methylamino]-2-propylsulfanyl-7H-purin-8-one (compound 15d). 6-Amino-9-[(3,4-difluorophenyl)methyl]-2-propylsulfanyl-7H-purin-8-one (600 mg, compound 27e) was obtained as a white solid. MS obsd. (ESI$^+$) [(M+H)$^+$]: 352.

Step 6: Preparation of 6-amino-2-propylsulfinyl-9-[3,4-difluorophenyl)methyl]-7H-purin-8-one

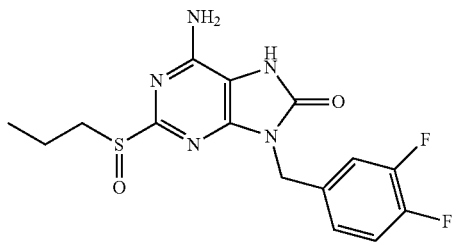

27f

Compound 27f was prepared in analogy to Example 15, Step 6 by using 6-amino-9-[(3,4-difluorophenyl)methyl]-2-propylsulfanyl-7H-purin-8-one (compound 27e) instead of 6-amino-9-[(2-chlorophenyl)methyl]-2-propylsulfanyl-7H-purin-8-one (compound 15e). 6-Amino-2-propylsulfinyl-9-[[3,4-difluorophenyl)methyl]-7H-purin-8-one (150 mg, compound 27f) was obtained as a white solid. MS obsd. (ESI+) [(M+H)+]: 368.

Step 7: Preparation of 6-amino-9-[(3,4-difluorophenyl)methyl]-2-(propylsulfonimidoyl)-7H-purin-8-one

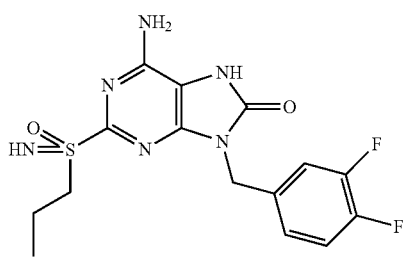

27

The title compound was prepared in analogy to Example 15, Step 7 by using 6-amino-9-[(3,4-difluorophenyl)methyl]-2-propylsulfinyl-7H-purin-8-one (compound 27f) instead 6-amino-9-[(2-chlorophenyl)methyl]-2-propylsulfinyl-7H-purin-8-one (compound 15f). 6-Amino-2-(propylsulfonimidoyl)-9-[[3,4-difluorophenyl)methyl]-7H-purin-8-one (60 mg, Example 27) was obtained as a white solid. $^1$H NMR (400 MHz, DMSO-$d_6$) δ ppm: 10.65 (br. s., 1H), 7.46-7.36 (m, 2H), 7.19-7.18 (m, 1H), 6.98 (br. s., 2H), 4.96 (s, 2H), 4.04 (s, 1H), 3.35-3.26 (m, 2H), 1.67-1.57 (m, 2H), 0.91 (t, J=8.0 Hz, 3H). MS obsd. (ESI+) [(M+H)+]: 383.

Example 28

6-Amino-9-[(4-chloro-3-methyl-phenyl)methyl]-2-(propylsulfonimidoyl)-7H-purin-8-one

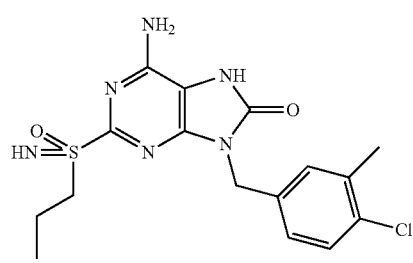

28

Step 1: Preparation of 4-chloro-3-methylbenzamide

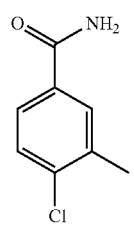

28a

To an ice cooled solution of 4-chloro-3-methylbenzoic acid (20.0 g, 117.2 mmol), HOBt (15.8 g, 117.2 mmol) and NH$_4$Cl (18.8 g, 351.7 mmol) in anhydrous DMF (200 mL) was added DIPEA (45.5 g, 351.7 mmol) followed by EDC.HCl (27.4 g, 152.4 mmol), then the mixture was warmed to 25° C. and stirred for 20 hrs. The reaction mixture was diluted with water (1.2 L) and extracted with EtOAC (200 mL) three times. The combined organic layer was washed with 1N HCl aq., sat. Na$_2$CO$_3$ aq., brine, dried over anhydrous sodium sulfate, filtered and concentrated in vacuo. The residue was triturated with MTBE to give 4-chloro-3-methylbenzamide (15 g, compound 28a) as a light yellow solid. $^1$H NMR (400 MHz, DMSO-$d_6$) δ ppm: 8.00 (s, 1H), 7.86 (s, 1H), 7.71 (dd, J=8.3 Hz, 1.5 Hz, 1H), 7.49 (d, J=8.3 Hz, 1H), 7.42 (s, 1H), 2.37 (s, 3H). MS obsd. (ESI+) [(M+H)+]: 170.

Step 2: Preparation of (4-chloro-3-methylphenyl)methylamine

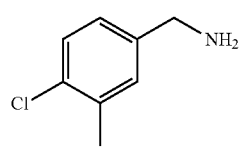

28b

To a suspension of LiAlH$_4$ (11.2 g, 294.8 mmol) in anhydrous THF (100 mL) was added 3-chloro-4-methylbenzamide (10 g, 58.96 mmol) in THF (100 mL) drop-wise. After the addition, the mixture was stirred at 28° C. for 2 hrs and then heated to 60° C. for 12 hrs. After the reaction mixture was cooled to 0° C., then 11.2 mL of water, 11.2 mL of 15% NaOH aq. and 33.6 mL of water was added sequentially. Anhydrous sodium sulfate (20 g) was added, and the resulting suspension was stirred for 30 min, and filtered. The filtrate was concentrated in vacuo to obtain (4-chloro-3-methyl-phenyl)methylamine as a colorless oil (8 g, compound 28b). MS obsd. (ESI$^+$) [(M+H)$^+$]: 156.

Step 3: Preparation of 6-chloro-N-[(4-chloro-3-methyl-phenyl)methyl]-5-nitro-2-propylsulfanyl-pyrimidin-4-amine

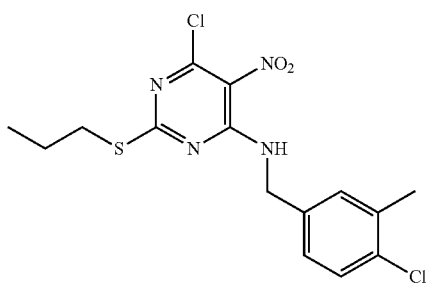

28c

Compound 28c was prepared in analogy to Example 15, Step 1 by using (4-chloro-3-methyl-phenyl)methylamine instead of (2-chlorophenyl)methylamine. 6-Chloro-N-[(4-chloro-3-methylphenylmethyl]-5-nitro-2-propylsulfanyl-pyrimidin-4-amine (8.0 g, compound 28c) was obtained as a white solid. MS obsd. (ESI$^+$) [(M+H)$^+$]: 387.

Step 4: Preparation of 6-chloro-N4-[(4-chloro-3-methyl-phenyl)methyl]-2-propylsulfanyl-pyrimidine-4,5-diamine

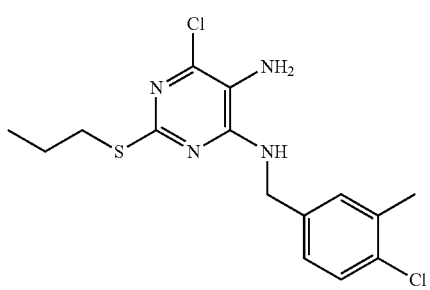

28d

Compound 28d was prepared in analogy to Example 15, Step 2 by using 6-chloro-N-[(4-chloro-3-methylphenyl)methyl]-5-nitro-2-propylsulfanyl-pyrimidin-4-amine (compound 28c) instead of 6-chloro-N-[(2-chlorophenyl)methyl]-5-nitro-2-propylsulfanyl-pyrimidin-4-amine (compound 15a). 6-Chloro-N-4-[(4-chloro-3-methylphenyl)methyl]-2-propylsulfanyl-pyrimidine-4,5-diamine (4.4 g, compound 28d) was obtained as a white solid. MS obsd. (ESI$^+$) [(M+H)$^+$]: 357.

Step 5: Preparation of 6-chloro-9-[(4-chloro-3-methyl-phenyl)methyl]-2-propylsulfanyl-7H-purin-8-one

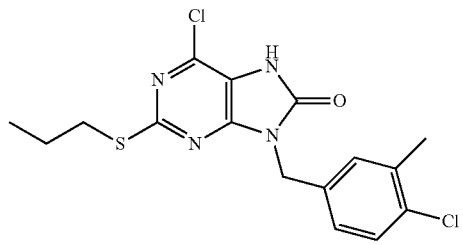

28e

Compound 28e was prepared in analogy to Example 15, Step 3 by using 6-chloro-N4-[(4-chloro-3-methylphenyl)methyl]-2-propylsulfanyl-pyrimidine-4, 5-diamine (compound 28d) instead of 6-chloro-N-4-[(2-chlorophenyl)methyl]-2-propylsulfanyl-pyrimidine-4,5-diamine (compound 15b). 6-Chloro-9-[(4-chloro-3-methyl-phenyl)methyl]-2-propylsulfanyl-7H-purin-8-one (4.6 g, compound 28e) was obtained as a white solid. MS obsd. (ESI$^+$) [(M+H)$^+$]: 383.

Step 6: Preparation of 9-[(4-chloro-3-methyl-phenyl)methyl]-6-[(4-methoxyphenyl)methylamino]-2-propylsulfanyl-7H-purin-8-one

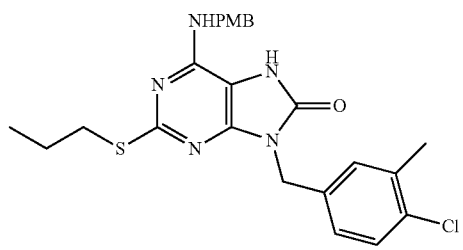

28f

Compound 28f was prepared in analogy to Example 15, Step 4 by using 6-chloro-9-[(4-chloro-3-methylphenyl)methyl]-2-propylsulfanyl-7H-purin-8-one (compound 28e) instead of 6-chloro-9-[(2-chlorophenyl)methyl]-2-propylsulfanyl-7H-purin-8-one (compound 15c). 9-[(3-Chloro-4-methyl-phenyl)methyl]-6-[(4-methoxyphenyl)methylamino]-2-propylsulfanyl-7H-purin-8-one (9 g, compound 28f) was obtained as a white solid. MS obsd. (ESI$^+$) [(M+H)$^+$]: 484.

Step 7: Preparation of 6-amino-9-[(4-chloro-3-methyl-phenyl)methyl]-2-propylsulfanyl-7H-purin-8-one

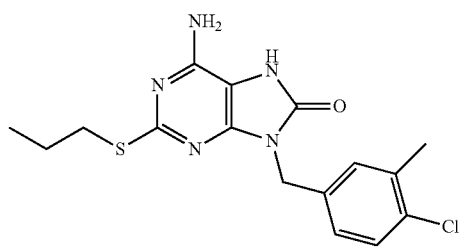

28g

Compound 28g was prepared in analogy to Example 15, Step 5 by using 9-[(4-chloro-3-methyl-phenyl)methyl]-6-[(4-methoxyphenyl)methylamino]-2-propylsulfanyl-7H-purin-8-one (compound 28f) instead of 9-[(2-chlorophenyl)methyl]-6-[(4-methoxyphenyl)methylamino]-2-propylsulfanyl-7H-purin-8-one (compound 15d). 6-Amino-9-[(4-chloro-3-methyl-phenyl)methyl]-2-propylsulfanyl-7H-purin-8-one (4.5 g, compound 28g) was obtained as a white solid. MS obsd. (ESI⁺) [(M+H)⁺]: 364.

Step 8: Preparation of 6-amino-2-propylsulfinyl-9-[4-chloro-3-methyl-phenyl methyl]-7H-purin-8-one

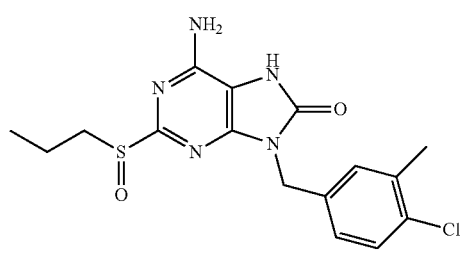

28h

Compound 28h was prepared in analogy to Example 15, Step 6 by using 6-amino-9-[(3-chloro-4-methyl-phenyl)methyl]-2-propylsulfanyl-7H-purin-8-one (compound 28g) instead of 6-amino-9-[(2-chlorophenyl)methyl]-2-propylsulfanyl-7H-purin-8-one (compound 15e). 6-Amino-2-propylsulfinyl-9-[[4-chloro-3-methyl-phenyl]methyl]-7H-purin-8-one (340 mg, compound 28h) was obtained as a white solid. MS obsd. (ESI⁺) [(M+H)⁺]: 380.

Step 9: Preparation of 6-amino-9-[(4-chloro-3-methyl-phenyl)methyl]-2-(propylsulfonimidoyl)-7H-purin-8-one

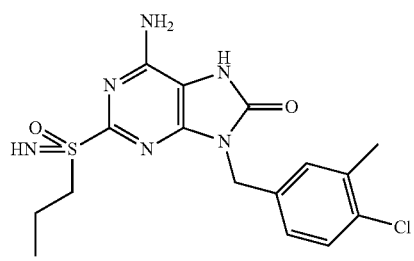

28

The title compound was prepared in analogy to Example 15, Step 7 by using 6-amino-9-[(4-chloro-3-methyl-phenyl)methyl]-2-propylsulfinyl-7H-purin-8-one (compound 28h) instead of 6-amino-9-[(2-chlorophenyl)methyl]-2-propylsulfinyl-7H-purin-8-one. 6-Amino-2-(propylsulfonimidoyl)-9-[[4-chloro-3-methyl-phenyl]methyl]-7H-purin-8-one (80 mg, Example 28) was obtained as a white solid. ¹H NMR (400 MHz, DMSO-d₆) δ ppm: 7.37-7.33 (m, 2H), 7.18-7.16 (m, 2H), 6.97 (br. s., 2H), 4.92 (s, 2H), 4.04 (s, 1H), 3.33-3.31 (m, 2H), 2.29 (s, 3H), 1.65-1.61 (m, 2H), 0.90 (t, J=7.6 Hz, 3H). MS obsd. (ESI⁺) [(M+H)⁺]: 395.

Example 29

6-Amino-2-(propylsulfonimidoyl)-9-(p-tolylmethyl)-7H-purin-8-one

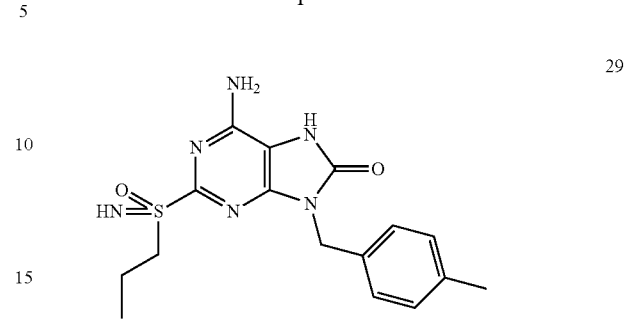

29

Step 1: Preparation of 6-chloro-N-[(p-tolylmethyl]-5-nitro-2-propylsulfanyl-pyrimidin-4-amine

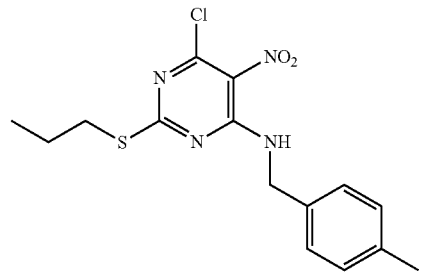

29a

Compound 29a was prepared in analogy to Example 15, Step 1 by using p-tolylmethylamine instead of (2-chlorophenyl)methylamine. 6-Chloro-N-[(p-tolylmethyl]-5-nitro-2-propylsulfanyl-pyrimidin-4-amine (3.9 g, compound 29a) was obtained as a white solid. MS obsd. (ESI⁺) [(M+H)⁺]: 353.

Step 2: Preparation of 6-chloro-N4-[(p-tolylmethyl]-2-propylsulfanyl-pyrimidine-4,5-diamine

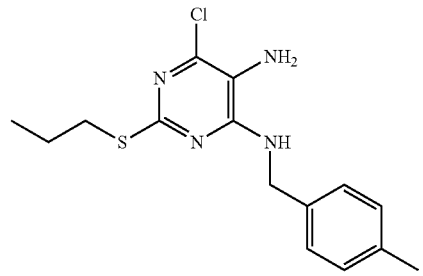

29b

Compound 29b was prepared in analogy to Example 15, Step 2 by using 6-chloro-N-[(p-tolylmethyl-5-nitro-2-propylsulfanyl-pyrimidin-4-amine (compound 29a) instead of 6-chloro-N-[(2-chlorophenyl)methyl]-5-nitro-2-propylsulfanyl-pyrimidin-4-amine (compound 15a). 6-Chloro-N4-(p-tolylmethyl)-2-propylsulfanyl-pyrimidine-4,5-diamine (2.2 g, compound 29b) was obtained as a white solid. MS obsd. (ESI⁺) [(M+H)⁺]: 323.

Step 3: Preparation of 6-chloro-9-[(p-tolylmethyl]-2-propylsulfanyl-7H-purin-8-one

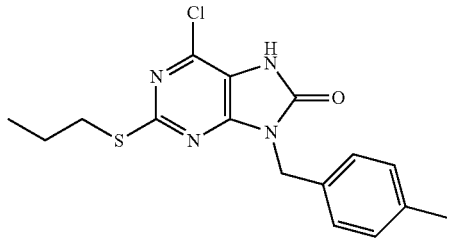

29c

Compound 29c was prepared in analogy to Example 15, Step 3 by using 6-chloro-N4-[(p-tolylmethyl]-2-propylsulfanyl-pyrimidine-4,5-diamine (compound 29b) instead of 6-chloro-N4-[(2-chlorophenyl)methyl]-2-propylsulfanyl-pyrimidine-4,5-diamine (compound 15b). 6-Chloro-9-[(p-tolylmethyl]-2-propylsulfanyl-7H-purin-8-one (2.2 g, compound 29c) was obtained as a white solid. MS obsd. (ESI$^+$) [(M+H)$^+$]: 349.

Step 4: Preparation of 9-[(p-tolylmethyl]-6-[(4-methoxyphenyl)methylamino]-2-propylsulfanyl-7H-purin-8-one

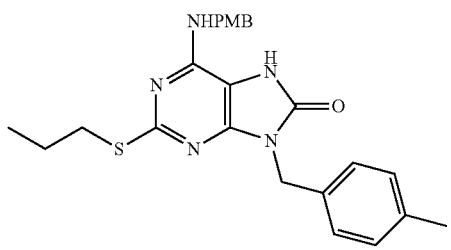

29d

Compound 29d was prepared in analogy to Example 15, Step 4, by using 6-chloro-9-[(p-tolylmethyl]-2-propylsulfanyl-7H-purin-8-one (compound 29c) instead of 6-chloro-9-[(2-chlorophenyl)methyl]-2-propylsulfanyl-7H-purin-8-one (compound 15c). 9-[(p-Tolylmethyl]-6-[(4-methoxyphenyl)methylamino]-2-propylsulfanyl-7H-purin-8-one (2.0 g, compound 29d) was obtained as a white solid. MS obsd. (ESI$^+$) [(M+H)$^+$]: 450.

Step 5: Preparation of 6-amino-2-propylsulfanyl-9-(p-tolylmethyl)-7H-purin-8-one

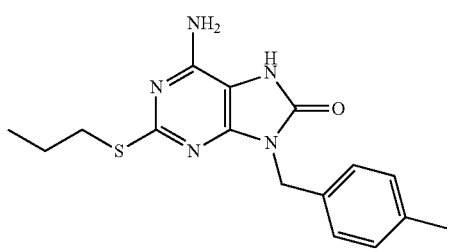

29e

Compound 29e was prepared in analogy to Example 15, Step 5 by using 9-[(p-tolylmethyl]-6-[(4-methoxyphenyl)methylamino]-2-propylsulfanyl-7H-purin-8-one (compound 29d) instead of 9-[(2-chlorophenyl)methyl]-6-[(4-methoxyphenyl)methylamino]-2-propylsulfanyl-7H-purin-8-one (compound 15d). 6-Amino-9-[(p-tolylmethyl]-2-propylsulfanyl-7H-purin-8-one (1.0 g, compound 29e) was obtained as a white solid. MS obsd. (ESI) [(M+H)$^+$]: 330.

Step 6: Preparation of 6-amino-2-propylsulfinyl-9-[p-tolylmethyl]-7H-purin-8-one

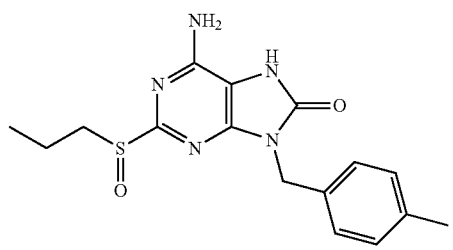

29f

Compound 29f was prepared in analogy to Example 15, Step 6 by using 6-amino-9-[(p-tolylmethyl)methyl]-2-propylsulfanyl-7H-purin-8-one (compound 29e) instead of 6-amino-9-[(2-chlorophenyl)methyl]-2-propylsulfanyl-7H-purin-8-one (compound 15e). 6-Amino-2-propylsulfinyl-9-[p-tolylmethyl]-7H-purin-8-one (220 mg, compound 29f) was obtained as a white solid MS obsd. (ESI$^+$) [(M+H)$^+$]: 345.

Step 7: Preparation of 6-amino-2-(propylsulfonimidoyl)-9-(p-tolylmethyl)-7H-purin-8-one

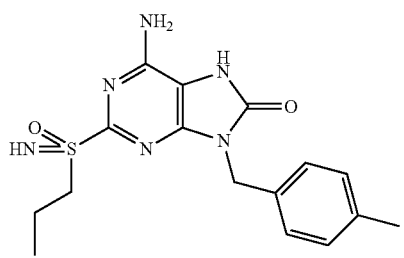

29

The title compound was prepared in analogy to Example 15, Step 7 by using 6-amino-9-[(p-tolylmethyl)methyl]-2-propylsulfinyl-7H-purin-8-one (compound 29f) instead 6-amino-9-[(2-chlorophenyl)methyl]-2-propylsulfinyl-7H-purin-8-one. 6-Amino-2-(propylsulfonimidoyl)-9-[[p-tolylmethyl]-7H-purin-8-one (127 mg, Example 29) was obtained as a white solid. $^1$H NMR (400 MHz, DMSO-d$_6$) δ ppm: 10.67 (br. s., 1H), 7.23 (d, J=8.0 Hz, 2H), 7.13 (d, J=8.0 Hz, 2H), 6.98 (br. s., 2H), 4.91 (s, 2H), 4.05 (s, 1H), 3.34-3.27 (m, 2H), 2.26 (s, 3H), 1.67-1.62 (m, 2H), 0.92 (t, J=8.0 Hz, 3H). MS obsd. (ESI$^+$) [(M+H)$^+$]: 361.

Separation of compound of Example 29 by chiral HPLC afforded Example 29-A (faster eluting, 50 mg) and Example 29-B (slower eluting, 49 mg) as white solid. (Separation condition: 30% isopropanol (0.05% DEA)/CO$_2$ on ChiralPak AD-3 column.)

Example 29-A

¹H NMR: (400 MHz, DMSO-d₆) δ ppm: 10.51 (s, 1H), 7.22 (d, J=8.0 Hz, 2H), 7.12 (d, J=8.0 Hz, 2H), 7.00 (s, 2H), 4.91 (s, 2H), 4.03 (s, 1H), 3.35-3.31 (m, 2H), 2.26 (s, 3H), 1.70-1.58 (m, 2H), 0.93 (t, J=7.40 Hz, 3H). MS obsd. (ESI⁺) [(M+H)⁺]: 361.

Example 29-B

¹H NMR: (400 MHz, DMSO-d₆) δ ppm: 10.54 (s, 1H), 7.23 (d, J=8.0 Hz, 2H), 7.13 (d, J=8.0 Hz, 2H), 6.97 (s, 2H), 4.91 (s, 2H), 4.04 (s, 1H), 3.34-3.30 (m, 2H), 2.26 (s, 3H), 1.72-1.57 (m, 2H), 0.93 (t, J=7.40 Hz, 3H). MS obsd. (ESI⁺) [(M+H)⁺]: 361.

Example 30

6-Amino-9-[(4-chloro-3-fluorophenyl)methyl]-2-(propylsulfonimidoyl)-7H-purin-8-one

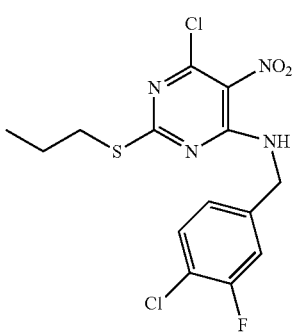

Step 1: Preparation of 6-chloro-N-[(4-chloro-3-fluoro-phenyl)methyl]-5-nitro-2-propylsulfanyl-pyrimidin-4-amine

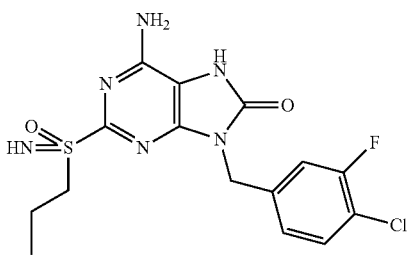

Compound 30a was prepared in analogy to Example 15, Step 1 by using 4-chloro-3-fluorophenyl)methylamine instead of (2-chlorophenyl)methylamine. 6-Chloro-N-[(4-chloro-3-fluoro-phenyl)methyl]-5-nitro-2-propylsulfanyl-pyrimidin-4-amine (6.2 g, compound 30a) was obtained. MS obsd. (ESI⁺) [(M+H)⁺]: 391.

Step 2: Preparation of 6-chloro-N4-[(4-chloro-3-fluoro-phenyl)methyl]-2-propylsulfanyl-pyrimidine-4,5-diamine

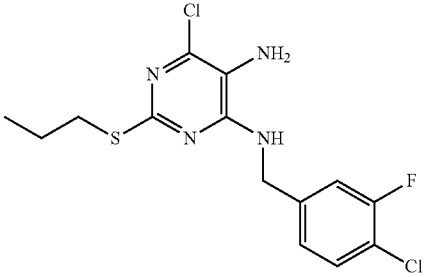

Compound 30b was prepared in analogy to Example 15, Step 2 by using 6-chloro-N-[(4-chloro-3-fluoro-phenyl)methyl]-5-nitro-2-propylsulfanyl-pyrimidin-4-amine (compound 30a) instead of 6-chloro-N-[(2-chlorophenyl)methyl]-5-nitro-2-propylsulfanyl-pyrimidin-4-amine (compound 15a). 6-Chloro-N4-[4-chloro-3-fluoro-phenyl)methyl]-2-propylsulfanyl-pyrimidine-4,5-diamine (4.7 g, compound 30b) was obtained as a brown solid. MS obsd. (ESI⁺) [(M+H)⁺]: 361.

Step 3: Preparation of 6-chloro-9-[(4-chloro-3-fluoro-phenyl)methyl]-2-propylsulfanyl-7H-purin-8-one

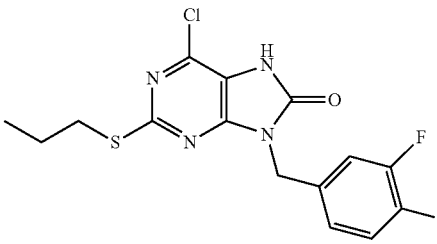

Compound 30c was prepared in analogy to Example 15, Step 3 by using 6-chloro-N-4-[(4-chloro-3-fluoro-phenyl)methyl]-2-propylsulfanyl-pyrimidine-4,5-diamine (compound 30b) instead of 6-chloro-N4-[(2-chlorophenyl)methyl]-2-propylsulfanyl-pyrimidine-4,5-diamine (compound 15b). 6-Chloro-9-[(4-chloro-3-fluoro-phenyl)methyl]-2-propylsulfanyl-7H-purin-8-one (3.8 g, compound 30c) was obtained as a gray solid. MS obsd. (ESI⁺) [(M+H)⁺]: 387.

Step 4: Preparation of 9-[(4-chloro-3-fluorophenyl)methyl]-6-[(4-methoxyphenyl)methylamino]-2-propylsulfanyl-7H-purin-8-one

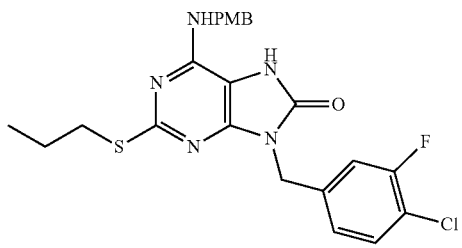

30d

Compound 30d was prepared in analogy to Example 15, Step 4 by using 6-chloro-9-[(4-chloro-3-fluoro-phenyl)methyl]-2-propylsulfanyl-7H-purin-8-one (compound 30c) instead of 6-chloro-9-[(2-chlorophenyl)methyl]-2-propyl-sulfanyl-7H-purin-8-one (compound 15c). 9-[(4-Chloro-3-fluoro-phenyl)methyl]-6-[(4-methoxyphenyl)methylamino]-2-propylsulfanyl-7H-purin-8-one (2.3 g, compound 30d) was obtained as a light yellow solid. MS obsd. (ESI⁺) [(M+H)⁺]: 488.

Step 5: Preparation of 6-amino-9-[(4-chloro-3-fluoro-phenyl)methyl]-2-propylsulfanyl-7H-purin-8-one

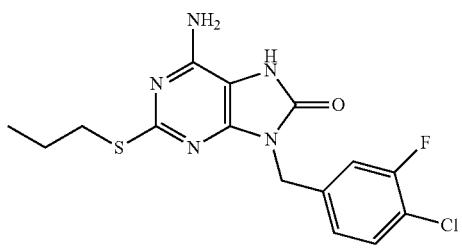

30e

Compound 30e was prepared in analogy to Example 15, Step 5 by using 9-[(4-chloro-3-fluoro-phenyl)methyl]-6-[(4-methoxyphenyl)methylamino]-2-propylsulfanyl-7H-purin-8-one (compound 30d) instead of 9-[(2-chlorophenyl)methyl]-6-[(4-methoxyphenyl)methylamino]-2-propylsulfanyl-7H-purin-8-one (compound 15d). 6-Amino-9-[(4-chloro-3-fluoro-phenyl)methyl)methyl]-2-propylsulfanyl-7H-purin-8-one (1.4 g, compound 30e) was obtained as a white solid. MS obsd. (ESI⁺) [(M+H)⁺]: 368.

Step 6: Preparation of 6-amino-2-propylsulfinyl-9-[4-chloro-3-fluoro-phenyl)methyl]-7H-purin-8-one

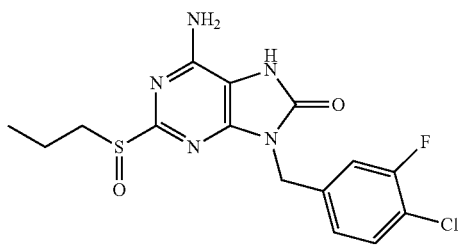

30f

Compound 30f was prepared in analogy to Example 15, Step 6 by using 6-amino-9-[(4-chloro-3-fluoro-phenyl)methyl]-2-propylsulfanyl-7H-purin-8-one (compound 30e) instead of 6-amino-9-[(2-chlorophenyl)methyl]-2-propyl-sulfanyl-7H-purin-8-one (compound 15e). 6-Amino-2-propylsulfinyl-9-[[4-chloro-3-fluoro-phenyl)methyl]-7H-purin-8-one (300 mg, compound 30O was obtained as a white solid MS obsd. (ESI⁺) [(M+H)⁺]: 384.

Step 7: Preparation of 6-amino-2-(propylsulfonimidoyl)-9-[[4-chloro-3-fluoro-phenyl)methyl]methyl]-7H-purin-8-one

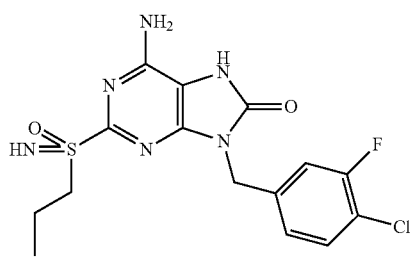

30

The title compound was prepared in analogy to Example 15, Step 7 by using 6-amino-9-[(4-chloro-3-fluoro-phenyl)methyl 2-propylsulfinyl-7H-purin-8-one (compound 30O instead of 6-amino-9-[(2-chlorophenyl)methyl]-2-propyl-sulfinyl-7H-purin-8-one (Example 30). 6-Amino-2-(propyl-sulfonimidoyl)-9-[[4-chloro-3-fluoro-phenyl)methyl]-7H-purin-8-one (63 mg, Example 30) was obtained as a white solid. $^1$H NMR (400 MHz, DMSO-$d_6$) δ ppm: 10.67 (br. s., 1H), 7.45-7.34 (m, 1H)), 7.31-7.22 (m, 1H), 7.09-7.03 (m, 1H), 7.00 (br. s., 2H), 4.99 (s, 2H), 3.98 (s, 1H), 3.31-3.26 (m, 2H), 1.72-1.50 (m, 2H), 0.91 (t, J=8.0 Hz, 3H). MS obsd. (ESI⁺) [(M+H)⁺]: 399.

Example 31

6-Amino-9-[(2,4-difluorophenyl)methyl]-2-(propyl-sulfonimidoyl)-7H-purin-8-one

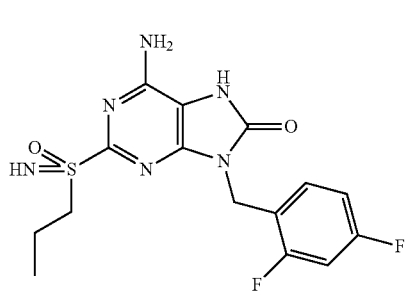

31

Step 1: Preparation of 6-chloro-N-[(2,4-difluorophenyl)methyl]-5-nitro-2-propylsulfanyl-pyrimidin-4-amine

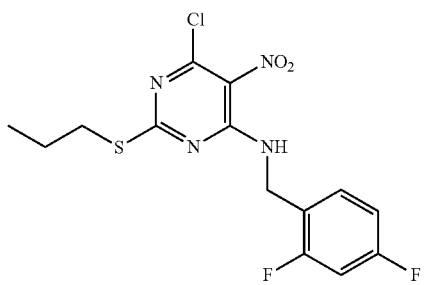

31a

Compound 31a was prepared in analogy to Example 15, Step 1 by using (2,4-difluorophenyl)methylamine instead of (2-chlorophenyl)methylamine. 6-Chloro-N-[(2,4-difluorophenyl)methyl]-5-nitro-2-propylsulfanyl-pyrimidin-4-amine (5.0 g, compound 31a) was obtained as a yellow solid. MS obsd. (ESI+) [(M+H)+]: 375.

Step 2: Preparation of 6-chloro-N4-[(2,4-difluorophenyl)methyl]-2-propylsulfanyl-pyrimidine-4,5-diamine

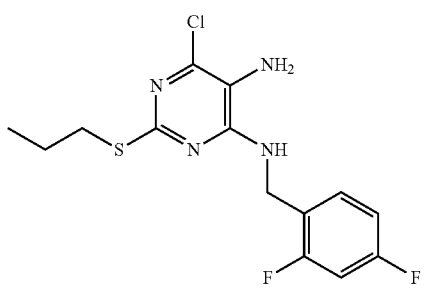

31b

Compound 31b was prepared in analogy to Example 15, Step 2 by using 6-chloro-N-[(2,4-difluorophenyl)methyl]-5-nitro-2-propylsulfanyl-pyrimidin-4-amine (compound 31a) instead of 6-chloro-N-[(2-chlorophenyl)methyl]-5-nitro-2-propylsulfanyl-pyrimidin-4-amine (compound 15a). 6-Chloro-N4-[(2,4-difluorophenyl)methyl]-2-propylsulfanyl-pyrimidine-4,5-diamine (4.0 g, compound 31b) was obtained as a white solid. MS obsd. (ESI+) [(M+H)+]: 345.

Step 3: Preparation of 6-chloro-9-[(2,4-difluorophenyl)methyl]-2-propylsulfanyl-7H-purin-8-one

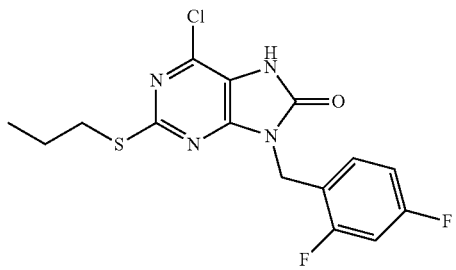

31c

Compound 31c was prepared in analogy to Example 15, Step 3 by using 6-chloro-N-4-[(2,4-difluorophenyl)methyl]-2-propylsulfanyl-pyrimidine-4,5-diamine (compound 31b) instead of 6-chloro-N4-[(2-chlorophenyl)methyl]-2-propylsulfanyl-pyrimidine-4,5-diamine (compound 15b). 6-Chloro-9-[(2,4-difluorophenyl)methyl]-2-propylsulfanyl-7H-purin-8-one (4.0 g, compound 31c) was obtained as a white solid. MS obsd. (ESI+) [(M+H)+]: 371.

Step 4: Preparation of 9-[(2,4-difluorophenyl)methyl]-6-[(4-methoxyphenyl)methylamino]-2-propylsulfanyl-7H-purin-8-one

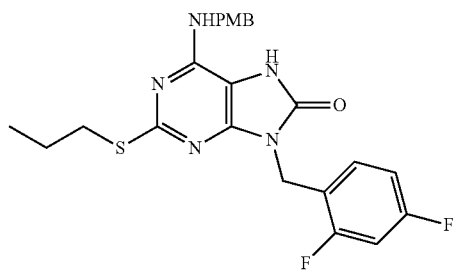

31d

Compound 31d was prepared in analogy to Example 15, Step 4 by using 6-chloro-9-[(2,4-difluorophenyl)methyl]-2-propylsulfanyl-7H-purin-8-one (compound 31c) instead of 6-chloro-9-[(2-chlorophenyl)methyl]-2-propylsulfanyl-7H-purin-8-one (compound 15c). 9-[(2,4-Difluorophenyl)methyl]-6-[(4-methoxyphenyl)methylamino]-2-propylsulfanyl-7H-purin-8-one (2.9 g, compound 31d) was obtained as a white solid. MS obsd. (ESI+) [(M+H)+]: 472.

Step 5: Preparation of 6-amino-9-[(2,4-difluorophenyl)methyl]-2-propylsulfanyl-7H-purin-8-one

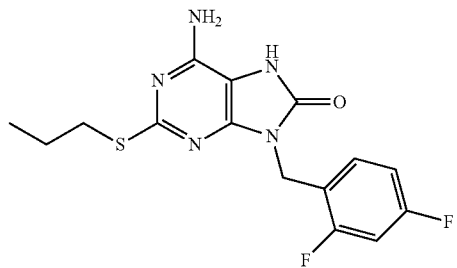

31e

Compound 31e was prepared in analogy to Example 15, Step 5 by using 9-[(2,4-difluorophenyl)methyl]-6-[(4-methoxyphenyl)methylamino]-2-propylsulfanyl-7H-purin-8-one (compound 31d) instead of 9-[(2-chlorophenyl)methyl]-6-[(4-methoxyphenyl)methylamino]-2-propylsulfanyl-7H-purin-8-one (compound 15d). 6-Amino-9-[(2,4-difluorophenyl)methyl]-2-propylsulfanyl-7H-purin-8-one (1.4 g, compound 31e) was obtained as a white solid. MS obsd. (ESI+) [(M+H)+]: 352.

Step 6: Preparation of 6-amino-2-propylsulfinyl-9-[(2,4-difluorophenyl)methyl]-7H-purin-8-one

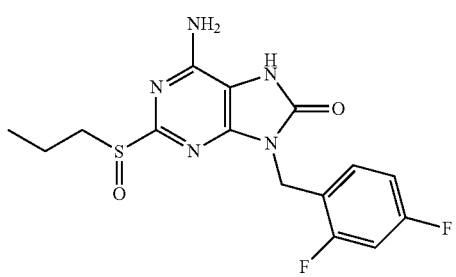

31f

Compound 31f was prepared in analogy to Example 15, Step 6 by using 6-amino-9-[(2,4-difluorophenyl)methyl]-2-propylsulfanyl-7H-purin-8-one (compound 31e) instead of 6-amino-9-[(2-chlorophenyl)methyl]-2-propylsulfanyl-7H-purin-8-one (compound 15e). 6-Amino-2-propylsulfinyl-9-[[(2,4-difluorophenyl)methyl]-7H-purin-8-one (290 mg, compound 31f) was obtained as a white solid. MS obsd. (ESI+) [(M+H)+]: 368.

Step 7: Preparation of 6-amino-2-(propylsulfonimidoyl)-9-[[(2,4-difluorophenyl)methyl]-7H-purin-8-one

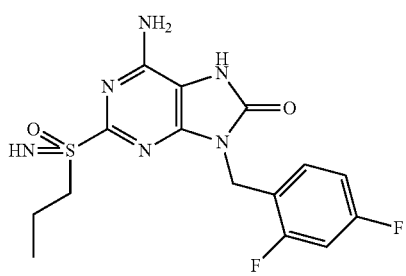

31

The title compound was prepared in analogy to Example 15, Step 7 by using 6-amino-9-[(2,4-difluorophenyl)methyl]-2-propylsulfinyl-7H-purin-8-one (compound 31f) instead of 6-amino-9-[(2-chlorophenyl)methyl]-2-propylsulfinyl-7H-purin-8-one (compound 15f). 6-Amino-2-(propylsulfonimidoyl)-9-[[(2,4-difluorophenyl)methyl]-7H-purin-8-one (33 mg, compound 31) was obtained as a white solid. $^1$H NMR (400 MHz, DMSO-d$_6$) δ ppm: 10.68 (br. s., 1H), 7.56 (t, J=8.0 Hz, 1H), 7.40 (d, J=8.0 Hz, 1H), 7.24-7.14 (m, 1H), 7.01 (br. s., 2H), 4.98 (s, 2H), 4.05 (s, 1H), 3.32-3.24 (m, 2H), 1.71-1.52 (m, 2H), 0.90 (t, J=8.0 Hz, 3H). MS obsd. (ESI+) [(M+H)+]: 383.

Example 32 & Example 33

4-[[6-Amino-8-oxo-2-(propylsulfonimidoyl)-7H-purin-9-yl]methyl]benzonitrile (compound 32) and 4-[[6-amino-8-oxo-2-(propylsulfonimidoyl)-7H-purin-9-yl]methyl]benzamide (compound 33)

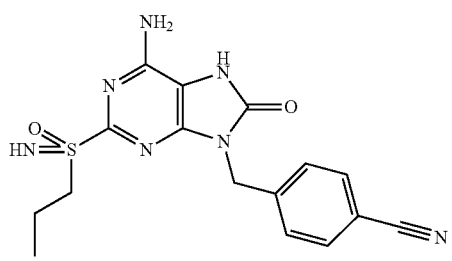

32

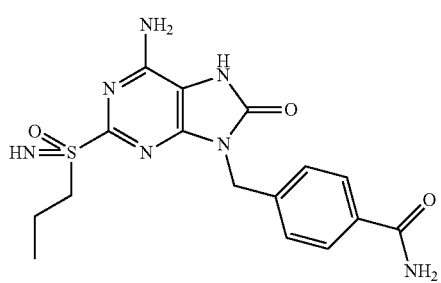

33

Step 1: Preparation of 4-[[(6-chloro-5-nitro-2-propylsulfanyl-pyrimidin-4-yl)amino]methyl]benzonitrile

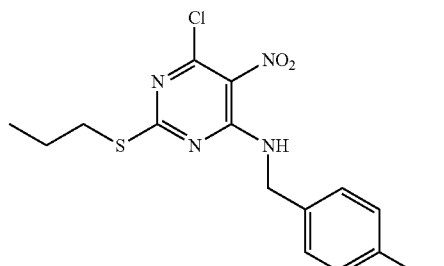

32a

Compound 32a was prepared in analogy to Example 15, Step 1 by using 4-(aminomethyl)benzonitrile instead of (2-chlorophenyl)methylamine. 4-[[(6-chloro-5-nitro-2-propylsulfanyl-pyrimidin-4-yl)amino]methyl]benzonitrile (5.5 g, compound 32a) was obtained as a yellow solid. MS obsd. (ESI+) [(M+H)+]: 364.

Step 2: Preparation of 4-[[(5-amino-6-chloro-2-propylsulfanyl-pyrimidin-4-yl)amino]methyl]benzonitrile

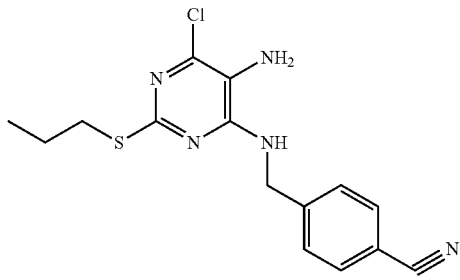

32b

Compound 32b was prepared in analogy to Example 15, Step 2 by using 4-[[(6-chloro-5-nitro-2-propylsulfanyl-pyrimidin-4-yl)amino]methyl]benzonitrile (compound 32a) instead of 6-chloro-N-[(2-chlorophenyl)methyl]-5-nitro-2-propylsulfanyl-pyrimidin-4-amine (compound 15a). 4-[[(5-Amino-6-chloro-2-propylsulfanyl-pyrimidin-4-yl)amino] methyl]benzonitrile (2.7 g, compound 32b) was obtained as a brown oil. MS obsd. (ESI$^+$) [(M+H)$^+$]: 334.

Step 3: Preparation of 4-[(6-chloro-8-oxo-2-propylsulfanyl-7H-purin-9-yl)methyl]benzonitrile

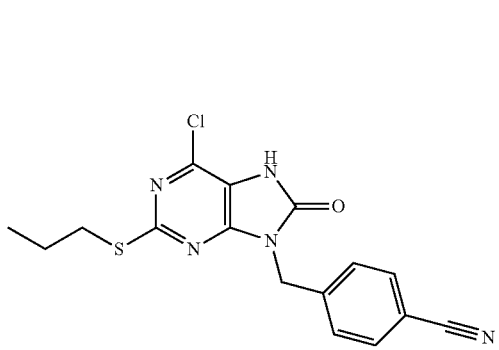

32c

Compound 32c was prepared in analogy to Example 15, Step 3 by using 4-[[(5-amino-6-chloro-2-propylsulfanyl-pyrimidin-4-yl)amino]methyl]benzonitrile (2.7 g, compound 32b) instead of 6-chloro-N4-[(2-chlorophenyl) methyl]-2-propylsulfanyl-pyrimidine-4,5-diamine (compound 15b). 4-[(6-Chloro-8-oxo-2-propylsulfanyl-7H-purin-9-yl)methyl]benzonitrile (2.5 g, compound 32c) was obtained as a light yellow solid. $^1$H NMR (400 MHz, DMSO-d$_6$) δ ppm: 10.14 (br. s., 1H), 7.82 (d, J=8.0 Hz, 2H), 7.51 (d, J=8.0 Hz, 2H), 5.06 (s, 2H), 3.01 (t, J=8.0 Hz, 2H), 1.68-1.53 (m, 2H), 0.91 (t, J=8.0 Hz, 3H). MS obsd. (ESI$^+$) [(M+H)$^+$]: 360.

Step 4: Preparation of 4-[[6-[(4-methoxyphenyl)methylamino]-8-oxo-2-propylsulfanyl-7H-purin-9-yl]methyl]benzonitrile

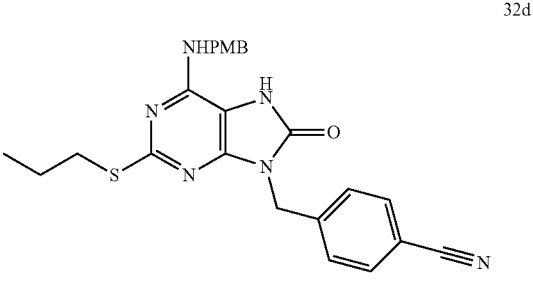

32d

Compound 32d was prepared in analogy to Example 15, Step 4 by using 4-[(6-chloro-8-oxo-2-propylsulfanyl-7H-purin-9-yl)methyl]benzonitrile (compound 32c) instead of 6-chloro-9-[(2-chlorophenyl)methyl]-2-propylsulfanyl-7H-purin-8-one (compound 15c). 4-[[6-[(4-Methoxyphenyl) methylamino]-8-oxo-2-propylsulfanyl-7H-purin-9-yl] methyl]benzonitrile (3.0 g, compound 32d) was obtained as a light red solid. MS obsd. (ESI$^+$) [(M+H)$^+$]: 461.

Step 5: Preparation of 4-[(6-amino-8-oxo-2-propylsulfanyl-7H-purin-9-yl)methyl]benzonitrile (compound 32e) and 4-[(6-amino-8-oxo-2-propylsulfanyl-7H-purin-9-yl)methyl]benzamide (compound 33a)

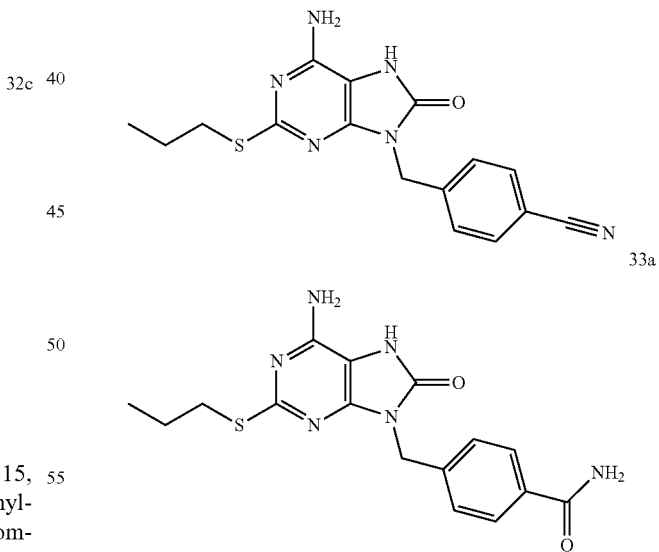

Compound 32e, 33a were prepared in analogy to Example 15, Step 5 by using 4-[[6-[(4-methoxyphenyl)methylamino]-8-oxo-2-propylsulfanyl-7H-purin-9-yl]methyl]benzonitrile (compound 32d) instead of 9-[(2-chlorophenyl) methyl]-6-[(4-methoxyphenyl)methylamino]-2-propylsulfanyl-7H-purin-8-one (compound 15d). 4-[(6-Amino-8-oxo-2-propylsulfanyl-7H-purin-9-yl)methyl] benzonitrile (compound 32e) and 4-[(6-amino-8-oxo-2- propylsulfanyl-7H-purin-9-yl)methyl]benzamide (compound 33a) was obtained as a mixture (1.5 g).

Step 6: Preparation of 4-[(6-amino-8-oxo-2-propyl-sulfinyl-7H-purin-9-yl)methyl]benzonitrile (compound 32f) and 4-[(6-amino-8-oxo-2-propylsulfinyl-7H-purin-9-yl)methyl]benzamide (compound 33b)

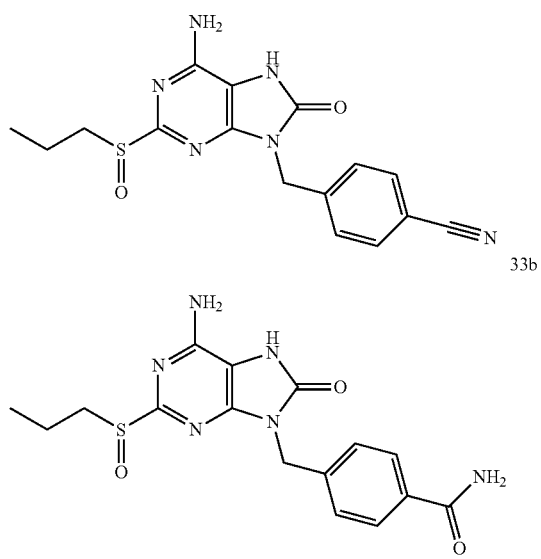

Compound 32f, 33b were prepared in analogy to Example 15, Step 6 by using the mixture of 4-[(6-amino-8-oxo-2-propylsulfanyl-7H-purin-9-yl)methyl]benzonitrile (compound 32e) and 4-[(6-amino-8-oxo-2-propylsulfanyl-7H-purin-9-yl)methyl]benzamide (compound 33a) instead of 6-amino-9-[(2-chlorophenyl)methyl]-2-propylsulfanyl-7H-purin-8-one (compound 15e). 4-[(6-Amino-8-oxo-2-propyl-sulfinyl-7H-purin-9-yl)methyl]benzonitrile (compound 32f) and 4-[(6-amino-8-oxo-2-propylsulfinyl-7H-purin-9-yl) methyl]benzamide (250 mg, compound 33b) was obtained as a mixture of white solid.

Step 7: Preparation of 4-[[6-amino-8-oxo-2-(propyl-sulfonimidoyl)-7H-purin-9-yl]methyl]benzonitrile (compound 32) and 4-[[6-amino-8-oxo-2-(propyl-sulfonimidoyl)-7H-purin-9-yl]methyl]benzamide (compound 33)

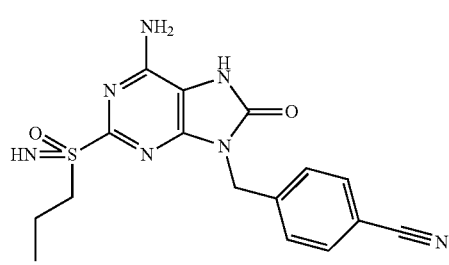

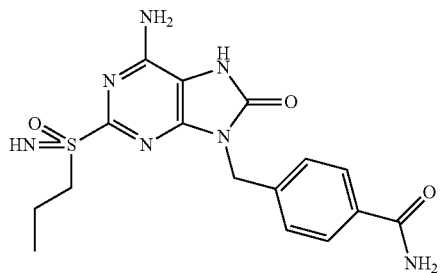

The title compound was prepared in analogy to Example 15, Step 7 by using the mixture of 4-[(6-amino-8-oxo-2-propylsulfinyl-7H-purin-9-yl)methyl]benzonitrile (compound 32f) and 4-[(6-amino-8-oxo-2-propylsulfinyl-7H-purin-9-yl)methyl]benzamide (compound 33b) instead of 6-amino-9-[(2-chlorophenyl)methyl]-2-propylsulfinyl-7H-purin-8-one (compound 15f). The residue was purified by prep-HPLC to give 4-[[6-amino-8-oxo-2-(propylsulfonimi-doyl)-7H-purin-9-yl]methyl]benzonitrile (24.7 mg, Example 32) and 4-[[6-amino-8-oxo-2-(propylsulfonimi-doyl)-7H-purin-9-yl]methyl]benzamide (18.8 mg, Example 33).

Example 32

$^1$H NMR (400 MHz, DMSO-d$_6$) δ ppm: 7.82 (d, J=8.0 Hz, 2H), 7.50 (d, J=8.0 Hz, 2H), 7.04 (br. s., 2H), 5.06 (s, 2H), 4.02 (s, 1H), 3.29-3.26 (m, 2H), 1.66-1.54 (m, 2H), 0.89 (t, J=8.0 Hz, 3H). MS obsd. (ESI$^+$) [(M+H)$^+$]: 372.

Example 33

$^1$H NMR (400 MHz DMSO-d$_6$) δ ppm: 10.73 (br. s., 1H), 7.94 (s, 1H), 7.82 (d, J=8.0 Hz, 2H), 7.38 (d, J=8.0 Hz, 2H), 7.34 (s, 1H), 7.02 (br. s., 2H), 5.01 (s, 2H), 4.03 (s, 1H), 3.31-3.27 (m, 2H), 1.68-1.56 (m, 2H), 0.90 (t, J=8.0 Hz, 3H). MS obsd. (ESI$^+$) [(M+H)$^+$]: 390.

Example 34

6-Amino-9-[(6-methyl-3-pyridyl)methyl]-2-(propyl-sulfonimidoyl)-7H-purin-8-one

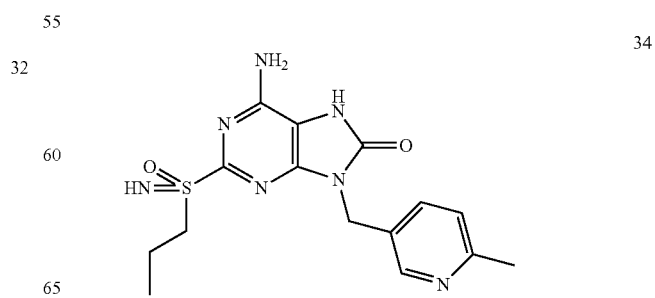

Step 1: Preparation of 6-methylpyridine-3-carbonitrile

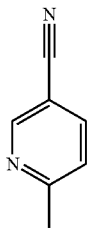

34a

To a suspension of 6-methylpyridine-3-carboxylic acid (17.0 g, 125 mmol) in toluene (200 mL) was added phosphoryl trichloride (84.24 g, 708 mmol) drop-wise. After the addition, the reaction mixture was stirred at 100° C. for 12 hrs. The mixture was cooled to RT and the solvent was removed in vacuo. The residue was suspended in EtOAc (400 mL), basified with sat. NaHCO$_3$ (400 mL), and extracted with EtOAc (300 mL) two times. The combined organic layer was dried over anhydrous sodium sulfate, filtered and concentrated in vacuo. The residue was purified by column chromatography on silica gel eluted with (PE/EtOAc from 10/1 to 5/1) to give 6-methylpyridine-3-carbonitrile (10.5 g, compound 34a) as a light yellow solid. MS obsd. (ESI$^+$) [(M+H)$^+$]: 119.

Step 2: Preparation of (6-methyl-3-pyridyl)methylamine

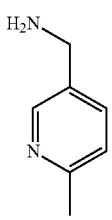

34b

To a solution of 6-methylpyridine-3-carbonitrile (10.5 g, 25.7 mmol) in MeOH (80 mL) and NH$_3$/MeOH (20 mL, 7 M) was added Raney-Ni (2.0 g) under N$_2$ atmosphere. The suspension was degassed in vacuo and refilled with H$_2$. The mixture was stirred for 12 hrs at 40° C. under H$_2$ (50 psi) atmosphere. The reaction mixture was filtered and the filtrate was concentrated in vacuo to give (6-methyl-3-pyridyl)methylamine (9.5 g, compound 34b) as a light oil. $^1$H NMR (400 MHz, DMSO-d$_6$) δ ppm: 8.36 (s, 1H), 7.62 (d, J=8.0 Hz, 1H), 7.18 (d, J=8.0 Hz, 1H), 3.69 (s, 2H), 2.42 (s, 3H). MS obsd. (ESI$^+$) [(M+H)$^+$]: 123.

Step 3: Preparation of 6-chloro-N-[(6-methyl-3-pyridyl)methyl]-5-nitro-2-propylsulfanyl-pyrimidin-4-amine

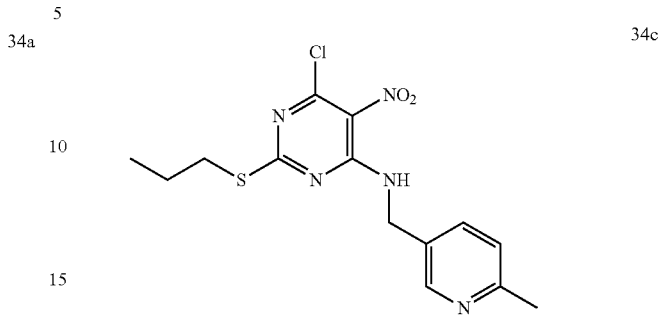

34c

Compound 34c was prepared in analogy to Example 15, Step 1 by using (6-methyl-3-pyridyl)methylamine (compound 34b) instead of (2-chlorophenyl)methylamine. 6-Chloro-N-[(6-methyl-3-pyridyl)methyl]-5-nitro-2-propylsulfanyl-pyrimidin-4-amine (15.5 mg, compound 34c) was obtained as a white solid. MS obsd. (ESI$^+$) [(M+H)$^+$]: 354.

Step 4: Preparation of 6-chloro-N-4-[(6-methyl-3-pyridyl)methyl]-2-propylsulfanyl-pyrimidine-4,5-diamine

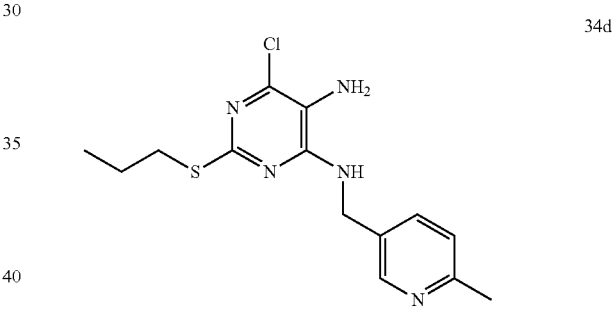

34d

Compound 34d was prepared in analogy to Example 15, Step 2 by using 6-chloro-N-[(6-methyl-3-pyridyl)methyl]-5-nitro-2-propylsulfanyl-pyrimidin-4-amine (compound 34c) instead of 6-chloro-N-[(2-chlorophenyl)methyl]-5-nitro-2-propylsulfanyl-pyrimidin-4-amine (compound 15a). 6-Chloro-N-4-[(6-methyl-3-pyridyl)methyl]-2-propylsulfanyl-pyrimidine-4,5-diamine (10.9 g, compound 34d) was obtained as a white solid. MS obsd. (ESI$^+$) [(M+H)$^+$]: 324.

Step 5: Preparation of 6-chloro-9-[(6-methyl-3-pyridyl)methyl]-2-propylsulfanyl-7H-purin-8-one

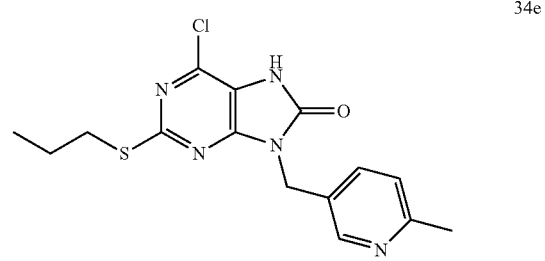 [SMILES: CCCSc1nc(Cl)c2[nH]c(=O)n(Cc3ccc(C)nc3)c2n1]

34e

Compound 34e was prepared in analogy to Example 15, Step 3 by using 6-chloro-N-4-[(6-methyl-3-pyridyl)methyl]-2-propylsulfanyl-pyrimidine-4,5-diamine (compound 34d) instead of 6-chloro-N4-[(2-chlorophenyl)methyl]-2-propylsulfanyl-pyrimidine-4,5-diamine (compound 15b). 6-Chloro-9-[(6-methyl-3-pyridyl)methyl]-2-propylsulfanyl-7H-purin-8-one (12.0 g, compound 34e) was obtained as a white solid. MS obsd. (ESI+) [(M+H)+]: 350.

Step 6: Preparation of 6-[(4-methoxyphenyl)methylamino]-9-[(6-methyl-3-pyridyl)methyl]-2-propylsulfanyl-7H-purin-8-one

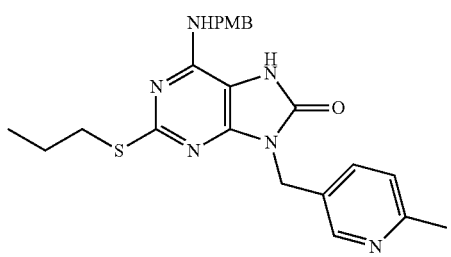

Compound 34f was prepared in analogy to Example 15, Step 4 by using 6-chloro-9-[(6-methyl-3-pyridyl)methyl]-2-propylsulfanyl-7H-purin-8-one (compound 34e) instead of 6-chloro-9-[(2-chlorophenyl)methyl]-2-propylsulfanyl-7H-purin-8-one (compound 15c). 6-[(4-Methoxyphenyl)methylamino]-9-[(6-methyl-3-pyridyl)methyl]-2-propylsulfanyl-7H-purin-8-one (15.0 g, compound 34f) was obtained as a white solid. MS obsd. (ESI+) [(M+H)+]: 451.

Step 7: Preparation of 6-amino-9-[(6-methyl-3-pyridyl)methyl]-2-propylsulfanyl-7H-purin-8-one

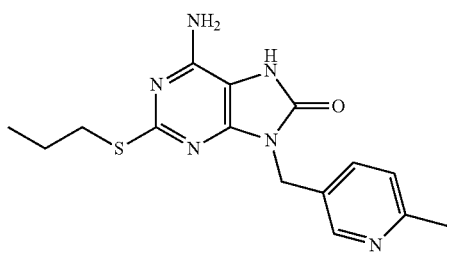

Compound 34g was prepared in analogy to Example 15, Step 5 by using 6-[(4-methoxyphenyl)methylamino]-9-[(6-methyl-3-pyridyl)methyl]-2-propylsulfanyl-7H-purin-8-one (compound 34f) instead of 9-[(2-chlorophenyl)methyl]-6-[(4-methoxyphenyl)methylamino]-2-propylsulfanyl-7H-purin-8-one (compound 15d). 6-Amino-9-[(6-methyl-3-pyridyl)methyl]-2-propylsulfanyl-7H-purin-8-one (7.9 g, compound 34g) was obtained as a white solid. MS obsd. (ESI+) [(M+H)+]: 331.

Step 8: Preparation of 6-amino-9-[(6-methyl-3-pyridyl)methyl]-2-propylsulfinyl-7H-purin-8-one

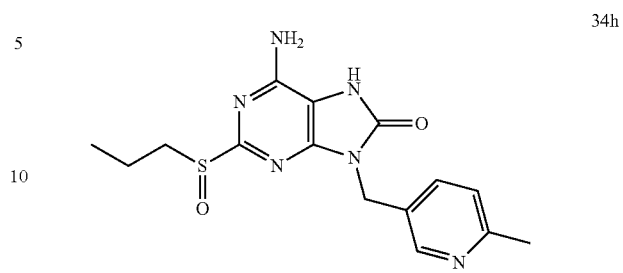

Compound 34h was prepared in analogy to Example 15, Step 6 by using 6-amino-9-[(6-methyl-3-pyridyl)methyl]-2-propylsulfanyl-7H-purin-8-one (compound 34g) instead 6-amino-9-[(2-chlorophenyl)methyl]-2-propylsulfanyl-7H-purin-8-one (compound 15e). 6-Amino-9-[(6-methyl-3-pyridyl)methyl]-2-propylsulfinyl-7H-purin-8-one (300 mg, compound 34h) was obtained as a white solid. MS obsd. (ESI+) [(M+H)+]: 347.

Step 9: Preparation of 6-amino-9-[(6-methyl-3-pyridyl)methyl]-2-(propylsulfonimidoyl)-7H-purin-8-one

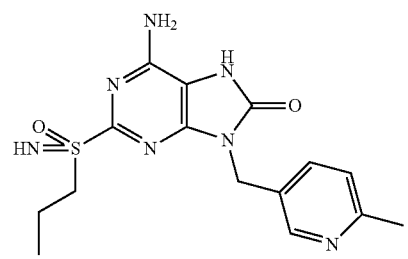

The title compound was prepared in analogy to Example 15, Step 7 by using 6-amino-9-[(6-methyl-3-pyridyl)methyl]-2-propylsulfinyl-7H-purin-8-one (compound 34h) instead of 6-amino-9-[(2-chlorophenyl)methyl]-2-propylsulfinyl-7H-purin-8-one (compound 15f). 6-Amino-9-[(6-methyl-3-pyridyl)methyl]-2-(propylsulfonimidoyl)-7H-purin-8-one (13 mg, Example 34) was obtained as a white solid. $^1$H NMR (400 MHz, DMSO-$d_6$) δ ppm: 8.47 (s, 1H), 7.63 (dd, J=8.0 Hz, 2.0 Hz, 1H), 7.21 (d, J=8.0 Hz, 1H), 7.07 (s, 2H), 4.95 (s, 2H), 4.06 (s, 1H), 3.32-3.29 (m, 2H), 2.42 (s, 3H), 1.71-1.57 (m, 2H), 0.92 (t, J=7.4 Hz, 3H) MS obsd. (ESI+) [(M+H)+]: 363.

Example 35

6-Amino-9-[(2-methyl-4-pyridyl)methyl]-2-(propylsulfonimidoyl)-7H-purin-8-one

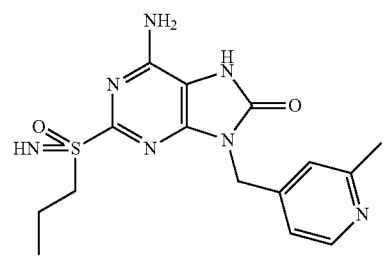 [SMILES: CCCS(=N)(=O)c1nc(N)c2[nH]c(=O)n(Cc3ccnc(C)c3)c2n1]

Step 1: Preparation of 2-methylpyridine-4-carbonitrile

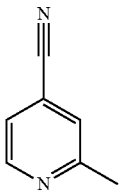

35a

A mixture of 2-chloropyridine-4-carbonitrile (30.0 g, 216.0 mol), AlMe$_3$ (11 mL, 220 mmol, 2 M in toluene) and Pd(PPh$_3$)$_4$ (2.3 g, 2.0 mmol) in dioxane (400 mL) was heated to 130° C. for 10 hrs under N$_2$ atmosphere. The mixture was cooled to RT, then poured into ice water (1000 mL), extracted with EtOAc. The combined organic layer was dried over anhydrous sodium sulfate and concentrated in vacuo. The residue was purified by column chromatography eluted with PE/EtOAc (2/1) to afford 2-methylpyridine-4-carbonitrile (compound 35a) as a yellow crystal. (5.2 g). $^1$H NMR (400 MHz, DMSO-d$_6$) □ ppm: 8.68 (d, J=5.0 Hz, 1H), 7.39 (s, 1H), 7.33 (d, J=5.0 Hz, 1H), 2.63 (s, 3H). MS obsd. (ESI$^+$) [(M+H)$^+$]: 119.

Step 2: Preparation of (2-methyl-4-pyridyl)methylanamine

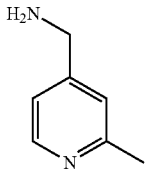

35b

To a solution of 2-methylpyridine-4-carbonitrile (1.6 g, 13 mmol, compound 35a) in MeOH (30 mL) and NH$_3$/MeOH (20 mL, 7 M) was added Raney-Ni (2.0 g) under N$_2$ atmosphere. The suspension was degassed in vacuo and purged with H$_2$ two times. The mixture was stirred under H$_2$ (50 psi) atmosphere at 40° C. for 12 hrs. The reaction mixture was then filtered and the filtrate was concentrated in vacuo to give (2-methyl-4-pyridyl)methylanamine ((1.6 g, compound 35b) as a brown oil. $^1$H NMR (400 MHz, DMSO-d$_6$) δ ppm: 8.41 (J=5.0 Hz, 1H), 7.12-7.04 (m, 2H), 3.86 (s, 2H), 2.54 (s, 3H). MS obsd. (ESI$^+$) [(M+H)$^+$]: 123.

Step 3: Preparation of 6-chloro-N-[(2-methyl-4-pyridyl)methyl]-5-nitro-2-propylsulfanyl-pyrimidin-4-amine

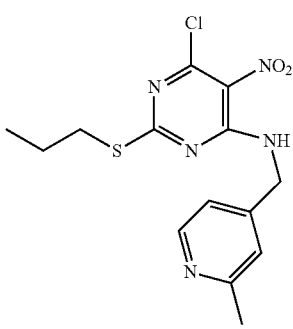

35c

Compound 35c was prepared in analogy to Example 15, Step 1 by using (2-methyl-4-pyridyl)methylamine (compound 35b) instead of (2-chlorophenyl)methanamine. 6-Chloro-N-[(2-methyl-4-pyridyl)methyl]-5-nitro-2-propyl-sulfanyl-pyrimidin-4-amine (4.3 g, compound 35c) was obtained as a white solid. MS obsd. (ESI$^+$) [(M+H)$^+$]: 354.

Step 4: Preparation of 6-chloro-N4-[(2-methyl-4-pyridyl)methyl]-2-propylsulfanyl-pyrimidine-4,5-diamine

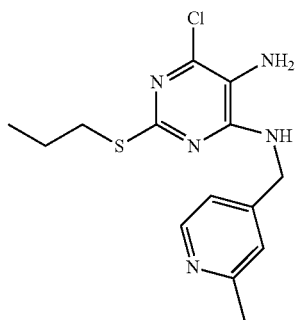

35d

Compound 35d was prepared in analogy to Example 15, Step 2 by 6-chloro-N-[(2-methyl-4-pyridyl)methyl]-5-nitro-2-propylsulfanyl-pyrimidin-4-amine (compound 35c) instead of 6-chloro-N-[(2-chlorophenyl)methyl]-5-nitro-2-propylsulfanyl-pyrimidin-4-amine (compound 15a). 6-Chloro-N-4-[(2-methyl-4-pyridyl)methyl]-2-propylsulfanyl-pyrimidine-4,5-diamine (2.0 g, compound 35d) was obtained as a white solid. MS obsd. (ESI$^+$) [(M+H)$^+$]: 324.

Step 5: Preparation of 6-chloro-9-[(2-methyl-4-pyridyl)methyl]-2-propylsulfanyl-7H-purin-8-one

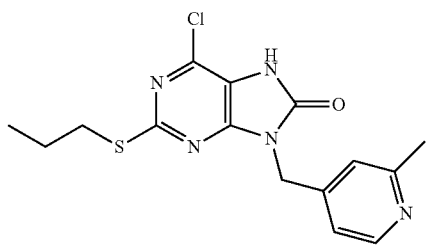

35e

Compound 35e was prepared in analogy to Example 15, Step 3 by using 6-chloro-N4-[(2-methyl-4-pyridyl)methyl]-2-propylsulfanyl-pyrimidine-4,5-diamine (compound 35d) instead of 6-chloro-N-4-[(2-chlorophenyl)methyl]-2-propyl-sulfanyl-pyrimidine-4,5-diamine (compound 15b). 6-Chloro-9-[(2-methyl-4-pyridyl)methyl]-2-propylsulfanyl-7H-purin-8-one (2.5 g, compound 35e) was obtained as a white solid. MS obsd. (ESI$^+$) [(M+H)$^+$]: 350.

Step 6: Preparation of 6-[(4-methoxyphenyl)methyl-amino]-9-[(2-methyl-4-pyridyl)methyl]-2-propylsulfanyl-7H-purin-8-one

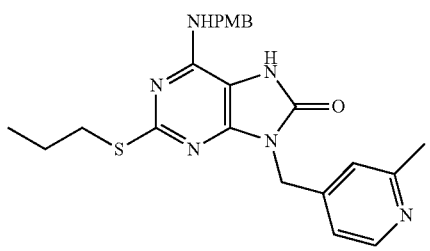

35f

Compound 35f was prepared in analogy to Example 15, Step 4 by using 6-chloro-9-[(2-methyl-4-pyridyl)methyl]-2-propylsulfanyl-7H-purin-8-one (compound 35e) instead of 6-chloro-9-[(2-methyl-4-pyridyl)methyl]-2-propylsulfanyl-7H-purin-8-one (compound 15c). 6-[(4-Methoxyphenyl)methylamino]-9-[(2-methyl-4-pyridyl)methyl]-2-propylsulfanyl-7H-purin-8-one (3.3 g, compound 35f) was obtained as a white solid. MS obsd. (ESI$^+$) [(M+H)$^+$]: 450.

Step 7: Preparation of 6-amino-9-[(2-methyl-4-pyridyl)methyl]-2-propylsulfanyl-7H-purin-8-one

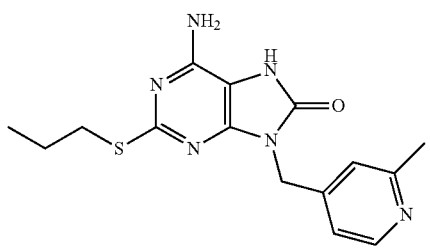

35g

Compound 35g was prepared in analogy to Example 15, Step 5 by using 6-[(4-methoxyphenyl)methylamino]-9-[(2-methyl-4-pyridyl)methyl]-2-propylsulfanyl-7H-purin-8-one (compound 35f) instead of 6-[(4-methoxyphenyl)methylamino]-2-propylsulfanyl-7H-purin-8-one (compound 15d). 6-Amino-9-[(2-methyl-4-pyridyl)methyl]-2-propylsulfanyl-7H-purin-8-one (compound 35g) was obtained as a white solid. MS obsd. (ESI$^+$) [(M+H)$^+$]: 331.

Step 8: Preparation of 6-amino-9-[(2-methyl-4-pyridyl)methyl]-2-propylsulfinyl-7H-purin-8-one

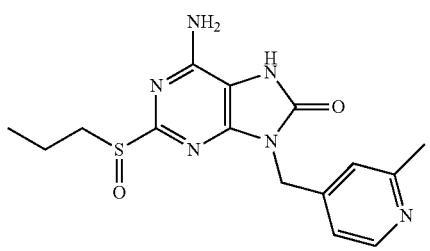

35h

Compound 35h was prepared in analogy to Example 15, Step 6 by using 6-amino-9-[(2-methyl-4-pyridyl)methyl]-2-propylsulfanyl-7H-purin-8-one (compound 35g) instead of 6-amino-9-[(2-chlorophenyl)methyl]-2-propylsulfanyl-7H-purin-8-one (compound 15e). 6-Amino-9-[(2-methyl-4-pyridyl)methyl]-2-propylsulfinyl-7H-purin-8-one (180 mg, compound 35h) was obtained as a white solid. MS obsd. (ESI$^+$) [(M+H)$^+$]: 347.

Step 9: Preparation of 6-amino-9-[(2-methyl-4-pyridyl)methyl]-2-(propylsulfonimidoyl)-7H-purin-8-one

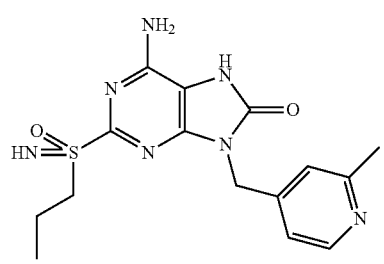

35

The title compound was prepared in analogy to Example 15, Step 7 by using 6-amino-9-[(2-methyl-4-pyridyl)methyl]-2-propylsulfinyl-7H-purin-8-one (compound 35h) instead of 6-amino-9-[(2-chlorophenyl)methyl]-2-propylsulfinyl-7H-purin-8-one (compound 15f). 6-Amino-2-(propylsulfonimidoyl)-9-[[(2,4-difluorophenyl)methyl]-7H-purin-8-one (21 mg, Example 35) was obtained as a white solid. $^1$H NMR (400 MHz, DMSO-d$_6$) δ ppm: 10.68 (br. s., 1H), 7.56 (t, J=8.0 Hz, 1H), 7.40 (d, J=8.0 Hz, 1H), 7.24-7.14 (m, 1H), 7.01 (br. s., 2H), 4.98 (s, 2H), 4.05 (s, 1H), 3.32-3.24 (m, 2H), 2.45 (s, 3H), 1.71-1.52 (m, 2H), 0.90 (t, J=8.0 Hz, 3H). MS obsd. (ESI$^+$) [(M+H)$^+$]: 362.

Example 36

6-Amino-9-[(3-chloro-4-methyl-phenyl)methyl]-2-(propylsulfonimidoyl)-7H-purin-8-one

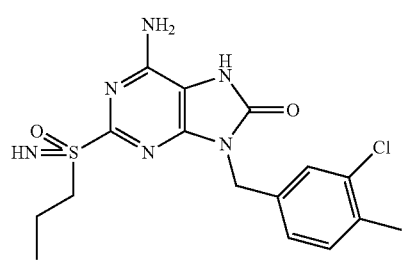

36

Step 1: Preparation of 6-chloro-N-[(2,4-difluoro-phenyl)methyl]-5-nitro-2-propylsulfanyl-pyrimidin-4-amine

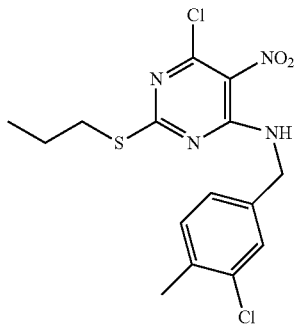
36a

Compound 36a was prepared in analogy to Example 15, Step 1 by using (3-chloro-4-methyl-phenyl)methylamine instead of (2-chlorophenyl)methylamine. 6-Chloro-N-[(3-chloro-4-methyl-phenyl)methyl]-5-nitro-2-propylsulfanyl-pyrimidin-4-amine (5.0 g, compound 36a) was obtained as a yellow solid. MS obsd. (ESI$^+$) [(M+H)$^+$]: 387.

Step 2: Preparation of 6-chloro-N4-[(3-chloro-4-methyl-phenyl)methyl]-2-propylsulfanyl-pyrimidine-4,5-diamine

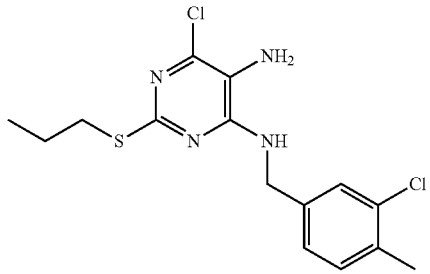
36b

Compound 36b was prepared in analogy to Example 15, Step 2 by using 6-chloro-N-[(3-chloro-4-methyl-phenyl)methyl]-5-nitro-2-propylsulfanyl-pyrimidin-4-amine (compound 36a) instead of 6-chloro-N-[(2-chlorophenyl)methyl]-5-nitro-2-propylsulfanyl-pyrimidin-4-amine (compound 15a). 6-Chloro-N4-[(3-chloro-4-methyl-phenyl)methyl]-2-propylsulfanyl-pyrimidine-4,5-diamine (4.0 g, compound 36b) was obtained as a white solid. MS obsd. (ESI$^+$) [(M+H)$^+$]: 357.

Step 3: Preparation of 6-chloro-9-[(3-chloro-4-methyl-phenyl)methyl]-2-propylsulfanyl-7H-purin-8-one

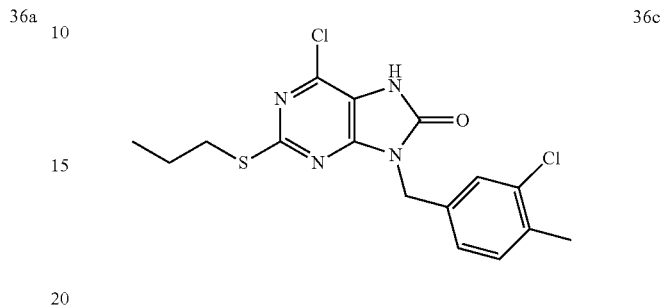
36c

Compound 36c was prepared in analogy to Example 15, Step 3 by using 6-chloro-N4-[(3-chloro-4-methyl-phenyl)methyl]-2-propylsulfanyl-pyrimidine-4,5-diamine (compound 36b) instead of 6-chloro-N4-[(2-chlorophenyl)methyl]-2-propylsulfanyl-pyrimidine-4,5-diamine (compound 15b). 6-Chloro-9-[(3-chloro-4-methyl-phenyl)methyl]-2-propylsulfanyl-7H-purin-8-one (compound 36c) was obtained as a white solid. MS obsd. (ESI$^+$) [(M+H)$^+$]: 383.

Step 4: Preparation of 9-[(3-chloro-4-methyl-phenyl)methyl]-6-[(4-methoxyphenyl)methylamino]-2-propylsulfanyl-7H-purin-8-one

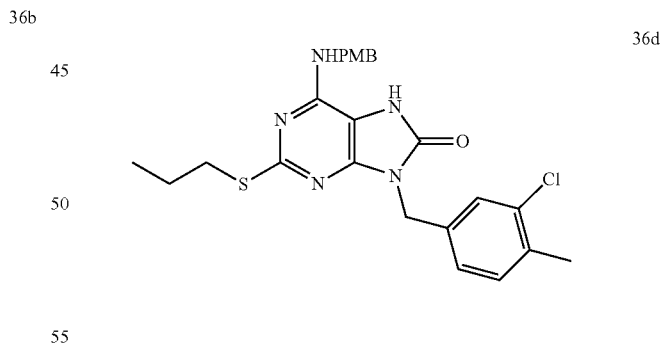
36d

Compound 36d was prepared in analogy to Example 15, Step 4 by using 6-chloro-9-[(3-chloro-4-methyl-phenyl)methyl]-2-propylsulfanyl-7H-purin-8-one (compound 36c) instead of 6-chloro-9-[(2-chlorophenyl)methyl]-2-propylsulfanyl-7H-purin-8-one (compound 15c). 9-[(3-Chloro-4-methyl-phenyl)methyl]-6-[(4-methoxyphenyl)methylamino]-2-propylsulfanyl-7H-purin-8-one (4.0 g, compound 36d) was obtained as a white solid. MS obsd. (ESI$^+$) [(M+H)$^+$]: 484.

Step 5: Preparation of 6-amino-9-[(3-chloro-4-methyl-phenyl)methyl]-2-propylsulfanyl-7H-purin-8-one

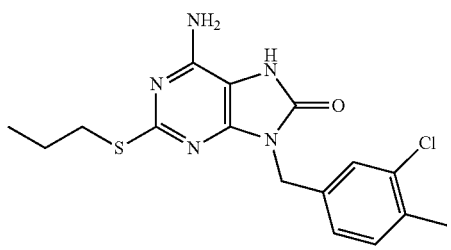

36e

Compound 36e was prepared in analogy to Example 15, Step 5 by using 9-[(3-chloro-4-methyl-phenyl)methyl]-6-[(4-methoxyphenyl)methylamino]-2-propylsulfanyl-7H-purin-8-one (compound 36d) instead of 9-[(2-chlorophenyl)methyl]-6-[(4-methoxyphenyl)methylamino]-2-propylsulfanyl-7H-purin-8-one. 6-Amino-9-[(3-chloro-4-methyl-phenyl)methyl]-2-propylsulfanyl-7H-purin-8-one (230 mg, compound 36e) was obtained as a white solid. MS obsd. (ESI$^+$) [(M+H)$^+$]: 364.

Step 6: Preparation of 6-amino-9-[(3-chloro-4-methyl-phenyl)methyl]-2-propylsulfinyl-7H-purin-8-one

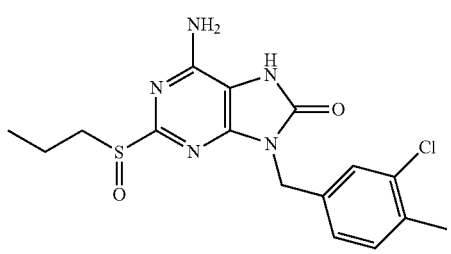

36f

Compound 36f was prepared in analogy to Example 15, Step 6 by using 6-amino-9-[(3-chloro-4-methyl-phenyl)methyl]-2-propylsulfanyl-7H-purin-8-one (compound 36e) instead of 6-amino-9-[(2-chlorophenyl)methyl]-2-propylsulfanyl-7H-purin-8-one (compound 15e). 6-Amino-9-[(3-chloro-4-methyl-phenyl)methyl]-2-propylsulfinyl-7H-purin-8-one (155 mg, compound 36f) was obtained as a white solid. MS obsd. (ESI$^+$) [(M+H)$^+$]: 380.

Step 7: Preparation of 6-amino-9-[(3-chloro-4-methyl-phenyl)methyl]-2-(propylsulfonimidoyl)-7H-purin-8-one

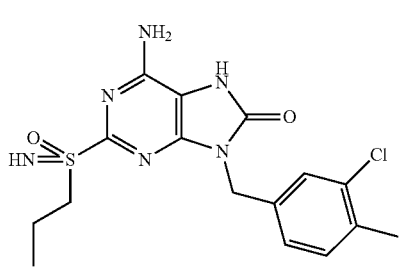

36

The title compound was prepared in analogy to Example 15, Step 7 by using 6-amino-9-[(3-chloro-4-methyl-phenyl)methyl]-2-propylsulfinyl-7H-purin-8-one (155 mg, compound 36f) instead of 6-amino-9-[(2-chlorophenyl)methyl]-2-propylsulfinyl-7H-purin-8-one (compound 15f). 6-Amino-9-[(3-chloro-4-methyl-phenyl)methyl]-2-(propylsulfonimidoyl)-7H-purin-8-one (34 mg, Example 36) was obtained as a gray solid. $^1$H NMR (400 MHz, DMSO-d$_6$) δ ppm: 7.39 (s, 1H), 7.31 (d, J=8.0 Hz, 1H), 7.20 (d, J=8.0 Hz, 1H), 7.03 (br. s., 2H), 4.93 (s, 2H), 4.02 (s, 1H), 3.30-3.27 (m, 2H), 1.72-1.54 (m, 2H), 0.91 (t, J=8.0 Hz, 3H). MS obsd. (ESI$^+$) [(M+H)$^+$]: 395.

Example 37

6-Amino-9-[(4-methylsulfonylphenyl)methyl]-2-(propylsulfonimidoyl)-7H-purin-8-one

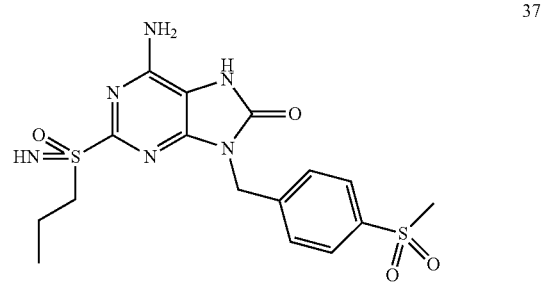 [SMILES: CCCS(=N)(=O)c1nc(N)c2[nH]c(=O)n(Cc3ccc(S(C)(=O)=O)cc3)c2n1]

37

Step 1: Preparation of 6-chloro-N-[(4-methylsulfonylphenyl)methyl]-5-nitro-2-propylsulfanyl-pyrimidin-4-amine

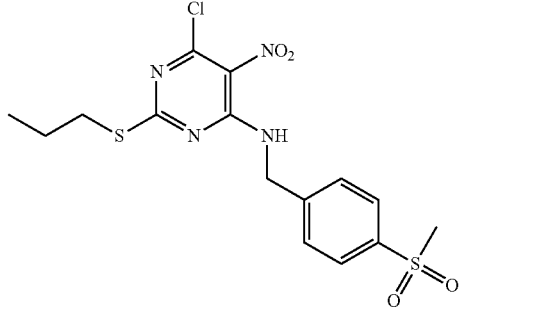

37a

Compound 37a was prepared in analogy to Example 15, Step 1 by using (4-methylsulfonylphenyl)methylamine instead of (2-chlorophenyl)methylamine. 6-Chloro-N-[(4-methylsulfonylphenyl)methyl]-5-nitro-2-propylsulfanyl-pyrimidin-4-amine (3.6 g, compound 37a) was obtained as a yellow solid. MS obsd. (ESI$^+$) [(M+H)$^+$]: 417.

Step 2: Preparation of 6-chloro-N4-[(4-methylsulfonylphenyl)methyl]-2-propylsulfanyl-pyrimidine-4,5-diamine

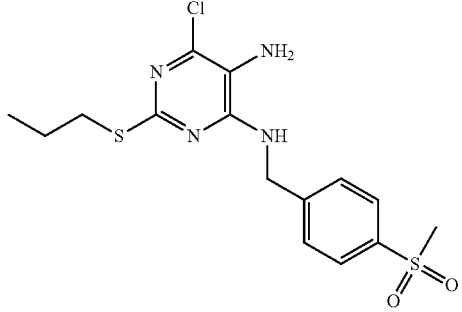

37b

Compound 37b was prepared in analogy to Example 15, Step 2 by using 6-chloro-N-[(4-methylsulfonylphenyl)methyl]-5-nitro-2-propylsulfanyl-pyrimidin-4-amine (compound 37a) instead of 6-chloro-N-[(2-chlorophenyl)methyl]-5-nitro-2-propylsulfanyl-pyrimidin-4-amine (compound 15a). 6-Chloro-N4-[(4-methylsulfonylphenyl)methyl]-2-propylsulfanyl-pyrimidine-4,5-diamine (3.2 g, compound 37b) was obtained as a white solid. MS obsd. (ESI+) [(M+H)+]: 387.

Step 3: Preparation of 6-chloro-9-[(4-methylsulfonylphenyl)methyl]-2-propylsulfanyl-7H-purin-8-one

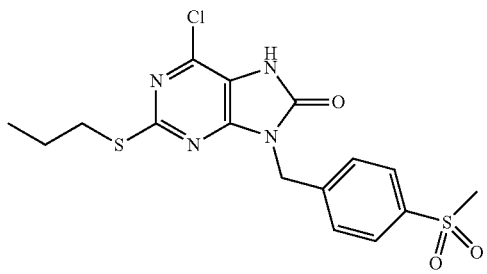

37c

Compound 37c was prepared in analogy to Example 15, Step 3 by using 6-chloro-N4-[(4-methylsulfonylphenyl)methyl]-2-propylsulfanyl-pyrimidine-4,5-diamine (compound 37b) instead of 6-chloro-N4-[(2-chlorophenyl)methyl]-2-propylsulfanyl-pyrimidine-4,5-diamine (compound 15b). 6-Chloro-9-[(4-methylsulfonylphenyl)methyl]-2-propylsulfanyl-7H-purin-8-one (2.0 g, compound 37c) was obtained as a white solid. MS obsd. (ESI+) [(M+H)+]: 413.

Step 4: Preparation of 6-[(4-methoxyphenyl)methylamino]-9-[(4-methylsulfonylphenyl)methyl]-2-propylsulfanyl-7H-purin-8-one

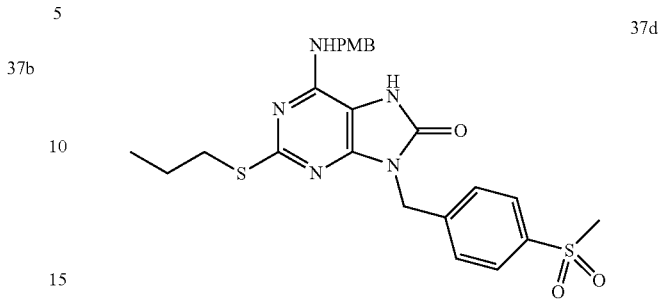

37d

Compound 37d was prepared in analogy to Example 15, Step 4 by using 6-chloro-9-[(4-methylsulfonylphenyl)methyl]-2-propylsulfanyl-7H-purin-8-one (compound 37c) instead of 6-chloro-9-[(2-chlorophenyl)methyl]-2-propylsulfanyl-7H-purin-8-one (compound 15c). 6-[(4-Methoxyphenyl)methylamino]-9-[(4-methylsulfonylphenyl)methyl]-2-propylsulfanyl-7H-purin-8-one (2.2 g, compound 37d) was obtained as a white solid. MS obsd. (ESI+) [(M+H)+]: 514.

Step 5: Preparation of 6-amino-9-[(4-methylsulfonylphenyl)methyl]-2-propylsulfanyl-7H-purin-8-one

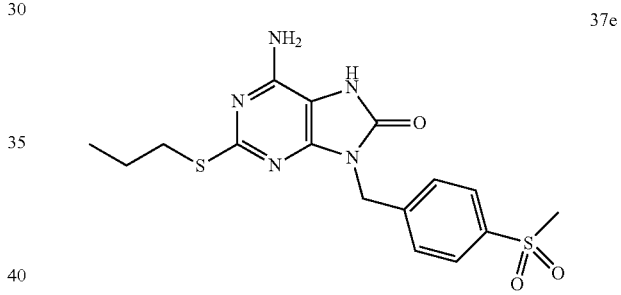

37e

Compound 37e was prepared in analogy to Example 15, Step 5 by using 6-[(4-methoxyphenyl)methylamino]-9-[(4-methylsulfonylphenyl)methyl]-2-propylsulfanyl-7H-purin-8-one (compound 36d) instead of 9-[(2-chlorophenyl)methyl]-6-[(4-methoxyphenyl)methylamino]-2-propylsulfanyl-7H-purin-8-one. 6-Amino-9-[(4-methylsulfonylphenyl)methyl]-2-propylsulfanyl-7H-purin-8-one (1.2 g, compound 37e) was obtained as a white solid. MS obsd. (ESI+) [(M+H)+]: 394.

Step 6: Preparation of 6-amino-9-[(4-methylsulfonylphenyl)methyl]-2-propylsulfinyl-7H-purin-8-one

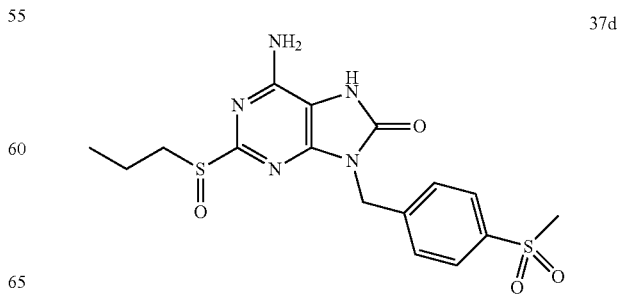

37d

Compound 37d was prepared in analogy to Example 15, Step 6 by using 6-amino-9-[(4-methylsulfonylphenyl)methyl]-2-propylsulfanyl-7H-purin-8-one (compound 37e) instead of 6-amino-9-[(2-chlorophenyl)methyl]-2-propylsulfanyl-7H-purin-8-one (compound 15e). 6-Amino-9-[(4-methylsulfonylphenyl)methyl]-2-propylsulfinyl-7H-purin-8-one (200 mg, compound 37f) was obtained as a white solid. MS obsd. (ESI$^+$) [(M+H)$^+$]: 410.

Step 7: Preparation of 6-amino-2-(propylsulfonimidoyl)-9-[[(2,4-difluorophenyl)methyl]-7H-purin-8-one

37

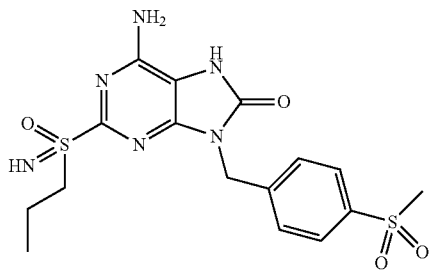

The title compound was prepared in analogy to Example 15, Step 7 by using 6-amino-9-[(4-methylsulfonylphenyl)methyl]-2-propylsulfinyl-7H-purin-8-one (compound 37f) instead of 6-amino-9-[(2-chlorophenyl)methyl]-2-propylsulfinyl-7H-purin-8-one (compound 15f). 6-Amino-9-[(4-methylsulfonylphenyl)methyl]-2-(propylsulfonimidoyl)-7H-purin-8-one (17 mg, Example 37) was obtained as a gray solid. $^1$H NMR (400 MHz, DMSO-d$_6$) δ ppm: 7.89 (d, J=8.0 Hz, 2H), 7.57 (d, J=8.0 Hz, 2H), 7.11 (br. s., 2H), 5.08 (s, 2H), 4.07 (s, 1H), 3.34-3.28 (m, 2H), 3.18 (s, 3H), 1.65-1.57 (m, 2H), 0.89 (t, J=8.0 Hz, 3H). MS obsd. (ESI$^+$) [(M+H)$^+$]: 425.

Example 38

Methyl 4-[[6-amino-8-oxo-2-(propylsulfonimidoyl)-7H-purin-9-yl]methyl]benzoate

38

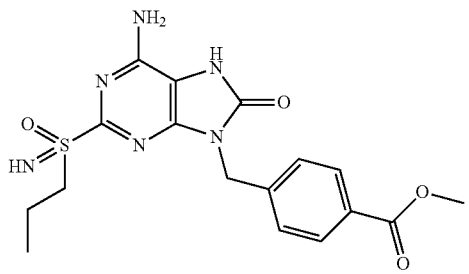

Step 1: Preparation of methyl 4-[[(6-chloro-5-nitro-2-propylsulfanyl-pyrimidin-4-yl)amino]methyl]benzoate

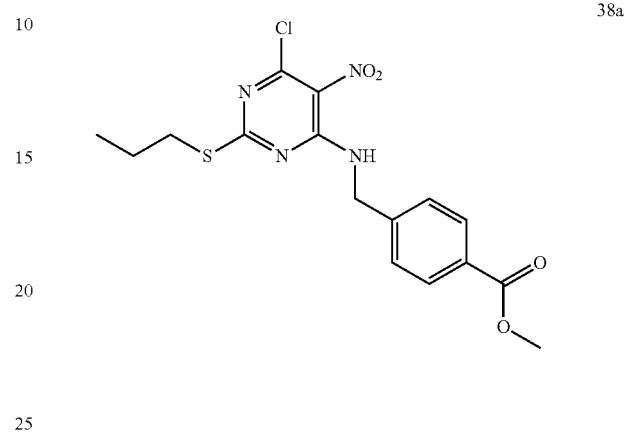

Compound 38a was prepared in analogy to Example 15, Step 1 by using methyl 4-(aminomethyl)benzoate instead of (2-chlorophenyl)methylamine. Methyl 4-[[(6-chloro-5-nitro-2-propylsulfanyl-pyrimidin-4-yl)amino]methyl]benzoate (compound 38a) was obtained as a white solid. MS obsd. (ESI$^+$) [(M+H)$^+$]: 397.

Step 2: Preparation of methyl 4-[[(6-chloro-5-methyl-2-propylsulfanyl-pyrimidin-4-yl)amino]methyl]benzoate

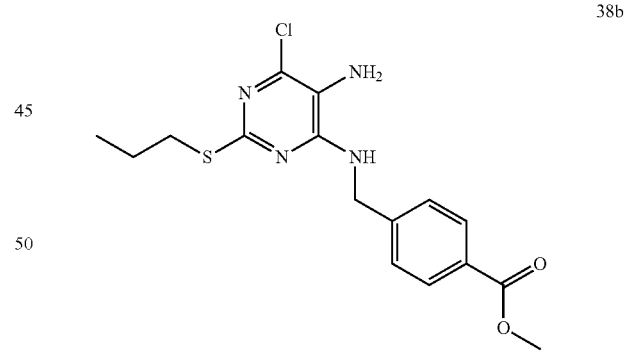

Compound 38b was prepared in analogy to Example 15, Step 2 by using methyl 4-[[(6-chloro-5-nitro-2-propylsulfanyl-pyrimidin-4-yl)amino]methyl]benzoate (compound 38a) instead of 6-chloro-N-[(2-chlorophenyl)methyl]-5-nitro-2-propylsulfanyl-pyrimidin-4-amine (compound 15a). Methyl 4-[[(6-chloro-5-methyl-2-propylsulfanyl-pyrimidin-4-yl)amino]methyl]benzoate (compound 38b) was obtained as a white solid. MS obsd. (ESI$^+$) [(M+H)$^+$]: 366.

Step 3: Preparation of methyl 4-[(6-chloro-8-oxo-2-propylsulfanyl-7H-purin-9-yl)methyl]benzoate

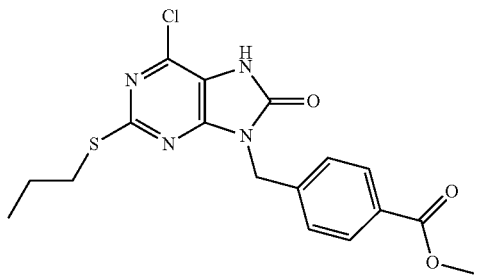

38c

Compound 38c was prepared in analogy to Example 15, Step 3 by using methyl 4-[[(6-chloro-5-methyl-2-propylsulfanyl-pyrimidin-4-yl)amino]methyl]benzoate (compound 38b) instead of 6-chloro-N4-[(2-chlorophenyl)methyl]-2-propylsulfanyl-pyrimidine-4,5-diamine (compound 15b). Methyl 4-[(6-chloro-8-oxo-2-propylsulfanyl-7H-purin-9-yl)methyl]benzoate (compound 38c) was obtained as a white solid. MS obsd. (ESI+) [(M+H)+]: 39.

Step 4: Preparation of methyl 4-[[6-[(4-methoxyphenyl)methylamino]-8-oxo-2-propylsulfanyl-7H-purin-9-yl]methyl]benzoate

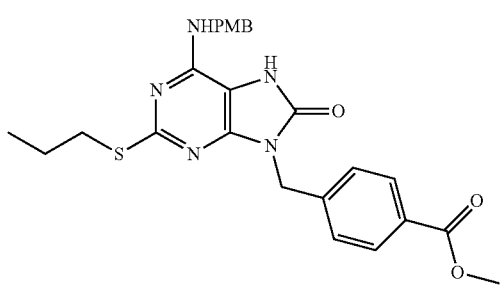

38d

Compound 38d was prepared in analogy to Example 15, Step 4 by using methyl 4-[(6-chloro-8-oxo-2-propylsulfanyl-7H-purin-9-yl)methyl]benzoate (compound 38c) instead of 6-chloro-9-[(2-chlorophenyl)methyl]-2-propylsulfanyl-7H-purin-8-one (compound 15c). Methyl 4-[[6-[(4-methoxyphenyl)methylamino]-8-oxo-2-propylsulfanyl-7H-purin-9-yl]methyl]benzoate (compound 38d) was obtained as a white solid. MS obsd. (ESI+) [(M+H)+]: 494.

Step 5: Preparation of methyl 4-[(6-amino-8-oxo-2-propylsulfanyl-7H-purin-9-yl)methyl]benzoate

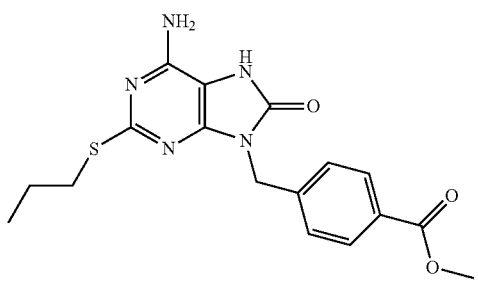

38e

Compound 38e was prepared in analogy to Example 15, Step 5 by using methyl 4-[[6-[(4-methoxyphenyl)methylamino]-8-oxo-2-propylsulfanyl-7H-purin-9-yl]methyl]benzoate (compound 38d) instead of 9-[(2-chlorophenyl)methyl]-6-[(4-methoxyphenyl)methylamino]-2-propylsulfanyl-7H-purin-8-one (compound 15d). Methyl 4-[(6-amino-8-oxo-2-propylsulfanyl-7H-purin-9-yl)methyl]benzoate (compound 38e) was obtained as a white solid. MS obsd. (ESI+) [(M+H)+]: 374.

Step 6: Preparation of methyl 4-[(6-amino-8-oxo-2-propylsulfinyl-7H-purin-9-yl)methyl]benzoate

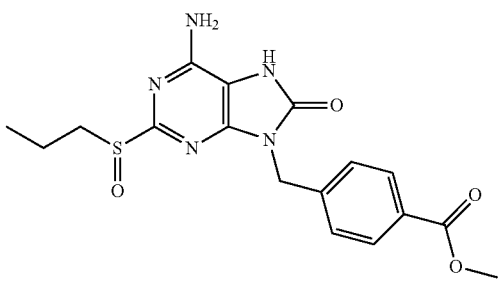

38f

Compound 38f was prepared in analogy to Example 15, Step 6 by using methyl 4-[(6-amino-8-oxo-2-propylsulfanyl-7H-purin-9-yl)methyl]benzoate (compound 38e) instead of 6-amino-9-[(2-chlorophenyl)methyl]-2-propylsulfanyl-7H-purin-8-one (compound 15e). Methyl 4-[(6-amino-8-oxo-2-propylsulfinyl-7H-purin-9-yl)methyl]benzoate (compound 38f) was obtained as a white solid MS obsd. (ESI+) [(M+H)+]: 390.

Step 7: Preparation of methyl 4-[[6-amino-8-oxo-2-(propylsulfonimidoyl)-7H-purin-9-yl]methyl]benzoate

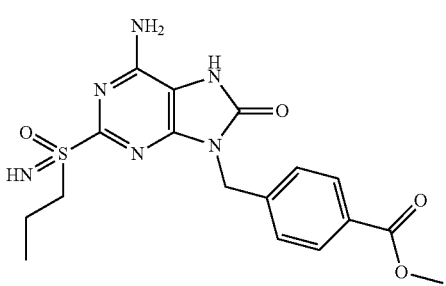

38

The title compound was prepared in analogy to Example 15, Step 7 by using methyl 4-[(6-amino-8-oxo-2-propylsulfinyl-7H-purin-9-yl)methyl]benzoate (compound 38f) instead of 6-amino-9-[(2-chlorophenyl)methyl]-2-propylsulfinyl-7H-purin-8-one. Methyl 4-[[6-amino-8-oxo-2-(propylsulfonimidoyl)-7H-purin-9-yl]methyl]benzoate (127 mg, Example 38) was obtained as a white solid. $^1$H NMR (400 MHz DMSO-$d_6$) δ ppm: 10.75 (br. s., 1H), 7.92 (d, J=8.0 Hz, 2H), 7.45 (d, J=8.0 Hz, 2H), 6.99 (br. s., 2H), 5.05 (s, 2H), 4.00 (s, 1H), 3.84 (s, 3H), 3.32-3.27 (m, 2H), 1.64-1.56 (m, 2H), 0.88 (t, J=8.0 Hz, 3H). MS obsd. (ESI+) [(M+H)+]: 405.

Example 39

4-[[6-Amino-8-oxo-2-(propylsulfonimidoyl)-7H-purin-9-yl]methyl]benzoic acid

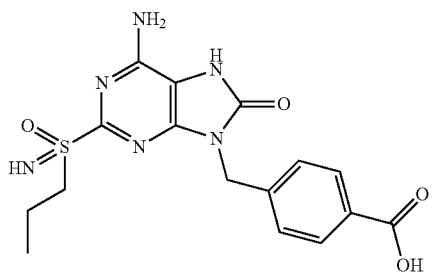

To a solution of methyl 4-[[6-amino-8-oxo-2-(propylsulfonimidoyl)-7H-purin-9-yl]methyl]benzoate (70 mg, compound 38) in THF/MeOH (2/1, V/V, 3 mL) was added aqueous LiOH (0.34 mL, 0.34 mmol, 1M) and the mixture was stirred at 25° C. for 3 hrs. Then the reaction mixture was acidified by the addition of 1N HCl. The formed solid was collected by filtration and purified by prep-HPLC to give 4-[[6-amino-8-oxo-2-(propylsulfonimidoyl)-7H-purin-9-yl]methyl]benzoic acid (38 mg, Example 39). $^1$H NMR (400 MHz DMSO-$d_6$) δ ppm: 10.76 (br. s., 1H), 7.89 (d, J=8.0 Hz, 2H), 7.41 (d, J=8.0 Hz, 2H), 7.03 (br. s., 2H), 5.04 (s, 2H), 4.05 (s, 1H), 3.32-3.27 (m, 2H), 1.63-1.55 (m, 2H), 0.88 (t, J=8.0 Hz, 3H). MS obsd. (ESI$^+$) [(M+H)$^+$]: 391.

Example 40

4-[[6-Amino-8-oxo-2-(propylsulfonimidoyl)-7H-purin-9-yl]methyl]-N-(2-methoxyethyl)benzamide

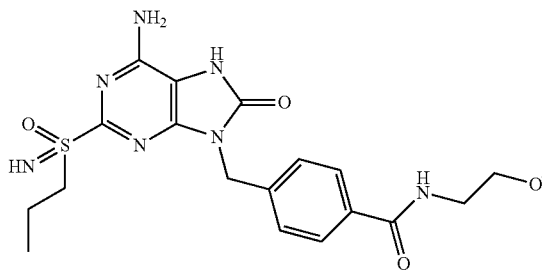

To a solution of 4-[[6-amino-8-oxo-2-(propylsulfonimidoyl)-7H-purin-9-yl]methyl]benzoic acid (100 mg, compound 39), HATU (146 mg, 0.38 mmol) and anhydrous DIPEA (89 μL, 0.51 mmol) in anhydrous DMF (5 mL) was added 2-methoxyethanamine (44 μL, 0.51 mmol). The reaction mixture was stirred at rt overnight and then evaporated in vacuo. The residue was purified by Prep-HPLC to give 4-[[6-amino-8-oxo-2-(propylsulfonimidoyl)-7H-purin-9-yl]methyl]-N-(2-methoxyethyl)benzamide (18 mg, Example 40) as a white solid. $^1$H NMR (400 MHz, DMSO-$d_6$) δ ppm: 10.59 (s, 1H), 8.44-8.61 (m, 1H), 7.80 (d, J=7.50 Hz, 2H), 7.40 (d, J=7.49 Hz, 2H), 6.98 (br. s., 2H), 5.01 (s, 2H), 4.04 (br. s., 1H), 3.38-3.44 (m, 4H), 3.29-3.30 (m, 2H), 3.25 (s, 3H), 1.58-1.66 (m, 2H), 0.91 (t, J=7.53 Hz, 3H). MS obsd. (ESI$^+$) [(M$^+$H)$^+$]: 448

Example 41

6-Amino-9-[[4-(piperidine-1-carbonyl)phenyl]methyl]-2-(propylsulfonimidoyl)-7H-purin-8-one

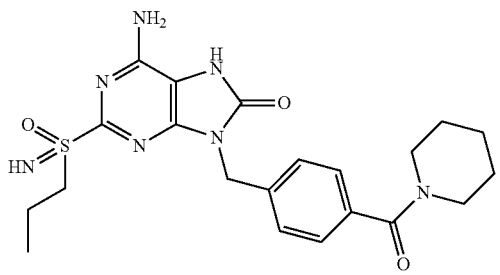

The title compound was prepared in analogy to Example 40 by using piperidine instead of 2-methoxyethanamine. 6-Amino-9-[[4-(piperidine-1-carbonyl)phenyl]methyl]-2-(propylsulfonimidoyl)-7H-purin-8-one (6.5 mg, Example 41) was obtained as a white solid. $^1$H NMR (400 MHz, DMSO-$d_6$) δ ppm: 10.80 (s, 1H), 7.31-7.39 (m, 4H), 7.04 (br. s., 2H), 5.00 (s, 2H), 4.03 (s, 1H), 3.55 (br. s., 2H), 3.26-3.39 (m, 4H), 1.43-1.68 (m, 8H), 0.93 (t, J=7.40 Hz, 3H). MS obsd. (ESI$^+$) [(M$^+$H)$^+$]: 458.

Example 42

6-Amino-2-(propylsulfonimidoyl)-9-[[4-(pyrrolidine-1-carbonyl)phenyl]methyl]-7H-purin-8-one

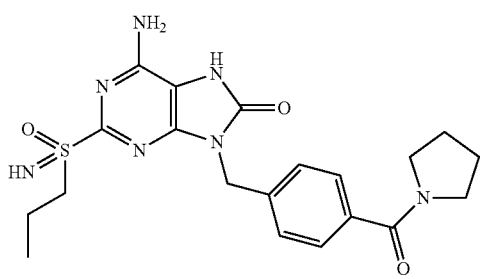

The title compound was prepared in analogy to Example 40 by using pyrrolidine instead of 2-methoxyethanamine. 6-Amino-2-(propylsulfonimidoyl)-9-[[4-(pyrrolidine-1-carbonyl)phenyl]methyl]-7H-purin-8-one (8.0 mg, Example 42) was obtained as a white solid. $^1$H NMR (400 MHz, DMSO-$d_6$) δ ppm: 10.60 (s, 1H), 7.48 (d, J=7.31 Hz, 2H), 7.37 (d, J=8.03 Hz, 2H), 6.99 (br. s., 2H), 5.00 (s, 2H), 4.10 (s, 1H), 3.40-3.46 (m, 2H), 3.31-3.34 (m, 4H), 1.62-1.67 (m, 4H), 1.62-1.67 (m, 2H), 0.91 (t, J=7.40 Hz, 3H). MS obsd. (ESI$^+$) [(M$^+$H)$^+$]: 444

Example 43

6-Amino-2-(propylsulfonimidoyl)-9-(pyrimidin-5-ylmethyl)-7H-purin-8-one

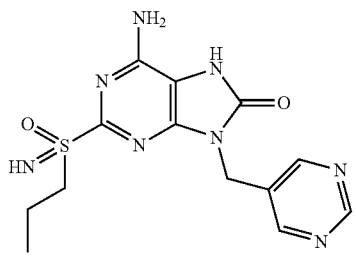

43

Step 1: Preparation of 6-chloro-5-nitro-2-propylsulfanyl-N-(pyrimidin-5-ylmethyl)pyrimidin-4-amine

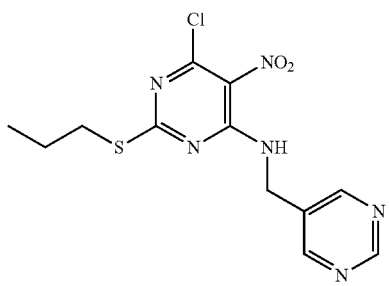

43a

Compound 43a was prepared in analogy to Example 15, Step 1 by using 4,6-dichloro-5-nitro-2-(propylthio)pyrimidine instead of (2-chlorophenyl)methylamine. 6-Chloro-5-nitro-2-(propylthio)-N-(pyrimidin-5-ylmethyl)-pyrimidin-4-amine (4.0 g, compound 43a) was obtained as a light yellow oil. MS obsd. (ESI$^+$) [(M+H)$^+$]: 341.

Step 2: Preparation of 6-chloro-2-propylsulfanyl-N4-(pyrimidin-5-ylmethyl)pyrimidine-4,5-diamine

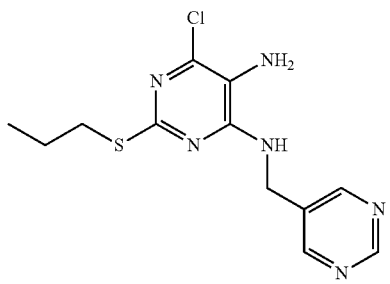

43b

Compound 43b was prepared in analogy to Example 15, Step 2 by using 6-chloro-5-nitro-2-(propylthio)-N-(pyrimidin-5-ylmethyl) pyrimidin-4-amine (compound 43a) instead of 6-chloro-N-[(2-chlorophenyl)methyl]-5-nitro-2-propylsulfanyl-pyrimidin-4-amine (compound 15a). 6-Chloro-2-propylsulfanyl-N4-(pyrimidin-5-ylmethyl)pyrimidine-4,5-diamine (1.0 g, compound 43b) was obtained as a white solid. MS obsd. (ESI$^+$) [(M+H)$^+$]: 311.

Step 3: Preparation of 6-chloro-2-propylsulfanyl-9-(pyrimidin-5-ylmethyl)-7H-purin-8-one

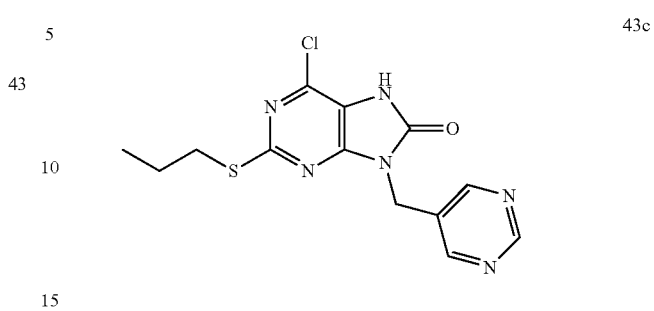

43c

Compound 43c was prepared in analogy to Example 15, Step 3 by using 6-Chloro-2-propylsulfanyl-N4-(pyrimidin-5-ylmethyl)pyrimidine-4,5-diamine (compound 43b) instead of 6-chloro-N4-[(2-chlorophenyl)methyl]-2-propyl-sulfanyl-pyrimidine-4,5-diamine (compound 15b). 6-Chloro-2-propylsulfanyl-9-(pyrimidin-5-ylmethyl)-7H-purin-8-one (0.5 g, compound 43c) was obtained as a white solid. MS obsd. (ESI$^+$) [(M+H)$^+$]: 337.

Step 4: Preparation of 6-[(4-methoxyphenyl)methylamino]-2-propylsulfanyl-9-(pyrimidin-5-ylmethyl)-7H-purin-8-one

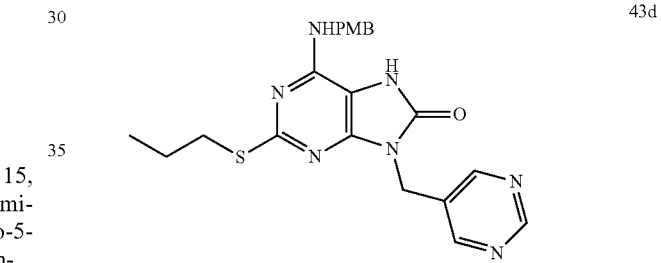

43d

Compound 43d was prepared in analogy to Example 15, Step 4 by using 6-chloro-2-propylsulfanyl-9-(pyrimidin-5-ylmethyl)-7H-purin-8-one (compound 43c) instead of 6-chloro-9-[(2-chlorophenyl)methyl]-2-propylsulfanyl-7H-purin-8-one (compound 15c). 6-[(4-Methoxyphenyl)methylamino]-2-propylsulfanyl-9-(pyrimidin-5-ylmethyl)-7H-purin-8-one (300 mg, compound 43d) was obtained as a white solid. MS obsd. (ESI$^+$) [(M+H)$^+$]: 438.

Step 5: Preparation of 6-[(4-methoxyphenyl)methylamino]-2-propylsulfinyl-9-(pyrimidin-5-ylmethyl)-7H-purin-8-one

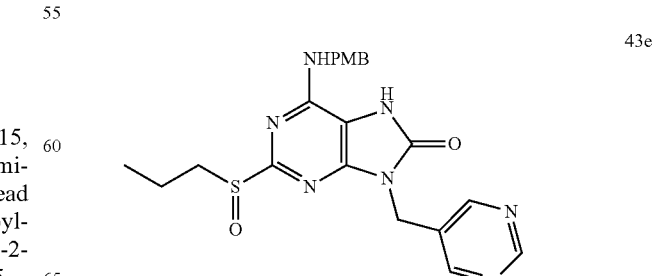

43e

Compound 43e was prepared in analogy to Example 15, Step 6 by using 6-[(4-methoxyphenyl)methylamino]-2-propylsulfanyl-9-(pyrimidin-5-ylmethyl)-7H-purin-8-one (compound 43d) instead of 6-amino-9-[(2-chlorophenyl)methyl]-2-propylsulfanyl-7H-purin-8-one (compound 15e). 6-[(4-Methoxyphenyl)methylamino]-2-propylsulfinyl-9-(pyrimidin-5-ylmethyl)-7H-purin-8-one (280 mg, compound 43e) was obtained as a white solid. MS obsd. (ESI⁺) [(M+H)⁺]: 454.

Step 6: Preparation of 6-amino-2-(propylsulfonimidoyl)-9-(pyrimidin-5-ylmethyl)-7H-purin-8-one

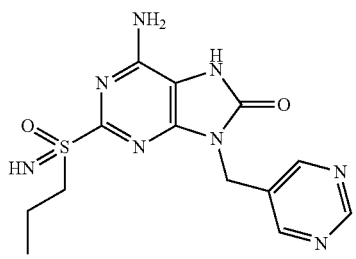

43

The title compound was prepared in analogy to Example 15, Step 7 by using 6-[(4-methoxyphenyl)methylamino]-2-propylsulfinyl-9-(pyrimidin-5-ylmethyl)-7H-purin-8-one (compound 43e) instead of 6-amino-9-[(2-chlorophenyl)methyl]-2-propylsulfinyl-7H-purin-8-one (compound 15f). 6-Amino-2-(propylsulfonimidoyl)-9-(pyrimidin-5-ylmethyl)-7H-purin-8-one (70 mg, Example 43) was obtained as a white solid. ¹H NMR (400 MHz, DMSO-d₆) δ ppm: 9.13 (s, 1H), 8.83 (s, 2H), 7.07 (br. s., 2H), 5.04 (s, 2H), 4.08 (s, 1H), 3.27-3.34 (m, 2H), 1.50-1.69 (m, 2H), 0.92 (t, J=7.2 Hz, 3H). MS obsd. (ESI⁺) [(M+H)⁺]: 349.

Example 44

6-Amino-9-[(2-methylpyrimidin-5-yl)methyl]-2-(propylsulfonimidoyl)-7H-purin-8-one

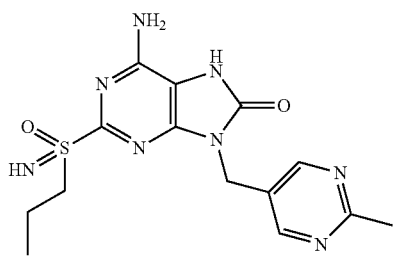

44

Step 1: Preparation of N,N'-[2-[1-(dimethylamino)methylidene]propane-1,3-diylidene]bis(N-methylmethanaminium) bis(tetrafluoroborate)

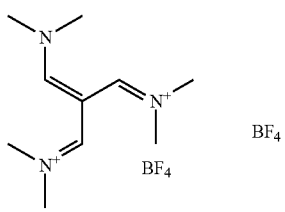

44a

To cooled DMF (400 mL) in a round-bottomed flask was added POCl₃ (165.5 g) at −10° C. The reaction mixture was stirred at 0° C. for 3 hrs. To this reaction mixture was added 2-bromoacetic acid (50 g, 360 mmol) at 0° C. The resulting reaction mixture was stirred at 80° C. for 16 hrs, then DMF was removed in vacuo. The dark red residue was cooled down to room temperature and sodium tetrafluoroborate (100 g, 911 mmol) was added into the residue. After the reaction mixture was cooled in ice bath, N,N'-[2-[1-(dimethylamino)methylidene]propane-1,3-diylidene]bis(N-methylmethanaminium) bis(tetrafluoroborate) (120 g, compound 44a) was obtained by filtration as a brown solid and used in next step without purification.

Step 2: Preparation of 2-methylpyrimidine-5-carbaldehyde

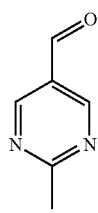

44b

To a mixture of N,N'-[2-[1-(dimethylamino)methylidene]propane-1,3-diylidene]bis(N-methylmethanaminium) bis(tetrafluoroborate) (70 g, 196 mmol, compound 44a) and acetamidine HCl (37 g, 392 mmol) in MeCN/H₂O (400 mL, V/V=1/1) was added NaOH (120 g, 3.0 mmol) at 15° C., and the resulting reaction mixture was stirred at 15° C. for 16 hrs. The reaction mixture was neutralized to pH 6-7 with AcOH, extracted by ethyl acetate (100 mL) three times. The separated organic layer was dried over sodium sulfate, filtered and concentrated in vacuo. The residue was purified by column chromatography to afford 2-methylpyrimidine-5-carbaldehyde (10 g, compound 44b) as a yellow solid.

Step 3: Preparation of (2-methylpyrimidin-5-yl)methanol

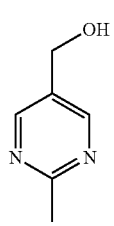

44c

To a mixture of 2-methylpyrimidine-5-carbaldehyde (8 g, 66 mmol, compound 44b) in MeOH (100 mL) was added NaBH₄ (7.5 g, 197 mmol) at 0° C., and the resulting reaction mixture was stirred at 15° C. for 3 hrs. Then the reaction mixture was quenched by saturated NH₄Cl solution (30 mL), extracted by ethyl acetate (20 mL) three times. The separated organic layer was dried over sodium sulfate, filtered and concentrated in vacuo. The residue was purified by column chromatography to afford (2-methylpyrimidin-5-yl)methanol (4.1 g, 51%, compound 44c) as a white solid.

Step 4: Preparation of 5-(azidomethyl)-2-methylpyrimidine

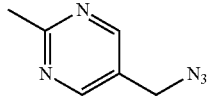

44d

To a mixture of (2-methylpyrimidin-5-yl)methanol (4.1 g, 33 mmol, compound 44c) in CHCl₃ (40 mL) and toluene (40 mL) was added DPPA (27 g, 83 mmol) and DBU (25 g, 164 mmol) at 0° C. and stirred at 15° C. for 16 hrs. The reaction mixture was diluted with DCM (100 mL) and washed with water (50 mL). The separated organic layer was dried over anhydrous sodium sulfate, filtered and concentrated in vacuo. The residue was purified by column chromatography to afford crude 5-(azidomethyl)-2-methylpyrimidine (2.8 g, compound 44d) as a light oil.

Step 5: Preparation of (2-methylpyrimidin-5-yl)methanamine

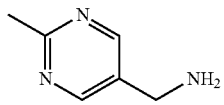

44e

A mixture of 5-(azidomethyl)-2-methylpyrimidine (2.8 g, 18.8 mmol, compound 44d) and Pd/C (500 mg) in MeOH (100 mL) was stirred under 1 atm of H₂ atmosphere at 15° C. for 1 hour. Then the reaction mixture was filtered, and the filtrate was concentrated in vacuo to afford (2-methylpyrimidin-5-yl)methanamine (1.8 g, 78%, compound 44e) as a white solid.

Step 6: 6-Chloro-N4-[(2-methylpyrimidin-5-yl)methyl]-5-nitro-2-propylsulfanyl-pyrimidin-4-amine

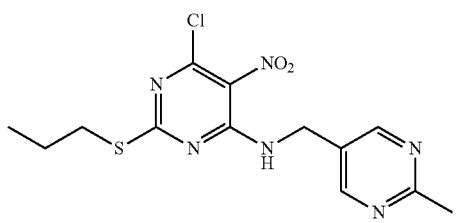

44f

Compound 44f was prepared in analogy to Example 15, Step 1 by using (2-methylpyrimidin-5-yl)methanamine (compound 44e) instead of (2-chlorophenyl)methylamine. 6-Chloro-N4-[(2-methylpyrimidin-5-yl)methyl]-5-nitro-2-propylsulfanyl-pyrimidin-4-amine (2.8 g, compound 44f) was obtained as a light yellow oil. MS obsd. (ESI⁺) [(M+H)⁺]: 355.

Step 7: Preparation of 6-chloro-N4-[(2-methylpyrimidin-5-yl)methyl]-2-propylsulfanyl-pyrimidine-4,5-diamine

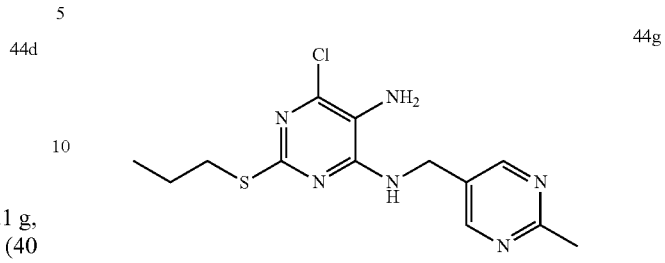

44g

Compound 44g was prepared in analogy to Example 15, Step 2 by using 6-chloro-N4-[(2-methylpyrimidin-5-yl)methyl]-2-propylsulfanyl-pyrimidine-4,5-diamine (compound 44f) instead of 6-chloro-N-[(2-chlorophenyl)methyl]-5-nitro-2-propylsulfanyl-pyrimidin-4-amine (compound 15a). 6-Chloro-N4-[(2-methylpyrimidin-5-yl)methyl]-2-propylsulfanyl-pyrimidine-4,5-diamine (2.1 g, compound 44g) was obtained and used in the next step without further purification. MS obsd. (ESI⁺) [(M+H)⁺]: 325.

Step 8: Preparation of 6-chloro-9-[(2-methylpyrimidin-5-yl)methyl]-2-propylsulfanyl-7H-purin-8-one

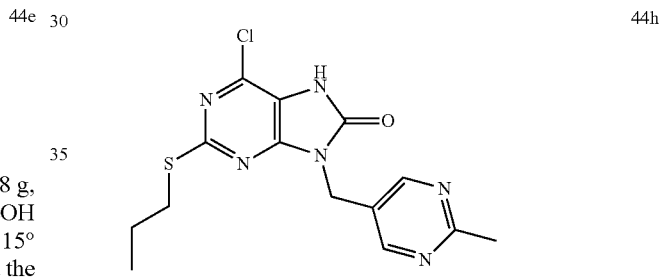

44h

Compound 44h was prepared in analogy to Example 15, Step 3 by using 6-chloro-N4-[(2-methylpyrimidin-5-yl)methyl]-2-propylsulfanyl-pyrimidine-4,5-diamine (compound 44g) instead of 6-chloro-N4-[(2-chlorophenyl)methyl]-2-propylsulfanyl-pyrimidine-4,5-diamine (compound 15b). 6-Chloro-9-[(2-methylpyrimidin-5-yl)methyl]-2-propylsulfanyl-7H-purin-8-one (1.8 g, compound 44h) was obtained as a white solid. MS obsd. (ESI⁺) [(M+H)⁺]: 351.

Step 9: Preparation of 6-[(4-methoxyphenyl)methylamino]-9-[(2-methylpyrimidin-5-yl)methyl]-2-propylsulfanyl-7H-purin-8-one

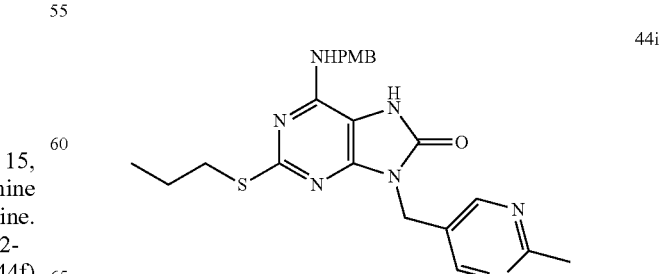

44i

Compound 44i was prepared in analogy to Example 15, Step 4 by using 6-chloro-9-[(2-methylpyrimidin-5-yl)methyl]-2-propylsulfanyl-7H-purin-8-one (compound 44h) instead of 6-chloro-9-[(2-chlorophenyl)methyl]-2-propylsulfanyl-7H-purin-8-one (compound 15c). 6-[(4-Methoxyphenyl)methylamino]-2-propylsulfanyl-9-(pyrimidin-5-ylmethyl)-7H-purin-8-one (500 mg, compound 44i) was obtained as a white solid. MS obsd. (ESI+) [(M+H)+]: 452.

Step 10: Preparation of 6-[(4-methoxyphenyl)methylamino]-9-[(2-methylpyrimidin-5-yl)methyl]-2-propylsulfinyl-7H-purin-8-one

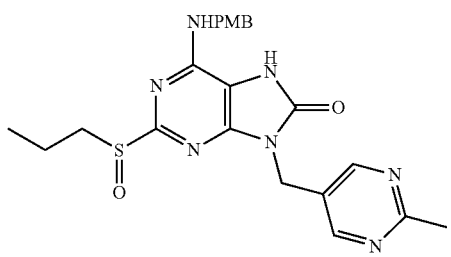

44j

Compound 44j was prepared in analogy to Example 15, Step 6 by using 6-[(4-methoxyphenyl)methylamino]-2-propylsulfanyl-9-(pyrimidin-5-ylmethyl)-7H-purin-8-one (compound 43i) instead of 6-amino-9-[(2-chlorophenyl)methyl]-2-propylsulfanyl-7H-purin-8-one (compound 15e). 6-[(4-Methoxyphenyl)methylamino]-9-[(2-methylpyrimidin-5-yl)methyl]-2-propylsulfinyl-7H-purin-8-one (420 mg, compound 44j) was obtained as a white solid. MS obsd. (ESI+) [(M+H)+]: 468.

Step 11: Preparation of 6-amino-9-[(2-methylpyrimidin-5-yl)methyl]-2-(propylsulfonimidoyl)-7H-purin-8-one

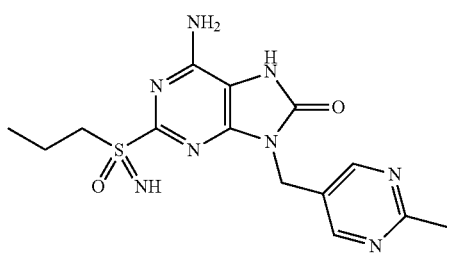

44

The title compound was prepared in analogy to Example 15, Step 7 by using 6-[(4-methoxyphenyl)methylamino]-9-[(2-methylpyrimidin-5-yl)methyl]-2-propylsulfinyl-7H-purin-8-one (compound 44j) instead of 6-amino-9-[(2-chlorophenyl)methyl]-2-propylsulfinyl-7H-purin-8-one (compound 15f). 6-Amino-9-[(2-methylpyrimidin-5-yl)methyl]-2-(propylsulfonimidoyl)-7H-purin-8-one (16.5 mg, Example 44) was obtained as a white solid. $^1$H NMR (400 MHz, DMSO-$d_6$) δ ppm: 8.71 (s, 2H), 6.98 (s, 2H), 4.99 (s, 2H), 4.10 (s, 2H), 3.35 (m, 2H), 2.59 (s, 3H), 1.65-1.62 (m, 2H), 0.95-0.91 (t, J=7.2 Hz, 3H). MS obsd. (ESI+) [(M+H)+]: 363.

Example 46

N-[(6-Amino-9-benzyl-8-oxo-7H-purin-2-yl)-oxo-propyl-λ$^4$-sulfanylidene]pentanamide

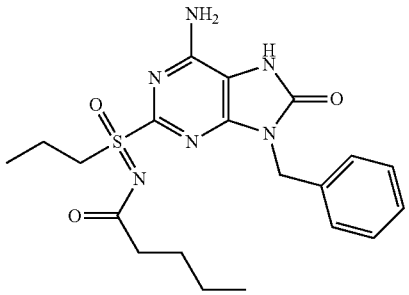

46

To the solution of 6-amino-9-benzyl-2-(propylsulfonimidoyl)-7H-purin-8-one (70 mg, 0.21 mmol, compound 4) in pyridine (2 mL) was added valeric acid anhydride (41 mg, 0.22 mmol). The reaction mixture was stirred at RT for 6 hrs. After reaction, the solvent was removed in vacuo. The residue was purified by prep-HPLC to give N-[(6-amino-9-benzyl-8-oxo-7H-purin-2-yl)-oxo-propyl-λ$^4$-sulfanylidene]pentanamide (13.7 mg, Example 46). $^1$H NMR (400 MHz, DMSO-$d_6$) δ ppm: 7.29-7.32 (m, 5H), 7.19 (br. s., 2H), 4.90 (m, 2H), 3.48-3.50 (m, 2H), 2.17 (t, J=7.2 Hz, 2H), 1.50-1.70 (m, 2H), 1.39-1.47 (m, 2H), 1.61-1.76 (m, 1H), 1.47-1.59 (m, 1H), 0.89 (t, J=7.40 Hz, 3H), 0.80 (t, J=7.39 Hz, 3H). MS obsd. (ESI+) [(M+H)+]: 431.

Example 47

N-[[6-Amino-9-[(4-chlorophenyl)methyl]-8-oxo-7H-purin-2-yl]-oxo-propyl-λ$^4$-sulfanylidene]acetamide

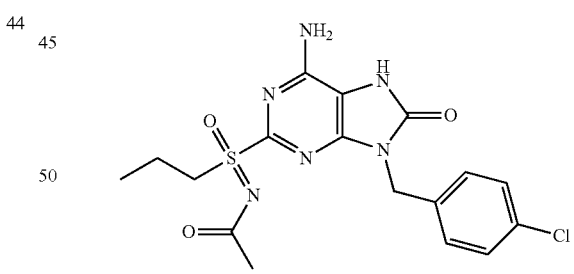

47

The title compound was prepared in analogy to Example 46 by using acetic anhydride and 6-amino-9-(4-chlorobenzylmethyl)-2-(propylsulfonimidoyl)-7H-purin-8-one (compound 9) instead of valeric acid anhydride and 6-amino-9-benzyl-2-(propylsulfonimidoyl)-7H-purin-8-one (Example 4). N-[[6-Amino-9-[(4-chlorophenyl)methyl]-8-oxo-7H-purin-2-yl]-oxo-propyl-λ$^4$-sulfanylidene]acetamide (2 mg, Example 47) was obtained as a white solid. $^1$H NMR (400 MHz, DMSO-$d_6$) δ ppm: 7.31-7.40 (m, 4H), 7.29 (br. s., 2H), 4.95 (s, 2H), 3.42-3.57 (m, 2H), 1.90 (s, 3H), 1.61-1.76 (m, 1H), 1.47-1.59 (m, 1H), 0.89 (t, J=7.40 Hz, 3H). MS obsd. (ESI+) [(M+H)+]: 423.

Example 48

N-[(6-Amino-9-benzyl-8-oxo-7H-purin-2-yl)-methyl-oxo-λ⁴-sulfanylidene]acetamide

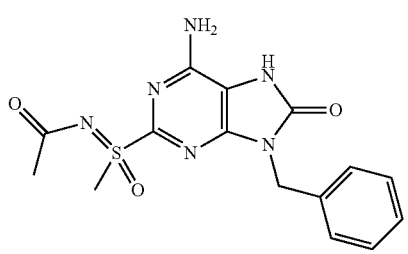

The title compound was prepared in analogy to Example 46 by using acetic anhydride instead of valeric acid anhydride. N-[(6-amino-9-benzyl-8-oxo-7H-purin-2-yl)-methyl-oxo-λ⁴-sulfanylidene]acetamide (44 mg, Example 48) was obtained as a white solid. $^1$H NMR (400 MHz, DMSO-$d_6$) δ ppm: 10.80 (br. s., 1H), 7.26-7.36 (m, 5H), 7.18 (br. s., 2H), 4.96 (s, 2H), 3.39 (s, 3H), 1.91 (s, 3H). MS obsd. (ESI$^+$) [(M+H)$^+$]: 361.

Example 49

4-[[(6-Amino-9-benzyl-8-oxo-7H-purin-2-yl)-oxo-propyl-λ⁴-sulfanylidene]amino]-4-oxo-butanoic acid

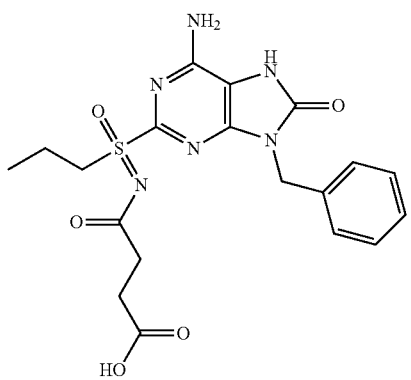

The title compound was prepared in analogy to Example 46 by using succinic anhydride instead of valeric acid anhydride. 4-[[[6-Amino-9-[(4-chlorophenyl)methyl]-8-oxo-7H-purin-2-yl]-oxo-propyl-λ⁴-sulfanylidene]amino]-4-oxo-butanoic acid (500 mg, Example 49) was obtained as a white solid. $^1$H NMR (400 MHz, DMSO-$d_6$) δ ppm: 7.31-7.41 (m, 5H), 7.21 (br. s., 2H), 4.88-5.00 (m, 2H), 3.40-3.64 (m, 2H), 2.41-2.46 (m, 2H), 2.30-2.36 (m, 2H), 1.56-1.66 (m, 2H), 0.89 (t, J=7.4 Hz, 3H). MS obsd. (ESI$^+$) [(M+H)$^+$]: 481.

Separation of compound of Example 49 by chiral HPLC afforded Example 49-A (faster eluting, 105 mg) and Example 49-B (slower eluting, 106.1 mg) as white solid. (Separation condition: methanol 5%-40% (0.05% DEA)/CO$_2$ on ChiralPak IC-3 column.)

Example 49-A $^1$H NMR (400 MHz, DMSO-$d_6$) δ ppm: 7.40 (m, 2H), 7.27-7.30 (m, 5H), 4.95 (s, 2H), 3.44-3.55 (m, 2H), 2.42-2.45 (m, 2H), 2.28-2.32 (m, 2H), 1.55-1.69 (m, 2H), 0.87-0.910.87 (t, J=7.8 Hz, 3H). MS obsd. (ESI$^+$) [(M+H)$^+$]: 481

Example 49-B $^1$H NMR (400 MHz, DMSO-$d_6$) δ ppm: 7.46 (s, 2H), 7.26-7.32 (m, 5H), 4.95 (s, 2H), 3.48-3.53 (m, 2H), 2.42-2.45 (m, 2H), 2.28-2.31 (m, 2H), 1.55-1.69 (m, 2H), 0.87-0.90 (t, J=7.8 Hz, 3H). MS obsd. (ESI$^+$) [(M+H)$^+$]: 481

Example 50

Ethyl 4-[[(6-amino-9-benzyl-8-oxo-7H-purin-2-yl)-oxo-propyl-λ⁴-sulfanylidene]amino]-4-oxo-butanoate

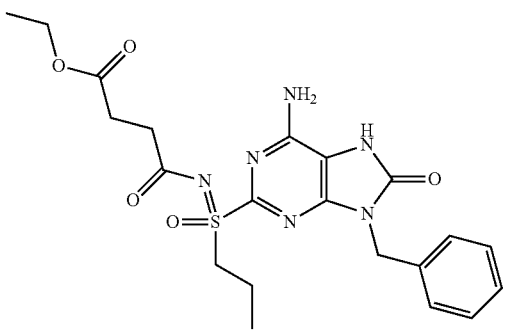 [SMILES: CCCS(=O)(=NC(=O)CCC(=O)OCC)c1nc(N)c2[nH]c(=O)n(Cc3ccccc3)c2n1]

The title compound was prepared in analogy to Example 46 by using ethyl 4-chloro-4-oxo-butanoate instead of valeric acid anhydride. N-[(6-Amino-9-benzyl-8-oxo-7H-purin-2-yl)-oxo-propyl-λ⁴-sulfanylidene]benzamide (30 mg, Example 50) was obtained as a white solid.

Separation of compound of Example 50 by chiral HPLC afforded Example 50-A (faster eluting, 11 mg) and Example 50-B (slower eluting, 12 mg) as white solid. (Separation condition: methanol 5%-40% (0.05% DEA)/CO$_2$ on ChiralPak OD-3 column.)

Example 50-A $^1$H NMR (400 MHz, DMSO-$d_6$) δ ppm: 7.28-7.35 (m, 5H), 7.22 (br. s., 2H), 4.94 (s, 2H), 3.98-4.03 (m, 2H), 3.48-3.51 (m, 2H), 2.33-2.40 (m, 4H), 1.55-1.69 (m, 2H), 1.14 (t, J=7.2 Hz, 3H), 0.90 (t, J=7.6 Hz, 3H). MS obsd. (ESI$^+$) [(M+H)$^+$]: 475.

Example 50-B $^1$H NMR (400 MHz, DMSO-$d_6$) δ ppm: 7.28-7.35 (m, 5H), 7.22 (br. s., 2H), 4.94 (s, 2H), 3.98-4.03 (m, 2H), 3.48-3.51 (m, 2H), 2.33-2.40 (m, 4H), 1.55-1.69 (m, 2H), 1.14 (t, J=7.2 Hz, 3H), 0.90 (t, J=7.6 Hz, 3H). MS obsd. (ESI$^+$) [(M+H)$^+$]: 475.

Example 51

N-[(6-Amino-9-benzyl-8-oxo-7H-purin-2-yl)-oxo-propyl-λ⁴-sulfanylidene]benzamide

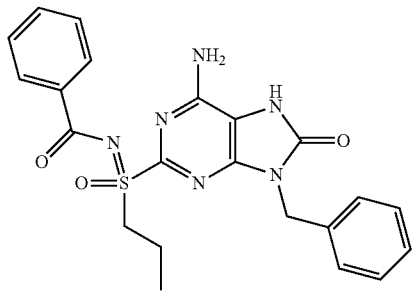 [SMILES: CCCS(=O)(=NC(=O)c1ccccc1)c1nc(N)c2[nH]c(=O)n(Cc3ccccc3)c2n1]

The title compound was prepared in analogy to Example 46 by using benzoyl benzoate instead of valeric acid anhydride. N-[(6-Amino-9-benzyl-8-oxo-7H-purin-2-yl)-oxo-propyl-λ⁴-sulfanylidene]benzamide (220 mg, Example 51) was obtained as a white solid. ¹H NMR (400 MHz, DMSO-$d_6$) δ ppm: 10.77 (br.s., 1H), 8.08-7.89 (m, 2H), 7.61-7.41 (m, 3H), 7.31-7.07 (m, 7H), 4.88 (d, J=3.8 Hz, 2H), 3.72-3.56 (m, 2H), 1.84-1.61 (m, 2H), 0.97 (t, J=7.8 Hz, 3H). MS obsd. (ESI⁺) [(M+H)⁺]: 451.

Separation of compound of Example 51 by chiral HPLC afforded Example 51-A (faster eluting, 50 mg) and Example 51-B (slower eluting, 50.5 mg) as white solid. (Separation condition: methanol 5%-40% (0.05% DEA)/CO₂ on ChiralPak OD-3S column.)

Example 51-A

¹H NMR (400 MHz, DMSO-$d_6$) δ ppm: 10.77 (br. s., 1H), 7.89-8.08 (m, 2H), 7.41-7.61 (m, 3H), 7.07-7.31 (m, 7H), 4.88 (d, J=3.8 Hz, 2H), 3.56-3.72 (m, 2H), 1.61-1.84 (m, 2H), 0.97 (t, J=7.8 Hz, 3H). MS obsd. (ESI⁺) [(M+H)⁺]: 451.

Example 51-B

¹H NMR (400 MHz, DMSO-$d_6$) δ ppm: 10.78 (br. s., 1H), 7.94-8.05 (m, 2H), 7.42-7.62 (m, 3H), 7.07-7.31 (m, 7H), 4.88 (d, J=3.8 Hz, 2H), 3.60-3.73 (m, 2H), 1.61-1.90 (m, 2H), 0.97 (t, J=7.8 Hz, 3H). MS obsd. (ESI⁺) [(M+H)⁺]: 451.

Example 52

9-Benzyl-6-(ethylamino)-2-(propylsulfonimidoyl)-7H-purin-8-one

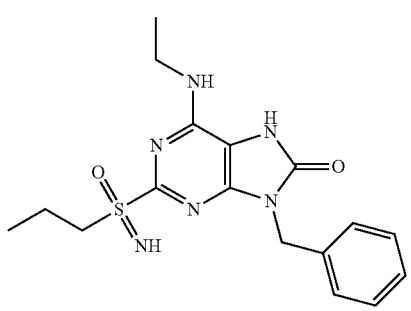

Step 1: Preparation of N-benzyl-6-chloro-5-nitro-2-(propylthio)pyrimidin-4-amine

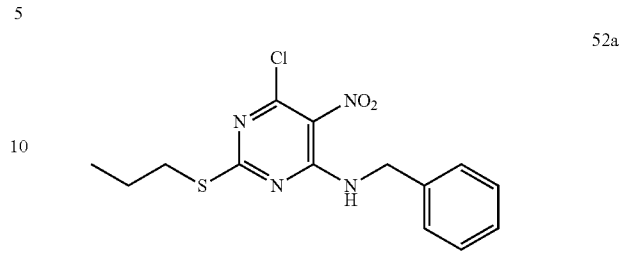

Compound 52a was prepared in analogy to Example 15, Step 1 by using benzylamine instead of (2-chlorophenyl)methylamine. N-Benzyl-6-chloro-5-nitro-2-(propylthio)pyrimidin-4-amine (35 g, compound 52a) was obtained as a yellow solid. MS obsd. (ESI⁺) [(M+H)⁺]: 339.

Step 2: Preparation of N4-benzyl-6-chloro-2-propylsulfanyl-pyrimidine-4,5-diamine

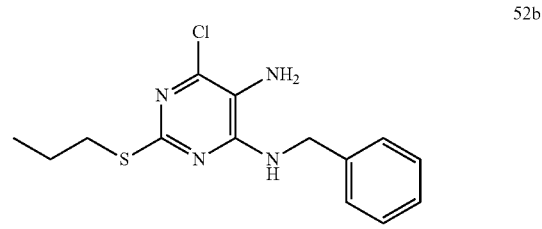 [SMILES: CCCSc1nc(Cl)c([N+](=O)[O-])c(NCc2ccccc2)n1]

Compound 52b was prepared in analogy to Example 15, Step 2 by using N-benzyl-6-chloro-5-nitro-2-(propylthio)pyrimidin-4-amine (compound 52a) instead of 6-chloro-N-[(2-chlorophenyl)methyl]-5-nitro-2-propylsulfanyl-pyrimidin-4-amine (compound 15a). N4-benzyl-6-chloro-2-propylsulfanyl-pyrimidine-4,5-diamine (28.0 g, compound 52b) was obtained as a brown solid. MS obsd. (ESI⁺) [(M+H)⁺]: 309.

Step 3: Preparation of 9-benzyl-6-chloro-2-propylsulfanyl-7H-purin-8-one

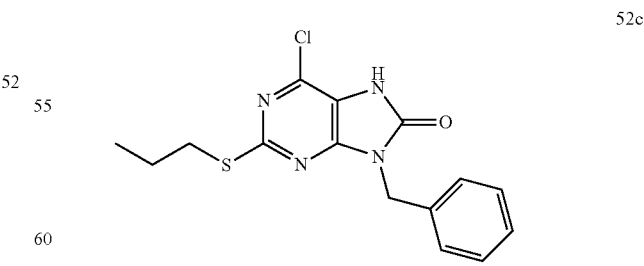

Compound 52c was prepared in analogy to Example 15, Step 3 by using N4-benzyl-6-chloro-2-propylsulfanyl-pyrimidine-4,5-diamine (compound 52b) instead of 6-chloro-N-4-[(2-chlorophenyl)methyl]-2-propylsulfanyl-pyrimidine-4,5-diamine (compound 15b). 9-Benzyl-6-chloro-2- propylsulfanyl-7H-purin-8-one (24.0 g, compound 52c) was obtained as a white solid. MS obsd. (ESI⁺) [(M+H)⁺]: 335.

Step 4: Preparation of 9-benzyl-6-(ethylamino)-2-propylsulfanyl-7H-purin-8-one

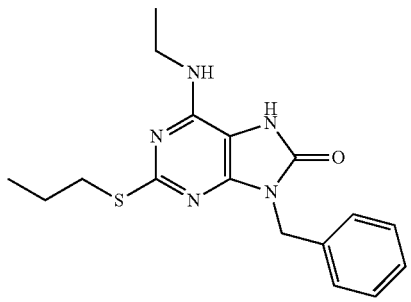
52d

To a solution of 9-benzyl-6-chloro-2-propylsulfanyl-7H-purin-8-one (2.3 g, 6.9 mmol, compound 52c) in n-BuOH (8 mL) was added EtNH₂.HCl (1.7 g, 20.6 mmol) and N-ethyl-N-isopropylpropan-2-amine (5.4 g, 41.4 mmol). The reaction vessel was sealed and heated in microwave at 130° C. for 2 hrs. The solvent was removed in vacuo. The residue was suspended in EtOAc (20 mL), washed with water (15 mL) two times and brine (30 mL). The separated organic layer was dried over anhydrous sodium sulfate and concentrated in vacuo to give 9-benzyl-6-(ethylamino)-2-propylsulfanyl-7H-purin-8-one (1.2 g, compound 52d) as light yellow solid. MS obsd. (ESI⁺) [(M+H)⁺]: 344

Step 5: Preparation of 9-benzyl-6-(ethylamino)-2-propylsulfinyl-7H-purin-8-one

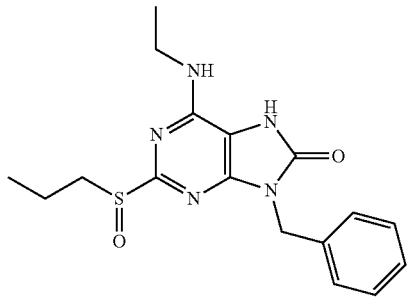
52e

To a solution of 9-benzyl-6-(ethylamino)-2-propylsulfanyl-7H-purin-8-one (682 mg, 2.0 mmol, compound 51d) in THF (8 mL) was added m-CPBA (415 mg, 2.4 mmol) in THF (2 mL) at 0° C. under N₂ atmosphere. After the addition, the mixture was stirred at this temperature for 30 min until a clear solution was formed. The reaction was quenched by the addition of saturated Na₂SO₃ (5 mL), extracted with i-PrOH/DCM (20 mL, V/V=1/3) two times. The combined organic layer was dried over Na₂SO₄ and concentrated to give 9-benzyl-6-(ethylamino)-2-propylsulfinyl-7H-purin-8-one (580 mg, compound 52e) as light yellow solid. MS obsd. (ESI⁺) [(M+H)⁺]: 360.

Step 6: Preparation of 9-benzyl-6-(ethylamino)-2-(propylsulfonimidoyl)-7H-purin-8-one

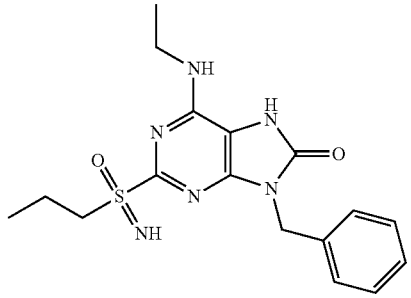
52

The title compound was prepared in analogy to Example 15, Step 7 by using 9-benzyl-6-(ethylamino)-2-propylsulfinyl-7H-purin-8-one (280 mg, compound 52e) instead of 6-amino-9-[(2-chlorophenyl)methyl]-2-propylsulfinyl-7H-purin-8-one (compound 15f). 9-Benzyl-6-(ethylamino)-2-(propylsulfonimidoyl)-7H-purin-8-one (94 mg, Example 52) was obtained as a white solid. ¹H NMR (400 MHz, DMSO-d₆) δ ppm: 10.65 (s, 1H), 7.50-7.22 (m, 5H), 7.14-6.97 (m, 1H), 4.97 (s, 2H), 4.07 (s, 1H), 3.58-3.44 (m, 2H), 3.36-3.28 (m, 2H), 1.78-1.54 (m, 2H), 1.21 (t, J=7.2 Hz, 3H), 0.93 (t, J=7.2 Hz, 3H). MS obsd. (ESI⁺) [(M+H)⁺]: 375.

Example 53

6-(Ethylamino)-9-[(6-methyl-3-pyridyl)methyl]-2-(propylsulfonimidoyl)-7H-purin-8-one

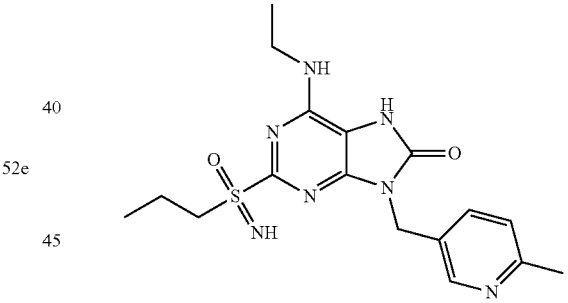

Step 1: Preparation of 6-(ethylamino)-9-[(6-methyl-3-pyridyl)methyl]-2-propylsulfanyl-7H-purin-8-one

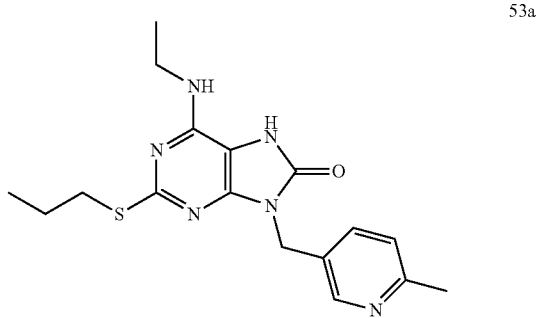
53a

Compound 53a was prepared in analogy to Example 52, Step 4 by using 6-chloro-9-[(6-methyl-3-pyridyl)methyl]-2-propylsulfanyl-7H-purin-8-one (compound 34e) instead of 9-benzyl-6-chloro-2-propylsulfanyl-7H-purin-8-one (compound 52c). 6-(Ethylamino)-9-[(6-methyl-3-pyridyl)methyl]-2-propylsulfanyl-7H-purin-8-one (810 mg, compound 53a) was obtained as light yellow solid. MS obsd. (ESI⁺) [(M+H)⁺]: 359.

Step 2: Preparation of 6-(ethylamino)-9-[(6-methyl-3-pyridyl)methyl]-2-propylsulfinyl-7H-purin-8-one

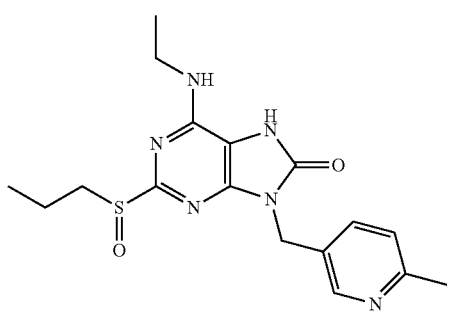

53b

Compound 53b was prepared in analogy to Example 52, Step 5 by using 6-chloro-9-[(6-methyl-3-pyridyl)methyl]-2-propylsulfanyl-7H-purin-8-one (compound 53a) instead of 9-benzyl-6-chloro-2-propylsulfanyl-7H-purin-8-one (compound 52d). 6-(Ethylamino)-9-[(6-methyl-3-pyridyl)methyl]-2-propylsulfinyl-7H-purin-8-one (380 mg, compound 53b) was obtained as light yellow solid. MS obsd. (ESI⁺) [(M+H)⁺]: 375.

Step 3: Preparation of 6-(ethylamino)-9-[(6-methyl-3-pyridyl)methyl]-2-(propylsulfonimidoyl)-7H-purin-8-one

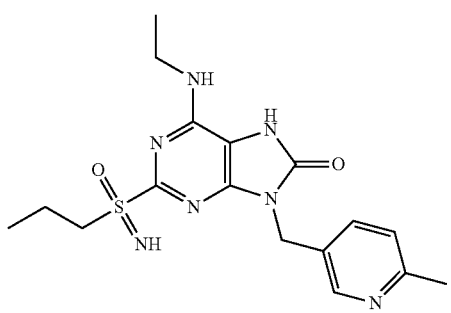 [SMILES: CCCS(=N)(=O)c1nc(NCC)c2[nH]c(=O)n(Cc3ccc(C)nc3)c2n1]

53

The title compound was prepared in analogy to Example 15, Step 7 by using 6-(ethylamino)-9-[(6-methyl-3-pyridyl)methyl]-2-propylsulfinyl-7H-purin-8-one (280 mg, compound 53b) instead of 6-amino-9-[(2-chlorophenyl)methyl]-2-propylsulfinyl-7H-purin-8-one (compound 15f). 6-(Ethylamino)-9-[(6-methyl-3-pyridyl)methyl]-2-(propylsulfonimidoyl)-7H-purin-8-one (78 mg, Example 53) was obtained as light yellow solid. ¹H NMR (400 MHz, DMSO-d₆) δ ppm: 10.56 (s, 1H), 8.47 (s, 1H), 7.62-7.64 (dd, J=8.0, 2.4 Hz, 1H), 7.20-7.22 (d, J=8.0 Hz, 1H), 7.00 (m, 1H), 4.95 (s, 2H), 4.21 (s, 1H), 3.50-3.45 (m, 2H), 3.39-3.35 (m, 2H), 2.42 (s, 3H), 1.61-1.71 (m, 2H), 1.18-1.21 (t, J=7.2 Hz, 3H), 0.95-0.95 (t, J=7.2 Hz, 3H). MS obsd. (ESI⁺) [(M+H)⁺]: 390.

Example 54

9-[(4-Chlorophenyl)methyl]-6-(ethylamino)-2-(propylsulfonimidoyl)-7H-purin-8-one

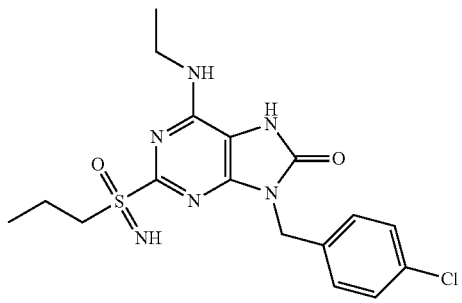 [SMILES: CCCS(=N)(=O)c1nc(NCC)c2[nH]c(=O)n(Cc3ccc(Cl)cc3)c2n1]

Step 1: Preparation of 6-chloro-N-[(4-chlorophenyl)methyl]-5-nitro-2-propylsulfanyl-pyrimidin-4-amine

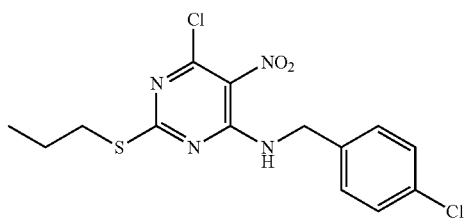

54a

Compound 54a was prepared in analogy to Example 15, Step 1 by using (4-Chlorophenyl)methylamine instead of (2-chlorophenyl)methylamine. 6-Chloro-N-[(4-chlorophenyl)methyl]-5-nitro-2-propylsulfanyl-pyrimidin-4-amine (11 g, compound 54a) was obtained as a yellow solid. MS obsd. (ESI⁺) [(M+H)⁺]: 373.

Step 2: Preparation of 6-chloro-N4-[(4-chlorophenyl)methyl]-2-propylsulfanyl-pyrimidine-4,5-diamine

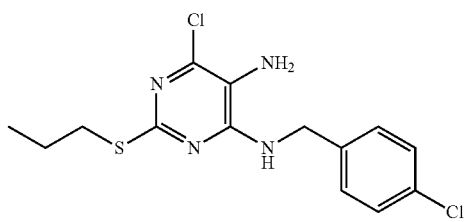

54b

Compound 54b was prepared in analogy to Example 15, Step 2 by using N-4-chlorobenzyl-6-chloro-5-nitro-2-(propylthio)pyrimidin-4-amine (compound 54a) instead of 6-chloro-N-[(2-chlorophenyl)methyl]-5-nitro-2-propylsulfanyl-pyrimidin-4-amine (compound 15a). 6-chloro-N4-[(4-chlorophenyl)methyl]-2-propylsulfanyl-pyrimidine-4,5-diamine (4.8 g, compound 54b) was obtained as a white solid. MS obsd. (ESI+) [(M+H)+]: 343.

Step 3: Preparation of 6-chloro-9-[(4-chlorophenyl)methyl]-2-propylsulfanyl-7H-purin-8-one

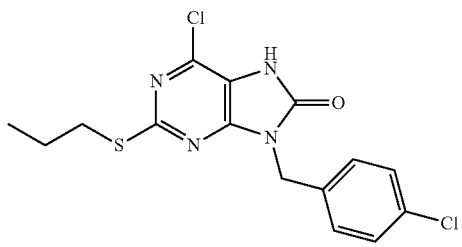

Compound 54c was prepared in analogy to Example 15, Step 3 by using 6-chloro-N4-[(4-chlorophenyl)methyl]-2-propylsulfanyl-pyrimidine-4,5-diamine (compound 54b) instead of 6-chloro-N-4-[(2-chlorophenyl)methyl]-2-propylsulfanyl-pyrimidine-4,5-diamine (compound 15b). 6-Chloro-9-[(4-chlorophenyl)methyl]-2-propylsulfanyl-7H-purin-8-one (4.5 g, compound 54c) was obtained as a white solid. MS obsd. (ESI+) [(M+H)+]: 369.

Step 4: Preparation of 9-[(4-chlorophenyl)methyl]-6-(ethylamino)-2-propylsulfanyl-7H-purin-8-one

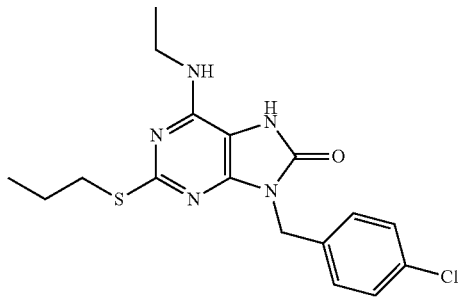

Compound 54d was prepared in analogy to Example 52, Step 4 by using 6-chloro-9-[(4-chlorophenyl)methyl]-2-propylsulfanyl-7H-purin-8-one (compound 54c) instead of 9-benzyl-6-chloro-2-propylsulfanyl-7H-purin-8-one (compound 52c). 9-[(4-Chlorophenyl)methyl]-6-(ethylamino)-2-propylsulfanyl-7H-purin-8-one (400 mg, compound 54d) was obtained as light yellow solid. MS obsd. (ESI+) [(M+H)+]: 378.

Step 5: Preparation of 9-[(4-chlorophenyl)methyl]-6-(ethylamino)-2-propylsulfinyl-7H-purin-8-one

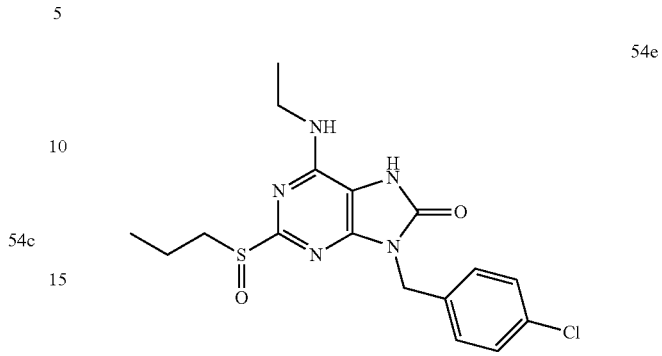

Compound 54e was prepared in analogy to Example 52, Step 5 by using 9-[(4-chlorophenyl)methyl]-6-(ethylamino)-2-propylsulfanyl-7H-purin-8-one (compound 54d) instead of 9-benzyl-6-chloro-2-propylsulfanyl-7H-purin-8-one (compound 52d). 9-[(4-Chlorophenyl)methyl]-6-(ethylamino)-2-propylsulfinyl-7H-purin-8-one (300 mg, compound 54e) was obtained as light yellow solid. MS obsd. (ESI+) [(M+H)+]: 394.

Step 6: Preparation of 9-[(4-chlorophenyl)methyl]-6-(ethylamino)-2-(propylsulfonimidoyl)-7H-purin-8-one

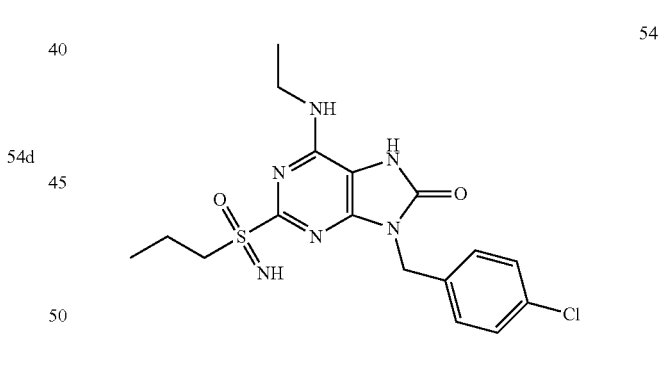

The title compound was prepared in analogy to Example 15, Step 7 by using 9-[(4-chlorophenyl)methyl]-6-(ethylamino)-2-propylsulfinyl-7H-purin-8-one (compound 54e) instead of 6-amino-9-[(2-chlorophenyl)methyl]-2-propylsulfinyl-7H-purin-8-one (compound 15e). 9-[(4-Chlorophenyl)methyl]-6-(ethylamino)-2-(propylsulfonimidoyl)-7H-purin-8-one (86 mg, Example 54) was obtained as light yellow solid. $^1$H NMR (400 MHz, DMSO-d$_6$) δ ppm: 10.50 (s, 1H), 7.31-7.42 (m, 3H), 6.97 (t, J=5.4 Hz, 1H), 4.96 (s, 2H), 4.18 (s, 1H), 3.42-3.59 (m, 2H), 3.30-3.39 (m, 2H), 1.54-1.76 (m, 2H), 1.15-1.28 (m, 3H), 0.86-0.99 (m, 3H). MS obsd. (ESI+) [(M+H)+]: 409.

Example 55

9-Benzyl-6-(propylamino)-2-(propylsulfonimidoyl)-7H-purin-8-one

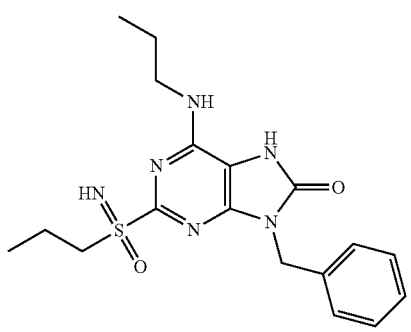

Step 1: Preparation of 9-benzyl-6-(propylamino)-2-propylsulfanyl-7H-purin-8-one

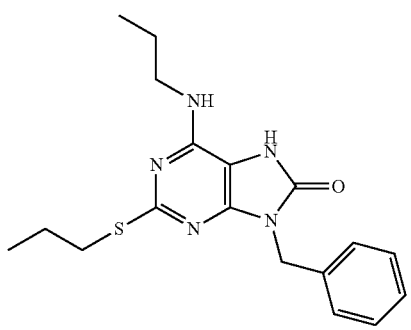

Compound 55a was prepared in analogy to Example 52, Step 4 by using propan-1-amine instead of EtNH$_2$.HCl. 9-Benzyl-6-(propylamino)-2-propylsulfanyl-7H-purin-8-one (820 mg, compound 55a) was obtained as a white solid. MS obsd. (ESI$^+$) [(M+H)$^+$]: 358.

Step 2: Preparation of 9-benzyl-6-(propylamino)-2-propylsulfinyl-7H-purin-8-one

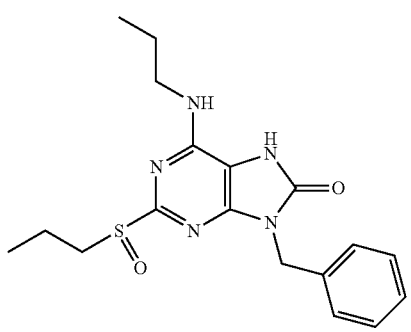

Compound 55b was prepared in analogy to Example 52, Step 5 by using 9-benzyl-6-(propylamino)-2-propylsulfanyl-7H-purin-8-one (compound 55a) instead of 9-benzyl-6-(ethylamino)-2-propylsulfanyl-7H-purin-8-one (compound 52d). 9-Benzyl-6-(propyl amino)-2-propylsulfanyl-7H-purin-8-one (400 mg, compound 55b) was obtained as a white solid. MS obsd. (ESI$^+$) [(M+H)$^+$]: 374.

Step 3: Preparation of 9-benzyl-6-(propylamino)-2-(propylsulfonimidoyl)-7H-purin-8-one

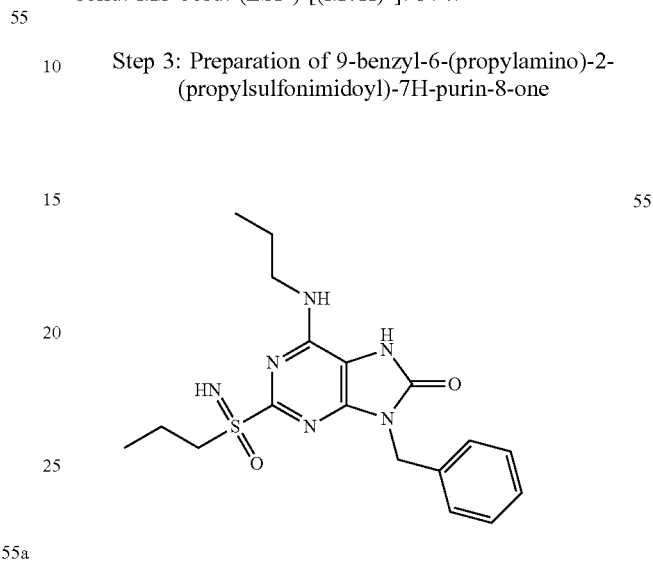

The title compound was prepared in analogy to Example 15, Step 7 by using 9-benzyl-6-(propylamino)-2-propylsulfinyl-7H-purin-8-one (compound 55b) instead of 6-amino-9-[(2-chlorophenyl)methyl]-2-propylsulfinyl-7H-purin-8-one (compound 15f). 9-Benzyl-6-(propylamino)-2-(propylsulfonimidoyl)-7H-purin-8-one (113.5 mg, Example 55) was obtained as a white solid. $^1$H NMR (400 MHz, DMSO-d$_6$) δ ppm: 10.67 (s, 1H), 7.45-7.19 (m, 5H), 7.16-7.01 (m, 1H), 4.97 (s, 2H), 4.17 (s, 1H), 3.52-3.40 (m, 2H), 3.36-3.28 (m, 2H), 1.81-1.44 (m, 4H), 1.06-0.79 (m, 6H). MS obs. (ESI$^+$) [(M+H)$^+$]: 389.

Example 56

9-Benzyl-6-(isopropylamino)-2-(propylsulfonimidoyl)-7H-purin-8-one

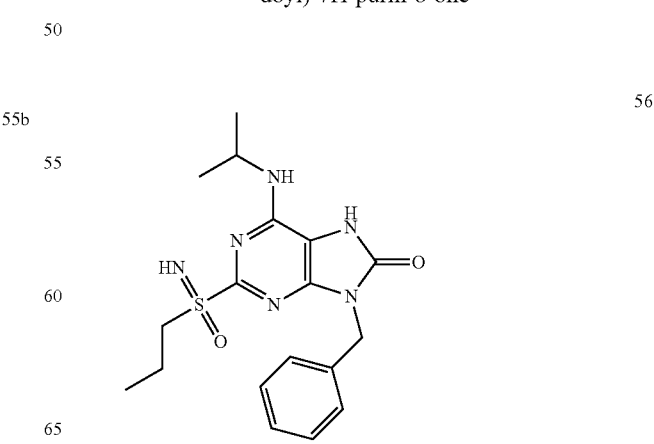

Step 1: Preparation of 9-benzyl-6-(isopropylamino)-2-propylsulfanyl-7H-purin-8-one

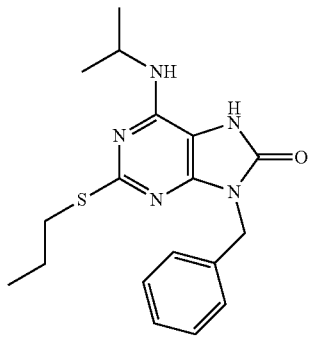

56a

Compound 56a was prepared in analogy to Example 52, Step 4 by using propan-2-amine instead of EtNH$_2$.HCl. 9-Benzyl-6-(isopropylamino)-2-propylsulfanyl-7H-purin-8-one (1.5 g, compound 56a) was obtained as a white solid. MS obsd. (ESI$^+$) [(M+H)$^+$]: 358.

Step 2: Preparation of 9-benzyl-6-(isopropylamino)-2-propylsulfinyl-7H-purin-8-one

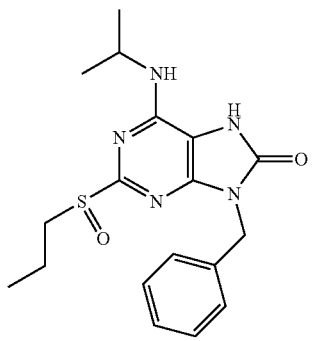

56b

Compound 56b was prepared in analogy to Example 52, Step 5 by using 9-benzyl-6-(isopropylamino)-2-propylsulfanyl-7H-purin-8-one (compound 56a) instead of 9-benzyl-6-(ethylamino)-2-propylsulfanyl-7H-purin-8-one (compound 52d). 9-Benzyl-6-(isopropylamino)-2-propylsulfinyl-7H-purin-8-one (1.35 g, compound 56b) was obtained as a white solid. MS obsd. (ESI$^+$) [(M+H)$^+$]: 373.

Step 3. Preparation of 9-benzyl-6-(isopropylamino)-2-(propylsulfonimidoyl)-7H-purin-8-one

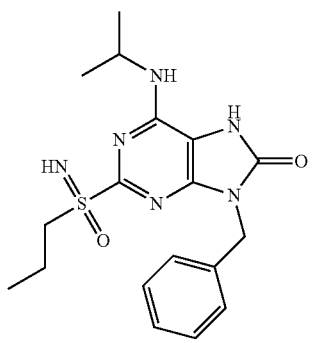

56

The title compound was prepared in analogy to Example 15, Step 7 by using 9-benzyl-6-(isopropylamino)-2-propylsulfinyl-7H-purin-8-one (compound 56b) instead of 6-amino-9-[(2-chlorophenyl)methyl]-2-propylsulfinyl-7H-purin-8-one (compound 15f). 9-Benzyl-6-(isopropylamino)-2-(propylsulfonimidoyl)-7H-purin-8-one (100 mg, Example 56) was obtained as a white solid. $^1$H NMR (400 MHz, DMSO-d$_6$) δ ppm: 10.45 (br. s., 1H), 7.47-7.21 (m, 5H), 6.93-6.80 (m, 1H), 4.95 (s, 2H), 4.26-4.17 (m, 1H), 4.14 (s, 1H), 3.38-3.37 (m, 2H), 1.65-1.55 (m, 2H), 1.23 (dd, J=6.4, 2.1 Hz, 6H), 0.92 (t, J=8.0 Hz, 3H). MS obsd. (ESI$^+$) [(M+H)$^+$]: 389.

Example 57

9-Benzyl-6-(cyclopropylamino)-2-(propylsulfonimidoyl)-7H-purin-8-one

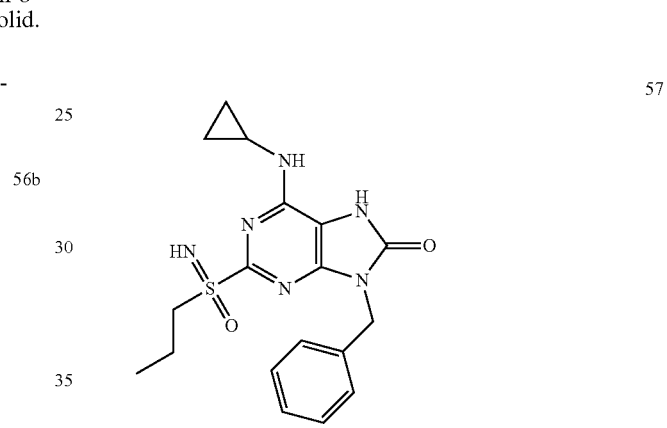

57

Step 1: Preparation of 9-benzyl-6-(cyclopropylamino)-2-propylsulfanyl-7H-purin-8-one

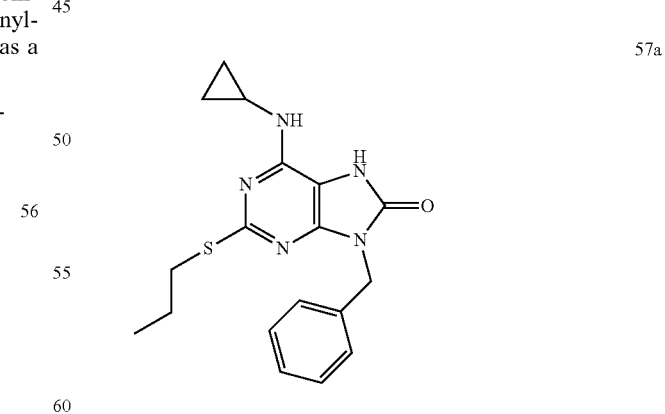

57a

Compound 57a was prepared in analogy to Example 52, Step 4 by using cyclopropanamine instead of EtNH$_2$.HCl. 9-Benzyl-6-(cyclopropylamino)-2-propylsulfanyl-7H-purin-8-on e (1.35 g, compound 57a) was obtained as a white solid. MS obsd. (ESI$^+$) [(M+H)$^+$]: 356.

Step 2: Preparation of 9-benzyl-6-(cyclopropylamino)-2-propylsulfinyl-7H-purin-8-one

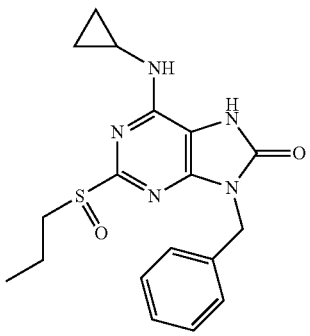

57b

Compound 57b was prepared in analogy to Example 52, Step 5 by using 9-benzyl-6-(cyclopropylamino)-2-propylsulfanyl-7H-purin-8-one instead of 9-benzyl-6-(ethylamino)-2-propylsulfanyl-7H-purin-8-one (52d). 9-Benzyl-6-(cyclopropylamino)-2-propylsulfinyl-7H-purin-8-one (1.35 g, compound 57b) was obtained as a white solid. MS obsd. (ESI+) [(M+H)+]: 372

Step 3: Preparation of 9-benzyl-6-(cyclopropylamino)-2-(propylsulfonimidoyl)-7H-purin-8-one

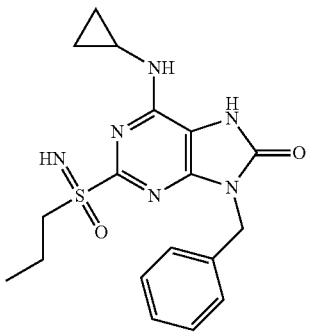

57

The title compound was prepared in analogy to Example 15, Step 7 by using 9-benzyl-6-(cyclopropylamino)-2-propylsulfinyl-7H-purin-8-one (compound 57b) instead of 6-amino-9-[(2-chlorophenyl)methyl]-2-propylsulfinyl-7H-purin-8-one (compound 15f). 9-Benzyl-6-(cyclopropylamino)-2-(propylsulfonimidoyl)-7H-purin-8-one (30.5 mg, Example 57) was obtained as a white solid. $^1$H NMR (400 MHz, DMSO-$d_6$) δ ppm: 7.40-7.57 (m, 1H), 7.28-7.34 (m, 5H), 4.97 (s, 2H), 4.12 (s, 1H), 3.38-3.40 (m, 2H), 1.65-1.70 (m, 2H), 0.94 (t, J=8.0 Hz, 3H), 0.80-0.81 (m, 2H), 0.52-0.59 (m, 2H). MS obsd. (ESI+) [(M+H)+]: 387.

Example 58

N-[9-[(4-Chlorophenyl)methyl]-8-oxo-2-(propylsulfonimidoyl)-7H-purin-6-yl]-2-propyl-pentanamide

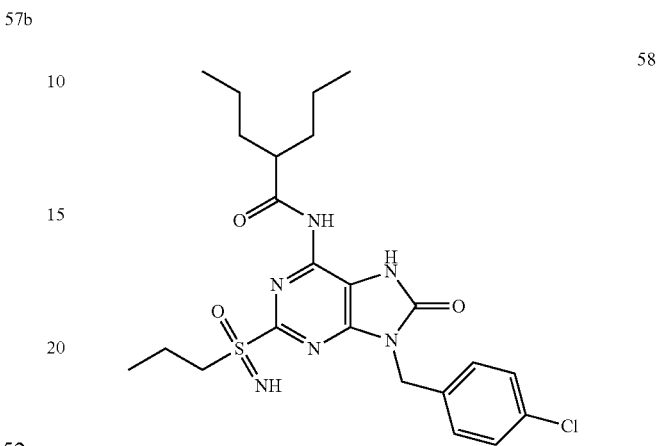

58

Step 1: Preparation of N-[9-[(4-chlorophenyl)methyl]-8-oxo-2-propylsulfanyl-7H-purin-6-yl]-2-propyl-pentanamide

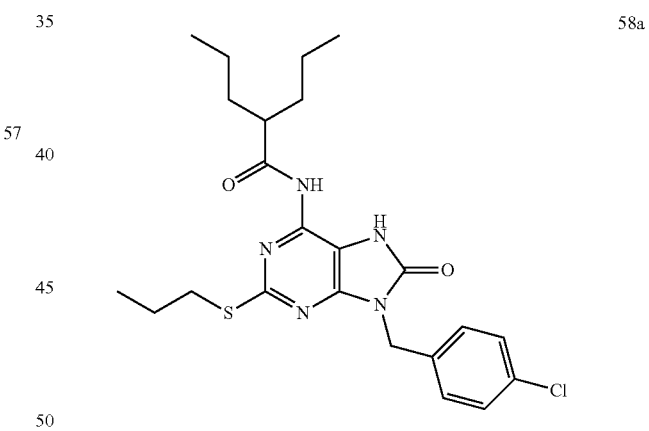

58a

To a 50 mL microwave vial was added 6-amino-9-[(4-chlorophenyl)methyl]-2-propylsulfanyl-7H-8-one (2.2 g, 6.29 mmol, compound 9c), 2-propylpentanoic anhydride (17 g, 62.9 mmol) and sulfuric acid (308 mg, 3.14 mmol). The vial was sealed and heated in the microwave at 70° C. for 10 min. Then the reaction mixture was diluted with $H_2O$ (50 mL) and neutralized with saturated sodium bicarbonate solution. The mixture was extracted with DCM. The organic layer was dried over $Na_2SO_4$ and concentrated in vacuo. The crude material was purified by flash chromatography (silica gel, 40 g, 100% DCM) to give N-[9-[(4-chlorophenyl)methyl]-8-oxo-2-propylsulfanyl-7H-purin-6-yl]-2-propyl-pentanamide (2.9 g, compound 58a) as a white solid. MS obsd. (ESI+) [(M+H)+]: 476.

Step 2: Preparation of N-[9-[(4-chlorophenyl)methyl]-8-oxo-2-propylsulfinyl-7H-purin-6-yl]-2-propyl-pentanamide

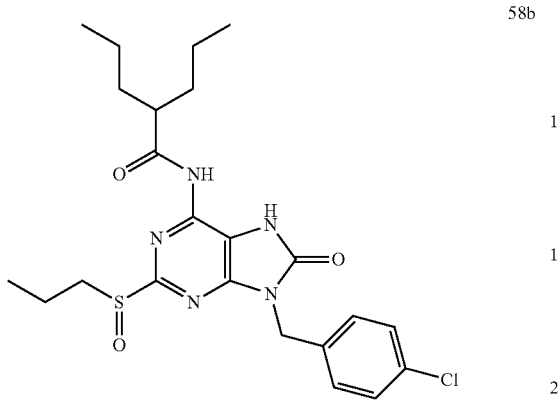

58b

Compound 58b was prepared in analogy to Example 15, Step 6 by using N-[9-[(4-chlorophenyl)methyl]-8-oxo-2-propylsulfanyl-7H-purin-6-yl]-2-propyl-pentanamide (2.9 g, compound 58a) instead of 6-amino-9-[(2-chlorophenyl)methyl]-2-propylsulfanyl-7H-purin-8-one (compound 15e). N-[9-[(4-Chlorophenyl)methyl]-8-oxo-2-propylsulfinyl-7H-purin-6-yl]-2-propyl-pentanamide (2.8 g, compound 58b) was obtained as a white solid. MS obsd. (ESI$^+$) [(M+H)$^+$]: 492.

Step 3: Preparation of N-[9-[(4-chlorophenyl)methyl]-8-oxo-2-(propylsulfonimidoyl)-7H-purin-6-yl]-2-propyl-pentanamide

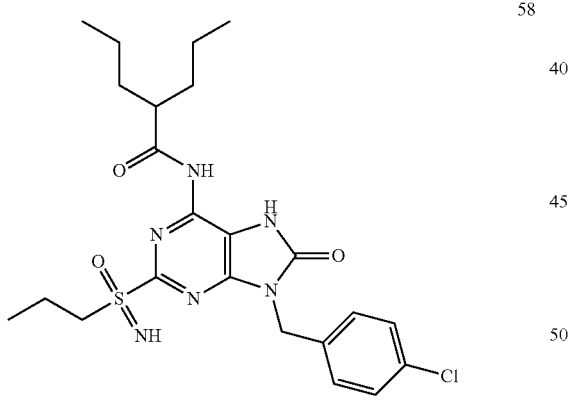

58

The title compound was prepared in analogy to Example 15, Step 7 by using N-[9-[(4-chlorophenyl)methyl]-8-oxo-2-propylsulfinyl-7H-purin-6-yl]-2-propyl-pentanamide (compound 58b) instead of 6-amino-9-[(2-chlorophenyl)methyl]-2-propylsulfinyl-7H-purin-8-one (compound 15f). N-[9-[(4-Chlorophenyl)methyl]-8-oxo-2-(propylsulfonimidoyl)-7H-purin-6-yl]-2-propyl-pentanamide (21 mg, Example 58) was obtained as a white solid. $^1$H NMR (400 MHz, DMSO-d$_6$) δ ppm: 11.15 (s, 1H), 10.45 (br. s, 1H), 7.39 (s, 4H), 5.04 (s, 2H), 4.27 (s, 1H), 3.37-3.44 (m, 2H), 2.68-2.73 (m, 1H), 1.56-1.65 (m, 4H), 1.24-1.42 (m, 6H), 0.90 (t, J=8 Hz, 3H), 0.88 (t, J=8 Hz, 6H). MS obsd. (ESI$^+$) [(M+H)$^+$]: 507.

Example 59

N-[9-[(4-Chlorophenyl)methyl]-8-oxo-2-(propylsulfonimidoyl)-7H-purin-6-yl]acetamide

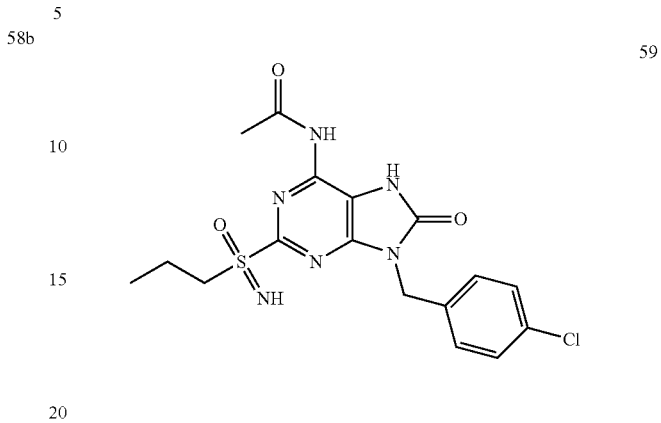

59

Step 1: Preparation of N-[9-[(4-chlorophenyl)methyl]-8-oxo-2-propylsulfanyl-7H-purin-6-yl]acetamide

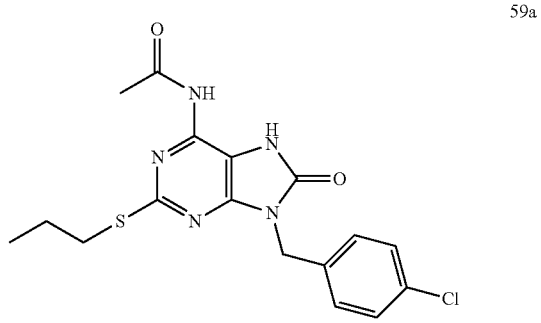 [SMILES: CCCSc1nc(NC(C)=O)c2[nH]c(=O)n(Cc3ccc(Cl)cc3)c2n1]

59a

Compound 59a was prepared in analogy to Example 58, Step 1 by using acetyl acetate instead of 2-propylpentanoic anhydride. N-[9-[(4-chlorophenyl)methyl]-8-oxo-2-propylsulfanyl-7H-purin-6-yl]acetamide (300 mg, compound 59a) was obtained as a white solid. MS obsd. (ESI$^+$) [(M+H)$^+$]: 392.

Step 2: Preparation of N-[9-[(4-chlorophenyl)methyl]-8-oxo-2-propylsulfinyl-7H-purin-6-yl]acetamide

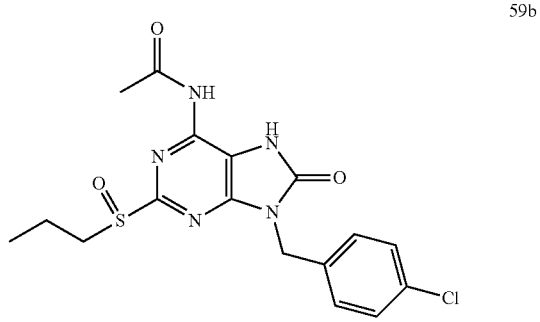 [SMILES: CCCS(=O)c1nc(NC(C)=O)c2[nH]c(=O)n(Cc3ccc(Cl)cc3)c2n1]

59b

Compound 59b was prepared in analogy to Example 58, Step 2 by using N-[9-[(4-chlorophenyl)methyl]-8-oxo-2- propylsulfanyl-7H-purin-6-yl]acetamide (300 mg, 0.76 mmol, compound 59a) instead of N-[9-[(4-chlorophenyl)methyl]-8-oxo-2-propylsulfanyl-7H-purin-6-yl]-2-propylpentanamide (compound 58a). N-[9-[(4-chlorophenyl)methyl]-8-oxo-2-propylsulfinyl-7H-purin-6-yl]acetamide (260 mg, compound 59b) was obtained as a white solid. MS obsd. (ESI$^+$) [(M+H)$^+$]: 408.

Step 3: Preparation of N-[9-[(4-chlorophenyl)methyl]-8-oxo-2-(propylsulfonimidoyl)-7H-purin-6-yl]acetamide

59

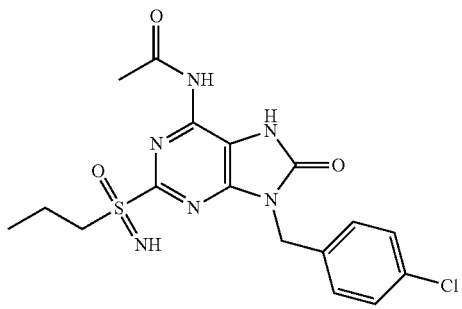

Compound 59 was prepared in analogy to Example 50, Step 3 by using N-[9-[(4-chlorophenyl)methyl]-8-oxo-2-propylsulfinyl-7H-purin-6-yl]acetamide (250 mg, 0.61 mmol, compound 59b) instead of N-[9-[(4-chlorophenyl)methyl]-8-oxo-2-propylsulfinyl-7H-purin-6-yl]-2-propyl-pentanamide (compound 58b). N-[9-[(4-chlorophenyl)methyl]-8-oxo-2-(propylsulfonimidoyl)-7H-purin-6-yl]acetamide (47 mg, Example 59) was obtained as a white solid. $^1$H NMR (400 MHz, DMSO-d$_6$) δ ppm: 11.04 (br. s, 1H), 10.34 (s, 1H), 7.40 (s, 4H), 5.03 (s, 2H), 4.29 (s, 1H), 3.37-3.44 (m, 2H), 2.16 (s, 3H), 1.60-1.66 (m, 2H), 0.91 (t, J=8 Hz, 3H). MS obsd. (ESI$^+$) [(M+H)$^+$]: 423.

Example 60

N-[9-Benzyl-8-oxo-2-(propylsulfonimidoyl)-7H-purin-6-yl]pentanamide

60

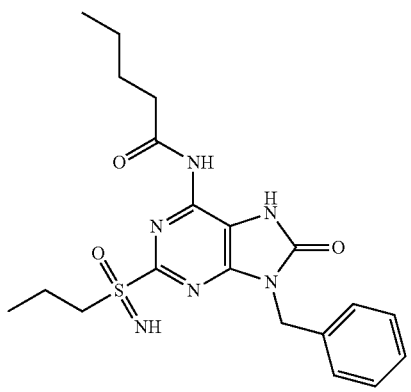

Step 1: Preparation of N-(9-benzyl-8-oxo-2-propylsulfanyl-7H-purin-6-yl)pentanamide 60a

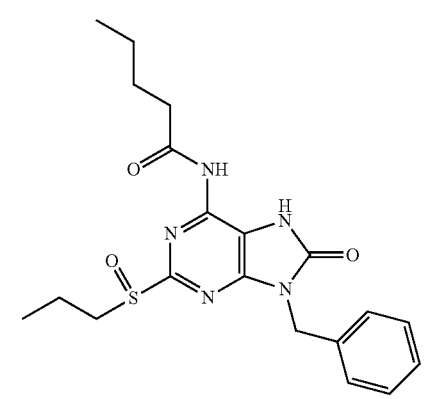

Compound 60a was prepared in analogy to Example 58, Step 1 by using pentanoyl pentanoate (TCI, Catalog number: V0006-25ML) and 6-amino-9-benzyl-2-propylsulfanyl-7H-purin-8-one (Example 50) instead of 2-propylpentanoic anhydride and 6-amino-9-[(4-chlorophenyl)methyl]-2-propylsulfanyl-7H-purin-8-one (compound 9c). N-(9-benzyl-8-oxo-2-propylsulfanyl-7H-purin-6-yl)pentanamide (320 mg, compound 60a) was obtained as a white solid. MS obsd. (ESI$^+$) [(M+H)$^+$]: 400.

Step 2: Preparation of N-(9-benzyl-8-oxo-2-propylsulfinyl-7H-purin-6-yl)pentanamide 60b Compound 60b was prepared in analogy to Example 58, Step 2 by using N-(9-benzyl-8-oxo-2-propylsulfanyl-7H-purin-6-yl)pentanamide (310 mg, 0.77 mmol, compound 60a) instead of N-[9-[(4-chlorophenyl)methyl]-8-oxo-2-propylsulfanyl-7H-purin-6-yl]-2-propyl-pentanamide (compound 58a). N-(9-benzyl-8-oxo-2-propylsulfinyl-7H-purin-6-yl)pentanamide (276 mg, compound 60b) was obtained as a white solid. MS obsd. (ESI$^+$) [(M+H)$^+$]: 416.

Step 3: Preparation of N-[9-benzyl-8-oxo-2-(propyl-sulfonimidoyl)-7H-purin-6-yl]pentanamide

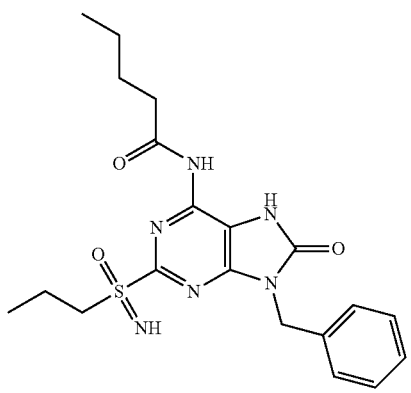

60

Compound 60 was prepared in analogy to Example 58, Step 3 by using N-(9-benzyl-8-oxo-2-propylsulfinyl-7H-purin-6-yl)pentanamide (200 mg, 0.48 mmol, compound 60b) instead of N-[9-[(4-chlorophenyl)methyl]-8-oxo-2-propylsulfinyl-7H-purin-6-yl]-2-propyl-pentanamide (compound 58b). N-[9-benzyl-8-oxo-2-(propylsulfonimidoyl)-7H-purin-6-yl]pentanamide (28 mg, Example 60) was obtained as a white solid. $^1$H NMR (400 MHz, DMSO-$d_6$) δ ppm: 10.98 (s, 1H), 7.27-7.39 (m, 5H), 5.04 (s, 2H), 4.27 (br. s., 1H), 3.24-3.44 (m, 2H), 2.46 (t, J=8.0 Hz, 2H), 1.58-1.71 (m, 4H), 1.32-1.37 (m, 2H), 0.90-0.93 (m, 6H). MS obsd. (ESI$^+$) [(M+H)$^+$]: 431.

Example 61

N-[9-[(4-Chlorophenyl)methyl]-8-oxo-2-(propylsulfonimidoyl)-7H-purin-6-yl]-2-ethyl-butanamide

61

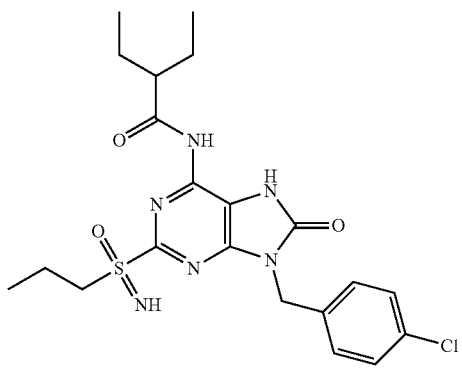

Step 1: Preparation of N-[9-[(4-chlorophenyl)methyl]-8-oxo-2-propylsulfanyl-7H-purin-6-yl]-2-ethyl-butanamide

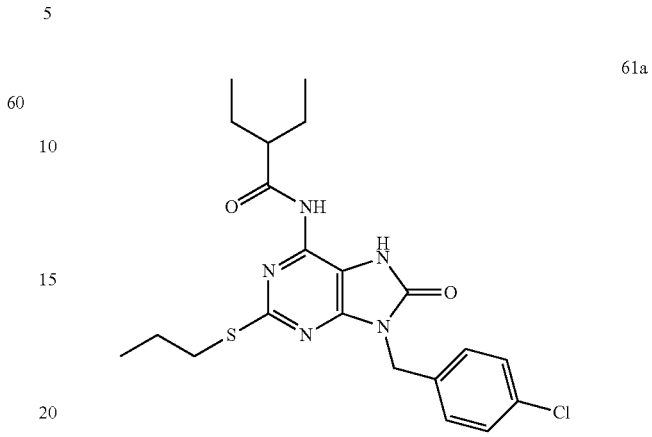

61a

Compound 61a was prepared in analogy to Example 58, Step 1 by using 2-ethylbutanoyl 2-ethylbutanoate instead of 2-propylpentanoic anhydride. N-[9-[(4-Chlorophenyl)methyl]-8-oxo-2-propylsulfanyl-7H-purin-6-yl]-2-ethyl-butanamide (150 mg, compound 61a) was obtained as a white solid. MS obsd. (ESI$^+$) [(M+H)$^+$]: 448.

Step 2: Preparation of N-[9-[(4-chlorophenyl)methyl]-8-oxo-2-propylsulfinyl-7H-purin-6-yl]-2-ethyl-butanamide

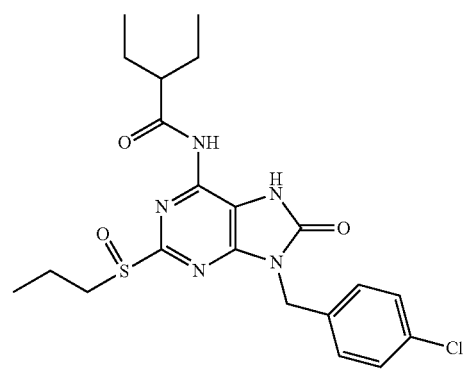

61b

Compound 61b was prepared in analogy to Example 58, Step 2 by using N-[9-[(4-chlorophenyl)methyl]-8-oxo-2-propylsulfanyl-7H-purin-6-yl]-2-ethyl-butanamide (136 mg, 0.30 mmol, compound 61a) instead of N-[9-[(4-chlorophenyl)methyl]-8-oxo-2-propylsulfanyl-7H-purin-6-yl]-2-propyl-pentanamide (compound 58a). N-[9-[(4-Chlorophenyl)methyl]-8-oxo-2-propylsulfinyl-7H-purin-6-yl]-2-ethyl-butanamide (126 mg, compound 61b) was obtained as a white solid. MS obsd. (ESI$^+$) [(M+H)$^+$]: 464.

Step 3: Preparation of N-[9-[(4-chlorophenyl)methyl]-8-oxo-2-(propylsulfonimidoyl)-7H-purin-6-yl]-2-ethyl-butanamide

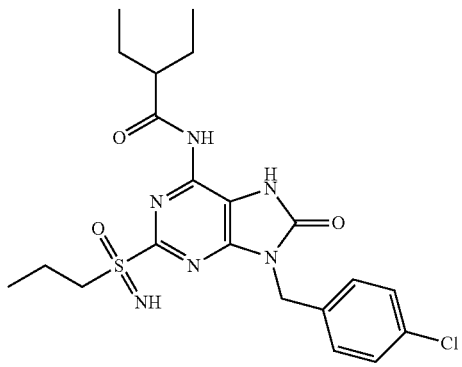

61

Compound 61 was prepared in analogy to Example 58, Step 3 by using N-[9-[(4-chlorophenyl)methyl]-8-oxo-2-propylsulfinyl-7H-purin-6-yl]-2-ethyl-butanamide (200 mg, 0.43 mmol, compound 61b) instead of N-[9-[(4-chlorophenyl)methyl]-8-oxo-2-propylsulfinyl-7H-purin-6-yl]-2-propyl-pentanamide (compound 58b). N-[9-[(4-chlorophenyl)methyl]-8-oxo-2-(propylsulfonimidoyl)-7H-purin-6-yl]-2-ethyl-butanamide (39 mg, Example 61) was obtained as a white solid. $^1$H NMR (400 MHz, DMSO-$d_6$) δ ppm: 11.15 (br. s., 1H), 10.50 (br. s., 1H), 7.36-7.41 (m, 4H), 5.05 (s, 2H), 4.22-4.36 (m, 1H), 3.29-3.40 (m, 2H), 2.67 (d, J=1.8 Hz, 1H), 1.43-1.69 (m, 4H), 1.15-1.38 (m, 2H), 0.86-0.94 (m, 9H). MS obsd. (ESI$^+$) [(M+H)$^+$]: 479.

Example 62

N-[9-[(4-Chlorophenyl)methyl]-8-oxo-2-(propylsulfonimidoyl)-7H-purin-6-yl]-3-methyl-butanamide

62

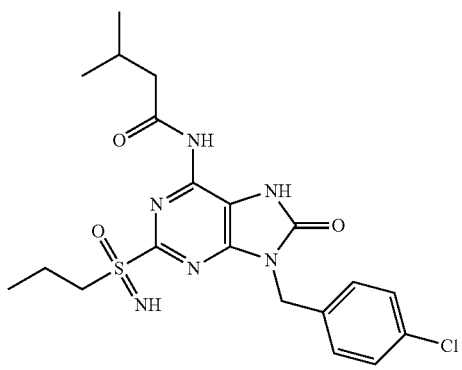

Step 1: Preparation of N-[9-[(4-chlorophenyl)methyl]-8-oxo-2-propylsulfanyl-7H-purin-6-yl]-3-methyl-butanamide

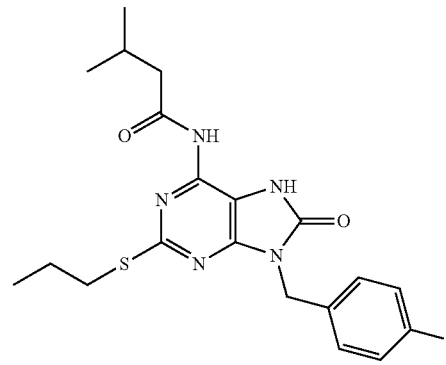

62a

Compound 62a was prepared in analogy to Example 58, Step 1 by using 2-methylbutanoyl 2-methylbutanoate (J&K, Catalog number: j20-038361-25g) instead of 2-propylpentanoic anhydride. N-[9-[(4-chlorophenyl)methyl]-8-oxo-2-propylsulfanyl-7H-purin-6-yl]-2-methyl-butanamide (390 mg, compound 62a) was obtained as a white solid. MS obsd. (ESI$^+$) [(M+H)$^+$]: 434.

Step 2: Preparation of N-[9-[(4-chlorophenyl)methyl]-8-oxo-2-propylsulfinyl-7H-purin-6-yl]-3-methyl-butanamide

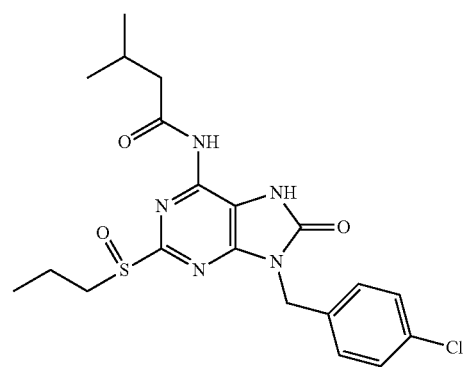

62b

Compound 62b was prepared in analogy to Example 58, Step 2 by using N-[9-[(4-chlorophenyl)methyl]-8-oxo-2-propylsulfanyl-7H-purin-6-yl]-2-methyl-butanamide (390 mg, 0.90 mmol, compound 62a) instead of N-[9-[(4-chlorophenyl)methyl]-8-oxo-2-propylsulfanyl-7H-purin-6-yl]-2-propyl-pentanamide (compound 58a). N-[9-[(4-chlorophenyl)methyl]-8-oxo-2-propylsulfinyl-7H-purin-6-yl]-2-methyl-butanamide (390 mg, compound 62b) was obtained as a white solid. MS obsd. (ESI$^+$) [(M+H)$^+$]: 450.

Step 3: Preparation of N-[9-[(4-chlorophenyl)methyl]-8-oxo-2-(propylsulfonimidoyl)-7H-purin-6-yl]-3-methyl-butanamide

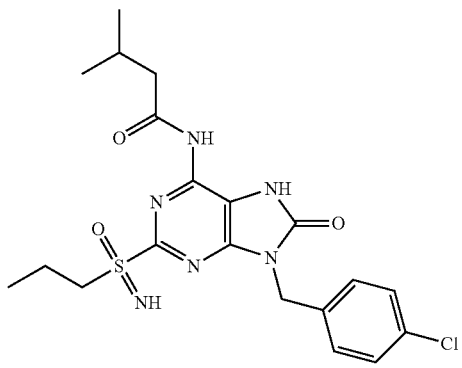

Example 62 was prepared in analogy to Example 58, Step 3 by using N-[9-[(4-chlorophenyl)methyl]-8-oxo-2-propylsulfinyl-7H-purin-6-yl]-2-methyl-butanamide (390 mg, 0.87 mmol, compound 62b) instead of N-[9-[(4-chlorophenyl)methyl]-8-oxo-2-propylsulfinyl-7H-purin-6-yl]-2-propyl-pentanamide (compound 58b). N-[9-[(4-chlorophenyl)methyl]-8-oxo-2-(propylsulfonimidoyl)-7H-purin-6-yl]-2-methyl-butanamide (89 mg, Example 62) was obtained as a white solid. $^1$H NMR (400 MHz, DMSO-d$_6$) δ ppm: 11.07 (br. s., 1H), 10.58 (br. s., 1H), 7.36-7.43 (m, 4H), 5.05 (s, 2H), 4.29 (s, 1H), 3.30-3.37 (m, 2H), 2.36 (d, J=7.0 Hz, 2H), 2.05-2.19 (m, 1H), 1.63 (sxt, J=7.6 Hz, 2H), 0.89-0.99 (m, 9H). MS obsd. (ESI$^+$) [(M+H)$^+$]: 465.

Example 63

N-[9-[(4-Chlorophenyl)methyl]-8-oxo-2-(propylsulfonimidoyl)-7H-purin-6-yl]-2-methyl-pentanamide

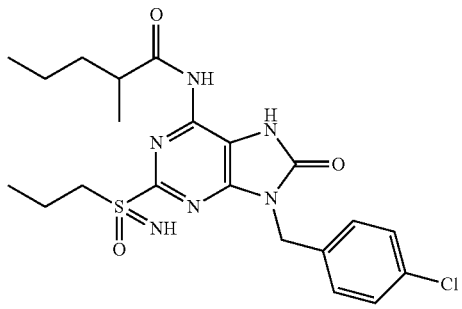

Step 1: Preparation of 2-methylpentanoyl 2-methylpentanoate

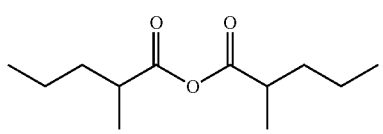

In a 250 mL three-necked flask, 2-methylpentanoic acid (11.6 g, 99.9 mmol). Di-tert-butyl dicarbonate (10.9 g, 49.9 mmol) and magnesium chloride (951 mg, 9.99 mmol) were dissolved in THF (100 mL) to give a colorless solution. The reaction mixture was stirred at 25° C. for 20 hrs. The reaction mixture was poured into H$_2$O (100 mL) and extracted with EtOAc (50 mL) three times. The organic layer was dried over MgSO$_4$ and concentrated in vacuo to give 2-methylpentanoyl-2-methylpentanoate (19 g, compound 63a) as a light yellow oil which was used in the next step without further purification.

Step 2: Preparation of N-[9-[(4-chlorophenyl)methyl]-8-oxo-2-propylsulfanyl-7H-purin-6-yl]-2-methyl-pentanamide

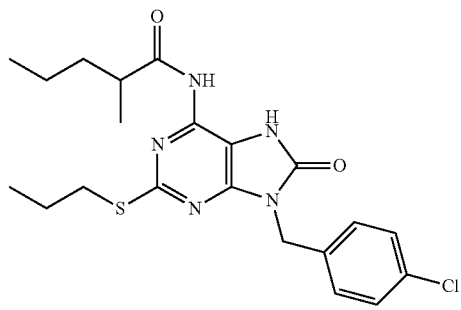

Compound 63b was prepared in analogy to Example 58, Step 1 by using 2-methylpentanoyl 2-methylpentanoate (compound 63b) instead of 2-propylpentanoic anhydride. N-[9-[(4-chlorophenyl)methyl]-8-oxo-2-propylsulfanyl-7H-purin-6-yl]-2-methyl-pentanamide (330 mg, compound 63b) was obtained as a white solid. MS obsd. (ESI$^+$) [(M+H)$^+$]: 448.

Step 3: Preparation of N-[9-[(4-chlorophenyl)methyl]-8-oxo-2-propylsulfinyl-7H-purin-6-yl]-2-methyl-pentanamide

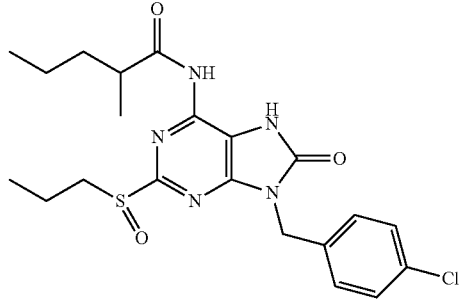

Compound 63c was prepared in analogy to Example 58, Step 2 by using N-[9-[(4-chlorophenyl)methyl]-8-oxo-2-propylsulfanyl-7H-purin-6-yl]-2-methyl-pentanamide (compound 63b) instead of N-[9-[(4-chlorophenyl)methyl]-8-oxo-2-propylsulfanyl-7H-purin-6-yl]-2-propyl-pentanamide (compound 58a). N-[9-[(4-chlorophenyl)methyl]-8-oxo-2-propylsulfinyl-7H-purin-6-yl]-2-methyl-pentanamide (250 mg, compound 63c) as a white solid. MS obsd. (ESI$^+$) [(M+H)$^+$]: 464.

Step 4: Preparation of N-[9-[(4-chlorophenyl)methyl]-8-oxo-2-(propylsulfonimidoyl)-7H-purin-6-yl]-2-methyl-pentanamide

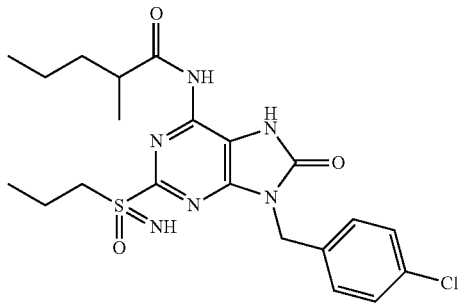

63

Example 63 was prepared in analogy to Example 58, Step 3 by using N-[9-[(4-chlorophenyl)methyl]-8-oxo-2-propylsulfinyl-7H-purin-6-yl]-2-methyl-pentanamide (250 mg, 0.87 mmol, compound 63c) instead of N-[9-[(4-chlorophenyl)methyl]-8-oxo-2-propylsulfinyl-7H-purin-6-yl]-2-propyl-pentanamide (compound 58b). N-[9-[(4-chlorophenyl)methyl]-8-oxo-2-(propylsulfonimidoyl)-7H-purin-6-yl]-2-methyl-pentanamide (122 mg, Example 63) as a white solid. $^1$H NMR (400 MHz, DMSO-$d_6$) δ ppm: 11.1 (s, 1H), 10.6 (s, 1H), 7.40 (m, 4H), 5.05 (s, 2H), 4.30 (s, 1H), 3.32-3.42 (m, 2H), 2.68-2.82 (m, 1H), 1.54-1.74 (m, 2H), 1.23-1.43 (m, 4H), 1.13 (d, J=8.0 Hz, 3H), 0.91 (t, J=7.2 Hz, 6H). MS obsd. (ESI$^+$) [(M+H)$^+$]: 479.

Example 64

N-[9-[(4-chlorophenyl)methyl]-8-oxo-2-(propylsulfonimidoyl)-7H-purin-6-yl]-2,2-dimethyl-propanamide

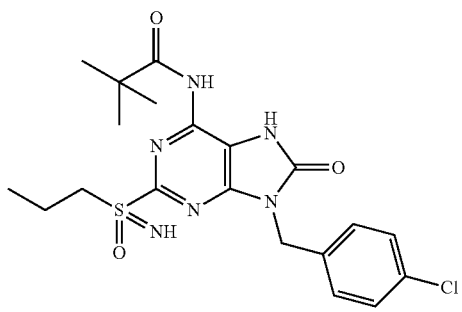

64

Step 1: Preparation of N-[9-[(4-chlorophenyl)methyl]-8-oxo-2-propylsulfanyl-7H-purin-6-yl]-2,2-dimethyl-propanamide

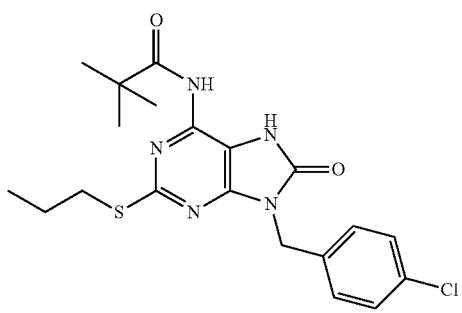

64a

Compound 64a was prepared in analogy to Example 58, Step 1 by using 2,2-dimethylpropanoyl 2,2-dimethylpropanoate (TCI, Catalog number: P1414-25ML) instead of 2-propylpentanoic anhydride. N-[9-[(4-chlorophenyl)methyl]-8-oxo-2-propylsulfanyl-7H-purin-6-yl]-2,2-dimethyl-propanamide (400 mg, compound 64a) was obtained as a white solid. MS obsd. (ESI$^+$) [(M+H)$^+$]: 434.

Step 2: Preparation of N-[9-[(4-chlorophenyl)methyl]-8-oxo-2-propylsulfinyl-7H-purin-6-yl]-2,2-dimethyl-propanamide

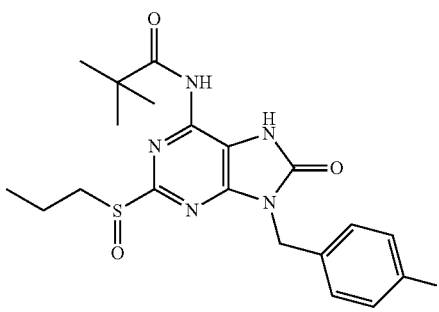

64b

Compound 64b was prepared in analogy to Example 58, Step 2 by using N-[9-[(4-chlorophenyl)methyl]-8-oxo-2-propylsulfanyl-7H-purin-6-yl]-2,2-dimethyl-propanamide (compound 64a) instead of N-[9-[(4-chlorophenyl)methyl]-8-oxo-2-propylsulfanyl-7H-purin-6-yl]-2-propyl-pentanamide (compound 58a). N-[9-[(4-chlorophenyl)methyl]-8-oxo-2-propylsulfinyl-7H-purin-6-yl]-2,2-dimethyl-propanamide (250 mg, compound 64b) was obtained as a white solid. MS obsd. (ESI$^+$) [(M+H)$^+$]: 450.

Step 3: Preparation of N-[9-[(4-chlorophenyl)methyl]-8-oxo-2-(propylsulfonimidoyl)-7H-purin-6-yl]-2,2-dimethyl-propanamide (64)

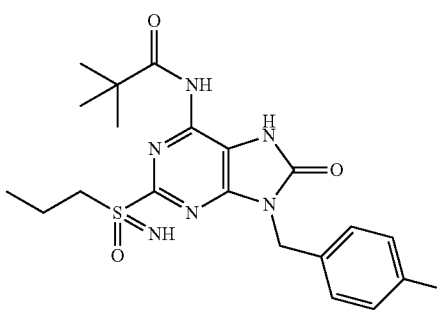

64

Example 64 was prepared in analogy to Example 58, Step 3 by using N-[9-[(4-chlorophenyl)methyl]-8-oxo-2-propylsulfinyl-7H-purin-6-yl]-2,2-dimethyl-propanamide (compound 64b) instead of N-[9-[(4-chlorophenyl)methyl]-8-oxo-2-propylsulfinyl-7H-purin-6-yl]-2-propyl-pentanamide (compound 58b). N-[9-[(4-chlorophenyl)methyl]-8-oxo-2-(propylsulfonimidoyl)-7H-purin-6-yl]-2,2-dimethyl-propanamide (33.5 mg, Example 64) was obtained as a white solid. $^1$H NMR (400 MHz, DMSO-$d_6$) δ ppm: 10.96 (s, 1H), 10.60 (s, 1H), 7.41 (m, 4H), 5.06 (s, 2H), 4.31 (s, 1H), 3.35-3.47 (m, 2H), 1.57-1.65 (m, 2H), 1.26 (m, 9H), 0.91 (t, J=8.0 Hz, 3H). MS obsd. (ESI+) [(M+H)+]: 465.

Example 65

N-[9-Benzyl-8-oxo-2-(propylsulfonimidoyl)-7H-purin-6-yl]-2-propyl-pentanamide

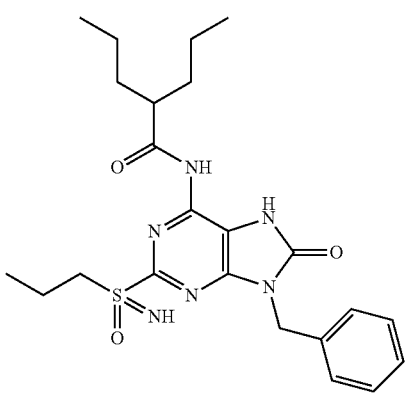

Step 1: Preparation of N-(9-benzyl-8-oxo-2-propyl-sulfanyl-7H-purin-6-yl)-2-propyl-pentanamide (65a)

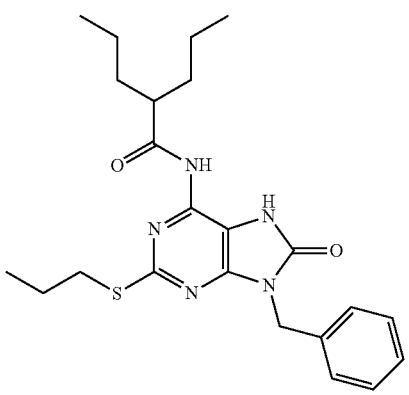

Compound 65a was prepared in analogy to Example 58, Step 1 by using 6-amino-9-benzyl-2-propylsulfanyl-7H-purin-8-one (compound 4a) instead of 6-amino-9-benzyl-2-propylsulfanyl-7H-purin-8-one (compound 9c). N-(9-Benzyl-8-oxo-2-propylsulfanyl-7H-purin-6-yl)-2-propyl-pentanamide (500 mg, compound 65a) was obtained as a white solid. MS obsd. (ESI+) [(M+H)+]: 442.

Step 2: Preparation of N-(9-benzyl-8-oxo-2-propyl-sulfinyl-7H-purin-6-yl)-2-propyl-pentanamide

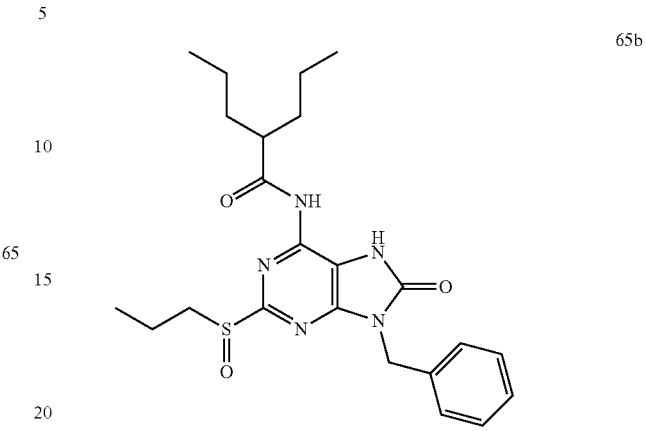

Compound 65b was prepared in analogy to Example 58, Step 2 by using N-(9-benzyl-8-oxo-2-propylsulfanyl-7H-purin-6-yl)-2-propyl-pentanamide (compound 65a) instead of N-[9-[(4-chlorophenyl)methyl]-8-oxo-2-propylsulfanyl-7H-purin-6-yl]-2-propyl-pentanamide (compound 50a). N-(9-benzyl-8-oxo-2-propylsulfinyl-7H-purin-6-yl)-2-propyl-pentanamide (400 mg, compound 65b) was obtained as a white solid. MS obsd. (ESI+) [(M+H)+]: 458.

Step 3: Preparation of N-[9-Benzyl-8-oxo-2-(propylsulfonimidoyl)-7H-purin-6-yl]-2-propyl-pentanamide

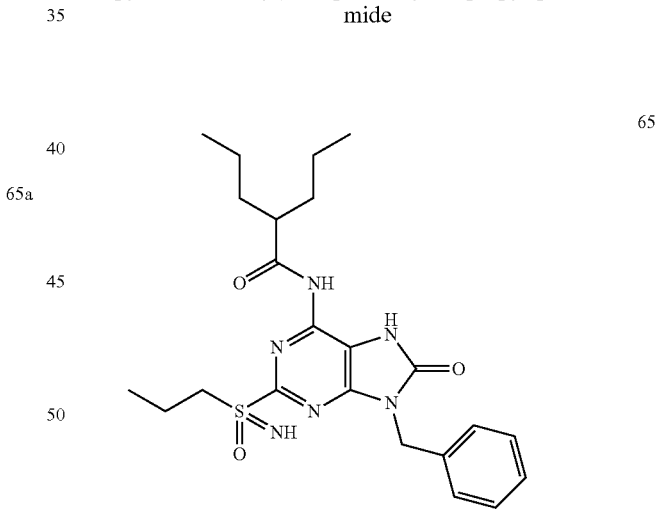

Example 65 was prepared in analogy to Example 58, Step 3 by using N-(9-benzyl-8-oxo-2-propylsulfinyl-7H-purin-6-yl)-2-propyl-pentanamide (compound 65b) instead of N-[9-[(4-chlorophenyl)methyl]-8-oxo-2-propylsulfinyl-7H-purin-6-yl]-2-propyl-pentanamide (compound 58b). N-[9-Benzyl-8-oxo-2-(propylsulfonimidoyl)-7H-purin-6-yl]-2-propyl-pentanamide (25 mg, Example 65) was obtained as a white solid. $^1$H NMR (400 MHz, DMSO-$d_6$) δ ppm: 11.15 (br. s., 1H), 10.45 (br. s., 1H), 7.27-7.39 (m, 5H), 5.06 (s, 2H), 4.29 (s, 1H), 3.31-3.37 (m, 2H), 2.61-2.87 (m, 1H), 1.50-1.75 (m, 4H), 1.23-1.43 (m, 6H), 0.81-0.97 (m, 9H). MS obsd. (ESI+) [(M+H)+]: 473.

Example 66

[6-Amino-9-benzyl-2-(methylsulfonimidoyl)-8-oxo-purin-7-yl]methyl acetate

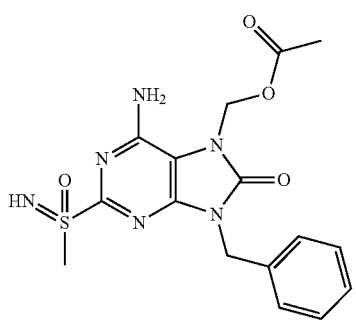

To a solution of 6-amino-9-benzyl-2-(methylsulfonimidoyl)-7H-purin-8-one (300 mg, 0.94 mmol, Example 1) in DMF (5 mL) was added NaH (45 mg, 1.13 mmol). The reaction was stirred for 10 min, then chloromethyl acetate (123 mg, 1.13 mmol) was added. The reaction mixture was stirred at RT for 0.5 hr, then quenched with sat. NH$_4$Cl and concentrated in vacuo. The residue was purified by prep-HPLC to give [6-amino-9-benzyl-2-(methylsulfonimidoyl)-8-oxo-purin-7-yl]methyl acetate (8.3 mg, Example 66) as a white solid. $^1$H NMR (400 MHz, CD$_3$OD) δ ppm: 7.48-7.35 (m, 2H), 7.33-7.26 (m, 3H), 6.01 (s, 2H), 5.12 (s, 2H), 3.35-3.33 (m, 3H), 2.11 (s, 3H). MS obsd. (ESI$^+$) [(M+H)$^+$]: 391.

Example 67

[6-Amino-9-benzyl-8-oxo-2-(propylsulfonimidoyl)purin-7-yl]methyl acetate

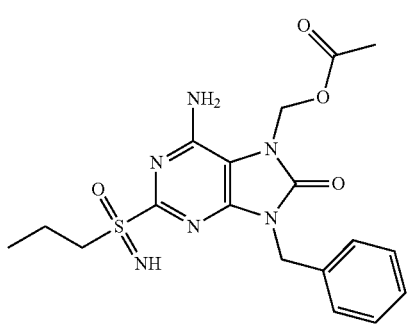

The title compound was prepared in analogy to Example 66 by using 6-amino-9-benzyl-2-(propylsulfonimidoyl)-7H-purin-8-one (Example 4) instead of 6-amino-9-benzyl-2-(methylsulfonimidoyl)-7H-purin-8-one (Example 1). [6-Amino-9-benzyl-2-(propylsulfonimidoyl)purin-8-yl]N-ethyl-N-methyl-carbamate (15 mg, Example 67) was obtained as a white solid. $^1$H NMR (400 MHz, CD$_3$OD) δ ppm: 7.45-7.43 (m, 2H), 7.35-7.28 (m, 3H), 6.01 (s, 2H), 5.12 (s, 2H), 3.55-3.44 (m, 2H), 2.12 (s, 3H), 1.81-1.74 (m, 2H), 1.02 (t, J=7.2 Hz, 3H). MS obsd. (ESI$^+$) [(M+H)$^+$]: 419.

Example 68

[6-Amino-9-benzyl-8-oxo-2-(propylsulfonimidoyl)purin-7-yl]methyl 2,2-dimethylpropanoate

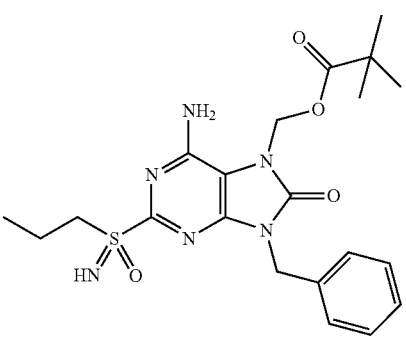

The title compound was prepared in analogy to Example 66 by using 6-amino-9-benzyl-2-(propylsulfonimidoyl)-7H-purin-8-one (Example 4) and chloromethyl 2,2-dimethylpropanoate instead of 6-amino-9-benzyl-2-(methylsulfonimidoyl)-7H-purin-8-one (Example 1) and chloromethyl acetate. [6-Amino-9-benzyl-8-oxo-2-(propylsulfonimidoyl)purin-7-yl]methyl 2,2-dimethylpropanoate (15.8 mg, Example 68) was obtained as a white solid. $^1$H NMR (400 MHz, CDCl$_3$) δ ppm: 7.48-7.50 (m, 2H), 7.31-7.36 (m, 3H), 6.01 (s, 2H), 5.95 (s, 2H), 5.12 (s, 2H), 3.58-3.44 (m, 2H), 1.85-1.94 (m, 2H), 1.24 (s, 9H), 1.07 (t, J=7.12 Hz, 3H). MS obsd. (ESI$^+$) [(M+H)$^+$]: 461.

Example 69

1-[6-Amino-9-benzyl-8-oxo-2-(propylsulfonimidoyl)purin-7-yl]ethyl acetate

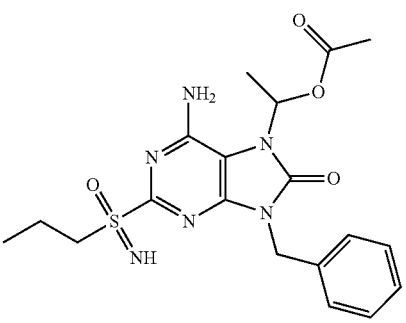 [SMILES: CCCS(=N)(=O)c1nc(N)c2c(n1)n(Cc1ccccc1)c(=O)n2C(C)OC(C)=O]

Step 1: Preparation of 1-chloroethyl acetate

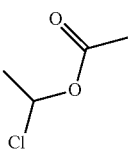

To a flask containing freshly dried catalytic amount of ZnCl₂ (680 mg, 5 mmol) under nitrogen was added acetyl chloride (3.9 g, 50 mmol) and the mixture was cooled to −5° C. to −10° C. Acetaldehyde (2.4 g, 55 mmol) was added dropwise and the resulting reaction mixture stirred at 22-33° C. for 1 hr. The mixture was concentrated in vacuo to afford 1-chloroethyl acetate which was used in the next step without further purification.

Step 2: Preparation of 1-[6-amino-9-benzyl-8-oxo-2-(propylsulfonimidoyl)purin-7-yl]ethyl acetate

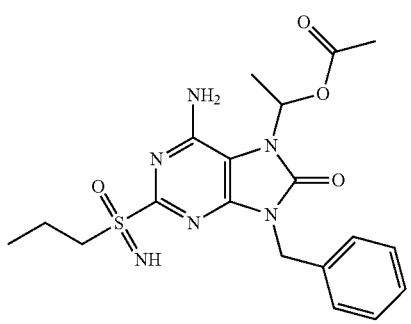 [SMILES: CCCS(=N)(=O)c1nc(N)c2c(n1)n(Cc1ccccc1)c(=O)n2C(C)OC(C)=O]

The title compound was prepared in analogy to Example 66 by using 6-amino-9-benzyl-2-(propylsulfonimidoyl)-7H-purin-8-one (Example 4) and 1-chloroethyl acetate instead of 6-amino-9-benzyl-2-(methylsulfonimidoyl)-7H-purin-8-one (Example 1) and chloromethyl acetate. 1-[6-Amino-9-benzyl-8-oxo-2-(propylsulfonimidoyl)purin-7-yl]ethyl acetate (9.3 mg, Example 69) was obtained as a white solid. ¹H NMR (400 MHz, CD₃OD) δ ppm: 7.44-7.30 (m, 5H), 7.05-7.03 (m, 1H), 5.12 (s, 2H), 3.33 (br. s., 2H), 2.14 (s, 3H), 1.74 (m, 2H), 1.72 (d, J=6.8 Hz, 3H), 1.04-1.00 (m, 3H). MS obsd. (ESI⁺) [(M+H)⁺]: 433.

Example 70

6-Amino-9-[(4-chlorophenyl)methyl]-2-(ethylsulfonimidoyl)-7H-purin-8-one

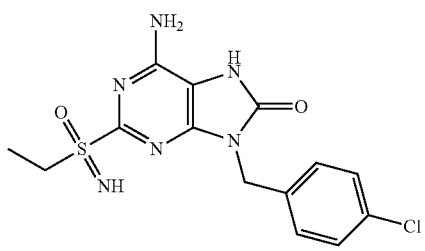

Step 1: Preparation of 6-amino-9-[(4-chlorophenyl)methyl]-2-ethylsulfanyl-7H-purin-8-one

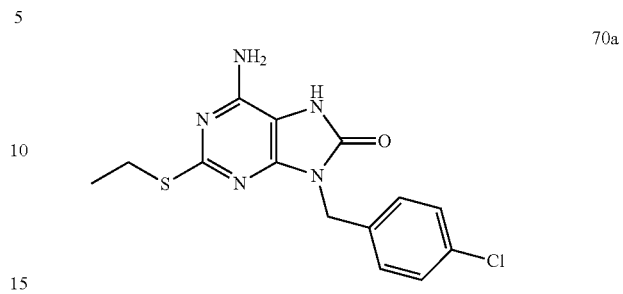

Compound 70a was prepared in analogy to Example 1, Step 3 by using iodoethane and 6-amino-9-[(4-chlorophenyl)methyl]-2-sulfanyl-7H-purin-8-one (compound 9b) instead of methyl iodide and 6-amino-9-phenylmethyl-2-sulfanyl-7H-purin-8-one (compound 1b). 6-Amino-9-[(4-chlorophenyl)methyl]-2-ethylsulfanyl-7H-purin-8-one (2.5 g, compound 70a) was obtained as a white solid. MS obsd. (ESI⁺) [(M+H)⁺]: 336.

Step 2: Preparation of 6-amino-9-(4-chlorobenzyl)-2-ethylsulfinyl-7H-purin-8-one

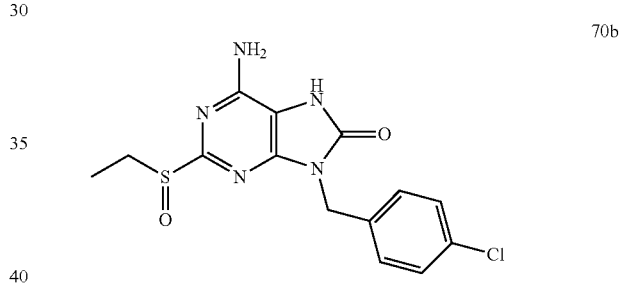

Compound 70b was prepared in analogy to Example 1, Step 4 by using 6-amino-9-[(4-chlorophenyl)methyl]-2-ethylsulfanyl-7H-purin-8-one (compound 70a) instead of 6-amino-9-benzyl-2-methylsulfanyl-7H-purin-8-one (compound 1c). 6-Amino-9-(4-chlorobenzyl)-2-ethylsulfinyl-7H-purin-8-one (1.94 g, compound 70b) was obtained as a white solid. MS obsd. (ESI⁺) [(M+H)⁺]: 352.

Step 3: Preparation of 6-amino-9-[(4-chlorophenyl)methyl]-2-(ethylsulfonimidoyl)-7H-purin-8-one

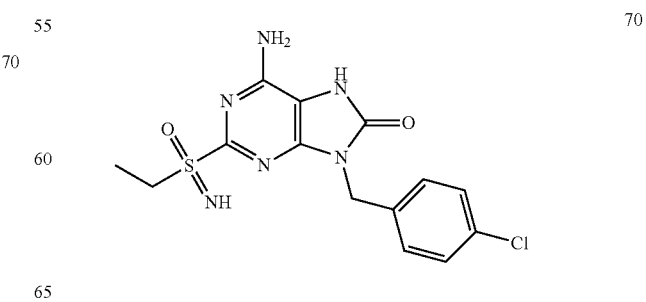

The title compound was prepared in analogy to Example 1, Step 5 by using 6-amino-9-(4-chlorobenzyl)-2-ethylsulfinyl-7H-purin-8-one (compound 70b) instead of 6-amino-9-benzyl-2-(2-methylsulfinyl)-7H-purin-8-one (compound 1d). 6-Amino-9-[(4-chlorophenyl)methyl]-2-(ethylsulfonimidoyl)-7H-purin-8-one (217 mg, Example 70) was obtained as a white solid. $^1$H NMR (400 MHz, DMSO-$d_6$) δ ppm: 10.61 (s, 1H), 7.42-7.35 (m, 4H), 6.98 (s, 2H), 4.96 (s, 2H), 4.05 (s, 1H), 3.42-3.37 (m, 2H), 1.16 (t, J=7.4 Hz, 3H). MS obsd. (ESI$^+$) [(M+H)$^+$]: 367.

Separation of compound of Example 70 by chiral HPLC afforded Example 70-A (faster eluting, 31.8 mg) and Example 70-B (slower eluting, 10 mg) as white solid. (Separation condition: methanol 5%-40% (0.05% DEA)/CO$_2$ on ChiralPak IC-3 column.)

Example 70-A $^1$H NMR (400 MHz, DMSO-$d_6$) δ ppm: 10.76 (s, 1H), 7.45-7.33 (m, 4H), 7.01 (s, 2H), 4.96 (s, 2H), 4.03 (s, 1H), 3.40-3.34 (m, 2H), 1.17 (t, J=7.4 Hz, 3H). MS obsd. (ESI$^+$) [(M+H)$^+$]: 367.

Example 70-B $^1$H NMR (400 MHz, DMSO-$d_6$) δ ppm: 10.70 (s, 1H), 7.46-7.28 (m, 4H), 7.01 (s, 2H), 4.96 (s, 2H), 4.03 (s, 1H), 3.44-3.36 (m, 2H), 1.17 (t, J=7.4 Hz, 3H). MS obsd. (ESI$^+$) [(M+H)$^+$]: 367.

Example 71

6-Amino-2-(ethylsulfonimidoyl)-9-(p-tolylmethyl)-7H-purin-8-one

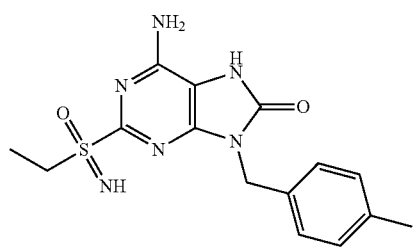

71

Step 1: Preparation of 4-amino-2-oxo-3-(p-tolylmethyl)-1H-imidazole-5-carbonitrile

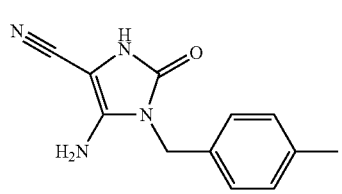

71a

Compound 71a was prepared in analogy to Example 9, Step 1 by using p-tolylmethanamine instead of 4-chlorophenylmethylamine. 4-Amino-2-oxo-3-(p-tolylmethyl)-1H-imidazole-5-carbonitrile (26.6 g, compound 71a) was obtained as a grey solid and used directly in next step without further purification. MS obsd. (ESI$^+$) [(M+H)$^+$]: 229.

Step 2: Preparation of 6-amino-9-(p-tolylmethyl)-2-sulfanyl-7H-purin-8-one

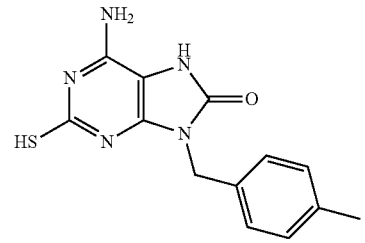

71b

Compound 71b was prepared in analogy to Example 9, Step 2 by using of 4-amino-2-oxo-3-(p-tolylmethyl)-1H-imidazole-5-carbonitrile (compound 71a) instead of 4-amino-3-[(4-chlorophenyl)methyl]-2-oxo-1H-imidazole-5-carbonitrile (compound 9a). 6-Amino-9-(p-tolylmethyl)-2-sulfanyl-7H-purin-8-one (20.0 g, compound 71b) was obtained as a yellow solid. MS obsd. (ESI$^+$) [(M+H)$^+$]: 288.

Step 3: Preparation of 6-amino-2-ethylsulfanyl-9-(p-tolylmethyl)-7H-purin-8-one

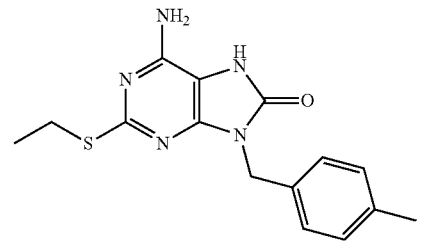

71c

Compound 71c was prepared in analogy to Example 1, Step 3 by using 6-amino-9-(p-tolylmethyl)-2-sulfanyl-7H-purin-8-one (compound 71b) and iodoethane instead of 6-amino-9-benzyl-2-ethylsulfanyl-7H-purin-8-one (compound 2a) and methyl iodide. 6-Amino-2-ethylsulfanyl-9-(p-tolylmethyl)-7H-purin-8-one (13 g, compound 71c) was obtained as a yellow solid. MS obsd. (ESI$^+$) [(M+H)$^+$]: 316.

Step 4: Preparation of 6-amino-2-ethylsulfinyl-9-(p-tolylmethyl)-7H-purin-8-one

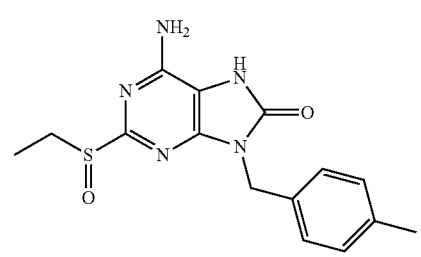

71d

Compound 71d was prepared in analogy to Example 1, Step 4 by using 6-amino-2-ethylsulfanyl-9-(p-tolylmethyl)-7H-purin-8-one (compound 71c) instead of 6-amino-9-benzyl-2-methylsulfanyl-7H-purin-8-one (compound 1c). 6-Amino-2-ethylsulfinyl-9-(p-tolylmethyl)-7H-purin-8-one6 (3.5 g, compound 71d) was obtained as a yellow solid. MS obsd. (ESI+) [(M+H)+]: 332.

Step 5: Preparation of 6-amino-2-(ethylsulfonimidoyl)-9-(p-tolylmethyl)-7H-purin-8-one

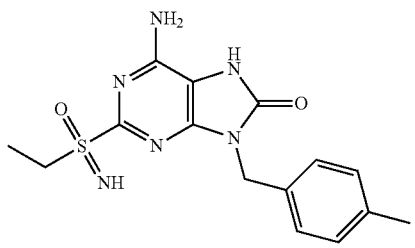

71

The title compound was prepared in analogy to Example 1, Step 5 by using 6-amino-2-ethylsulfinyl-9-(p-tolylmethyl)-7H-purin-8-one (compound 71d) instead of 6-amino-9-benzyl-2-methylsulfinyl-7H-purin-8-one (compound 1d). 6-Amino-2-(ethylsulfonimidoyl)-9-(p-tolylmethyl)-7H-purin-8-one (530 mg, Example 71) was obtained as a yellow solid. 1H NMR (400 MHz, DMSO-d6) δ ppm: 10.53 (s, 1H), 7.24 (d, J=8.03 Hz, 2H), 7.13 (d, J=8.03 Hz, 2H), 6.94 (br. s., 2H), 4.91 (s, 2H), 4.03 (s, 1H), 3.36-3.41 (m, 2H), 2.26 (s, 3H), 1.18 (t, J=7.28 Hz, 3H). MS obsd. (ESI+) [(M+H)+]: 347.

Separation of compound of Example 71 by chiral HPLC afforded Example 71-A (faster eluting, 56.8 mg) and Example 71-B (slower eluting, 56.7 mg) as white solid. (Separation condition: methanol 5%-40% (0.05% DEA)/CO2 on ChiralPak AD-3 column.)

Example 71-A

1H NMR (400 MHz, DMSO-d6) δ ppm: 10.52 (br. s., 1H), 7.24 (d, J=8.0 Hz, 2H), 7.13 (d, J=7.9 Hz, 2H), 6.94 (br. s., 2H), 4.91 (s, 2H), 4.02 (s, 1H), 3.43-3.33 (m, 2H), 2.26 (s, 3H), 1.18 (t, J=7.3 Hz, 3H). MS obsd. (ESI+) [(M+H)+]: 347.

Example 71-B

1H NMR (400 MHz, DMSO-d6) δ ppm: 10.52 (br. s., 1H), 7.24 (d, J=8.0 Hz, 2H), 7.13 (d, J=8.0 Hz, 2H), 6.94 (br. s., 2H), 4.91 (s, 2H) 4.02 (s, 1H), 3.42-3.33 (m, 2H), 2.26 (s, 3H), 1.18 (t, J=7.3 Hz, 3H). MS obsd. (ESI+) [(M+H)+]: 347.

Example 72

6-Amino-2-(ethylsulfonimidoyl)-9-[(4-fluorophenyl)methyl]-7H-purin-8-one

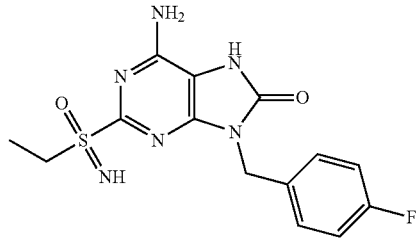

72

Step 1: Preparation of 4-amino-3-[(4-fluorophenyl)methyl]-2-oxo-1H-imidazole-5-carbonitrile

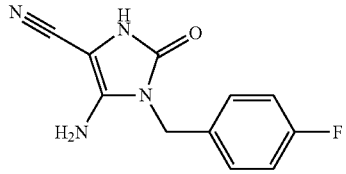

72a

Compound 72a was prepared in analogy to Example 9, Step 1 by using (4-fluorophenyl)methylamine instead of 4-chloropenylmethylamine. 4-Amino-3-[(4-fluorophenyl)methyl]-2-oxo-1H-imidazole-5-carbonitrile (48 g, compound 72a) was obtained as a light yellow solid and used directly in next step without further purification. MS obsd. (ESI+) [(M+H)+]: 233.

Step 2: Preparation of 6-amino-9-[(4-fluorophenyl)methyl]-2-sulfanyl-7H-purin-8-one

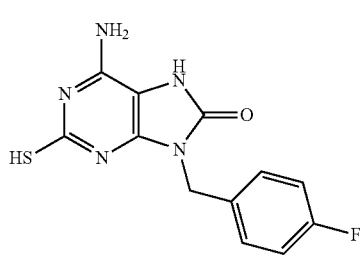

72b

Compound 72b was prepared in analogy to Example 9, Step 2 by using of 4-amino-3-[(4-fluorophenyl)methyl]-2-oxo-1H-imidazole-5-carbonitrile (compound 72a) instead of 4-amino-3-[(4-chlorophenyl)methyl]-2-oxo-1H-imidazole-5-carbonitrile (compound 9a). 6-Amino-9-[(4-fluorophenyl)methyl]-2-sulfanyl-7H-purin-8-one (32.0 g, compound 72b) was obtained as a yellow solid. MS obsd. (ESI+) [(M+H)+]: 292.

Step 3: Preparation of 6-amino-2-ethylsulfanyl-9-[(4-fluorophenyl)methyl]-7H-purin-8-one

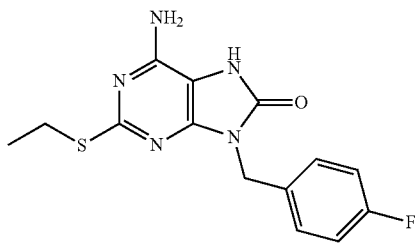

Compound 72c was prepared in analogy to Example 1, Step 3 by using 6-amino-9-[(4-fluorophenyl)methyl]-2-sulfanyl-7H-purin-8-one (compound 72b) and iodoethane instead of 6-amino-9-benzyl-2-sulfanyl-7H-purin-8-one (compound 1b) and methyl iodide. 6-Amino-2-ethylsulfanyl-9-[(4-fluorophenyl)methyl]-7H-purin-8-one (5.6 g, compound 72c) was obtained as a yellow solid. MS obsd. (ESI$^+$) [(M+H)$^+$]: 320.

Step 4: Preparation of 6-amino-2-ethylsulfinyl-9-[(4-fluorophenyl)methyl]-7H-purin-8-one

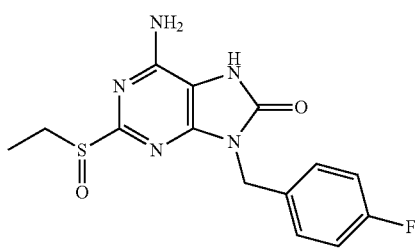

Compound 72d was prepared in analogy to Example 1, Step 4 by using 6-amino-2-ethylsulfanyl-9-[(4-fluorophenyl)methyl]-7H-purin-8-one (compound 72c) instead of 6-amino-9-benzyl-2-methylsulfanyl-7H-purin-8-one (compound 1c). 6-Amino-2-ethylsulfinyl-9-[(4-fluorophenyl) methyl]-7H-purin-8-one (4.8 g, compound 72d) was obtained as a yellow solid. MS obsd. (ESI$^+$) [(M+H)$^+$]: 332.

Step 5: Preparation of 6-amino-2-(ethylsulfonimidoyl)-9-[(4-fluorophenyl)methyl]-7H-purin-8-one

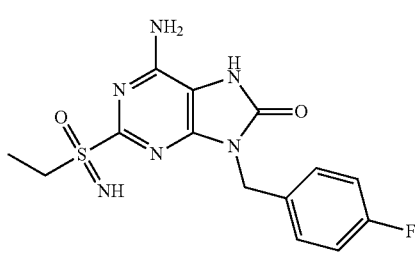

The title compound was prepared in analogy to Example 1, Step 5 by using 6-amino-2-ethylsulfinyl-9-[(4-fluorophenyl)methyl]-7H-purin-8-one (compound 72d) instead of 6-amino-9-benzyl-2-methylsulfinyl-7H-purin-8-one (compound 1d). 6-Amino-2-(ethylsulfonimidoyl)-9-[(4-fluorophenyl)methyl]-7H-purin-8-one (2.9 g, Example 72) was obtained as a yellow solid. $^1$H NMR (400 MHz, DMSO-d$_6$) δ ppm: 10.57 (br. s., 1H), 7.40 (dd, J=8.5, 5.5 Hz, 2H), 7.16 (t, J=8.9 Hz, 2H), 6.97 (br. s., 2H), 4.94 (s, 2H), 4.07 (s, 1H), 3.43-3.36 (m, 2H), 1.17 (t, J=7.4 Hz, 3H). MS obsd. (ESI$^+$) [(M+H)$^+$]: 351.

Separation of compound of Example 72 by chiral HPLC afforded Example 72-A (faster eluting, 85.4 mg) and Example 72-B (slower eluting, 36.4 mg) as white solid. (Separation condition: methanol 5%-40% (0.05% DEA)/CO$_2$ on ChiralPak AD-3 column.)

Example 72-A $^1$H NMR (400 MHz, DMSO-d$_6$) δ ppm: 10.53 (br. s., 1H), 7.41 (dd, J=8.5, 5.5 Hz, 2H), 7.17 (t, J=8.9 Hz, 2H), 6.98 (br. s., 2H), 4.95 (s, 2H), 4.07 (s, 1H), 3.45-3.36 (m, 2H), 1.17 (t, J=7.3 Hz, 3H). MS obsd. (ESI$^+$) [(M+H)$^+$]: 351.

Example 72-B $^1$H NMR (400 MHz, DMSO-d$_6$) δ ppm: 10.53 (br. s., 1H), 7.41 (dd, J=8.5, 5.5 Hz, 2H), 7.17 (t, J=8.9 Hz, 2H), 6.98 (br. s., 2H), 4.95 (s, 2H), 4.07 (s, 1H), 3.44-3.37 (m, 2H) 1.17 (t, J=7.3 Hz, 3H). MS obsd. (ESI$^+$) [(M+H)$^+$]: 351.

Example 73

HEK-Blue-hTLR 7 Cells Assay

A stable HEK-Blue-hTLR7 cell line was purchased from InvivoGen (Cat.#: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue-hTLR7 cells with TLR7 ligands. Therefore the reporter expression was regulated by the NF-κB promoter upon stimulation of human TLR7 for 20 hrs. The cell culture supernatant SEAP reporter activity was determined using QUANTI-Blue™ kit (Cat.#: rep-qb1, Invivogen, San Diego, Ca, USA) at a wavelength of 640 nm, a detection medium that turns purple or blue in the presence of alkaline phosphatase.

HEK-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (V/V) heat-inactivated fetal bovine serum for 24 hrs. Then the HEK-Blue-hTLR-7 cells were incubated with addition of 20 μL test compound in a serial dilution in the presence of final DMSO at 1% and perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002)).

The compounds of the present invention were tested in HEK-Blue-hTLR7 assay for their TLR7 agonism activity as described herein and results are listed in Table 1. The Examples were found to have $EC_{50}$ of about 0.01 μM to about 0.7 μM. Particular compounds of the present invention were found to have $EC_{50}$ of about 0.01 μM to about 0.1 μM.

TABLE 1

Activity of Compounds in HEK-Blue-hTLR7 assay in vitro

| Example No. | HEK-Blue-hTLR7 ($EC_{50}$ (μM)) |
|---|---|
| GS-9620 | 0.80 |
| S-1 | 0.37 |
| P-2 | 0.27 |
| P-5 | 3.14 |
| 1 | 0.30 |
| 1-B | 0.18 |
| 2 | 0.20 |
| 3 | 0.33 |
| 3-A | 0.27 |
| 3-B | 0.55 |
| 4 | 0.065 |
| 4-A | 0.067 |
| 4-B | 0.086 |
| 5 | 0.32 |
| 6 | 0.43 |
| 7 | 0.18 |
| 9 | 0.012 |
| 9-A | 0.014 |
| 9-B | 0.011 |
| 10 | 0.074 |
| 11 | 0.066 |
| 13 | 0.043 |
| 14 | 0.017 |
| 15 | 0.19 |
| 16 | 0.22 |
| 16-A | 0.76 |
| 16-B | 0.15 |
| 17 | 0.068 |
| 18 | 0.047 |
| 19 | 0.67 |
| 20 | 0.26 |
| 22 | 0.042 |
| 23 | 0.016 |
| 24 | 0.037 |
| 25 | 0.0096 |
| 26 | 0.021 |
| 27 | 0.036 |
| 28 | 0.021 |
| 29 | 0.027 |
| 29-A | 0.019 |
| 29-B | 0.022 |
| 30 | 0.018 |
| 31 | 0.040 |
| 32 | 0.054 |
| 33 | 0.066 |
| 34 | 0.030 |
| 35 | 0.12 |
| 36 | 0.022 |
| 37 | 0.023 |
| 38 | 0.075 |
| 39 | 0.17 |
| 40 | 0.15 |
| 41 | 0.084 |
| 42 | 0.09 |
| 43 | 0.24 |
| 44 | 0.136 |
| 70 | 0.057 |
| 70-A | 0.054 |
| 70-B | 0.077 |
| 71 | 0.098 |
| 71-A | 0.134 |
| 71-B | 0.087 |

Example 74

HEK-Blue-hTLR8 Cells Assay and Selectivity Index ($EC_{50(TLR8)}/EC_{50(TLR7)}$)

A stable HEK-Blue-hTLR8 cell line was purchased from InvivoGen (Cat.#: HEK-Blue-htlr8, San Diego, Calif., USA). These cells were designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue-hTLR8 cells with TLR8 ligands. Therefore the reporter expression was regulated by the NF-κB promoter upon stimulation of human TLR8 for 20 hrs. The cell culture supernatant SEAP reporter activity was determined using QUANTI-Blue™ kit (Cat.#: rep-qb1, Invivogen, San Diego, Ca, USA) at a wavelength of 640 nm, a detection medium that turns purple or blue in the presence of alkaline phosphatase.

HEK-Blue-hTLR8 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (V/V) heat-inactivated fetal bovine serum for 24 hrs. Then the HEK-Blue-hTLR8 cells were incubated with addition of 20 μL test compound in a serial dilution in the presence of final DMSO at 1% and perform incubation under 37° C. in a $CO_2$ incubator for 20 hrs. Then 20 μL of the supernatant from each well was incubated with 180 μL Quanti-blue substrate solution at 37° C. for 2 hours and the absorbance was read at 620~655 nm using a spectrophotometer. The signalling pathway that TLR8 activation leads to downstream NF-κB activation has been widely accepted, and therefore similar reporter assay was also widely used for evaluating TLR8 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002)).

The compounds of the present invention were tested in HEK-Blue-hTLR8 assay for their TLR8 agonism activity as described herein and results are listed in Table 2. The ratio of TLR8 agonism activity compared to TLR7 agonism activity was defined as the selectivity index ($EC_{50\ (TLR8)}$ value/$EC_{50(TLR7)}$ value) and calculated accordingly. Since TLR7 and TLR8 agonists differ in their target cell selectivity and cytokine induction profile, and TLR7-specific agonists activate plasmacytoid DCs (pDCs) and B cells and induce mainly IFN-α and IFN-regulated cytokines, which may be potentially beneficial as the HBV therapy. The higher selectivity index the compound shows, the more TLR7 specific the compound is. The compounds of present invention showed comparable or better selectivity index over reference compounds.

TABLE 2

Activity of Compounds in HEK Blue-hTLR-8 assay in vitro and selective index

| Example No. | HEK Blue hTLR-8 EC50 (μM) | Selective index |
|---|---|---|
| GS-9620 | 11.6 | 14 |
| S-1 | >1000 | >2703 |
| P-2 | >1000 | >3707 |
| P-5 | >1000 | >318 |
| 1 | 652.4 | 2175 |
| 1-B | 535.7 | 2976 |
| 13 | 300 | 6977 |
| 16 | >1000 | >4546 |
| 20 | >1000 | >3846 |
| 70 | 90.0 | 1579 |
| 70-A | >1000 | >18518 |

Example 75

Lysa Solubility

LYSA solubility assay is used to determine the aqueous solubility of a compound.

Samples were prepared in duplicate from 10 mM DMSO stock solution. After evaporation of DMSO with a centrifugal vacuum evaporator, the compounds were dissolved in 0.05 M phosphate buffer (pH 6.5), stirred for one hour and shaken for two hours. After one night, the solutions were filtered using a microtiter filter plate. Then the filtrate and its 1/10 dilution were analyzed by HPLC-UV. In addition a four-point calibration curve was prepared from the 10 mM stock solutions and used for the solubility determination of the compounds. The results are in μg/mL and summarized in Table 3. Compounds with higher solubility could broaden its suitability for different dosage forms and increase the chance to achieve desired concentration in systemic circulation, which in turn can potentially lower the required dose. The exemplified compounds of present invention showed much improved solubility compared to S-1, P-2 and P-5.

TABLE 3

Solubility data of compounds of present invention

| Example No. | LYSA (μg/mL) |
|---|---|
| S-1 | 0.5 |
| P-2 | 1 |
| P-5 | 1 |
| 1-A | 85 |
| 1-B | 98 |
| 2 | 29 |
| 3 | 300 |
| 4 | 21 |
| 4-A | 56 |
| 4-B | 50 |
| 5 | 40 |
| 6 | 89 |
| 7 | 18 |
| 11 | 18 |
| 13 | 10 |
| 18 | 166 |
| 19 | >428 |
| 21 | 121 |
| 24 | 12 |
| 27 | 7 |
| 29-A | 6 |
| 29-B | 11 |
| 32 | 18 |
| 33 | 79 |
| 39 | >520 |
| 40 | 168 |
| 43 | >465 |
| 44 | 357 |
| 70 | 7 |
| 70-B | 5 |
| 71 | 12 |
| 71-A | 13 |
| 71-B | 13 |
| 72 | 152 |
| 72-A | 90 |
| 72-B | 115 |

Example 76

Metabolic Stability in Human Liver Microsomes

The human microsomal stability assay is used for early assessment of metabolic stability of a test compound in human liver microsomes.

Human liver microsomes (Cat. NO.: 452117, Corning, USA; Cat. NO.: H2610, Xenotech, USA) were preincubated with test compound for 10 minutes at 37° C. in 100 mM potassium phosphate buffer, pH 7.4. The reactions were initiated by adding NADPH regenerating system. The final incubation mixtures contained 1 μM test compound, 0.5 mg/mL liver microsomal protein, 1 mM $MgCL_2$, 1 mM NADP, 1 unit/mL isocitric dehydrogenase and 6 mM isocitric acid in 100 mM potassium phosphate buffer, pH 7.4. After incubation times of 0, 3, 6, 9, 15 and 30 minutes at 37° C., 300 μL of cold ACN (including internal standard) was added to 100 μL incubation mixture to terminate the reaction. Following precipitation and centrifugation, the amount of compound remaining in the samples were determined by LC-MS/MS. Controls of no NADPH regenerating system at zero and 30 minutes were also prepared and analyzed. The results were categorized as: low (<7.0 mL/min/kg), medium (7.0-16.2 mL/min/kg) and high (16.2-23.2 mL/min/kg). Results of metabolic stability study in human liver microsomes are given in Table 4. Exemplified compounds of this invention showed low clearance in human liver microsomes, while reference compounds GS-9620 and P-2 were categorized as high and medium respectively.

TABLE 4

Metabolic stability in human liver microsomes of compounds of this invention.

| Example No. | Human Liver Microsome Clearance (mL/min/kg) |
|---|---|
| GS-9620 | 17.8 |
| P-2 | 7.3 |
| 1 | <6.15* |
| 1-A | <6.15 |
| 1-B | <6.15 |
| 2 | <6.15 |
| 3 | <6.15 |
| 3-A | <6.15 |
| 4 | <6.15 |
| 5 | <6.15 |
| 29-A | <6.15 |
| 31 | <6.15 |
| 32 | <6.15 |

TABLE 4-continued

Metabolic stability in human liver microsomes of compounds of this invention.

| Example No. | Human Liver Microsome Clearance (mL/min/kg) |
|---|---|
| 33 | <6.15 |
| 34 | <6.15 |
| 35 | <6.15 |
| 37 | <6.15 |
| 39 | <6.15 |
| 40 | <6.15 |
| 43 | <6.15 |
| 44 | <6.15 |
| 70-A | <6.15 |
| 70-B | <6.15 |
| 71-A | <6.15 |
| 71-B | <6.15 |
| 72 | <6.15 |
| 72-A | <6.15 |
| 72-B | <6.15 |

*6.15 mL/min/kg is the limitation of assay sensitivity.

Example 77

Cytochrome P450 (Cyp450) Induction Screening Assay mRNA Induction

Induction of cytochrome P450 enzymes is associated with an increased prevalence of clinical drug-drug interactions. The clinical consequences of induction may be therapeutic failure caused by a decreased systemic exposure of the drug itself or a co-administered therapy, or toxicity as a result of increased bioactivation. Cytochrome P450 (CYP450) induction assay has been used to understand the potential drug-drug interaction liabilities in drug discovery stage.

Cell Culture

Human cryopreserved hepatocytes (Life Technologies, Carlsbad, USA) were thawed and cultured in collagen I coated 96-well plates with a density of 52,000 cells/well. After attachment, hepatocyte maintenance medium (HMM; Lonza, Switzerland) was changed after cells were pre-cultured overnight.

Test compounds were dosed to the cells next morning at an indicated concentration (up to 10 µM) in HMM culture medium containing gentamycin and a constant 0.1% DMSO. Similarly, dilutions of the positive inducer compounds omeprazole (prototypical inducer of human CYP1A2; final concentrations: 1 and 10 µM), phenobarbital (prototypical inducer of human CYP2B6; final concentrations: 100 and 1000 µM) and rifampicin (prototypical inducer of human CYP3A4; final concentrations: 1 and 10 µM) were prepared from 1000 fold DMSO stock solutions in HMM containing gentamycin. Medium change was then performed and cells were exposed for 24 hours to test compounds, positive inducer compounds, or vehicle (0.1% DMSO), respectively.

At the end of the compound exposure period, medium was removed and cells lysed using 100 µL/well MagNA Pure LC RNA isolation tissue lysis buffer (Roche Diagnostics AG, Rotkreuz, Switzerland). Plates were then sealed and frozen at −80° C. until further workup.

mRNA Isolation, Processing and qRT-PCR mRNA isolation was performed using the MagNA Pure 96 system (Roche Diagnostics AG, Rotkreuz, Switzerland) and the respective cellular RNA large volume kit (Roche Diagnostics AG, Rotkreuz, Switzerland) from thawed samples diluted 1:1 with PBS. The volume of the cell lysis and an elution volume of 100 µL were used. 20 µL of the resulting mRNA suspension was then used for reverse transcription using 20 µL of the transcript or first stand cDNA synthesis kit (Roche prime Supply, Mannheim, Germany). The resulting cDNA was diluted with 40 µL of $H_2O$ before using for qRT-PCR. qRT-PCR was performed by using the forward and the reverse primer, the corresponding Universal Probe Library (all from Microsynth, Balgach, Switzerland) and the Taqman Fast advanced master mix (Applied Biosystems), on an ABI 7900 machine (Applied Biosystems).

Calculations qRT-PCR Ct-values for the respective P450s were put into relation to the Ct-value of RN18S1 (microsynth, Balgach, Switzerland) of the same sample. Doing so, a respective Δct-value was calculated. Using the average of all Δct-values for the vehicle control samples, a ΔΔct-value was calculated for each sample (ΔΔct-value(sample)=Δct-value(sample)−average of Δct-value of all vehicle controls). The fold induction of the respective sample was calculated as $2^{(-\Delta\Delta ct)}$. The individual fold induction values were then averaged per treatment condition (usually n=3 biological replicates).

Relative induction values to the respective positive inducer compound condition (10 µM omeprazole for CYP1A2; 1000 µM Phenobarbital for CYP2B6; 10 µM Rifampicin for CYP3A4) were then calculated from the fold induction values as follows:

Relative induction (%)=100×(T−V)/(P−V)

T: fold induction of test compound condition
P: fold induction of positive inducer compound
V: fold induction of vehicle controls Results of CYP3A4 induction are given in Table 5. Exemplified compounds of present invention did not cause a significant change in CYP 3A4 mRNA at any concentration. The results indicated that exemplified compounds had no CYP induction liability, which can avoid potential drug interaction in clinical application.

TABLE 5

Relative induction values of compounds of present invention to 10 µM Rifampicin

| Example No. | Relative induction of Positive control (10 µM Rifampicin) (%) |
|---|---|
| 4-A | −0.63 |
| 4-B | −0.90 |
| 24 | −0.72 |
| 70-A | 0.42 |
| 70-B | −0.42 |
| 71-A | −0.10 |

Example 78

Ames Microsuspension Assay

The Ames microsuspension assay examines if a compound causes DNA mutations. The method was based on a modified pre-incubation version described by Kado et al (see references: B. N. Ames, J. McCann, E. Yamasaki, Mutation Res. 1975, 31, 347-364 N.Y. Kado, D. Langley, and E. Eisenstadt, Mutation Res. 1983, 121, 25-32). Five *Salmonella typhimurium* tester strains (TA1535, TA97, TA98, TA100, and TA102) were treated with the test compound in absence and in presence of an exogenous metabolic activation system (S9). The bacteria were pre-incubated for 1 h, the pre-incubation volume is 210 µL (100 µL of overnight culture, 100 µL of S9 mix (10% S9) or 100 µL phosphate buffer, and 10 µL test compound solution). The overnight cultures were resuspended for the test in cold phosphate buffer. The S9 mix contains potassium chloride, magnesium chloride, sodium phosphate buffered saline, NADP$^+$ and glucose-6-phosphate. The test tubes are incubated and shaken for 60 minutes at 37° C. 2.2 mL soft agar supplemented with L-histidine and biotin was added afterwards and the content of the tubes were mixed and poured on Vogel-Bonner minimal agar plates.

Three replicate plates for the test compound and negative control or two replicate plates for the positive controls were incubated at 37° C., upside down, for 2 days. Colonies were counted electronically using an automatic image analysis system after having inspected the background lawn for signs of toxicity. Plates exhibiting precipitate or contamination were counted manually.

S9 is an in vitro metabolic system which is obtained from liver homogenates by centrifuging them at 9000 g for 20 minutes. It contains CYP450 isoforms, phase-II metabolic enzymes, etc. In the Ames microsuspension assay test, S9 is used to assess mutagenicity of compounds, some of which require metabolic activation to become mutagenic.

Criteria of the Ames microsuspension assay: a positive result is defined as a reproducible, dose-related increase in the number of revertant colonies in at least one of the strains. For TA1535 and TA98, the positive threshold is a 2-fold increase over control. For TA97, TA100 and TA102, the threshold is a 1.5-fold increase.

Results of Ames microsuspension assay are given in Table 6. Exemplified compounds of present invention showed negative results suggesting that there was no indication of mutagenicity of the compounds tested in the Ames microsuspension assay.

TABLE 6

Ames microsuspension assay results

| Compound NO. | Ames result |
|---|---|
| 1-B | negative |
| 4 | negative |
| 4-A | negative |
| 4-B | negative |
| 9 | negative |
| 27 | negative |
| 29-A | negative |
| 29-B | negative |
| 34 | negative |
| 39 | negative |
| 70-A | negative |
| 70-B | negative |
| 71-A | negative |

Example 79 hERG Channel Inhibition Assay

The hERG channel inhibition assay is a highly sensitive measurement that identifies compounds exhibiting hERG inhibition related to cardiotoxicity in vivo. The hERG K$^+$ channels were cloned in humans and stably expressed in a CHO (Chinese hamster ovary) cell line. CHO$_{hERG}$ cells were used for patch-clamp (voltage-clamp, whole-cell) experiments. Cells were stimulated by a voltage pattern to activate hERG channels and conduct I$_{KhERG}$ currents (rapid delayed outward rectifier potassium current of the hERG channel). After the cells were stabilized for a few minutes, the amplitude and kinetics of I$_{KhERG}$ were recorded at a stimulation frequency of 0.1 Hz (6 bpm). Thereafter, the test compound was added to the preparation at increasing concentrations. For each concentration, an attempt was made to reach a steady-state effect, usually, this was achieved within 3-10 min at which time the next highest concentration was applied. The amplitude and kinetics of I$_{KhERG}$ are recorded in each concentration of the drug which were compared to the control values (taken as 100%). (references: Redfern W S, Carlsson L, Davis A S, Lynch W G, MacKenzie I, Palethorpe S, Siegl P K, Strang I, Sullivan A T, Wallis R, Camm A J, Hammond T G. 2003; Relationships between preclinical cardiac electrophysiology, clinical QT interval prolongation and torsade de pointes for a broad range of drugs: evidence for a provisional safety margin in drug development. Cardiovasc. Res. 58:32-45, Sanguinetti M C, Tristani-Firouzi M. 2006; hERG potassium channels and cardiac arrhythmia. Nature 440:463-469, Webster R, Leishman D, Walker D. 2002; Towards a drug concentration effect relationship for QT prolongation and torsades de pointes. Curr. Opin. Drug Discov. Devel. 5:116-26).

Results of hERG are given in Table 7. A safety ratio (hERG IC$_{20}$/EC$_{50}$)>30 suggests a low potential of hERG related cardiotoxicity.

TABLE 7 hERG results and safety ratio.

| Compound NO. | hERG IC$_{20}$ (µM) | hERG IC$_{50}$ (µM) | Safety ratio (hERG IC$_{20}$/EC$_{50}$) |
|---|---|---|---|
| 1-B | >10 | >20 | >56 |
| 4 | >10 | >20 | >154 |
| 4-A | >10 | >20 | >149 |
| 4-B | >10 | >20 | >116 |
| 9 | >10 | >20 | >833 |
| 27 | >10 | >20 | >278 |
| 29-A | >10 | >20 | >526 |
| 29-B | >10 | >20 | >546 |
| 34 | >10 | >20 | >333 |
| 39 | >10 | >20 | >59 |
| 71-A | >10 | >20 | >75 |

Example 80

GSH Adduct Screening Assay

The formation of reactive metabolites is an unwanted drug property because of the idiosyncratic clinical adverse effect. GSH adduct formation is used to evaluate the formation of reactive metabolites in vitro. Positive controls were Diclofenac, Troglitazone, Nefazodone and mGluR5. Solvent control was DMSO.

Incubation

All compounds including positive and solvent control were incubated using a 96-deep-well plate (Eppendorf) at 20 µM (addition of 1 µL of 10 mM DMSO stock solution) in 450 µL of 0.1 M sodium phosphate buffer at pH 7.4 containing rat liver microsomes (RLM) and human liver microsomes (HLM). Microsomal protein concentration is 1 mg/mL. Pipetting was performed using a TECAN pipetting robot. The buffer was prepared at room temperature by combining 2.62 g NaH$_2$PO$_4$.1H$_2$O and 14.43 g Na$_2$HPO$_4$.2H$_2$O dissolved in H$_2$O (Millipore, >18 MΩ) to a weight of 1000 g (pH 7.4). After 5 minutes of pre-incubation at 37° C. the reaction was started by adding 50 µL of buffer containing GSH (100 mM) and NADPH (20 mM). Fresh stock solutions of GSH and NADPH were prepared straight before each experiment. The final concentrations were 5 mM for GSH and 1 mM for NADPH. After 60 minutes of incubation at 37° C. (shaking at 800 rpm) the reaction is quenched with 500 µL of cold acetonitrile and centrifuged at 5000×g at 25° C. for 11 minutes. Before LC-MS/MS analysis the supernatant was split to two fractions, 450 µL and 400 each followed by evaporation using a $N_2$ stream at 35° C. to a volume of approximately 150 pt.

Liquid Chromatography

Sample clean-up and chromatography of analytes were performed on-line by a column-switching set-up of two HPLC columns. From each sample 50 µL were injected (Shimadzu SilHTC) and loaded with water containing 0.1% formic acid onto a trapping column (Waters Oasis HLB 2.1×10 mm, 25 µm) with a flow rate of 0.3 mL/min. After 1.5 min the trapped analytes were then flushed (included a change in flow direction on the trapping column) onto an analytical column (Waters Atlantis T3 2.1×100 mm, 3 µm) with a total flow of 0.2 mL/min starting with 95/5% water containing 0.1% formic acid/acetonitrile. The fraction of acetonitrile was increased to 20% acetonitrile between 2 and 2.5 minutes, to 70% at 10 minutes and to 98% at 11 minutes. After 12 minutes the analytical column was equilibrated to start conditions (5% acetonitrile). The trapping column was washed with acetonitrile for 1 minute at a flow rate of 1.5 mL/min and equilibrated for 1.25 minutes with water containing 0.1% formic acid at a flow rate of 1.5 mL/min. The total running time was 14 min per sample.

Mass Spectrometry

A triple quadrupole-linear ion trap mass spectrometer 4000 Qtrap equipped with an electrospray ionization source (Turbo V) was used, both from Applied Biosystems/MDS Sciex. Based on a published method of Dieckhaus et al. (2005) a precursor ion survey scan (PreIS) method was used to detect GSH-conjugates in negative ion mode. Briefly, as survey scan ions (400 to 900 amu within 2 seconds) are scanned for precursors of m/z 272 amu, the ion spray voltage was −4200 V, the source temperature 500° C., nitrogen was used as curtain and collision gas. If the parent molecule exceeds a molecular mass of 500 the scan range was changed to 500 amu to 1000 amu within 2 seconds. For signals in the survey scan exceeding 7500 cts (that was approximately 5 times of the background signal), enhanced resolution scan and enhanced product ion scan were triggered which allowed isotope determination and confirmation of a positive GSH adduct by the presence of diagnostic fragment ions. Further instrument settings were as following: Curtain gas: 30 psi, CAD gas: 10 psi Gas 1: 30 psi, Gas 2: 50 psi, declustering potential: −70 V, entrance potential: −10 V, collision energy: −24 V, and cell exit potential −15 V. Data acquisition was performed using Analyst 1.4.2, data analysis, i.e. sample control (solvent) comparisons were performed with Metabolite ID 1.3 (Applied Biosystems/MDS Sciex). (reference: Dieckhaus, C. M., Fernandez-Metzler, C. L., King, R., Krolikowski, P. H., and Baillie, T. A. (2005). Negative ion tandem mass spectrometry for the detection of glutathione conjugates. Chem Res Toxicol 18, 630-638).

Results of GSH are given in Table 8. Exemplified compounds of present invention showed no flag in GSH assay indicating that no potential reactive metabolite formation which might lead to idiosyncratic hepatotoxicity.

TABLE 8

GSH results

| Compound NO. | GSH results* |
|---|---|
| 4 | No flag |
| 4-A | No flag |
| 4-B | No flag |
| 9 | No flag |
| 27 | No flag |
| 29-A | No flag |
| 34 | No flag |
| 39 | No flag |
| 70-A | No flag |
| 70-B | No flag |
| 71-A | No flag |

*No Flag: no GSH adduct formation observed when compared to control (DMSO).

Example 81

Comparison of the Mean Plasma Concentration and PK Parameters after 1 mg/kg Intravenous Dosing to Rat The single dose PK in Male Wister-Han Rats was performed to assess pharmacokinetic properties of tested compounds. Two groups of animals were dosed via bolus intravenous (IV) of the respective compound. Blood samples (approximately 20 µL) were collected via Jugular vein or an alternate site at 5 min, 15 min, 30 min, 1 hr, 2 hr, 4 hr, 7 hr and 24 hr post-dose for IV group. Blood samples were placed into tubes containing EDTA-K2 anticoagulant and centrifuged at 5000 rpm for 6 min at 4° C. to separate plasma from the samples. Following centrifugation, the resulting plasma was transferred to clean tubes for bioanalysis on LC/MS/MS. The pharmacokinetic parameters were calculated using non-compartmental module of WinNonlin® Professional 6.2.

Results of PK parameters are given in Table 9. Exemplified compounds of present invention clearly showed unexpected superior PK profile on C0, CL and AUC compared to GS-9620 and S-1 in rat PK study with 5-10 folds higher C0, 3-5 folds lower systemic clearance (CL) and 5-10 folds higher exposure (AUC). Therefore, compounds of present invention potentially could lead to less dose frequency and lower dose in clinical application.

TABLE 9 the mean plasma concentration and PK parameters

| | Mean plasma concentration (nM) Dose compound | | | | |
|---|---|---|---|---|---|
| | GS-9620* | S-1 | Example 70-A | Example 70-B | Example 71-A |
| | Test Compound | | | | |
| | GS-9620 | S-1 | Example 70-A | Example 70-B | Example 71-A |
| | IV | IV | IV | IV | IV |
| Time (h) | (1 mpk) | (1 mpk) | (1 mpk) | (1 mpk) | (1 mpk) |
| 0.083 | 170 | 534 | 3052 | 2782 | 1848 |
| 0.25 | 102 | 236 | 1342 | 1434 | 1003 |
| 0.5 | 65.4 | 125 | 718 | 862 | 537 |
| 1 | 48.1 | 38 | 354 | 461 | 292 |
| 2 | 21.6 | 9 | 110 | 173 | 115 |
| 4 | 13 | ND | 20.5 | 29.1 | 18.2 |
| 8** | 4.17 | ND | 6.28 | 16.7 | ND |
| 24 | ND | ND | ND | ND | ND |

TABLE 9-continued the mean plasma concentration and PK parameters

| | Mean plasma concentration (nM) Dose compound | | | | |
|---|---|---|---|---|---|
| | GS-9620* | S-1 | Example 70-A | Example 70-B | Example 71-A |
| | | | Test Compound | | |
| Time (h) | GS-9620 IV (1 mpk) | S-1 IV (1 mpk) | Example 70-A IV (1 mpk) | Example 70-B IV (1 mpk) | Example 71-A IV (1 mpk) |
| C0 (nM) | 220 | 534 | 3052 | 2782 | 1848 |
| CL (mL/min/kg) | 205 | 261 | 56 | 48.7 | 84.6 |
| AUC0-inf (nM · hr) | 201 | 201 | 1627 | 1894 | 1182 |

*GS-9620 data were available from WO2016023511.
**7 hrs for Example 70-A, Example 70-B and Example 71-A.

The invention claimed is:

1. A compound of formula (I),

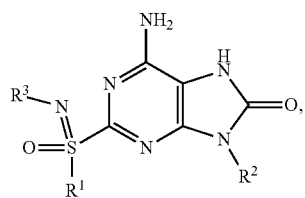

(I)

wherein
$R^1$ is $C_{1-6}$alkyl, halo$C_{1-6}$alkyl, $C_{3-7}$cylcoalkyl$C_{1-6}$alkyl, $C_{1-6}$alkoxy$C_{1-6}$alkyl or pyrrolidinyl$C_{1-6}$alkyl;
$R^2$ is $C_{1-6}$alkyl, phenyl$C_{1-6}$alkyl, pyridinyl$C_{1-6}$alkyl or pyrimidinyl$C_{1-6}$alkyl, said phenyl$C_{1-6}$alkyl, pyridinyl$C_{1-6}$alkyl and pyrimidinyl$C_{1-6}$alkyl are unsubstituted or substituted by one, two or three substituents independently selected from halogen, $C_{1-6}$alkyl, $C_{1-6}$alkoxy, cyano, carboxy, carbamoyl, halo$C_{1-6}$alkyl, $C_{1-6}$alkylsulfonyl, $C_{1-6}$alkoxycarbonyl, $C_{1-6}$alkoxy$C_{1-6}$alkylaminocarbonyl, pyrrolidinylcarbonyl and piperidinylcarbonyl;
$R^3$ is H;
or a pharmaceutically acceptable salt, enantiomer or diastereomer thereof.

2. The compound according to claim 1, wherein
$R^1$ is methyl, ethyl, propyl, butyl, chloropropyl, cyclohexylmethyl, methoxyethyl, methoxypropyl, pyrrolidinylpropyl or trifluoroethyl;
$R^2$ is isobutyl, benzyl, chlorobenzyl, fluorobenzyl, bromobenzyl, chlorofluorobenzyl, chloromethylbenzyl, dichlorobenzyl, difluorobenzyl, methylbenzyl, methoxybenzyl, cyanobenzyl, carbamoylbenzyl, trifluoromethylbenzyl, methylsulfonylbenzyl, methoxycarbonylbenzyl, carboxybenzyl, methoxyethylaminocarbonylbenzyl, piperidinylcarbonylbenzyl, pyrrolidinylcarbonylbenzyl, pyridinylmethyl, chloropyridinylmethyl, methylpyridinylmethyl, pyrimidinylmethyl or methylpyrimidinylmethyl;
$R^3$ is H;
or a pharmaceutically acceptable salt, enantiomer or diastereomer thereof.

3. The compound according to claim 1, or a pharmaceutically acceptable salt, enantiomer or diastereomer thereof, wherein $R^1$ is $C_{1-6}$alkyl, halo$C_{1-6}$alkyl or $C_{1-6}$alkoxy$C_{1-6}$alkyl.

4. The compound according to claim 3, or a pharmaceutically acceptable salt, enantiomer or diastereomer thereof, wherein $R^1$ is methyl, ethyl, propyl, butyl, chloropropyl, trifluoroethyl, methoxyethyl or methoxypropyl.

5. The compound according to claim 3, or a pharmaceutically acceptable salt, enantiomer or diastereomer thereof, wherein $R^1$ is $C_{1-6}$alkyl.

6. The compound according to claim 5, or a pharmaceutically acceptable salt, enantiomer or diastereomer thereof, wherein $R^1$ is methyl, ethyl or propyl.

7. The compound according to claim 6, or a pharmaceutically acceptable salt, enantiomer or diastereomer thereof, wherein $R^1$ is ethyl.

8. The compound according to claim 1, or a pharmaceutically acceptable salt, enantiomer or diastereomer thereof, wherein $R^2$ is
phenyl$C_{1-6}$alkyl, said phenyl$C_{1-6}$alkyl is unsubstituted or substituted by halogen, carbamoyl, $C_{1-6}$alkyl, carboxy, cyano, $C_{1-6}$alkoxy, $C_{1-6}$alkylsulfonyl and $C_{1-6}$alkoxy$C_{1-6}$alkylaminocarbonyl;
pyridinyl$C_{1-6}$alkyl, said pyridinyl$C_{1-6}$alkyl is unsubstituted or substituted by $C_{1-6}$alkyl; or
pyrimidinyl$C_{1-6}$alkyl, said pyrimidinyl$C_{1-6}$alkyl is unsubstituted or substituted by $C_{1-6}$alkyl.

9. The compound according to claim 8, or a pharmaceutically acceptable salt, enantiomer or diastereomer thereof, wherein $R^2$ is benzyl, methylbenzyl, chlorobenzyl, fluorobenzyl, difluorobenzyl, cyanobenzyl, carboxybenzyl, methoxybenzyl, methylsulfonylbenzyl, methoxyethylaminocarbonylbenzyl, pyridinylmethyl, methylpyridinylmethyl, pyrimidinylmethyl or methylpyrimidinylmethyl.

10. The compound according to claim 9, or a pharmaceutically acceptable salt, enantiomer or diastereomer thereof, wherein $R^2$ is benzyl, methylbenzyl, chlorobenzyl, fluorobenzyl, difluorobenzyl, carboxybenzyl or methylpyridinylmethyl.

11. The compound according to claim 10, or a pharmaceutically acceptable salt, enantiomer or diastereomer thereof, wherein $R^2$ is methylbenzyl or chlorobenzyl.

12. The compound according to claim 1, wherein
$R^1$ is $C_{1-6}$alkyl or $C_{1-6}$alkoxy$C_{1-6}$alkyl;
$R^2$ is phenyl$C_{1-6}$alkyl, said phenyl$C_{1-6}$alkyl is unsubstituted or substituted by halogen, carbamoyl, $C_{1-6}$alkyl, carboxy, cyano and $C_{1-6}$alkoxy$C_{1-6}$alkylaminocarbonyl; or
pyrimidinyl$C_{1-6}$alkyl, said pyrimidinyl$C_{1-6}$alkyl is unsubstituted or substituted by $C_{1-6}$alkyl;
$R^3$ is H;
or a pharmaceutically acceptable salt, enantiomer or diastereomer thereof.

13. The compound according to claim 12, wherein
$R^1$ is methyl, ethyl, propyl, butyl or methoxyethyl;
$R^2$ is benzyl, methylbenzyl, chlorobenzyl, fluorobenzyl, cyanobenzyl, carboxybenzyl, methoxyethylaminocarbonylbenzyl, pyrimidinylmethyl or methylpyrimidinylmethyl;
$R^3$ is H;
or a pharmaceutically acceptable salt, enantiomer or diastereomer thereof.

14. The compound according to claim 1, wherein
$R^1$ is $C_{1-6}$alkyl;
$R^2$ is phenyl$C_{1-6}$alkyl, said phenyl$C_{1-6}$alkyl is unsubstituted or substituted by halogen or $C_{1-6}$alkyl;

R³ is H;
or a pharmaceutically acceptable salt, enantiomer or diastereomer thereof.

15. The compound according to claim 14, wherein
R¹ is ethyl or propyl;
R² is benzyl, chlorobenzyl or methylbenzyl;
R³ is H;
or a pharmaceutically acceptable salt, enantiomer or diastereomer thereof.

16. The compound according to claim 1 selected from a group consisting of:
6-Amino-9-benzyl-2-(methylsulfonimidoyl)-7H-purin-8-one;
6-Amino-9-benzyl-2-(ethylsulfonimidoyl)-7H-purin-8-one;
6-Amino-9-benzyl-2-(2-methoxyethylsulfonimidoyl)-7H-purin-8-one;
6-Amino-9-benzyl-2-(propylsulfonimidoyl)-7H-purin-8-one;
6-Amino-9-benzyl-2-(butylsulfonimidoyl)-7H-purin-8-one;
6-Amino-9-benzyl-2-(3-methoxypropylsulfonimidoyl)-7H-purin-8-one;
6-Amino-9-benzyl-2-(2,2,2-trifluoroethylsulfonimidoyl)-7H-purin-8-one;
6-Amino-9-benzyl-2-(cyclohexylmethylsulfonimidoyl)-7H-purin-8-one;
6-Amino-9-[(4-chlorophenyl)methyl]-2-(propylsulfonimidoyl)-7H-purin-8-one;
6-Amino-9-[(4-methoxyphenyl)methyl]-2-(methylsulfonimidoyl)-7H-purin-8-one;
6-Amino-2-(3-chloropropylsulfonimidoyl)-9-[(4-methoxyphenyl)methyl]-7H-purin-8-one;
6-Amino-9-[(4-methoxyphenyl)methyl]-2-(3-pyrrolidin-1-ylpropylsulfonimidoyl)-7H-purin-8-one;
6-Amino-9-[(4-chlorophenyl)methyl]-2-(methylsulfonimidoyl)-7H-purin-8-one;
6-Amino-9-[(6-chloro-3-pyridyl)methyl]-2-(propylsulfonimidoyl)-7H-purin-8-one;
6-Amino-9-[(2-chlorophenyl)methyl]-2-(propylsulfonimidoyl)-7H-purin-8-one;
6-Amino-2-(methylsulfonimidoyl)-9-(3-pyridylmethyl)-7H-purin-8-one;
3-[[6-Amino-8-oxo-2-(propylsulfonimidoyl)-7H-purin-9-yl]methyl]benzonitrile;
3-[[6-amino-8-oxo-2-(propylsulfonimidoyl)-7H-purin-9-yl]methyl]benzamide;
6-Amino-2-(methylsulfonimidoyl)-9-(2-pyridylmethyl)-7H-purin-8-one;
6-Amino-2-(methylsulfonimidoyl)-9-(4-pyridylmethyl)-7H-purin-8-one;
6-Amino-9-isobutyl-2-(propylsulfonimidoyl)-7H-purin-8-one;
6-Amino-9-[(3-chlorophenyl)methyl]-2-(propylsulfonimidoyl)-7H-purin-8-one;
6-Amino-2-(propylsulfonimidoyl)-9-[[4-(trifluoromethyl)phenyl]methyl]-7H-purin-8-one;
6-Amino-9-[(4-fluorophenyl)methyl]-2-(propylsulfonimidoyl)-7H-purin-8-one;
6-Amino-9-[(4-bromophenyl)methyl]-2-(propylsulfonimidoyl)-7H-purin-8-one;
6-Amino-9-[(3,4-dichlorophenyl)methyl]-2-(propylsulfonimidoyl)-7H-purin-8-one;
6-Amino-9-(3,4-difluorophenylmethyl)-2-(propylsulfonimidoyl)-7H-purin-8-one;
6-Amino-9-[(4-chloro-3-methyl-phenyl)methyl]-2-(propylsulfonimidoyl)-7H-purin-8-one;
6-Amino-2-(propylsulfonimidoyl)-9-(p-tolylmethyl)-7H-purin-8-one;
6-Amino-9-[(4-chloro-3-fluorophenyl)methyl]-2-(propylsulfonimidoyl)-7H-purin-8-one;
6-Amino-9[(2,4-difluorophenyl)methyl]-2-(propylsulfonimidoyl)-7H-purin-8-one;
4-[[6-Amino-8-oxo-2-(propylsulfonimidoyl)-7H-purin-9-yl]methyl]benzonitrile;
4-[[6-Amino-8-oxo-2-(propylsulfonimidoyl)-7H-purin-9-yl]methyl]benzamide;
6-Amino-9-[(6-methyl-3-pyridyl)methyl]-2-(propylsulfonimidoyl)-7H-purin-8-one;
6-Amino-9-[(2-methyl-4-pyridyl)methyl]-2-(propylsulfonimidoyl)-7H-purin-8-one;
6-Amino-9-[(3-chloro-4-methyl-phenyl)methyl]-2-(propylsulfonimidoyl)-7H-purin-8-one;
6-Amino-9[(4-methylsulfonylphenyl)methyl]-2-(propylsulfonimidoyl)-7H-purin-8-one;
Methyl 4-[[6-amino-8-oxo-2-(propylsulfonimidoyl)-7H-purin-9-yl]methyl]benzoate;
4-[[6-Amino-8-oxo-2-(propylsulfonimidoyl)-7H-purin-9-yl]methyl]benzoic acid;
4-[[6-Amino-8-oxo-2-(propylsulfonimidoyl)-7H-purin-9-yl]methyl]-N-(2-methoxyethyl)benzamide;
6-Amino-9-[[4-(piperidine-1-carbonyl)phenyl]methyl]-2-(propylsulfonimidoyl)-7H-purin-8-one;
6-Amino-2-(S-propylsulfonimidoyl)-9-[[4-(pyrrolidine-1-carbonyl)phenyl]methyl]-7H-purin-8-one;
6-Methyl-2-(propylsulfonimidoyl)-9-(pyrimidin-5-ylmethyl)-7H-purin-8-one;
6-Methyl-9-[(2-methylpyrimidin-5-yl)methyl]-2-(propylsulfonimidoyl)-7H-purin-8-one;
6-Amino-9[(4-chlorophenyl)methyl]-2-(ethylsulfonimidoyl)-7H-purin-8-one;
6-Amino-2-(ethylsulfonimidoyl)-9-(p-tolylmethyl)-7H-purin-8-one; and
6-Amino-2-(ethylsulfonimidoyl)-9[(4-fluorophenyl)methyl]-7H-purin-8-one;
or a pharmaceutically acceptable salt, enantiomer or diastereomer thereof.

17. The compound according to claim 1 selected from a group consisting of:
6-Amino-9-benzyl-2-(propylsulfonimidoyl)-7H-purin-8-one;
6-Amino-9[(4-chlorophenyl)methyl]-2-(propylsulfonimidoyl)-7H-purin-8-one;
6-Amino-9-[(6-chloro-3-pyridyl)methyl]-2-(propylsulfonimidoyl)-7H-purin-8-one;
6-Amino-9[(4-fluorophenyl)methyl]-2-(propylsulfonimidoyl)-7H-purin-8-one;
6-Amino-9[(4-bromophenyl)methyl]-2-(propylsulfonimidoyl)-7H-purin-8-one;
6-Amino-2-(propylsulfonimidoyl)-9-(p-tolylmethyl)-7H-purin-8-one;
6-Amino-9-[(6-methyl-3-pyridyl)methyl]-2-(propylsulfonimidoyl)-7H-purin-8-one;
Methyl 4-[[6-amino-8-oxo-2-(propylsulfonimidoyl)-7H-purin-9-yl]methyl]benzoate;
4-[[6-Amino-8-oxo-2-(propylsulfonimidoyl)-7H-purin-9-yl]methyl]benzoic acid;
6-Methyl-9-[(2-methylpyrimidin-5-yl)methyl]-2-(propylsulfonimidoyl)-7H-purin-8-one;
6-Amino-9-[(4-chlorophenyl)methyl]-2-(ethylsulfonimidoyl)-7H-purin-8-one; and
6-Amino-2-(ethylsulfonimidoyl)-9-(p-tolylmethyl)-7H-purin-8-one;

or a pharmaceutically acceptable salt, enantiomer or diastereomer thereof.

18. The compound according to claim 1 selected from a group consisting of:
6-Amino-9-[(4-chlorophenyl)methyl]-2-(ethylsulfonimidoyl)-7H-purin-8-one; and
6-Amino-2-(ethylsulfonimidoyl)-9-(p-tolylmethyl)-7H-purin-8-one;
or a pharmaceutically acceptable salt, enantiomer or diastereomer thereof.

19. A pharmaceutical composition comprising a compound according to claim 1 and a therapeutically inert carrier.

20. The compound which is 6-Amino-9-[(4-chlorophenyl)methyl]-2-(ethylsulfonimidoyl)-7H-purin-8-one, or a pharmaceutically acceptable salt thereof.

21. The compound which is 6-Amino-2-(ethylsulfonimidoyl)-9-(p-tolylmethyl)-7H-purin-8-one, or a pharmaceutically acceptable salt thereof.

* * * * *